(12) United States Patent
Barbas, III et al.

(10) Patent No.: US 9,902,962 B2
(45) Date of Patent: Feb. 27, 2018

(54) CHIMERIC POLYPEPTIDES HAVING TARGETED BINDING SPECIFICITY

(71) Applicant: THE SCRIPPS RESEARCH INSTITUTE, La Jolla, CA (US)

(72) Inventors: Carlos F. Barbas, III, La Jolla, CA (US); Andrew Mercer, Poolesville, MD (US); Brian M. Lamb, San Diego, CA (US); Thomas Gaj, Solana Beach, CA (US)

(73) Assignee: The Scripps Research Institute, La Jolla, CA (US)

( * ) Notice: Subject to any disclaimer, the term of this patent is extended or adjusted under 35 U.S.C. 154(b) by 80 days.

(21) Appl. No.: 14/425,944

(22) PCT Filed: Sep. 4, 2013

(86) PCT No.: PCT/US2013/058100
§ 371 (c)(1),
(2) Date: Mar. 4, 2015

(87) PCT Pub. No.: WO2014/039585
PCT Pub. Date: Mar. 13, 2014

(65) Prior Publication Data
US 2015/0284728 A1 Oct. 8, 2015

Related U.S. Application Data

(60) Provisional application No. 61/696,689, filed on Sep. 4, 2012, provisional application No. 61/753,763, filed (Continued)

(51) Int. Cl.
*C12N 15/62* (2006.01)
*C12N 9/16* (2006.01)
*C12N 9/22* (2006.01)

(52) U.S. Cl.
CPC .............. *C12N 15/62* (2013.01); *C12N 9/16* (2013.01); *C12N 9/22* (2013.01); *C07K 2319/80* (2013.01)

(58) Field of Classification Search
None
See application file for complete search history.

(56) References Cited

U.S. PATENT DOCUMENTS

| 2010/0086532 A1* | 4/2010 | Barbas, III | C12N 15/1082 424/94.5 |
| 2011/0301073 A1* | 12/2011 | Gregory | C12N 15/62 514/1.1 |

(Continued)

FOREIGN PATENT DOCUMENTS

WO    WO 2012033462 A1 *    3/2012    ........... C07K 14/415

OTHER PUBLICATIONS

U.S. Appl. No. 61/560,630, filed Nov. 16, 2011, Specification, Drawings and Abstract.*

(Continued)

*Primary Examiner* — Richard Ekstrom
(74) *Attorney, Agent, or Firm* — Hugh Wang; Thomas Fitting; Stephen Whiteside

(57) ABSTRACT

Disclosed herein are chimeric polypeptides, including compositions thereof, expression vectors, and methods of use thereof, for the generation of transgenic cells, tissues, plants, and animals. The compositions, vectors, and methods of the present invention are also useful in gene therapy techniques. The invention provides a chimeric polypeptide. The polypeptide includes: a) a recombinase, nuclease or transcription factor, or fragment thereof; and b) a transcription activator-like effector (TALE) protein.

9 Claims, 30 Drawing Sheets

Related U.S. Application Data on Jan. 17, 2013, provisional application No. 61/818,364, filed on May 1, 2013.

(56) References Cited

U.S. PATENT DOCUMENTS

| | | | |
|---|---|---|---|
| 2012/0178131 A1* | 7/2012 | Voytas | C12N 9/22 435/91.52 |
| 2013/0196373 A1* | 8/2013 | Gregory | C07K 14/195 435/69.1 |

* cited by examiner

| | | | | | | | | | | | | | | | | | | | | | | | | | | |
|---|---|---|---|---|---|---|---|---|---|---|---|---|---|---|---|---|---|---|---|---|---|---|---|---|---|---|
| AvrXa7 | NI | HG | NI | NI | NS | HD | NN | HD | HD | HD | NS | N* | N* | HD | HD | NS | NS | NN | NN | NI | NG | NN | NI | N* | NS | N* |
| Target Sequence | A | T | A | A | A | C | C | C | C | C | T | C | C | A | A | C | C | A | G | G | T | G | C | T | A | A |
| Synthetic | NI | NG | NI | NI | NI | HD | HD | HD | HD | HD | NG | HD | HD | NI | NI | HD | HD | NI | NN | NN | NG | NN | HD | NG | NI | NI |

FIG. 7

TALE and TALER sequences
AvrXa7 protein:
MDPIRSRTPSPARELLPGPQPDRVQPTADRGGAPPAGGPLDGLPARRTMSRTRLPSPPAPSPA
FSAGSFSDLLRQFDPSLLDTSLLDSMPAVGTPHTAAAPAECDEVQSGLRAADDPPPTVRVAV
TAARPPRAKPAPRRRAAQPSDASPAAQVDLRTLGYSQQQQEKIKPKVRSTVAQHHEALVGH
GFTHAHIVALSQHPAALGTVAVTYQDIIRALPEATHEDIVGVGKQWSGARALEALLTEAGEL
RGPPLQLDTGQLLKIAKRGGVTAVEAVHAWRNALTGAPLNLTPDQVVAIASNIGGKQALET
VQRLLPVLCQDHGLTPDQVVAIASHGGGKQALETVQRLLPVLCQDHGLTPDQVVAIASNIG
GKQALETVQRLLPVLCQAHGLTPDQVVAIASNIGGKQALETVQRLLPVLCQDHGLTPAQVV
AIASNSGGKQALETVQRLLPVLCQDHGLTPDQVVAIASHDGGKQALETLQRLLPVLCQDHG
LTPDQVVAIANNNGGKQALETLQRLLPVLCQDHGLTPDQVVAIASHDGGKQALETVQRLLP
VLCQDHGLTPDQVVAIASHDGGKQALETVQRLLPVLCQDHGLTPAQVVAIASHDGGKQAL
ETVQRLLPVLCQDHGLTPDQVVAIASNSGGKQALETVQRLLPVLCQDHGLTPDQVVAIASN
GGKQALETVQRLLPVLCQDHGLTPDQVVAIASNGGKQALETVQRLLPVQRLLPVLCQDHG
LTQDQVVAIASHDGGKQALETVQRLLPVLCQDHGLTPDQVVAIASHDGGKQALETVQRLLP
VLCQDHGLTPDQVVAIASNSGGKQALETVQRLLPVLCQDHGLTPDQVVAIASNSGGKQALE
TVQRLLPVLCQDHGLTPDQVVAIASNNGGKQALETVQRLLPVLCQDHGLTPDQVVAIANN
NGGKQALETVQRLLPVLCQDHGLTPAQVVAIASNIGGKQALETVQRLLPVLCQDHGLTLDQ
VVAIASNGGSKQALETVQRLLPVLCQDHGLTPDQVVAIANNNGGKQALETVQRLLPVLCQ
DHGLTPDQVVAIASNIGGKQALETVQRLLPVLCQDHGLTLDQVVAIASNGGKQALETVQRL
LPVLCQDHGLTPNQVVAIASNSGGKQALETVQRLLPVLCQDHGLTPNQVVAIASNGGKQAL
ESIVAQLSRPDPALAALTNDHLVALACLGGRPALDAVKKGLPHAPELIRRINRRIPERTSHRV
PDLAHVVRVLGFFQSHSHPAQAFDDAMTQFEMSRHGLVQLFRRVGVTEFEARYGTLPPASQ
RWDRILQASGMKRAKPSPTSAQTPDQASLHAFADSLERDLDAPSPMHEGDQTRASSRKRSR
SDRAVTGPSTQQSFEVRVPEQQDALHLPLSWRVKRPRTRIGGGLPDPGTPIAADLAASSTVM
WEQDAAPFAGAADDFPAFNEEELAWLMELLPQSGSVGGTI

FIG. 8

AvrXa7 gene:
ATGGATCCCATTCGTTCGCGCACGCCAAGTCCTGCCCGCGAGCTTCTGCCCGGACCCCA
ACCGGATAGGGTTCAGCCGACTGCAGATCGGGGGGGGGCTCCGCCTGCTGGCGGCCCC
CTGGATGGCTTGCCCGCTCGGCGGACGATGTCCCGGACCCGGCTGCCATCTCCCCCTGC
GCCCTCGCCTGCGTTCTCGGCGGGCAGCTTCAGCGATCTGCTCCGTCAGTTCGATCCGTC
GCTTCTTGATACATCGCTTCTTGATTCGATGCCTGCCGTCGGCACGCCGCATACAGCGGC
TGCCCCAGCAGAGTGCGATGAGGTGCAATCGGGTCTGCGTGCAGCCGATGACCCGCCAC
CCACCGTGCGTGTCGCTGTCACTgcgGCGCGGCCGCCGCGCGCCAAGCCGGCCCCGCGAC
GGCGTGCGGCGCAACCCTCCGACGCTTCGCCGGCCGCGCAGGTGGATCTACGCACGCTC
GGCTACAGTCAGCAGCAGCAAGAGAAGATCAAACCGAAGGTGCGTTCGACAGTGGCGC
AGCACCACGAGGCACTGGTGGGCCATGGGTTTACACACGCGCACATCGTTGCGCTCAGC
CAACACCCGGCAGCGTTAGGGACCGTTGCTGTCACGTATCAGGACATAATCAGGGCGTT
GCCAGAGGCGACACACGAAGACATCGTTGGCGTCGGCAAACAGTGGTCCGGCGCACGC
GCTCTGGAGGCCTTGCTCACGGAGGCGGGGGAGTTGAGAGGTCCGCCGTTACAGTTGGA
CACAGGCCAACTTCTCAAGATTGCAAAACGTGGCGGCGTGACCGCAGTGGAGGCAGTG
CATGCATGGCGCAATGCACTGACGGGTGCCCCCCTGAACCTGACCCCGGACCAAGTGGT
GGCCATCGCCAGCAATATTGGCGGCAAGCAGGCGCTGGAGACGGTACAGCGGCTGTTG
CCGGTGCTGTGCCAGGACCATGGCCTGACCCCGGACCAGGTCGTGGCCATCGCCAGCCA
TGGCGGCGGCAAGCAGGCGCTGGAGACGGTGC

FIG. 9

AGCGGCTGTTGCCGGTGCTGTGCCAGGACCATGGCCTGACCCCGGACCAGGTGGTGGCC
ATCGCCAGCAATATTGGCGGCAAGCAGGCGCTAGAGACGGTGCAGCGGCTGTTGCCGG
TGCTGTGCCAGGCCCATGGCCTGACCCCGGACCAGGTCGTGGCCATCGCCAGCAATATT
GGCGGCAAGCAGGCGCTGGAGACGGTGCAGCGGCTGTTGCCGGTGCTGTGCCAGGACC
ATGGCCTGACCCCGGCCCAGGTGGTGGCCATCGCCAGCAATAGTGGCGGCAAGCAGGC
GCTGGAGACGGTGCAGCGGCTGTTGCCGGTGCTGTGCCAGGACCATGGCCTGACCCCGG
ACCAAGTCGTGGCCATCGCCAGCCACGATGGCGGCAAGCAGGCGCTGGAGACGCTGCA
GCGGCTGTTGCCGGTGCTGTGCCAGGACCATGGCCTGACCCCGGACCAGGTCGTGGCCA
TCGCCAACAATAACGGCGGCAAGCAGGCGCTGGAGACGCTGCAGCGGCTGTTGCCGGT
GCTGTGCCAGGACCATGGCCTGACCCCGGACCAAGTGGTGGCCATCGCCAGCCACGATG
GCGGCAAGCAGGCGCTGGAGACGGTGCAGCGGCTGTTGCCGGTGCTGTGCCAGGACCA
TGGCCTGACCCCGGACCAGGTGGTGGCCATCGCCAGCCACGATGGCGGCAAGCAGGCG
CTGGAGACGGTGCAGCGGCTGTTGCCGGTGCTGTGCCAGGACCATGGCCTGACCCCGGC
CCAAGTGGTGGCCATCGCCAGCCACGATGGCGGCAAGCAGGCGCTGGAGACGGTGCAG
CGGCTGTTGCCGGTGCTGTGCCAGGACCATGGCCTGACCCCGGACCAGGTGGTGGCCAT
CGCCAGCAATAGCGGCGGCAAGCAGGCGCTGGAGACGGTACAGCGGCTGTTGCCGGTG
CTGTGCCAGGACCATGGACTGACCCCGGACCAGGTCGTGGCCATCGCCAGCAATGGCG
GCAAGCAGGCGCTGGAGACGGTACAGCGGCTGTTGCCGGTGCTGTGCCAGGACCATGG
CCTGACCCCGGACCAGGTCGTGGCCATCGCCAGCAATGGCGGCAAGCAGGCGCTGGAG
ACGGTGCAGCGGCTGTTGCCGGTACAGCGGCTGTTGCCGGTGCTGTGCCAGGACCATGG
CCTGACCCAGGACCAGGTGGTGGCCATCGCCAGCCACGATGGCGGCAAGCAGGCGCTG
GAGACGGTGCAGCGGCTGTTGCCGGTGCTGTGCCAGGACCATGGCCTGACCCCGGACCA
AGTGGTGGCCATCGCCAGCCACGATGGCGGCAAACAGGCGCTGGAGACGGTGCAGCGG
CTGTTGCCGGTGCTGTGCCAGGACCATGGCCTGACCCCGGACCAGGTGGTGGCCATCGC
CAGCAATAGTGGCGGCAAGCAGGCGCTGGAGACGGTGCAGCGGCTGTTGCCGGTGCTG
TGCCAGGACCATGGCCTGACCCCGGACCAAGTGGTGGCCATCGCCAGCAATAGTGGCG
GCAAGCAGGCGCTGGAGACGGTGCAGCGGCTGTTGCCGGTGCTGTGCCAGGACCATGG
CCTGACCCCGGACCAGGTGGTGGCCATCGCCAGCAATAACGGCGGCAAGCAGGCGCTG
GAGACGGTGCAGCGGCTGTTGCCGGTGCTGTGCCAGGACCATGGCCTGACCCCGGACCA
GGTCGTGGCCATCGCCAACAATAACGGCGGCAAGCAGGCGCTGGAGACGGTGCAGCGG
CTGTTGCCGGTGCTGTGCCAGGACCATGGCCTGACCCCGGCGCAGGTGGTGGCCATCGC
CAGCAATATTGGCGGCAAGCAGGCGCTGGAGACGGTGCAGCGGCTGTTGCCGGTGCTGT
GCCAGGACCATGGCCTGACCCTGGACCAGGTGGTGGCCATTGCCAGCAATGGCGGCAG
CAAACAGGCGCTAGAGACGGTGCAGCGGCTGTTGCCGGTGCTGTGCCAGGACCATGGC
CTGACCCCGGACCAAGTGGTGGCCATCGCCAACAATAACGGCGGCAAGCAGGCGCTGG
AGACGGTGCAGCGGCTGTTGCCGGTGCTGTGCCAGGACCATGGCCTGACCCCGGACCAG
GTCGTGGCCATCGCCAGCAATATTGGCGGCAAGCAGGCGCTGGAGACGGTGCAGCGGC
TGTTGCCGGTGCTGTGCCAGGACCATGGCCTGACCCTGGACCAGGTGGTGGCCATCGCC
AGCAATGGCGGCAAGCAGGCGCTGGAGACGGTGCAGCGGCTGTTGCCGGTGCTGTGCC
AGGACCATGGCCTGACCCCGAACCAGGTGGTGGCCATCGCCAGCAATAGTGGCGGCAA
GCAGGCGCTGGAGACGGTGCAGCGGCTGTTGCCGGTGCTGTGCCAGGACCATGGCCTGA
CCCCGAACCAGGTGGTGGCCATCGCCAGCAATGGCGGCAAGCAGGCGCTGGAGAGCAT
TGTTGCCCAGTTATCTCGCCCTGATCCGGCGTTGGCCGCGTTGACCAACGACCACCTCGT
CGCCTTGGCCTGCCTCGGCGGACGTCCTGCCCTGGATGCAGTGAAAAAGGGATTGCCGC
ACGCGCCGGAATTGATCAGAAGAATCAATCGCCGCATTCCCGAACGCACGTCCCATCGC
GTTCCCGACCTCGCGCACGTGGTTCGCGTGCTTGGTTTTTTCCAGAGCCACTCCCACCCA
GCGCAAGCATTCGATGACGCCATGACGCAGTTCGAGATGAGCAGGCACGGCTTGGTAC
AGCTCTTTCGCAGAGTGGGCGTCACCGAATTCGAAGCCCGCTACGGAACGCTCCCCCCA
GCCTCGCAGCGTTGGGACCGTATCCTCCAGGCATCAGGG

FIG. 9 (cont.)

```
ATGAAAAGGGCCAAACCGTCCCCTACTTCAGCTCAAACACCGGATCAGGCGTCTTTGCA
TGCATTCGCCGATTCGCTGGAGCGTGACCTTGATGCGCCCAGCCCAATGCACGAGGGAG
ATCAGACGCGGGCAAGCAGCCGTAAACGGTCCCGATCGGATCGTGCTGTCACCGGCCCC
TCCACACAGCAATCTTTCGAGGTGCGCGTTCCCGAACAGCAAGATGCGCTGCATTTGCC
CCTCAGCTGGAGGGTAAAACGCCCGCGTACCAGGATCGGGGGCGGCCTCCCGGATCCT
GGTACGCCCATCGCTGCCGACCTGGCAGCGTCCAGCACCGTGATGTGGGAACAAGATGC
GGCCCCCTTCGCAGGGGCAGCGGATGATTTCCCGGCATTCAACGAAGAGGAGCTCGCAT
GGTTGATGGAGCTATTGCCTCAGTCAGGCTCAGTCGGAGGGACGATCTGA
```

FIG. 9 (cont.)

Gin-AvrΔ74

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSPRQFDPSLLDTSLLDSMPAVGTPHTAAAPAECDEVQS
GLRAADDPPPTVRVAVTAARPPRAKPAPRRRAAQPSDASPAAQVDLRTLGYSQQQQEKIKP
KVRSTVAQHHEALVGHGFTHAHIVALSQHPAALGTVAVTYQDIIRALPEATHEDIVGVGKQ
WSGARALEALLTEAGELRGPPLQLDTGQLLKIAKRGGVTAVEAVHAWRNALTGAPLNLTP
DQVVAIASNIGGKQALETVQRLLPVLCQDHGLTPDQVVAIASHGGGKQALETVQRLLPVLC
QDHGLTPDQVVAIASNIGGKQALETVQRLLPVLCQAHGLTPDQVVAIASNIGGKQALETVQ
RLLPVLCQDHGLTPAQVVAIASNSGGKQALETVQRLLPVLCQDHGLTPDQVVAIASHDGGK
QALETLQRLLPVLCQDHGLTPDQVVAIANNNGGKQALETLQRLLPVLCQDHGLTPDQVVAI
ASHDGGKQALETVQRLLPVLCQDHGLTPDQVVAIASHDGGKQALETVQRLLPVLCQDHGL
TPAQVVAIASHDGGKQALETVQRLLPVLCQDHGLTPDQVVAIASNSGGKQALETVQRLLPV
LCQDHGLTPDQVVAIASNGGKQALETVQRLLPVLCQDHGLTPDQVVAIASNGGKQALETV
QRLLPVQRLLPVLCQDHGLTQDQVVAIASHDGGKQALETVQRLLPVLCQDHGLTPDQVVAI
ASHDGGKQALETVQRLLPVLCQDHGLTPDQVVAIASNSGGKQALETVQRLLPVLCQDHGL
TPDQVVAIASNSGGKQALETVQRLLPVLCQDHGLTPDQVVAIASNNGGKQALETVQRLLPV
LCQDHGLTPDQVVAIANNNGGKQALETVQRLLPVLCQDHGLTPAQVVAIASNIGGKQALET
VQRLLPVLCQDHGLTLDQVVAIASNGGSKQALETVQRLLPVLCQDHGLTPDQVVAIANNN
GGKQALETVQRLLPVLCQDHGLTPDQVVAIASNIGGKQALETVQRLLPVLCQDHGLTLDQV
VAIASNGGKQALETVQRLLPVLCQDHGLTPNQVVAIASNSGGKQALETVQRLLPVLCQDHG
LTPNQVVAIASNGGKQALESIVAQLSRPDPALAALTNDHLVALACLG

FIG. 10

Gin-AvrΔ87

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSPDSMPAVGTPHTAAAPAECDEVQSGLRAADDPPPTV
RVAVTAARPPRAKPAPRRRAAQPSDASPAAQVDLRTLGYSQQQQEKIKPKVRSTVAQHHE
ALVGHGFTHAHIVALSQHPAALGTVAVTYQDIIRALPEATHEDIVGVGKQWSGARALEALL
TEAGELRGPPLQLDTGQLLKIAKRGGVTAVEAVHAWRNALTGAPLNLTPDQVVAIASNIGG
KQALETVQRLLPVLCQDHGLTPDQVVAIASHGGGKQALETVQRLLPVLCQDHGLTPDQVV
AIASNIGGKQALETVQRLLPVLCQAHGLTPDQVVAIASNIGGKQALETVQRLLPVLCQDHGL
TPAQVVAIASNSGGKQALETVQRLLPVLCQDHGLTPDQVVAIASHDGGKQALETLQRLLPV
LCQDHGLTPDQVVAIANNNGGKQALETLQRLLPVLCQDHGLTPDQVVAIASHDGGKQALE
TVQRLLPVLCQDHGLTPDQVVAIASHDGGKQALETVQRLLPVLCQDHGLTPAQVVAIASHD
GGKQALETVQRLLPVLCQDHGLTPDQVVAIASNSGGKQALETVQRLLPVLCQDHGLTPDQ
VVAIASNGGKQALETVQRLLPVLCQDHGLTPDQVVAIASNGGKQALETVQRLLPVQRLLPV
LCQDHGLTQDQVVAIASHDGGKQALETVQRLLPVLCQDHGLTPDQVVAIASHDGGKQALE
TVQRLLPVLCQDHGLTPDQVVAIASNSGGKQALETVQRLLPVLCQDHGLTPDQVVAIASNS
GGKQALETVQRLLPVLCQDHGLTPDQVVAIASNNGGKQALETVQRLLPVLCQDHGLTPDQ
VVAIANNNGGKQALETVQRLLPVLCQDHGLTPAQVVAIASNIGGKQALETVQRLLPVLCQD
HGLTLDQVVAIASNGGSKQALETVQRLLPVLCQDHGLTPDQVVAIANNNGGKQALETVQR
LLPVLCQDHGLTPDQVVAIASNIGGKQALETVQRLLPVLCQDHGLTLDQVVAIASNGGKQA
LETVQRLLPVLCQDHGLTPNQVVAIASNSGGKQALETVQRLLPVLCQDHGLTPNQVVAIAS
NGGKQALESIVAQLSRPDPALAALTNDHLVALACLG

FIG. 11

Gin-AvrΔ120

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSTVRVAVTAARPPRAKPAPRRRAAQPSDASPAAQVDL
RTLGYSQQQQEKIKPKVRSTVAQHHEALVGHGFTHAHIVALSQHPAALGTVAVTYQDIIRA
LPEATHEDIVGVGKQWSGARALEALLTEAGELRGPPLQLDTGQLLKIAKRGGVTAVEAVHA
WRNALTGAPLNLTPDQVVAIASNIGGKQALETVQRLLPVLCQDHGLTPDQVVAIASHGGGK
QALETVQRLLPVLCQDHGLTPDQVVAIASNIGGKQALETVQRLLPVLCQAHGLTPDQVVAI
ASNIGGKQALETVQRLLPVLCQDHGLTPAQVVAIASNSGGKQALETVQRLLPVLCQDHGLT
PDQVVAIASHDGGKQALETLQRLLPVLCQDHGLTPDQVVAIANNNGGKQALETLQRLLPVL
CQDHGLTPDQVVAIASHDGGKQALETVQRLLPVLCQDHGLTPDQVVAIASHDGGKQALET
VQRLLPVLCQDHGLTPAQVVAIASHDGGKQALETVQRLLPVLCQDHGLTPDQVVAIASNSG
GKQALETVQRLLPVLCQDHGLTPDQVVAIASNGGKQALETVQRLLPVLCQDHGLTPDQVV
AIASNGGKQALETVQRLLPVQRLLPVLCQDHGLTQDQVVAIASHDGGKQALETVQRLLPVL
CQDHGLTPDQVVAIASHDGGKQALETVQRLLPVLCQDHGLTPDQVVAIASNSGGKQALET
VQRLLPVLCQDHGLTPDQVVAIASNSGGKQALETVQRLLPVLCQDHGLTPDQVVAIASNNG
GKQALETVQRLLPVLCQDHGLTPDQVVAIANNNGGKQALETVQRLLPVLCQDHGLTPAQV
VAIASNIGGKQALETVQRLLPVLCQDHGLTLDQVVAIASNGGSKQALETVQRLLPVLCQDH
GLTPDQVVAIANNNGGKQALETVQRLLPVLCQDHGLTPDQVVAIASNIGGKQALETVQRLL
PVLCQDHGLTLDQVVAIASNGGKQALETVQRLLPVLCQDHGLTPNQVVAIASNSGGKQALE
TVQRLLPVLCQDHGLTPNQVVAIASNGGKQALESIVAQLSRPDPALAALTNDHLVALACLG

FIG. 12

Gin-AvrΔ120*

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSTVRVAVTAARPPHAVAGPAAQVDLRTLGYSQQQQE
KIKPKVRSTVAQHHEALVGHGFTHAHIVALSQHPAALGTVAVTYQDIIRALPEATHEDIVGV
GKQWSGARALEALLTEAGELRGPPLQLDTGQLLKIAKRGGVTAVEAVHAWRNALTGAPLN
LTPDQVVAIASNIGGKQALETVQRLLPVLCQDHGLTPDQVVAIASHGGGKQALETVQRLLP
VLCQDHGLTPDQVVAIASNIGGKQALETVQRLLPVLCQAHGLTPDQVVAIASNIGGKQALE
TVQRLLPVLCQDHGLTPAQVVAIASNSGGKQALETVQRLLPVLCQDHGLTPDQVVAIASHD
GGKQALETLQRLLPVLCQDHGLTPDQVVAIANNNGGKQALETLQRLLPVLCQDHGLTPDQ
VVAIASHDGGKQALETVQRLLPVLCQDHGLTPDQVVAIASHDGGKQALETVQRLLPVLCQ
DHGLTPAQVVAIASHDGGKQALETVQRLLPVLCQDHGLTPDQVVAIASNSGGKQALETVQ
RLLPVLCQDHGLTPDQVVAIASNGGKQALETVQRLLPVLCQDHGLTPDQVVAIASNGGKQA
LETVQRLLPVQRLLPVLCQDHGLTQDQVVAIASHDGGKQALETVQRLLPVLCQDHGLTPDQ
VVAIASHDGGKQALETVQRLLPVLCQDHGLTPDQVVAIASNSGGKQALETVQRLLPVLCQD
HGLTPDQVVAIASNSGGKQALETVQRLLPVLCQDHGLTPDQVVAIASNNGGKQALETVQRL
LPVLCQDHGLTPDQVVAIANNNGGKQALETVQRLLPVLCQDHGLTPAQVVAIASNIGGKQA
LETVQRLLPVLCQDHGLTLDQVVAISNGGSKQALETVQRLLPVLCQDHGLTPDQVVAIAN
NNGGKQALETVQRLLPVLCQDHGLTPDQVVAIASNIGGKQALETVQRLLPVLCQDHGLTLD
QVVAIASNGGKQALETVQRLLPVLCQDHGLTPNQVVAIASNSGGKQALETVQRLLPVLCQD
HGLTPNQVVAIASNGGKQALESIVAQLSRPDPALAALTNDHLVALACLG

FIG. 13

Gin-AvrΔ147

MLIGYVRVSTNDQNTDLQRNALV

Gin-Avr15Δ128-synthetic DNA:
ATGCTGATTGGCTATGTAAGGGTATCAACAAATGACCAGAATACAGACCTGCAACGAA
ACGCTCTTGTTTGTGCAGGATGTGAACAAATATTTGAAGATAAATTAAGCGGAACAAGG
ACAGACCGACCGGGATTAAAACGCGCTTTAAAGCGCCTTCAAAAAGGTGACACACTGG
TTGTCTGGAAACTGGATCGCCTCGGGCGAAGCATGAAACATTTGATTTCTCTCGTAGGG
GAATTACGAGAGCGAGGGATTAATTTTCGCAGTCTTACTGACAGTATTGATACGTCATC
TCCAATGGGGCGTTTTTTCTTCTACGTTATGGGTGCCCTGGCTGAAATGGAACGAGAACT
AATTATCGAGCGAACGATGGCTGGACTTGCTGCCGCCAGAAATAAAGGCCGTATTGGAG
GTCGCCCGCGTAAATCGGGGTCTGGATCCCCCGCGCGGCCGCCGCGCGCCAAGCCGGCC
CCGCGACGGCGTGCTGCGCAACCCTCCGACGCTTCGCCGGCCGCGCAGGTGGATCTACG
CACGCTCGGCTACAGTCAGCAGCAGCAAGAGAAGATCAAACCGAAGGTGCGTTCGACA
GTGGCGCAGCACCACGAGGCACTGGTGGGCCATGGGTTTACACACGCGCACATCGTTGC
GCTCAGCCAACACCCGGCAGCGTTAGGGACCGTCGCTGTCACGTATCAGCACATAATCA
CGGCGTTGCCAGAGGCGACACACGAAGACATCGTTGGCGTCGGCAAACAGTGGTCCGG
CGCACGCGCCCTGGAGGCCTTGCTCACGGATGCGGGGGAGTTGAGAGGTCCGCCGTTAC
AGTTGGACACAGGCCAACTTGTGAAGATTGCAAAACGTGGCGGCGTGACCGCAATGGA
GGCAGTGCATGCATCGCGCAATGCACTGACGGGTGCCCCCCTGGAGCTGACTCCGGACC
AAGTGGTGGCTATCGCCAGCAACATTGGCGGCAAGCAAGCGCTCGAAACGGTGCAGCG
GCTGTTGCCGGTGCTGTGCCAGGACCATGGCCTGACTCCGGACCAAGTGGTGGCTATCG
CCAGCAACGGTGGCGGCAAGCAAGCGCTCGAAACGGTGCAGCGGCTGTTGCCGGTGCT
GTGCCAGGACCATGGCCTGACTCCGGACCAAGTGGTGGCTATCGCCAGCAACATTGGCG
GCAAGCAAGCGCTCGAAACGGTGCAGCGGCTGTTGCCGGTGCTGTGCCAGGACCATGG
CCTGACTCCGGACCAAGTGGTGGCTATCGCCAGCAACATTGGCGGCAAGCAAGCGCTCG
AAACGGTGCAGCGGCTGTTGCCGGTGCTGTGCCAGGACCATGGCCTGACTCCGGACCAA
GTGGTGGCTATCGCCAGCAACATTGGCGGCAAGCAAGCGCTCGAAACGGTGCAGCGGC
TGTTGCCGGTGCTGTGCCAGGACCATGGCCTGACTCCGGACCAAGTGGTGGCTATCGCC
AGCCACGATGGCGGCAAGCAAGCGCTCGAAACGGTGCAGCGGCTGTTGCCGGTGCTGT
GCCAGGACCATGGCCTGACTCCGGACCAAGTGGTGGCTATCGCCAGCCACGATGGCGG
CAAGCAAGCGCTCGAAACGGTGCAGCGGCTGTTGCCGGTGCTGTGCCAGGACCATGGC
CTGACTCCGGACCAAGTGGTGGCTATCGCCAGCCACGATGGCGGCAAGCAAGCGCTCG
AAACGGTGCAGCGGCTGTTGCCGGTGCTGTGCCAGGACCATGGCCTGACTCCGGACCAA
GTGGTGGCTATCGCCAGCCACGATGGCGGCAAGCAAGCGCTCGAAACGGTGCAGCGGC
TGTTGCCGGTGCTGTGCCAGGACCATGGCCTGACTCCGGACCAAGTGGTGGCTATCGCC
AGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCGG
CAAGCAAGCGCTCGAAACGGTGCAGCGGCTGTTGCCGGTGCTGTGCCAGGACCATGGC
CTGACTCCGGACCAAGTGGTGGCTATCGCCAGCCACGATGGCGGCAAGCAAGCGCTCG
AAACGGTGCAGCGGCTGTTGCCGGTGCTGTGCCAGGACCATGGCCTGACTCCGGACCAA
GTGGTGGCTATCGCCAGCCACGATGGCGGCAAGCAAGCGCTCGAAACGGTGCAGCGGC
TGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACATTGGCGG
CAAGCAAGCGCTCGAAAGCATTGTGGCCCAGCTGAGCCGGCCTGATCCGGCGTTGGCCG
CGTTGACCAACGACCACCTCGTCGCCTTGGCCTGCCTCGGCCCCAAGAAGAAGCGCAAG
GTGTAG

FIG. 16

GinAvr15Δ128-synthetic protein:

*MLIGYVRVSTNDQNTDLQRNALVCAGCEQIFEDKLSGTRTDRPGLKR*
*ALKRLQKGDTLVVWKLDRLGRSMKHLISLVGELRERGINFRSLTDSI*
*DTSSPMGRFFFYVMGALAEMERELIIERTMAGLAAARNKGRIGGRPR*
*KSGSGS*<u>PALRPPRAKPAPRRRAAQPSDASPAAQVDLRTLGYSQQQQE</u>
<u>KIKPKVRSTVAQHHEALVGHGFTHAHIVALSQHPAALGTVAVTYQHI</u>
<u>ITALPE</u>
<u>ATHEDIVGVGKQWSGARALEALLTDAGELRGPPLQ</u>    (-1)
<u>LDTGQLVKIAKRGGVTAMEAVHASRNALTGAPLN</u>    (0)T
LTPDQVVAIASNIGGKQALETVQRLLPVLCQDHG    (1)A
LTPDQVVAIASNGGGKQALETVQRLLPVLCQDHG    (2)T
LTPDQVVAIASNIGGKQALETVQRLLPVLCQDHG    (3)A
LTPDQVVAIASNIGGKQALETVQRLLPVLCQDHG    (4)A
LTPDQVVAIASNIGGKQALETVQRLLPVLCQDHG    (5)A
LTPDQVVAIASHDGGKQALETVQRLLPVLCQDHG    (6)C
LTPDQVVAIASHDGGKQALETVQRLLPVLCQDHG    (7)C
LTPDQVVAIASHDGGKQALETVQRLLPVLCQDHG    (8)C
LTPDQVVAIASHDGGKQALETVQRLLPVLCQDHG    (9)C
LTPDQVVAIASHDGGKQALETVQRLLPVLCQDHG    (10)C
LTPDQVVAIASNGGGKQALETVQRLLPVLCQDHG    (11)T
LTPDQVVAIASHDGGKQALETVQRLLPVLCQDHG    (12)C
LTPDQVVAIASHDGGKQALETVQRLLPVLCQDHG    (13)C
LTPDQVVAIASNIGGKQALETVQRLLPVLCQDHG    (14)A
LTPDQVVAIASNIGGKQALE            (15)A
<u>SIVAQLSRPDPALAALTNDHLVALACLGPKKKRKV</u>

Key:
Gin Recombinase (italics)
TALE N-terminal framework (double underline)
RVD (DNA binding domains) (emboldened)
TALE C-terminal framework (dotted underline)

FIG. 17

```
TALE-G      QVDLRTLGYSQQQQEKIKPKVRSTVAQHHEALVGHGFTHAHIVALSQHPAALGTVAVTYQ  60
Brg11       ---MAALGYSREQIRKLKQESLSGVARYHAPLTRHGFTHTDICRISRRWQSLRMVAKNYP  57
             :****::*  .*:*  :  * **::*  .*, *****:.*  *::   :*  **  .*

TALE-G      HIITALPEATHEDIVGVG░░░░░RALEALLTDAGELRGFPLQLDTGQLVKIAKRGGVTA  120
Brg11       KLIAALPDLTRTHIVDIA░░░░░LALEALLFVATALAAAPLRLRASQIAIIAQCGERPA  117
             ::*:****: *:..*.:.  .:  ******. *  *  ..**:* :.*:. **: *   .*

TALE-G      MEAVHASRWALTGAP  135
Brg11       ILALHRLRRKLTGAP  132
             : *:*  *:. *****
```

| TALEN Pair | NTD | % Editing | Indels |
|---|---|---|---|
| 1: T1/T2 | NT-T | 16.6% | |
| 2: T1/T2 | NT-G | 7.5% | |
| 3: T1/T2 | NT-βN | 11.3% | |
| 4: T1/T2 | NT-αN | 12.9% | |
| 5: T1/T2 | NT-dHax3 | 20.1% | |
| 6: G1/G2 | NT-T | 4.4% | |
| 7: G1/G2 | NT-G | 15.2% | (9/30) |
| 8: G1/G2 | NT-αN | 4.9% — 3x Ave = 14.4% | |
| 9: G1/G2 | NT-βN | 28.9% | (10/30) |
| 10: G1/G2 | NT-dHax3 | 6.2% | |
| 11: A1/A2 | NT-T | 1% | |
| 12: A1/A2 | NT-G | 0.7% | |
| 13: A1/A2 | NT-βN | 0.4% | |
| 14: A1/A2 | NT-αN | 9.1% | (3/30) |
| 15: A1/A2 | NT-dHax3 | 1.2% | |
| 16: C1/C2 | NT-T | 8.6% | |
| 17: C1/C2 | NT-G | 8.9% | |
| 18: C1/C2 | NT-βN | 13.4% | (9/30) |
| 19: C1/C2 | NT-αN | 17.9% | (8/30) |
| 20: C1/C2 | NT-dHax3 | 9.1% | |

TALEN Pair 7 (9/30)
```
CCR5 (x20) TGGAAATTCTTCCAGAATTGATACTGACTGTATGGAAAATGAGAGCTGCAGGTGTAATGAAGACCTTCTTTTTGAGATCTGGT
   -6 (x3) TGGAAATTCTTCCATAATTGATATTGACTGTATGGA------AGGCTGCGGGTGTAATGAATACCTTCTTTTTGAGATCTGGT
   -6      TGGAAATTCTTCCAGAATTGATACTGACTGTATGGAAAA------CTGCAGGTGTAATGAAGACCTTCTTTTTGAGATCTGGT
   -6      TGGAAATTCTTCCAGAATTGATACTGACTGTATGGAA------AGCTGCAGGTGTAATGAAGACCTTCTTTTTGAGATCTGGT
   -7      TGGAAATTCTTCCAGAATTGATACTGACTGTATGGAA-------GCTGCAGGTGTAATGAAGACCTTCTTTTTGAGATCTGGT
   -10     TGGAAATTCTTCCAGAATTGATACTGACTGTAG----------AGCTGCAGGTGTAATGAAGACCTTCTTTTTGAGATCTGGT
   -11     TGGAAATTCTTCCAGAATTGATACTGACTGTAT-----------GCTGCAGGTGTAATGAAGACCTTCTTTTTGAGATCTGGT
   -13     TGGAAATTCTTCCAGAATTGATACTGACTGT-------------GCTGCAGGTGTAATGAAGACCTTCTTTTTGAGATCTGGT
```

TALEN pair 9 (10/30)
(CCR5 WT X 21)
```
         TGGAAATTCTTCCAGAATTGATACTGACTGTATGGAAAATGAGAGCTGCAGGTGTAATGAAGACCTTCTTTTTGAGATCTGGT
   -4      TGGAAATTCTTCCAGAATTGATACTGACTGTATGGAAA----GAGCTGCAGGTGTAATGAAGACCTTCTTTTTGAGATCTGGT
   -5      TGGAAATTCTTCCAGAATTGATACTGACTGTATGGAA-----GAGCTGCAGGTGTAATGAAGACCTTCTTTTTGAGATCTGGT
   -6      TGGAAATTCTTCCAGAATTGATACTGACTGTATGGA------GAGCTGCAGGTGTAATGAAGACCTTCTTTTTGAGATCTGGT
   -9       TGGAAATTCTTCCAGAATTGATACTGACT---------ATGAGAGCTGCAGGTGTAATGAAGACCTTCTTTTTGAGATCTGGT
   -10 (x2) TGGAAATTCTTCCAGAATTGATACTGACTGTA----------GAGCTGCAGGTGTAATGAAGACCTTCTTTTTGAGATCTGGT
   -11     TGGAAATTCTTCCAGAATTGATACTGAC-----------TGAGAGCTGCAGGTGTAATGAAGACCTTCTTTTTGAGATCTGGT
   -11     TGGAAATTCTTCCAGGATTGATACTGACT-----------GAGAGCTGCAGGTGTAATGAAGACCTTCTTTTTGAGATCTGGT
   -11     TGGAAATTCTTCCAGAATTGATACTGACT-----------GAGAGCTGCAGGTGTAATGAAGACCTTCTTTTTGAGATCTGGT
   -11     TGGAAATTCTTCCAGAATTGATACTGACT-----------AGGAGCTGCAGGTGTAATGAAGACCTTCTTTTTGAGATCTGGT
```

TALEN pair 14 (3/30)
(CCR5 WT X27)
```
       TGGAAATTCTTCCAGAATTGATACTGACTGTATGGAAAATGAGAGCTGCAGGTGTAATGAAGACCTTCTTTTTGAGATCTGGT
   -2    TGGAAATTCTTCCAGAATTGATACTGACT--ATGGAAAATGAGAGCTGCAGGTGTAATGAAGACCTTCTTTTTGAGATCTGGT
   -3    TGGAAATTCTTCCTCAATTGATACTGA---TATGGAAAATGAGAGCTGCAGGTGTAATGAAGACCTTCTTTTTGAGATCTGGT
   -9      TGGAAATTCTTCCAGAATTGATA---------TGGAAAATGAGAGCTGCAGGTGTAATGAAGACCTTCTTTTTGAGATCTGGT
```

TALEN Pair 18 (9/30)
(CCR5 WT X 20)
```
      TGGAAATTCTTCCAGAATTGATACTGACTGTATGGAAAATGAGAGCTGCAGGTGTAATGAAGACCTTCTTTTTGAGATCTGGT
   -4    TGGAAATTCTTCCAGAATTGATACTGACTGTATGA----TGAGAGCTGCAGGTGTAATGAAGACCTTCTTTTTGAGATCTGGT
   -4    TGGAAATTCTTCCAGAATTGATACTGACTGTATGG----TGAGAGCTGCAGGTGTAATGAAGACCTTCTTTTTGAGATCTGGT
   -5    TGGAAATTCTTCCAGAATTGATACTGACTGTA-----AATGAGAGCTGCAGGTGTAATGAAGACCTTCTTTTTGAGATCTGGT
   -5    TGGAAATTCTTCCAGAATTGATACTGACTGTATG-----TGAGAGCTGCAGGTGTAATGAAGACCTTCTTTTTGAGATCTGGT
   -9     TGGAAATTCTTCCAGAATTGATACTGA---------AAATGAGAGCTGCAGGTGTAATGAAGACCTTCTTTTTGAGATCTGGT
   -9     TGGAAATTCTTCCAGAATTGATACTGACTGTATGGA---------CTGCAGGTGTAATGAAGACCTTCTTTTTGAGATCTGGT
   -10    TGGAAATTCTTCCAGAATTGATACTGACTG---------TGAGAGCTGCAGGTGTAATGAAGACCTTCTTTTTGAGATCTGGT
   +3/-10 TGGAAATTCTTCCAGAATTGATACTgta----------TGAGAGCTGCAGGTGTAATGAAGACCTTCTTTTTGAGATCTGGT
   -12    TGGAAATTCTTCCAGAATTGATACTGACTGT-------------AGCTGCAGGTGTAATGAAGACCTTCTTTTTGAGATCTGGT
```

TALEN Pair 19 (8/30)
(CCR5 WT (x 23))
```
      TGGAAATTCTTCCAGAATTGATACTGACTGTATGGAAAATGAGAGCTGCAGGTGTAATGAAGACCTTCTTTTTGAGATCTGGT
   -7    TGGAAATTCTTCCAGAATTGATACTGACTGTATGGAAA-------CTGC-GGTGTAATGAAGACCTTCTTTTTGAGATCTGGT
   -7    TGGAAATTCTTCCAGAATTGATACTGACTGTA-------TGAGAGCTGCAGGTGTAATGAAGACCTTCTTTTTGAGATCTGGT
   -9    TGGAAATTCTTCCAGAATTAATACTGACTGT---------GAGAGCTGCAGGTGTAATGAAGACCTTCTTTTTGAGATCTGGT
   -10   TGGAAATTCTTCCAGAATTGATACTGACTG----------GAGAGCTGCAGGTGTAATGAAGACCTTCTTTTTGAGATCTGGT
   -11   TGGAAATTCTTCCAGAATTGATACTGACT-----------GAGAGCTGCAGGTGTAATGAAGACCTTCTTTTTGAGATCTGGT
   -15     TGGAAATTCTTCCAGAATTGATACTGACTG---------------CTGCAGGTGTAATGAAGACCTTCTTTTTGAGATCTGGT
   -18      TGGAAATTCTTCCAGAATTGATACTGACTGT------------------ATGTGTAATGAAGACCTTCTTTTTGAGATCTGGT
           -44      TGGAAATTCTTCCAGAATTGATA--------------------------------------CTTTTTGAGATCTGGT
```

FIG. 28

CHIMERIC POLYPEPTIDES HAVING TARGETED BINDING SPECIFICITY

CROSS REFERENCE TO RELATED APPLICATION(S)

This application claims benefit of priority under 35 U.S.C. § 119(e) of U.S. Ser. No. 61/696,689, filed Sep. 4, 2012; U.S. Ser. No. 61/753,763, filed Jan. 17, 2013; and U.S. Ser. No. 61/818,364, filed May 1, 2013, the entire contents of which are incorporated herein by reference in their entireties.

BACKGROUND OF THE INVENTION

Field of the Invention

The present invention relates generally to the field of biotechnology, and more specifically to chimeric recombinases that recognize specific DNA sequences.

Background Information

The ability of proteins to recognize DNA in a sequence-dependent manner is central to life, as a variety of protein domains have evolved to provide sequence-specific DNA recognition. DNA recognition by a select few of these domains is also the foundation for a wide variety of biotechnological applications. In particular, $C_2H_2$ zinc-finger proteins (ZFPs) were among the first DNA-binding proteins to be engineered to recognize user-defined DNA sequences and have been used with varying degrees of success for many applications, including transcriptional regulation, genome engineering and epigenetic modification. Modular assembly of ZFPs has facilitated these approaches. However, despite the advances and promise of ZFP technology, construction of specific, high-affinity ZFPs for certain sequences remains difficult and in select cases requires the use of time-consuming and labor-intensive selection systems not readily adopted by non-specialty laboratories.

Transcription activator-like effector (TALE) domains are a class of naturally occurring DNA-binding domains (DBDs) that represent a potential alternative to ZFP technology. TALEs, which are found in the plant pathogen *Xanthomonas*, contain a series of 33 to 35 amino acid repeats that function to selectively bind target DNA sequences. These repeats are identical with the exception of two adjacent repeat variable di-residues (RVDs) that confer DNA specificity by mediating binding to a single nucleotide. Arrays of over 30 repeats have been described that bind to DNA sites of similar numbers of base pairs (bps). Although there is inherent degeneracy in the binding of each RVD, recent reports have indicated that synthetic TALE proteins are specific enough to target single loci within the human genome.

The introduction of DNA double-strand breaks (DSBs) by chimeric nucleases, such as zinc-finger nucleases (ZFNs) can be used to knockout gene function or in the presence of exogenously added DNA drive cassette integration at the targeted loci. ZFNs have been extensively studied over the last decade and in some cases are approaching clinical use for gene therapy. Recently, a number of groups have explored the use of TALE DNA-binding domains fused to nucleases (TALENs) for targeted genome editing. Indeed, much of the work with ZFNs has been replicated with TALE nucleases, as TALENs may have advantages over ZFNs in regards to DNA-binding modularity. However, despite impressive research with ZFNs and TALENs, questions remain about their safety and specificity. In particular, off-target cleavage events remain difficult to detect, as the most likely result of an off-target DSB is the introduction of small insertions or deletions. Additionally, repair of DSBs relies on cell machinery that varies with cell type.

An alternate approach for achieving targeted genomic modifications is the use of site-specific recombinases (SSRs). SSRs, such as the tyrosine recombinases Cre and Flp, are valuable molecular biology tools that are routinely used to manipulate chromosome structure inside cells. Because these enzymes rely on a number of complex protein-protein and protein-DNA interactions to coordinate catalysis, SSRs exhibit remarkable target site specificity. To date, however, altering the specificity of many SSRs has proven difficult. Serine recombinases of the resolvase/invertase type provide a versatile alternative to tyrosine recombinases for genome engineering. In nature, these enzymes function as multi-domain protein complexes that coordinate recombination in a highly modular manner. However, mutants of several serine recombinases have been identified that do not require accessory factors for recombination. Additionally, numerous studies have shown that the native DBDs of serine recombinases can be replaced with custom-designed ZFPs to generate chimeric zinc-finger recombinases (ZFRs). In principle, ZFRs capable of recognizing an extended number of sequences could be generated, however, the lack of zinc-finger domains capable of recognizing all possible DNA triplets limits the potential modular targeting capacity of these enzymes.

ZFRs are composed of an activated catalytic domain derived from the resolvase/invertase family of serine recombinases and a zinc-finger DNA-binding domain that can be custom-designed to recognize almost any DNA sequence (FIG. 30A). ZFRs catalyze recombination between specific ZFR target sites that consist of two-inverted zinc-finger binding sites (ZFBS) flanking a central 20-bp core sequence recognized by the recombinase catalytic domain (FIG. 30B). In contrast to zinc-finger nucleases (ZFNs) and TAL effector nucleases (TALENs), ZFRs function autonomously and can excise and integrate transgenes in human and mouse cells without activating the cellular DNA damage response pathway. However, as with conventional site-specific recombinases, applications of ZFRs have been restricted by sequence requirements imposed by the recombinase catalytic domain, which dictate that ZFR target sites contain a 20-bp core derived from a native serine resolvase/invertase recombination site.

Site-specific DNA recombination systems such as Cre-loxP, FLP-FRT and ^C31-att have emerged as powerful tools for genetic engineering. The site-specific recombinases that promote these DNA rearrangements recognize short (30- to 40-bp) sequences and coordinate DNA cleavage, strand exchange and re-ligation by a mechanism that does not require DNA synthesis or a high-energy cofactor. This simplicity has allowed researchers to study gene function with extraordinary spatial and temporal sensitivity. However, the strict sequence requirements imposed by site-specific recombinases have limited their application to cells and organisms that contain artificially introduced recombination sites. In order to address this limitation, directed evolution has been used to alter the sequence specificity of several recombinases toward naturally occurring DNA sequences. Despite advances, the need for complex mutagenesis and selection strategies and the finding that re-engineered recombinase variants routinely exhibit relaxed substrate specificity have hindered the widespread adoption of this technology.

Accordingly, there is a need for a more generalized method of catalyzing targeted and site-specific recombination of the endogenous genome, particularly for gene therapy, as well as for enzymes that can catalyze such targeted and site-specific recombination. This is particularly useful for gene therapy, but would have many other applications in molecular biology, including in gene cloning and use in modification of industrial organisms and agricultural plants and animals.

SUMMARY OF THE INVENTION

Disclosed herein are targeted chimeric polypeptides, including compositions thereof, expression vectors, and methods of use thereof, for the generation of transgenic cells, tissues, plants, and animals. The compositions, vectors, and methods of the present invention are also useful in gene therapy techniques.

In one aspect, the invention provides a chimeric polypeptide. The polypeptide includes: a) a recombinase, nuclease or transcription factor, or fragment thereof; and b) a transcription activator-like effector (TALE) protein. In various embodiments, the TALE protein is truncated and includes a C-terminal or N-terminal truncation. In embodiments, the TALE protein is AcrXa7, Tal1c, and PthXo1. In embodiments, the TALE protein includes all or a portion an amino acid sequence as set forth in SEQ ID NO: 2. In some embodiments, the TALE protein is truncated between amino acid residues 27 and 268, 92 and 134, 120 and 129, 74 and 147, or 87 and 120 of SEQ ID NO: 2. In some embodiments, the TALE protein is truncated at amino acid residue 28, 74, 87, 92, 95, 120, 124, 128, 129, 147 and 150 of SEQ ID NO: 2.

In another aspect, the invention provides a method of generating a transcription activator-like effector (TALE) protein binding domain which specifically binds a desired nucleotide. The method includes a) randomizing the amino acid sequence of the TALE protein binding domain by mutating an amino acid residue within a variable di-residue (RVD), or within 1 to 2 amino acid residues N-terminal or C-terminal of the RVD; and b) selecting for the randomized TALE protein binding domain of (a), wherein the TALE protein binding domain specifically binds to the desired nucleotide.

In another aspect, the invention provides an isolated polypeptide comprising a *Xanthamonus* derived transcription activator-like effector (TALE) protein, the TALE protein having an N-terminal domain (NTD) comprising an amino acid sequence as set forth in SEQ ID NO: 3 (VGKQWSGARAL) having one or more mutations or deletions selected from: Q is Y, Q is S, Q is R, W is R, W is G, W is deleted, S is R, S is H, S is A, S is N, and S is T.

In another aspect, the invention provides an isolated polypeptide including a *Ralstonia* derived transcription activator-like effector (TALE) protein, the TALE protein having an N-terminal domain (NTD) including an amino acid sequence as set forth in SEQ ID NO: 8 (IVDIAR$_1$QR$_2$SGDLA) having one or more mutations or deletions selected from: R$_1$ is K, Q is Y, Q is S, Q is R, R$_2$ is W, R$_2$ is G, R$_2$ is deleted, S is R, S is H, S is A, S is N, and S is T.

In another embodiment, the invention provides a method of generating a transcription activator-like effector (TALE) protein N-terminal domain (NTD). The method includes: a) randomizing an amino acid sequence of the NTD by mutating or deleting one or more amino acid residues within the NTD, wherein the amino acid sequence is SEQ ID NO: 14 (VGKXXXGAR) or SEQ ID NO: 15 (VDIAXXXXGDLA); and b) selecting for the randomized TALE protein NTD of (a), wherein the TALE protein NTD specifically binds to a desired nucleotide or exhibits enhanced activity.

Also disclosed herein are chimeric proteins including a serine recombinase and one or more zinc finger binding domains, methods of generating ZFRs, compositions thereof, expression vectors, and methods of use thereof, for the generation of transgenic cells, tissues, plants, and animals. The compositions, vectors, and methods of the present invention are also useful in gene therapy techniques.

In one aspect, the invention provides a method of generating a plurality of zinc finger recombinase (ZFRs) proteins having catalytic specificity greater than the corresponding wild type recombinase. The method includes performing random mutagenesis on a recombinase catalytic domain at positions equivalent to Gin Ile120, Thr123, Leu127, Ile136 and Gly137 or a combination thereof, mutating the DNA at positions 2 and 3 for each amino acid; fusing the recombinase catalytic domain with a plurality of zinc finger binding domains to form ZFRs, and enriching for ZFRs having catalytic specificity greater than the corresponding wild type recombinase. In embodiments the ZFRs have increased catalytic activity on DNA targets selected from GC, GT, CA, TT and AC. In one embodiment, the recombinase catalytic domain is mutagenized at Ile136 and/or Gly137.

In various aspects, the chimeric polypeptides described herein include a recombinase catalytic domain derived from or randomly mutagenized as disclosed herein from: a) Tn3, also known as EcoTn3; Hin, also known as StyHin; Gin, also known as MuGin; Sin; Beta; Pin; Min; Din; Cin; EcoTn21; SfaTn917; BmeTn5083; Bme53; Cpe; SauSK1; SauSK41; SauTn552; Ran; Aac; Lla; pMER05; Mlo92; Mlo90; Rrh; Pje; Req; PpsTn5501; Pae; Xan; ISXc5; Spy; RhizY4cG; SarpNL1; SsolSC1904a; SsolSC1904b; SsolSC1913; Aam606; MjaM0014; Pab; HpyIS607; MtuIS_Y349; MtuRv2792c; MtuRv2979c; MtuRv3828c; MtuRv0921; McoRv0921; TnpX; TndX; WwK; lactococcal phage TP901-1 serine recombinase; *S. pyogenes* phage φ370.1 serine recombinase; *S. pyogenes* phage φFC1 serine recombinase; *Listeria* phage A118 serine recombinase; *S. coelicolor* chromosome SC3C8.24 serine recombinase; *S. coelicolor* chromosome SC2E1.37 serine recombinase; *S. coelicolor* chromosome SCD78.04c serine recombinase; *S. coelicolor* chromosome SC8F4.15c serine recombinase; *S. coelicolor* chromosome SCD12A.23 serine recombinase; *S. coelicolor* chromosome SCH10.38c serine recombinase; *S. coelicolor* chromosome SCC88.14 serine recombinase; *Streptomyces* phage φC31 serine recombinase; *Streptomyces* phage R4 serine recombinase; *Bacillus* phage φ105 serine recombinase; *Bacillus* phage SPBc2 serine recombinase; *Bacillus* prophage SKIN serine recombinase; *S. aureus* ccrA serine recombinase; *S. aureus* ccrB serine recombinase; *M. tuberculosis* phage Bxb1 serine recombinase; *M. tuberculosis* prophage φRV1 serine recombinase; YBCK_ECOLI; Y4bA; Bja; Spn; Cac 1956; and Cac 1954; or b) muteins of a).

In yet another aspect, the invention provides an isolated nucleic acid molecule encoding the chimeric polypeptide described herein.

In yet another aspect, the invention provides an expression cassette including the nucleic acid molecule the chimeric polypeptide described herein.

In yet another aspect, the invention provides a vector including the expression cassette described herein.

In yet another aspect, the invention provides an isolated host cell containing the vector described herein.

In yet another aspect, the invention provides a method for site-specific integration into a DNA sequence. The method includes contacting the DNA sequence with a chimeric polypeptide of the present invention, wherein the chimeric polypeptide catalyzes site-specific integration.

In yet another aspect, the invention provides a method for gene therapy. The method includes administering to a subject a composition comprising a nucleic acid molecule encoding the chimeric polypeptide described herein, wherein upon expression of the nucleic acid molecule, a gene present in the genome of the subject is specifically removed or inactivated.

In yet another aspect, the invention provides a pharmaceutical composition. The composition includes the chimeric polypeptide described herein; and a pharmaceutically acceptable carrier. In another aspect, the composition includes a nucleic acid molecule encoding the chimeric polypeptide described herein; and a pharmaceutically acceptable carrier.

In yet another aspect, the invention provides a transgenic organism produced by recombination catalyzed by the chimeric polypeptide of the present invention.

In yet another aspect, the invention provides a method for gene therapy. The method includes administering to a subject a cell comprising a nucleic acid molecule having the DNA sequence generated by the method of site-specific integration described herein.

In another aspect, the invention provides an isolated nucleic acid molecule encoding the chimeric protein described herein.

In another aspect, the invention provides a method for site-specific recombination. The method includes: a) providing a DNA sequence comprising at least two binding sites for specifically interacting with the chimeric protein described herein; and b) reacting the DNA sequence with the chimeric protein, wherein the chimeric protein catalyzes a site-specific recombination event in which both strands of the DNA sequence are cleaved between the two sites specifically interacting with the chimeric protein.

BRIEF DESCRIPTION OF THE DRAWINGS

FIG. 3 is a series of graphical representations regarding TALER variants selected from incremental truncation library. A) Frequency of selected TALER truncation variants. After 3 rounds of selection, incrementally truncated Gin-AvrXa7 variants were isolated and DNA sequencing was used to determine truncation length. B) Activity of incrementally truncated TALER variants (between Δ92 and Δ134 in length) against the Avr-32G DNA target. For reference, the shortest (Δ145) and longest (Δ74) truncation variants, as well as Δ87 were included. C) Activity of Gin-AvrΔ74, Gin-AvrΔ128 and Gin-AvrΔ145 against a diverse panel of cognate and non-cognate DNA targets. Error bars indicate s.d. (n=3).

FIG. 6 is a diagrammatic representation of location of primers for N-terminal designed truncations of AvrXa7 (SEQ ID NO: 1 DNA sequence; SEQ ID NO: 2 amino acid sequence). Star denotes the location of Δ120 fusion point.

FIG. 7 is a diagrammatic representation of a comparison of native wild-type and synthetic RDV domains for the AvrXa7 target sequence (SEQ ID NOs: 16-18).

FIG. 8 is a diagrammatic representation of TALE and TALER amino acid sequences of AvrXa7 protein (SEQ ID NO: 19).

FIG. 9 is a diagrammatic representation of construct AvrXa7 DNA sequence (SEQ ID NO: 20).

FIG. 10. is a diagrammatic representation of construct Gin-AvrΔ74 amino acid sequence (SEQ ID NO: 21).

FIG. 11 is a diagrammatic representation of construct Gin-AvrΔ87 amino acid sequence (SEQ ID NO: 22).

FIG. 12 is a diagrammatic representation of construct Gin-AvrΔ120 amino acid sequence (SEQ ID NO: 23).

FIG. 13 is a diagrammatic representation of construct Gin-AvrΔ120*amino acid sequence (SEQ ID NO: 24).

FIG. 14 is a diagrammatic representation of construct Gin-AvrΔ147 amino acid sequence (SEQ ID NO: 25).

FIG. 15 is a diagrammatic representation of construct GinAvr15Δ128-synthetic protein amino acid sequence (SEQ ID NO: 26).

FIG. 16 is a diagrammatic representation of construct Gin-Avr15Δ128-synthetic protein DNA sequence (SEQ ID NO: 27).

FIG. 17 is a diagrammatic representation of construct GinAvr15Δ128-synthetic protein amino acid sequence (SEQ ID NO: 28).

FIG. 18D is an alignment of optimized TALE NTDs SEQ ID NOs: 33-36), illustrating sequence differences in the N-1 hairpin. E) Comprehensive comparison of optimized NTD activities in the context of MBP-TALE AvrXa7. (*=p<0.05, =p<0.01, *=p<0.001, compared to wild type and 5'A/G/C).

FIG. 28 is a diagrammatic representation showing alignment indel sequencing of selected TALEN experiments from FIG. 27 (SEQ ID NOs: 292-332 from top to bottom).

DETAILED DESCRIPTION OF THE INVENTION

The present provides the first disclosure of a TALE recombinase (TALER). Using a library of incrementally truncated TALE domains, optimized TALER architecture that can be used to recombine DNA in bacterial and mammalian cells was identified. Any customized TALE repeat array can be inserted into the TALER architecture described herein, thus dramatically expanding the targeting capacity of engineered recombinases for applications in biotechnology and medicine.

Transcription activator-like effector (TALE) proteins can be designed to bind virtually any DNA sequence. General guidelines for design of TALE DNA-binding domains suggest that the 5'-most base of the DNA sequence bound by the TALE (the $N_0$ base) should be a thymine. The $N_0$ requirement was quantified by analysis of the activities of TALE transcription factors (TALE-TF), TALE recombinases (TALE-R) and TALE nucleases (TALENs) with each DNA base at this position. In the absence of a 5' T, decreases in TALE activity up to >1000-fold in TALE-TF activity, up to 100-fold in TALE-R activity and up to 10-fold reduction in TALEN activity compared with target sequences containing a 5' T was observed. To develop TALE architectures that recognize all possible $N_0$ bases, structure-guided library design coupled with TALE-R activity selections were used to evolve novel TALE N-terminal domains to accommodate any N0 base. A G-selective domain and broadly reactive domains were isolated and characterized. The engineered TALE domains selected in the TALE-R format demonstrated modularity and were active in TALE-TF and TALEN architectures. Evolved N-terminal domains provide effective and unconstrained TALE-based targeting of any DNA sequence as TALE binding proteins and designer enzymes.

Figure 35:
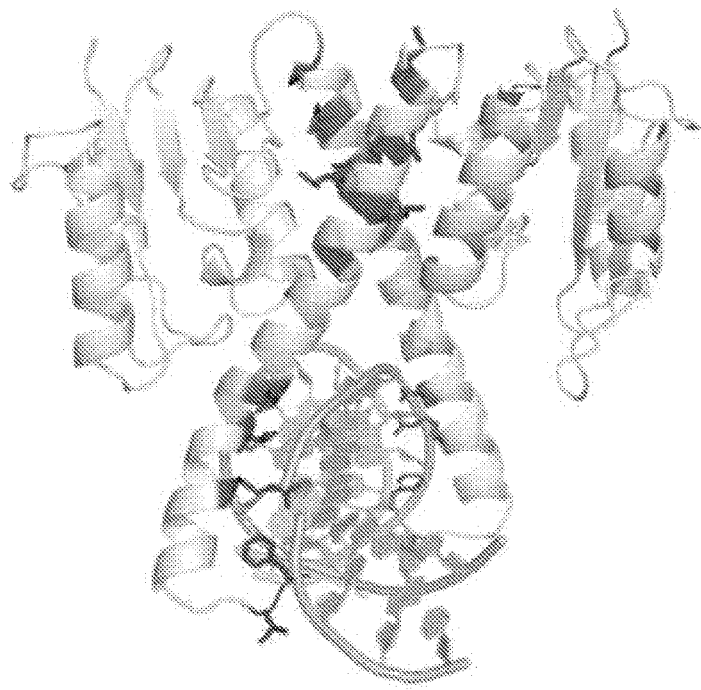
FIG. 35 is a diagrammatic representation of recombinase DNA-binding residues are located outside the dimer interface. The γδ resolvase in complex with target DNA. Catalytic domain dimer is colored cyan. DNA is colored grey. Arm region residues are shown as red sticks. Residues at the dimer interface are shown as purple sticks (PDB ID: 1GDT).

Additionally, in order to address sequence requirement limitations, a knowledge-base approach was described for re-engineering serine recombinase catalytic specificity. This strategy, which was based on the saturation mutagenesis of specificity-determining DNA-binding residues, was used to generate recombinase variants that showed a >10,000-fold shift in specificity. Importantly, this approach focused exclusively on amino acid residues located outside the recombinase dimer interface (FIG. 35). As a result, it was determined that re-engineered catalytic domains could associate to form ZFR heterodimers and that these designed ZFR pairs recombine pre-determined DNA sequences with exceptional specificity. Together, these results led us to hypothesize that an expanded catalog of specialized catalytic domains developed by this method could be used to generate ZFRs with custom specificity. Here, a combination of substrate specificity analysis and directed evolution is used to develop a diverse collection of Gin recombinase catalytic domains that are capable of recognizing an estimated 4×10⁸ unique 20-bp core sequences. It is shown that ZFRs assembled from these re-engineered catalytic domains recombine user-defined sequences with high specificity and integrate DNA into targeted endogenous loci in human cells. These results demonstrate the potential of ZFR technology for a wide variety of applications, including genome engineering and gene therapy.

Before the present compositions and methods are described, it is to be understood that this invention is not limited to the particular compositions, methods, and experimental conditions described, as such devices, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the composition" or "the method" includes one or more compositions and methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

"Recombinases" are a family of enzymes that mediate site-specific recombination between specific DNA sequences recognized by the recombinase (Esposito, D., and Scocca, J. J., Nucleic Acids Research 25, 3605-3614 (1997); Nunes-Duby, S. E., et al., Nucleic Acids Research 26, 391-406 (1998); Stark, W. M., et al., Trends in Genetics 8, 432-439 (1992)).

As used herein, the term "chimeric TALE recombinase" includes without limitation recombinases having a TALE domain derived from a naturally-occurring TALE protein or a synthetically derived TALE protein or domain with sequence-specific binding activity.

As used herein, the term "chimeric zinc finger recombinase" includes without limitation recombinases having a zinc finger binding domain derived from a naturally-occurring zinc finger DNA binding protein or a synthetically derived zinc finger binding protein or domain with sequence-specific binding activity.

As used herein, the term "zinc finger," "zinc finger nucleotide binding domain," or similar terminology refers both to naturally occurring and artificially produced zinc fingers. Such zinc fingers can have various framework structures, such as, but not limited to, C2H2, C4, H4, H3C, C3X, H3X, C2X2, and H2X2, where X is a zinc ligating amino acid. In these framework structures, as is conventional in the recitation of zinc finger structures, "C" represents a cysteine residue and "H" represents a histidine residue. Zinc fingers having the framework C2H2 include, but are not limited to, zinc fingers described, for example, in International Publication Number WO2008/006028 to Barbas et al., U.S. Pat. No. 7,101,972 to Barbas, U.S. Pat. No. 7,067,617 to Barbas to Barbas et al., U.S. Pat. No. 6,790,941 to Barbas et al., U.S. Pat. No. 6,610,512 to Barbas, U.S. Pat. No. 6,242,568 to Barbas et al., U.S. Pat. No. 6,140,466 to Barbas et al., U.S. Pat. No. 6,140,081 to Barbas, United States Patent Application Publication No. 20060223757 by Barbas, United States Patent Application Publication No. 20060211846 by Barbas et al., United States Patent Application Publication No. 20060078880 by Barbas et al., United States Patent Application Publication No. 20050148075 by Barbas, United States Patent Application Publication No. 20050084885 by Barbas et al., United States Patent Application Publication No. 20040224385 by Barbas et al., United States Patent Application Publication No. 20030059767 by Barbas et al., and United States Patent Application Publication No. 20020165356 by Barbas et al., all of which are incorporated herein by this reference. Other zinc fingers are described in: U.S. Pat. No. 7,067,317 to Rebar et al.; U.S. Pat. No. 7,030,215 to Liu et al.; U.S. Pat. No. 7,026,462 to Rebar et al.; U.S. Pat. No. 7,013,219 to Case et al.; U.S. Pat. No. 6,979,539 to Cox III et al.; U.S. Pat. No. 6,933,113 to Case et al.; U.S. Pat. No. 6,824,978 to Cox III et al.; U.S. Pat. No. 6,794,136 to Eisenberg et al.; U.S. Pat. No. 6,785,613 to Eisenberg et al.; U.S. Pat. No. 6,777,185 to Case et al.; U.S. Pat. No. 6,706,470 to Choo et al.; U.S. Pat. No. 6,607,882 to Cox I M et al.; U.S. Pat. No. 6,599,692 to Case et al.; U.S. Pat. No. 6,534,261 to Cox I I et al.; U.S. Pat. No. 6,503,717 to Case et al.; U.S. Pat. No. 6,453,242 to Eisenberg et al.; United States Patent Application Publication No. 2006/0246588 to Rebar et al.; United States Patent Application Publication No. 2006/0246567 to Rebar et al.; United States Patent Application Publication No. 2006/0166263 to Case et al.; United States Patent Application Publication No. 2006/0078878 to Cox H I et at.; United States Patent Application Publication No. 2005/0257062 to Rebar et al.; United States Patent Application Publication No. 2005/0215502 to Cox III et al.; United States Patent Application Publication No. 2005/0130304 to Cox M l et al.; United States Patent Application Publication No. 2004/0203064 to Case et al.; United States Patent Application Publication No. 2003/0166141 to Case et al.; United States Patent Application Publication No. 2003/0134318 to Case et al.; United States Patent Application Publication No. 2003/0105593 to Eisenberg et al.; United States Patent Application Publication No. 2003/0087817 to Cox I M et al.; United States Patent Application Publication No. 2003/0021776 to Rebar et al.; and United States Patent Application Publication No. 2002/0081614 to Case et al., all of which are incorporated herein by this reference. For example, one alternative described in these patents and patent publications involves the use of so-called "D-able sites" and zinc finger modules or zinc finger DNA binding domains that can bind to such sites. A "D-able" site is a region of a target site that allows an appropriately designed zinc finger module or zinc finger DNA binding domain to bind to four bases rather than three of the target strand. Such a zinc finger module or zinc finger DNA binding domain binds to a triplet of three bases on one strand of a double-stranded DNA target segment (target strand) and a fourth base on the other, complementary, strand. Binding of a single zinc finger to a four base target segment imposes constraints both on the sequence of the target strand and on the amino acid sequence of the zinc finger.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. Watson et al. Molecular Biology of the Gene, 4th Edition, 1987, Benjamin/Cummings, p. 224). In particular, such a conservative variant has a modified amino acid sequence, such that the change(s) do not substantially alter the protein's (the conservative variant's) structure and/or activity, e.g., antibody activity, enzymatic activity, or receptor activity. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (I or Ile), leucine (L or Leu), methionine (M or Met), valine (V or Val); and (6) phenylalanine (F or Phe), tyrosine (Y or Tyr), tryptophan (W or Trp); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations" when the three-dimensional structure and the function of the protein to be delivered are conserved by such a variation.

As used herein, the term "expression vector" refers to a plasmid, virus, phagemid, or other vehicle known in the art that has been manipulated by insertion or incorporation of heterologous DNA, such as nucleic acid encoding the fusion proteins herein or expression cassettes provided herein. Such expression vectors typically contain a promoter sequence for efficient transcription of the inserted nucleic acid in a cell. The expression vector typically contains an origin of replication, a promoter, as well as specific genes that permit phenotypic selection of transformed cells.

As used herein, the term "host cells" refers to cells in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art.

As used herein, genetic therapy involves the transfer of heterologous DNA to the certain cells, target cells, of a mammal, particularly a human, with a disorder or conditions for which such therapy is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product, or it may encode a product, such as a peptide or RNA that in some manner mediates, directly or indirectly, expression of a therapeutic product. Genetic therapy may also be used to deliver nucleic acid encoding a gene product that replaces a defective gene or supplements a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof. Genetic therapy may also involve delivery of an inhibitor or repressor or other modulator of gene expression.

As used herein, heterologous DNA is DNA that encodes RNA and proteins that are not normally produced in vivo by the cell in which it is expressed or that mediates or encodes mediators that alter expression of endogenous DNA by affecting transcription, translation, or other regulatable biochemical processes. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

Hence, herein heterologous DNA or foreign DNA, includes a DNA molecule not present in the exact orientation and position as the counterpart DNA molecule found in the genome. It may also refer to a DNA molecule from another organism or species (i.e., exogenous).

As used herein, a therapeutically effective product is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease. Typically, DNA encoding a desired gene product is cloned into a plasmid vector and introduced by routine methods, such as calcium-phosphate mediated DNA uptake (see, (1981) Somat. Cell. Mol. Genet. 7:603-616) or microinjection, into producer cells, such as packaging cells. After amplification in producer cells, the vectors that contain the heterologous DNA are introduced into selected target cells.

As used herein, an expression or delivery vector refers to any plasmid or virus into which a foreign or heterologous DNA may be inserted for expression in a suitable host cell—i.e., the protein or polypeptide encoded by the DNA is synthesized in the host cell's system. Vectors capable of directing the expression of DNA segments (genes) encoding one or more proteins are referred to herein as "expression vectors". Also included are vectors that allow cloning of cDNA (complementary DNA) from mRNAs produced using reverse transcriptase.

As used herein, a gene refers to a nucleic acid molecule whose nucleotide sequence encodes an RNA or polypeptide. A gene can be either RNA or DNA. Genes may include regions preceding and following the coding region (leader and trailer) as well as intervening sequences (introns) between individual coding segments (exons).

As used herein, the term "isolated" with reference to a nucleic acid molecule or polypeptide or other biomolecule means that the nucleic acid or polypeptide has been separated from the genetic environment from which the polypeptide or nucleic acid were obtained. It may also mean that the biomolecule has been altered from the natural state. For example, a polynucleotide or a polypeptide naturally present in a living animal is not "isolated," but the same polynucleotide or polypeptide separated from the coexisting materials of its natural state is "isolated," as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith et al. (1988) Gene 67:3140. The terms isolated and purified are sometimes used interchangeably.

Thus, by "isolated" is meant that the nucleic acid is free of the coding sequences of those genes that, in a naturally-occurring genome immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

"Isolated" or "purified" as those terms are used to refer to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. Particularly for proteins, the procedures may include for example, but are not limited to, ammonium sulfate fractionation, gel filtration, ion exchange change chromatography, affinity chromatography, density gradient centrifugation, electrofocusing, chromatofocusing, and electrophoresis.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

As used herein, a promoter region of a gene includes the regulatory element or elements that typically lie 5' to a structural gene; multiple regulatory elements can be present, separated by intervening nucleotide sequences. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product. The promoter region may be a normal cellular promoter or, for example, an onco-promoter. An onco-promoter is generally a virus-derived promoter. Viral promoters to which zinc finger binding polypeptides may be targeted include, but are not limited to, retroviral long terminal repeats (LTRs), and Lentivirus promoters, such as promoters from human T-cell lymphotrophic virus (HTLV) 1 and 2 and human immunodeficiency virus (HIV) 1 or 2.

As used herein, the term "truncated" or similar terminology refers to a polypeptide derivative that contains less than the full amino acid sequence of a native protein, such as a ZFP, TALE or serine recombinase.

As used herein, a polypeptide "variant" or "derivative" refers to a polypeptide that is a mutagenized form of a polypeptide or one produced through recombination but that still retains a desired activity, such as the ability to bind to a ligand or a nucleic acid molecule or to modulate transcription.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier. Vectors include, but are not necessarily limited to, expression vectors.

As used herein with regard to nucleic acid molecules, including DNA fragments, the phrase "operatively linked" means the sequences or segments have been covalently joined, preferably by conventional phosphodiester bonds, into one strand of DNA, whether in single or double-stranded form such that operatively linked portions function as intended. The choice of vector to which transcription unit or a cassette provided herein is operatively linked depends directly, as is well known in the art, on the functional properties desired, e.g., vector replication and protein expression, and the host cell to be transformed, these being limitations inherent in the art of constructing recombinant DNA molecules.

As used herein, administration of a therapeutic composition can be effected by any means, and includes, but is not limited to, oral, subcutaneous, intravenous, intramuscular, intrasternal, infusion techniques, intraperitoneal administration and parenteral administration.

Methods of transforming cells are well known in the art. By "transformed" it is meant a heritable alteration in a cell resulting from the uptake of foreign DNA. Suitable methods include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCE package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

As such, the invention provides nucleic acid and amino acid sequences encoding chimeric polypeptides of the invention which are substantially homologous and encode polypeptides that retain equivalent biological activity.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule Inhibition of hybridization of the completely identical sequence can be assessed using hybridization assays that are well known in the art (e.g., Southern blot, Northern blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.)

A first polynucleotide is "derived from" a second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

Site-specific recombinases are powerful tools for genome engineering. Hyperactivated variants of the resolvase/invertase family of serine recombinases function without accessory factors, and thus can be re-targeted to sequences of interest by replacing native DNA-binding domains with engineered zinc-finger proteins (ZFPs).

The zinc finger recombinases described herein are chimeric enzymes composed of an activated catalytic domain derived from the resolvase/invertase family of serine recombinases and a custom-designed zinc-finger DNA-binding domain. The ZFRs assembled from engineered catalytic domains efficiently recombine user-defined DNA targets with high specificity and designed ZFRs integrate DNA into targeted endogenous loci in human cells.

In one aspect, the invention provides a method of generating a plurality of zinc finger recombinase (ZFRs) proteins having catalytic specificity greater than the corresponding wild type recombinase. The method includes performing random mutagenesis on a recombinase catalytic domain at positions equivalent to Gin Ile120, Thr123, Leu127, Ile136 and Gly137 or a combination thereof with reference to a wild-type Gin catalytic domain, mutating the DNA at positions 2 and 3 for each amino acid; fusing the recombinase catalytic domain with a plurality of zinc finger binding domains to form ZFRs, and enriching for ZFRs having catalytic specificity greater than the corresponding wild type recombinase. In embodiments the ZFRs have increased catalytic activity on DNA targets selected from GC, GT, CA, TT and AC. In one embodiment, the recombinase catalytic domain is mutagenized at Ile136 and/or Gly137.

As used herein, a wild-type Gin catalytic domain refers to a Gin catalytic domain including all or a portion of a polypeptide having the amino acid sequence set forth as SEQ ID NO: 56 as follows:

```
MLIGYVRVSTNDQNTDLQRNALVCAGCEQIFEDKLSGTRTDRPGL

KRALKRLQKGDTLVVWKLDRLGRSMKHLISLVGELRERGINFRSL

TDSIDTSSPMGRFFFYVMGALAEMERELIIERTMAGLAAARNKGR

IGGRPPKLTKAEWEQAGRLLAQGIPRKQVALIYDVALSTLYKKHP
```

In various embodiments, the chimeric polypeptides of the invention include a Gin catalytic domain, such as those generated by the method of the invention. Particular Gin catalytic domains include those set forth in Table 1.

TABLE 1

Gin catalytic domains.
Gin catalytic domains.

| Variant | SEQ ID NO: | Sequence |
|---|---|---|
| Gin α | 57 | MLIGYVRVSTNDQNTDLQRNALVCAGCEQIFEDKLSGTRTDRPGLKRA<br>LKRLQKGDTLVVWKLDRLGRSMKHLISLVGELRERGINFRSLTDSIDTS<br>SPMGRFFF<u>Y</u>VMGALAEMERELI<u>IERT</u>MAG<u>L</u>AAARNKGR<u>I</u>GGRPPKSG |
| Gin β | 58 | MLIGYVRVSTNDQNTDLQRNALVCAGCEQIFEDKLSGTRTDRPGLKRA<br>LKRLQKGDTLVVWKLDRLGRSMKHLISLVGELRERGINFRSLTDSIDTS<br>SPMGRFFF<u>Y</u>VMGALAEMERELI<u>IERT</u>MAG<u>I</u>AAARNKGR<u>RF</u>GRPPKS |
| Gin γ | 59 | MLIGYVRVSTNDQNTDLQRNALVCAGCEQIFEDKLSGTRTDRPGLKRA<br>LKRLQKGDTLVVWKLDRLGRSMKHLISLVGELRERGINFRSLTDSIDTS<br>SPMGRFFF<u>Y</u>VMGALAEMERELI<u>LERV</u>MAG<u>I</u>AAARNKGR<u>RW</u>GRPPKSG |
| Gin δ | 60 | MLIGYVRVSTNDQNTDLQRNALVCAGCEQIFEDKLSGTRTDRPGLKRA<br>LKRLQKGDTLVVWKLDRLGRSMKHLISLVGELRERGINFRSLTDSIDTS<br>SPMGREFF<u>Y</u>VMGALAEMERELI<u>IERV</u>MAG<u>L</u>AAARNKGR<u>RF</u>GRPPKSG |
| Gin ε | 61 | MLIGYVRVSTNDQNTDLQRNALVCAGCEQIFEDKLSGTRTDRPGLKRA<br>LKRLQKGDTLVVWKLDRLGRSMKHLISLVGELRERGINFRSLTDSIDTS<br>SPMGRFFF<u>Y</u>VMGALAEMER<u>LSI</u>LER<u>P</u>MAG<u>H</u>AAARNKGR<u>RF</u>GRPPKSG |

TABLE 1-continued

Gin catalytic domains.
Gin catalytic domains.

| Variant | SEQ ID NO: | Sequence |
|---|---|---|
| Gin ζ | 62 | MLIGYVRVSTNDQNTDLQRNALVCAGCEQIFEDKLSGTRTDRPGLKRA LKRLQKGDTLVVWKLDRLGRSMKHLISLVGELRERGINFRSLTDSIDTS SPMGRFFFYVMGALAEMERELIIERTSAGRAAAINKGRIMGRPRKSG |

Targeted arm region positions are double underlined.
Random substitutions are emboldened and underlined.
The hyperactivating H106Y mutation is underlined.

In various embodiments, the ZFRs generated by the method of the invention include a Gin catalytic domain operatively linked to a plurality of zinc finger binding domains. Exemplary ZFRs generated by the invention include those set forth in Table 2.

TABLE 2

ZFRs.
Amino acid sequences of exemplary ZFRs.

| | | |
|---|---|---|
| ZFR-1 Left | SEQ ID NO: 63 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGREFFYVMGALAEMERELIIERTMAGLAAARNKGRIGG RPPKSGTGEKPYKCPECGKSFSTSGNLVRHQRTHTGEKPYKCPECG KSFSQSGDLRRHQRTHTGEKPYKCPECGKSFSTSGNLVRHQRTHTG EKPYKCPECGKSFSTSGELVRHQRTHTGKKTSGQAGQ |
| ZFR-1 Right | SEQ ID NO: 64 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGREFFYVMGALAEMERELIIERTMAGLAAARNKGRIGG RPPKSGTGEKPYKCPECGKSFSHRTTLTNHQRTHTGEKPYKCPECG KSFSQSGDLRRHQRTHTGEKPYKCPECGKSFSQSGDLRRHQRTHTG EKPYKCPECGKSFSQSGDLRRHQRTHTGKKTSGQAGQ |
| ZFR-2 Left | SEQ ID NO: 65 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELIIERTMAGLAAARNKGRIGG RPPKSGTGEKPYKCPECGKSFSQSGDLRRHQRTHTGEKPYKCPECG KSFSQRAHLERHQRTHTGEKPYKCPECGKSFSTSGNLVRHQRTHTG EKPYKCPECGKSFSRSDELVRHQRTHTGKKTSGQAGQ |
| ZFR-2 Right | SEQ ID NO: 66 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELIIERTMAGLAAARNKGRIGG RPPKSGTGEKPYKCPECGKSFSRSDKLVRHQRTHTGEKPYKCPECG KSFSRKDNLKNHQRTHTGEKPYKCPECGKSFSTSGELVRHQRTHTG EKPYKCPECGKSFSRSDKLVRHQRTHTGKKTSGQAGQ |
| ZFR-3 Left | SEQ ID NO: 67 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGREFFYVMGALAEMERELIIERTMAGLAAARNKGRIGG RPPKSGTGEKPYKCPECGKSFSTTGNLTVHQRTHTGEKPYKCPECG KSFSDPGALVRHQRTHTGEKPYKCPECGKSFSQSSNLVRHQRTHTG EKPYKCPECGKSFSRSDHLTNHQRTHTGKKTSGQAGQ |
| ZFR-3 Right | SEQ ID NO: 68 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELIIERTMAGLAAARNKGRIGG RPPKSGTGEKPYKCPECGKSFSRKDNLKNHQRTHTGEKPYKCPECG KSFSRSDHLTNHQRTHTGEKPYKCPECGKSFSDPGNLVRHQRTHTG EKPYKCPECGKSFSRKDNLKNHQRTHTGKKTSGQAGQ |
| ZFR-4 Left | SEQ ID NO: 69 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELILERVMAGIAAARNKGRRW GRPPKSGTGEKPYKCPECGKSFSQRANLRAHQRTHTGEKPYKCPEC GKSFSQSSSLVRHQRTHTGEKPYKCPECGKSFSTTGNLTVHQRTHT GEKPYKCPECGKSFSQRAHLERHQRTHTGKKTSGQAGQ |
| ZFR-4 Right | SEQ ID NO: 70 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELILERVMAGIAAARNKGRRW GRPPKSGTGEKPYKCPECGKSFSQRANLRAHQRTHTGEKYYKCPEC |

TABLE 2-continued

ZFRs.
Amino acid sequences of exemplary ZFRs.

|  |  |  |
|---|---|---|
|  |  | GKSFS<u>RRDELNV</u>HQRTHTGEKPYKCPECGKSFS<u>QLAHLRA</u>HQRTHT<br>GEKPYKCPECGKSFS<u>QRAHLER</u>HQRTHTGKKTSGQAGQ |
| ZFR-5 Left | SEQ ID NO: 71 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELILE͇RV̲MAGI̲AAARNKGR<u>RW</u><br>GRPPKSGTGEKPYKCPECGKSFS<u>RRDELNV</u>HQRTHTGEKPYKCPEC<br>GKSFS<u>RSDHLTN</u>HQRTHTGEKPYKCPECGKSFS<u>QLAHLRA</u>HQRTHT<br>GEKPYKCPECGKSFS<u>QRAHLER</u>HQRTHTGKKTSGQAGQ |
| ZFR-5 Right | SEQ ID NO: 72 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELI̲I̲ER̲T̲MAGL̲AAARNKGRI̲G̲G̲<br>RPPKSGTGEKPYKCPECGKSFS<u>TSGSLVR</u>HQRTHTGEKPYKCPECG<br>KSFS<u>RSDKLVR</u>HQRTHTGEKPYKCPECGKSFS<u>QSGDLRR</u>HQRTHTG<br>EKPYKCPECGKSFS<u>TSGELVR</u>HQRTHTGKKTSGQAGQ |
| ZFR-6 Left | SEQ ID NO: 73 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELIIERT̲SAGR̲AAAINKGRI̲MGR̲<br>P̲R̲KSGTGEKPYKCPECGKSFS<u>QLAHLRA</u>HQRTHTGEKPYKCPECGK<br>SFS<u>QLAHLRA</u>HQRTHTGEKPYKCPECGKSFS<u>DPGHLVR</u>HQRTHTGE<br>KPYKCPECGKSFS<u>DSGNLRV</u>HQRTHTGKKTSGQAGQ |
| ZFR-6 Right | SEQ ID NO: 74 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELILE͇RV̲MAGI̲AAARNKGR<u>RW</u><br>GRPPKSGTGEKPYKCPECGKSFS<u>QRAHLER</u>HQRTHTGEKPYKCPEC<br>GKSFS<u>TTGNLTV</u>HQRTHTGEKPYKCPECGKSFS<u>DSGNLRV</u>HQRTHT<br>GEKPYKCPECGKSFS<u>QSSNLVR</u>HQRTHTGKKTSGQAGQ |
| ZFR-7 Left | SEQ ID NO: 75 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELHE͇RTMAGI̲AAARNKGRR<u>FGR</u><br>PPKSGTGEKPYKCPECGKSFS<u>THLDLIR</u>HQRTHTGEKPYKCPECGKS<br>FS<u>TTGNLTV</u>HQRTHTGEKPYKCPECGKSFS<u>QSSSLVR</u>HQRTHTGEKP<br>YKCPECGKSFS<u>RSDNLVR</u>HQRTHTGKKTSGQAGQ |
| ZFR-7 Right | SEQ ID NO: 76 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELHE͇RTMAGI̲AAARNKGRR<u>FGR</u><br>PPKSGTGEKPYKCPECGKSFS<u>RSDKLVR</u>HQRTHTGEKPYKCPECGK<br>SFS<u>RRDELNV</u>HQRTHTGEKPYKCPECGKSFS<u>QSSSLVR</u>HQRTHTGE<br>KPYKCPECGKSFS<u>RSDHLTN</u>HQRTHTGKKTSGQAGQ |
| ZFR-8 Left | SEQ ID NO: 77 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELI̲I̲ER̲T̲MAGL̲AAARNKGRI̲G̲G̲<br>RPPKSGTGEKPYKCPECGKSFS<u>QRAHLER</u>HQRTHTGEKPYKCPECG<br>KSFS<u>TSGNLVR</u>HQRTHTGEKPYKCPECGKSFS<u>RSDELVR</u>HQRTHTG<br>EKPYKCPECGKSFS<u>HKNALQN</u>HQRTHTGKKTSGQAGQ |
| ZFR-8 Right | SEQ ID NO: 78 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELI̲I̲ER̲T̲MAGL̲AAARNKGRI̲G̲G̲<br>RPPKSGTGEKPYKCPECGKSFS<u>RRDELNV</u>HQRTHTGEKPYKCPECG<br>KSFS<u>QSSNLVR</u>HQRTHTGEKPYKCPECGKSFS<u>QSSSLVR</u>HQRTHTGE<br>KPYKCPECGKSFS<u>TTGNLTV</u>HQRTHIGKKTSGQAGQ |
| ZFR-9 Left | SEQ ID NO: 79 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELILE͇RV̲MAGI̲AAARNKGR<u>RW</u><br>GRPPKSGTGEKPYKCPECGKSFS<u>TTGNLTV</u>HQRTHTGEKPYKCPEC<br>GKSFS<u>QSSNLVR</u>HQRTHTGEKPYKCPECGKSFS<u>QRAHLER</u>HQRTHT<br>GEKPYKCPECGKSFS<u>QKSSLIA</u>HQRTHTGKKTSGQAGQ |
| ZFR-9 Right | SEQ ID NO: 80 | MLIGYVRVSTNDQNTDLQRNALVCAGCEQIFEDKLSGTRTDRPGLK<br>RALKRLQKGDTLVVWKLDRLGRSMKHLISLVGELRERGINFRSLTD<br>SIDTSSPMGRFFFYVMGALAEMERELIIERT̲SAGR̲AAAINKGRI̲MGR̲<br>P̲R̲KSGTGEKPYKCPECGKSFS<u>DPGALVR</u>HQRTHTGEKPYKCPECGK<br>SFS<u>QSSSLVR</u>HQRTHTGEKPYKCPECGKSFS<u>QLAHLRA</u>HQRTHTGE<br>KPYKCPECGKSFS<u>QRANLRA</u>HQRTHTGKKTSGQAGQ |

Arm region mutations are double underlined.
Specificity-determining α-helical zinc-finger residues are underlined.

While the Examples illustrate generation of ZFRs having a Gin catalytic domain, the methods may be applied to catalytic domains of a number of other recombinases. Such recombinases include: a) Tn3, also known as EcoTn3; Hin, also known as StyHin; MuGin; Sin; Beta; Pin; Min; Din; Cin; EcoTn21; SfaTn917; BmeTn5083; Bme53; Cpe; SauSK1; SauSK41; SauTn552; Ran; Aac; Lla; pMER05; Mlo92; Mlo90; Rrh; Pje; Req; PpsTn5501; Pae; Xan; ISXc5; Spy; RhizY4cG; SarpNL1; SsolSC1904a; SsolSC1904b; SsolSC1913; Aam606; MjaM0014; Pab; HpylS607; MtulS_Y349; MtuRv2792c; MtuRv2979c; MtuRv3828c; MtuRv0921; MceRv0921; TnpX; TndX; WwK; lactococcal phage TP901-1 serine recombinase; *S. pyogenes* phage φ370.1 serine recombinase; *S. pyogenes* phage φFC1 serine recombinase; *Listeria* phage A118 serine recombinase; *S. coelicolor* chromosome SC3C8.24 serine recombinase; *S. coelicolor* chromosome SC2E1.37 serine recombinase; *S. coelicolor* chromosome SCD78.04c serine recombinase; *S. coelicolor* chromosome SC8F4.15c serine recombinase; *S. coelicolor* chromosome SCD12A.23 serine recombinase; *S. coelicolor* chromosome SCH10.38c serine recombinase; *S. coelicolor* chromosome SCC88.14 serine recombinase; *Streptomyces* phage φC31 serine recombinase; *Streptomyces* phage R4 serine recombinase; *Bacillus* phage φ105 serine recombinase; *Bacillus* phage SPBc2 serine recombinase; *Bacillus* prophage SKIN serine recombinase; *S. aureus* ccrA serine recombinase; *S. aureus* ccrB serine recombinase; *M. tuberculosis* phage Bxb1 serine recombinase; *M. tuberculosis* prophage φRV1 serine recombinase; YBCK_ECOLI; Y4bA; Bja; Spn; Cac 1956; and Cac 1954; and b) muteins of a).

Imperfect modularity with particular domains, lack of high-affinity binding to all DNA triplets, and difficulty in construction has hindered the widespread adoption of ZFPs in unspecialized laboratories. The discovery of a novel type of DNA-binding domain in transcription activator-like effector (TALE) proteins from *Xanthomonas* provides an alternative to ZFPs. Described herein are chimeric TALE recombinases (TALERs): engineered fusions between a hyperactivated catalytic domain from the DNA invertase Gin and an optimized TALE architecture. A library of incrementally truncated TALE variants was identified to identify TALER fusions that modify DNA with efficiency and specificity comparable to zinc-finger recombinases in bacterial cells. Also shown in the Examples, TALERs recombine DNA in mammalian cells. The TALER architecture described herein provides a platform for insertion of customized TALE domains, thus significantly expanding the targeting capacity of engineered recombinases and their potential applications in biotechnology and medicine.

Transcription activator-like effector (TALE) proteins can be designed to bind virtually any DNA sequence. General guidelines for design of TALE DNA-binding domains suggest that the 5'-most base of the DNA sequence bound by the TALE (the $N_0$ base) should be a thymine. We quantified the $N_0$ requirement by analysis of the activities of TALE transcription factors (TALE-TF), TALE recombinases (TALE-R) and TALE nucleases (TALENs) with each DNA base at this position. In the absence of a 5' T, we observed decreases in TALE activity up to >1000-fold in TALE-TF activity, up to 100-fold in TALE-R activity and up to 10-fold reduction in TALEN activity compared with target sequences containing a 5' T. To develop TALE architectures that recognize all possible $N_0$ bases, a structure-guided library design coupled with TALE-R activity selections was used to evolve novel TALE N-terminal domains to accommodate any $N_0$ base. A G-selective domain and broadly reactive domains were isolated and characterized. The engineered TALE domains selected in the TALE-R format demonstrated modularity and were active in TALE-TF and TALEN architectures. Evolved N-terminal domains provide effective and unconstrained TALE-based targeting of any DNA sequence as TALE binding proteins and designer enzymes.

In one aspect, the invention provides a method of generating a transcription activator-like effector (TALE) protein binding domain which specifically binds a desired nucleotide. As shown in the Examples, the method includes a) randomizing the amino acid sequence of the TALE protein binding domain by mutating an amino acid residue within a variable di-residue (RVD), or within 1 to 2 amino acid residues N-terminal or C-terminal of the RVD; and b) selecting for the randomized TALE protein binding domain of (a), wherein the TALE protein binding domain specifically binds to the desired nucleotide.

Sequence-specific nucleases, recombinases, nucleases and transcription factors are provided herein. The sequence-specific polypeptides include customized TAL effector DNA binding domains. As such, in another aspect, the invention provides a chimeric polypeptide. The polypeptide includes: a) a recombinase, a transcription factor or nuclease; and b) a transcription activator-like effector (TALE) protein.

TALEs are proteins of plant pathogenic bacteria that are injected by the pathogen into the plant cell, where they travel to the nucleus and function as transcription factors to turn on specific plant genes. The primary amino acid sequence of a TALE dictates the nucleotide sequence to which it binds. Thus, target sites can be predicted for TALE, and TALE also can be engineered and generated for the purpose of binding to particular nucleotide sequences, as described herein.

Fused to the TALE-encoding nucleic acid sequences are sequences encoding a nuclease, transcription factor or recombinase, or a portion thereof. Many such proteins are known in art that may be used in the present invention.

In various embodiments, the chimeric polypeptide includes a catalytic domain of a recombinase. As discussed above, catalytic domains of a number of recombinases may be utilized. Such recombinases include: a) Tn3, also known as EcoTn3; Hin, also known as StyHin; Gin, also known as MuGin; Sin; Beta; Pin; Min; Din; Cin; EcoTn21; SfaTn917; BmeTn5083; Bme53; Cpe; SauSK1; SauSK41; SauTn552; Ran; Aac; Lla; pMER05; Mlo92; Mlo90; Rrh; Pje; Req; PpsTn5501; Pae; Xan; ISXc5; Spy; RhizY4cG; SarpNL1; SsolSC1904a; SsolSC1904b; SsoISC1913; Aam606; MjaM0014; Pab; HpylS607; MtulS_Y349; MtuRv2792c; MtuRv2979c; MtuRv3828c; MtuRv0921; MceRv0921; TnpX; TndX; WwK; lactococcal phage TP901-1 serine recombinase; *S. pyogenes* phage φ370.1 serine recombinase; *S. pyogenes* phage φFC1 serine recombinase; *Listeria* phage A118 serine recombinase; *S. coelicolor* chromosome SC3C8.24 serine recombinase; *S. coelicolor* chromosome SC2E1.37 serine recombinase; *S. coelicolor* chromosome SCD78.04c serine recombinase; *S. coelicolor* chromosome SC8F4.15c serine recombinase; *S. coelicolor* chromosome SCD12A.23 serine recombinase; *S. coelicolor* chromosome SCH10.38c serine recombinase; *S. coelicolor* chromosome SCC88.14 serine recombinase; *Streptomyces* phage φC31 serine recombinase; *Streptomyces* phage R4 serine recombinase; *Bacillus* phage φ105 serine recombinase; *Bacillus* phage SPBc2 serine recombinase; *Bacillus* prophage SKIN serine recombinase; *S. aureus* ccrA serine recombinase; *S. aureus* ccrB serine recombinase; *M. tuberculosis* phage Bxb1 serine recombinase; *M. tuberculosis* prophage φRV1 serine recombinase; YBCK_ECOLI; Y4bA; Bja; Spn; Cac 1956; and Cac 1954; and b) muteins of a). In preferred embodiments, a highly active Gin catalytic domain is utilized. Such a domain may be generated using the methods of the present invention as described herein.

As described herein, TALEs may include a number of imperfect repeats that determine the specificity with which they interact with DNA. Each repeat binds to a single base, depending on the particular di-amino acid sequence at residues 12 and 13 of the repeat. Thus, by engineering the repeats within a TALE, particular DNA sites can be targeted. Such engineered TALEs can be used, for example, as transcription factors targeted to particular DNA sequences.

As illustrated in the Examples, the chimeric proteins of the present invention are exemplified by the variants and portions thereof (e.g., RVDs and NTDs) as set forth in Table 3.

TABLE 3

| Variant | SEQ ID NO: | Sequence |
|---|---|---|
| TALEN (Goldy) NT-T T1 Protein Sequence | 81 | MRSPKKKRKVQVDLRTLGYSQQQQEK IKPKVRSTVAQHHEALVGHGFTHAHI VALSQHPAALGTVAVTYQHIITALPE ATHEDIVGVGKQWSGARALEALLTDA GELRGPPLQLDTGQLVKIAKRGGVTA MEAVHASRNALTGAPLNLTPDQVVAI ASNGGGKQALETVQRLLPVLCQDHGL TPDQVVAIASHDGGKQALETVQRLLP VLCQDHGLTPDQVVAIASNIGGKQAL ETVQRLLPVLCQDHGLTPDQVVAIAS NGGGKQALETVQRLLPVLCQDHGLTP DQVVAIASNGGGKQALETVQRLLPVL CQDHGLTPDQVVAIASNIGGKQALET VQRLLPVLCQDHGLTPDQVVAIASHD GGKQALETVQRLLPVLCQDHGLTPDQ VVAIASNIGGKQALETVQRLLPVLCQ DHGLTPDQVVAIVSHDGGKQALETVQ RLLPVLCQDHGLTPDQVVAIVSHDGG KQALETVQRLLPVLCQDHGLTPDQVV AIVSNGGGKQALETVQRLLPVLCQDH GLTPDQVVAIASNNGGKQALETVQRL LPVLCQDHGLTPDQVVAIASHDGGKQ ALETVQRLLPVLCQDHGLTPDQVVAI ASNIGGKQALETVQRLLPVLCQDHGL TPDQVVAIASNNGGKQALETVQRLLP VLCQDHGLTPDQVVAIASHDGGKQAL ESIVAQLSRPDPALAALTNDHLVALA CLGGRPAMDAVKKGLPHAPELIRRVN RRIGERTSHRVAGSQLVKSELEEKKS ELRHKLKYVPHEYIELIEIARNSTQD RILEMKVMEFFMKVYGYRGKHLGGSR KPDGAIYTVGSPIDYGVIVDTKAYSG GYNLPIGQADEMQRYVEENQTRNKHI NPNEWWKVYPSSVTEFKFLFVSGHFK GNYKAQLTRLNHITNCNGAVLSVEEL LIGGEMIKAGTLTLEEVRRKFNNGEI NF = N-Terminal Domain (NTD) -varied as shown below |

TALEN RVD Sequences

| G1 | 82 | NG-NN-HD-NG-HD-NI-NG-NG-NI-HD-HD-HD-NG-NN-HD-NI targeting (TCTTCATTACAC CTGCA; SEQ ID NO: 280) |
| G2 | 83 | HD-NI-NN-NG-HD-NI-NN-NG-NI-NG-HD-NI-NI-NG-NG targeting (CAGTCAGTATCAATT; SEQ ID NO: 281) |
| A1 | 84 | HD-HD-NG-NN-HD-NI-NN-HD-NG-HD-NG-HD-NI-NG-NG-NG targeting (CCTGCAGCTCTCATT TT; SEQ ID NO: 282) |

TABLE 3-continued

| Variant | SEQ ID NO: | Sequence |
|---|---|---|
| A2 | 85 | NI-NG-NG-HD-NG-NG-HD-HD-NI-NN-NI-NG-NG-NN-NI targeting (ATTCTTCCAGAATTG A; SEQ ID NO: 283) |
| C2 | 86 | HD-NI-NN-NI-NI-NG-NG-NN-NI-NG-NI-HD-NG-NN-NI-HD-NG targeting (CAGAATTGATACTGA CT; SEQ ID NO: 284) |
| T1 | 87 | NG-HD-NI-NG-NG-NI-HD-NI-HD-HD-NG-NN-HD-NI-NN-HD targeting (TCATTACACCTGCAG C; SEQ ID NO: 285) |
| T2 | 88 | HD-NG-NG-HD-HD-NI-NN-NI-NI-NG-NG-NN-NI-NG-NI-HD-NG-NN targeting (CTTCCAGAA TTGATACTG; SEQ ID NO: 286) |

N-Terminal Domains

| NTD = dHax3-TALEN DNA Sequence | 89 | ATGAGATCTCCTAAGAAAAAGAGGAAG ATGGTGGACTTGAGGACACTCGGTTAT TCGCAACAGCAACAGGAGAAAATCAAG CCTAAGGTCAGGAGCACCGTCGCGCAA CACCACGAGGCGCTTGTGGGGCATGGC TTCACTCATGCGCATATTGTCGCGCTT TCACAGCACCCTGCGGCGCTTGGGACG GTGGCTGTCAAATACCAAGATATGATT GCGGCCCTGCCCGAAGCCACGCACGAG GCAATTGTAGGGGTCGGTAAACAGTGG TCGGGAGCGCGAGCACTTGAGGCGCTG CTGACTGTGGCGGGTGAGCTTAGGGGG CCTCCGCTCCAGCTCGACACCGGCCAG CTGCTGAAGATCGCGAAGAGAGGGGA GTAACAGCGGTAGAGGCAGTGCATGCA TCGCGCAATGCACTGACGGGTGCCCCC |
| NTD = dHax3-TALEN | 90 | MRSPKKKRKMVDLRTLGYSQQQQEKIK PKVRSTVAQHHEALVGHGFTHAHIVAL SQHPAALGTVAVKYQDMIAALPEATHE AIVGVGKQWSGARALEALLTVAGELRG PPLQLDTGQLLKIAKRGGVTAVEAVHA SRNALTGAP ... repeat variable diresidues |
| NTD = NT-βN TALEN DNA Sequence | 91 | ATGAGATCTCCTAAGAAAAAGAGGAAG GTGCAGGTGGATCTACGCACGCTCGGC TACAGTCAGCAGCAGCAAGAGAAGATC AAACCGAAGGTGCGTTCGACAGTGGCG CAGCACCACGAGGCACTGGTGGGCCAT GGGTTTACACACGCGCACATCGTTGCG CTCAGCCAACACCCGGCAGCGTTAGGG ACCGTCGCTGTCACGTATCAGCACATA ATCACGGCGTTGCCAGAGGCGACACAC GAAGACATCGTTGGCGTCGGCAAATAT CATGGGGCACGCGCTCTGGAGGCCTTG CTCACGGATGCGGGGGAGTTGAGAGGT CCGCCGTTACAGTTGGACACAGGCCAA CTTGTGAAGATTGCAAAACGTGGCGGC GTGACCGCAATGAGGCAGTGCATGCA TCGCGCAATGCACTGACGGGTGCCCCC |
| NTD = NT-βN TALEN | 92 | MRSPKKKRKVQVDLRTLGYSQQQQEKI KPKVRSTVAQHHEALVGHGFTHAHIVA LSQHPAALGTVAVTYQHIITALPEATH EDIVGVGKYHGARALEALLTDAGELRG PPLQLDTGQLVKIAKRGGVTAMEAVHA SRNALTGAP ... repeat variable diresidues |
| NTD NT-G TALEN DNA Sequence | 93 | ATGAGATCTCCTAAGAAAAAGAGGAAG GTGCAGGTGGATCTACGCACGCTCGGC TACAGTCAGCAGCAGCAAGAGAAGATC AAACCGAAGGTGCGTTCGACAGTGGCG CAGCACCACGAGGCACTGGTGGGCCAT |

TABLE 3-continued

| Variant | SEQ ID NO: | Sequence |
|---|---|---|
| | | GGGTTTACACACGCGCACATCGTTGCG CTCAGCCAACACCCGGCAGCGTTAGGG ACCGTCGCTGTCACGTATCAGCACATA ATCACGGCGTTGCCAGAGGCGACACAC GAAGACATCGTTGGCGTCGGCAAATCG CGGTCGGGGGCACGCGCTCTGGAGGCC TTGCTCACGGATCGGGGGAGTTGAGA GGTCCGCCGTTACAGTTGGACACAGGC CAACTTGTGAAGATTGCAAAACGTGGC GGCGTGACCGCAATGGAGGCAGTGCAT GCATCGCGCAATGCACTGACGGGTGCC CCC |
| NTD NT-G TALEN Protein Sequence | 94 | MRSPKKKRKVQVDLRTLGYSQQQQEKI KPKVRSTVAQHHEALVGHGFTHAHIVA LSQHPAALGTVAVTYQHIITALPEATH EDIVGVGKSRSGARALEALLTDAGELR GPPLQLDTGQLVKIAKRGGVTAMEAVH ASRNALTGAP ... repeat variable diresidues |
| NTD = NT-αN TALEN DNA Sequence | 95 | ATGAGATCTCCTAAGAAAAAGAGGAAG GTGCAGGTGGATCTACGCACGCTCGGC TACAGTCAGCAGCAGCAAGAGAAGATC AAACCGAAGGTGCGTTCGACAGTGGCG CAGCACCACGGGGCACTGGTGGGCCAT GGGTTTACACACGCGCACATCGTTGCG CTCAGCCAACACCCGGCAGCGTTAGGG ACCGTCGCTGTCACGTATCAGCACATA ATCACGGCGTTGCCAGAGGCGACACAC GAAGACATCGTTGGCGTCGGCAAACGG GGGGCTGGTGCACGCGCTCTGGAGGCC TTGCTCACGGATCGGGGGAGTTGAGA GGTCCGCCGTTACAGTTGGACACAGGC CAACTTGTGAAGATTGCAAAACGTGGC GGCGTGACCGCAATGGAGGCAGTGCAT GCATCGCGCAATGCACTGACGGGTGCC CCC |
| NTD = NT-αN TALEN Protein | 96 | MRSPKKKRKVQVDLRTLGYSQQQQEKI KPKVRSTVAQHHEALVGHGFTHAHIVA LSQHPAALGTVAVTYQHIITALPEATH EDIVGVGKRGARALEALLTDAGELR GPPLQLDTGQLVKIAKRGGVTAMEAVH ASRNALTGAP ... repeat variable diresidues |
| NTD = NT-T T-1 TALEN DNA | 97 | ATGAGATCTCCTAAGAAAAAGAGGAAG GTGCAGGTGGATCTACGCACGCTCGGC TACAGTCAGCAGCAGCAAGAGAAGATC AAACCGAAGGTGCGTTCGACAGTGGCG CAGCACCACGAGGCACTGGTGGGCCAT GGGTTTACACACGCGCACATCGTTGCG CTCAGCCAACACCCGGCAGCGTTAGGG ACCGTCGCTGTCACGTATCAGCACATA ATCACGGCGTTGCCAGAGGCGACACAC GAAGACATCGTTGGCGTCGGCAAACAG TGGTCCGGCGCACGCGCCCTGGAGGCC TTGCTCACGGATGCGGGGGAGTTGAGA GGTCCGCCGTTACAGTTGGACACAGGC CAACTTGTGAAGATTGCAAAACGTGGC GGCGTGACCGCAATGGAGGCAGTGCAT GCATCGCGCAATGCACTGACGGGTGCC CCC |
| MBP-TALE Protein Sequence | 98 | MKIEEGKLVIWINGDKGYNGLAEVGKK FEKDTGIKVTVEHPDKLEEKFPQVAAT GDGPDIIFWAHDRFGGYAQSGLLAEIT PDKAFQDKLYPFTWDAVRYNGKLIAYP IAVEALSLIYNKDLLPNPPKTWEEIPA LDKELKAKGKSALMFNLQEPYFTWPLI AADGGYAFKYENGKYDIKDVGVDNAGA KAGLTFLVDLIKNKHMNADTDYSIAEA AFNKGETAMTINGPWAWSNIDTSKVNY GVTVLPTFKGQPSKPFVGVLSAGINAA SPNKELAKEFLENYLLTDEGLEAVNKD KPLGAVALKSYEEELAKDPRIAATMEN AQKGEIMPNIPQMSAFWYAVRTAVINA ASGRQTVDEALKDAQTNSSSNNNNNNN NNNLGIEGRISEFGSPARPPRAKPAPR RRSAQPSDASPAAQVDLRTLGYSQQQQ EKIKPKVRSTVAQHHEALVGHGFTHAH IVALSQHPAALGTVAVTYQHIITALPE ATHEDIVGVGK[XXX]GARALEALLTD AGELLRGPPLQLDTGQLVKIAKRGGVT AMEAVHASRNALTGAPLNLTPDQVVAI ASNIGGKQALETVQRLLPVLCQDHGLT PDQVVAIASNGGGKQALETVQRLLPVL CQDHGLTPDQVVAIASNIGGKQALETV QRLLPVLCQDHGLTPDQVVAIASNIGG KQALETVQRLLPVLCQDHGLTPDQVVA IASNIGGKQALETVQRLLPVLCQDHGL TPDQVVAIASHDGGKQALETVQRLLPV LCQDHGLTPDQVVAIASHDGGKQALET VQRLLPVLCQDHGLTPDQVVAIVSHDG GKQALETVQRLLPVLCQDHGLTPDQVV AIVSHDGGKQALETVQRLLPVLCQDHG LTPDQVVAIVSNGGGKQALETVQRLLP VLCQDHGLTPDQVVAIVSNGGGKQALE TVQRLLPVLCQDHGLTPDQVVAIASHD GGKQALETVQRLLPVLCQDHGLTPDQV VAIASHDGGKQALETVQRLLPVLCQDH GLTPDQVVAIASNIGGKQALETVQRLL PVLCQDHGLTPDQVVAIASNIGGKQAL ESIVAQLSRPDPALAALTNDHLVALAC LG XXX: NT-T = QWS NT-G = SRS; NT-αN = RGA; NT-βN = Y-H |
| TALE-R Protein Sequence | 99 | MLIGYVRVSTNDQNTDLQRNALVCAGC KQIFEDKLSGTRTDRPGLKRALKRLQK GDTLVVVVKLDRLGRSMKHLISLVGHL RHRGINFRSLTDSIDTSSPMGRFFFYV MGALAEMERELIIERTMAGLAAARNKG RIGGRPPKSGSPRPPRAKPAPRRRAAQ PSOASPAAQVDLRTLGYSQQQQEKIKP KVRSTVAQHHEALFVGHGFTHAHIVALS QHPAALGTVAVTYQHIITALPEATHRD IVGVGK[XXX]GARALEALLTDAGELR GPPLQLDTGDLVKIAKRGGVTAMEAVH ASRNALTGAPLNLTPDQVVAIASNIGG KQALETVQRLLPVLCQDHGLTPDQVVA IASNGGGKQALETVQRLLPVLCQDHGL TPDQVVAIASNIGGKQALETVQRLLPV LCQDHGLTPDQVVAIASNIGGKQALET VQRLLPVLCQDHGLTPDQWAIASNIGG KQALETVQRLLPVLCQDHGLTPDQVVA IASHDGGKQALETVQRLLPVLCQDHGL TPDQVVAIASHDGGKQALETVQRLLPV LCQDHGLTPDQVVAIASHDGGKQALET VQRLLPVLCQDHGLTPDQVVAIVSHDG GKQALETVQRLLPVLCQDHGLTPDQVV AIVSHDGGKQALETVQRLLPVLCQDHG LTPDQVVAIVSNGGGKQALETVQRLLP VLCQDHGLTPDQVVAIASHDGGKQALE TVQRLLPVLCQDIIGLTPDQVVAIASH DGGKQALETVQRLLPVLCQDHGLTPDQ VVAIASNIGGKQALHTVQRLLPVLCQD HGLTPDQVVAIASNIGGKQALESIVAQ LSRPDPALAALTNDHLVALACLG XXX: NT-T = QWS NT-G = SRS; NT-αN = RGA; NT-βN = Y-H |
| Avr15 TALE-TF Protein Sequence | 100 | MAQAASGSPRPPRAKPAPRRRAAQPSD ASPAAQVDLRTLGYSQQQQEKIKPKVR STVAQHHEALVGIIGFTHAHIVALSQH PAALGTVAVTYQHIITALPEATHEDIV GVGK[XXX]GARALEALLTDAGELRGP PLQLDTGQLVKIAKRGGVTAMEAVHAS RNALTGAPLNLTPDQVVAIASNIGGKQ ALHTVQRLLPVLCQDHGLTPDQWAIAS NGGGKQALETVQRLLPVLCQDHGLTPD |

TABLE 3-continued

| Variant | SEQ ID NO: | Sequence |
|---|---|---|
| | | QVVAIASNIGGKQALETVQRLLPVLCQ<br>DHGLTPDQWAIASNIGGKQALETVQRL<br>LPVLCQDHGLTPDQWAIASNIGGKQAL<br>ETVQRLLPVLCQDHGLTPDQVVAIASH<br>DGGKQALETVQRLLPVLCQDHGLTPDQ<br>WAIASHDGGKQALETVQRLLPVLCQDH<br>GLTPDQVVAIASHDGGKQALETVQRLL<br>PVLCQDHGLTPDQVVAIVSHDGGKQAL<br>ETVQRLLPVLCQDHGLTPDQVVAIVSH<br>DGGKQALETVQRLLPVLCQDHGLTPDQ<br>VVAIVSNGGGKQALETVQRLLPVLCQD<br>HGLTPDQVVAIASHDGGKQALETVQRL<br>LPVLCQOHGLTPDQVVAIASHDGGKQA<br>LETVQRLLPVLCQDHGLTPDQVVAIAS<br>NIGGKQALETVQRLLPVLCQDHGLTPD<br>QVVAIASNIGGKQALESIVAQLSRPDP<br>ALAALTNDHLVALACLGGRPAMDAVKK<br>GLPHAPELIRRVNRRIGERTSHRVADY<br>AQVVRVLEFFQCHSHPAYAFDEAMTQF<br>GMSGQAGQASPKKRKVGRADALDDFD<br>LDMLGSDALDDFDLDMLGSDALDDFDL<br>DMLGSDALDDFDLDMLINYPYDVPDYA<br>S<br>XXX: NT-T = QWS NT-G = SRS;<br>NT-αN = RGA;<br>NT-βN = Y-H |
| Avr15 RVD Sequence (for TALE-R, TALE-TF, MBP-TALE) | 101 | NI-NG-NI-NI-NI-HD-HD-HD-HD-<br>HD-NI-HD-HD-NI-NI targeting<br>(ATAAACCCCTCCAA;<br>SEQ ID NO: 287) |

In various embodiments, chimeric protein includes a TALE protein having a C-terminal or N-terminal truncation. For example, the TALE protein may include all or a portion of SEQ ID NO: 2. In embodiments, the TALE protein is truncated between amino acid residues 27 and 268, 92 and 134, 120 and 129, 74 and 147, or 87 and 120, such at amino acid residue 28, 74, 87, 92, 95, 120, 124, 128, 129, 147 and 150.

In another embodiment, a isolated polypeptide comprising a transcription activator-like effector (TALE) protein is provided in which the TALE protein has an N-terminal domain (NTD) comprising an amino acid sequence as set forth in SEQ ID NO: 3 (VGKQWSGARAL) having one or more mutations or deletions selected from: Q is Y, Q is S, Q is R, W is R, W is G, W is deleted, S is R, S is H, S is A, S is N, and S is T.

In some embodiments, the NTD comprises an amino acid sequence selected from:

VGKYRGARAL, (SEQ ID NO: 4)

VGKSRSGARAL, (SEQ ID NO: 5)

VGKYHGARAL, (SEQ ID NO: 6)
and

VGKRGAGARAL. (SEQ ID NO: 7)

In another embodiment, an isolated polypeptide comprising a transcription activator-like effector (TALE) protein is provided in which the TALE protein has an N-terminal domain (NTD) comprising an amino acid sequence as set forth in SEQ ID NO: 8 (IVDIAR$_1$QR$_2$SGDLA) having one or more mutations or deletions selected from: R$_1$ is K, Q is Y, Q is S, Q is R, R$_2$ is W, R$_2$ is G, R$_2$ is deleted, S is R, S is H, S is A, S is N, and S is T.

In some embodiments, the NTD comprises an amino acid sequence selected from:

IVDIARQWSGDLA, (SEQ ID NO: 9)

IVDIARYRGDLA, (SEQ ID NO: 10)

IVDIARSRSGDLA, (SEQ ID NO: 11)

IVDIARYHGDLA, (SEQ ID NO: 12)
and

IVDIARRGAGDLA. (SEQ ID NO: 13)

In another embodiment, the TALE protein includes a modified N$_0$ domain having an amino acid sequence set forth as follows:

LTPDQLVKIA<u>KRGG</u>TAMEAVHASRNALTGAPLN. (SEQ ID NO: 102)

In various embodiments, the TALE protein includes a mutated variant in which

KRGG (SEQ ID NO: 103)
of SEQ ID NO: 102 is selected from

LDYE, (SEQ ID NO: 104)

INLV, (SEQ ID NO: 105)

YSKK, (SEQ ID NO: 106)

NMAH, (SEQ ID NO: 107)

SPTN, (SEQ ID NO: 108)

SNTR, (SEQ ID NO: 109)

LTTT, (SEQ ID NO: 110)

VADL, (SEQ ID NO: 111)

MVLS, (SEQ ID NO: 112)

YNGR, (SEQ ID NO: 113)

RIPR, (SEQ ID NO: 114)

YSKI, (SEQ ID NO: 115)

LTQY, (SEQ ID NO: 116)

YLSK, (SEQ ID NO: 117)

-continued

LRPN, (SEQ ID NO: 118)

LFTN, (SEQ ID NO: 119)

LLTN, (SEQ ID NO: 120)

EEDK, (SEQ ID NO: 121)

VTAM, (SEQ ID NO: 122)

CPSR, (SEQ ID NO: 123)

LTRV, (SEQ ID NO: 124)

KGDL, (SEQ ID NO: 125)

QKAL, (SEQ ID NO: 126)

LYLL, (SEQ ID NO: 127)

WISV, (SEQ ID NO: 128)

GDQV and (SEQ ID NO: 129)

CPSR. (SEQ ID NO: 130)

In another embodiment, the TALE protein includes a modified $N_{-1}$ domain having an amino acid sequence set forth as follows: MRSPKKKRKVQVDL-RTLGYSQQQQEKIKPKVRSTVAQHH EALVGHG-FTHAHIVALSQHPAALGTVAVTYQHIITALPEATHEDI-VGVG<u>XXXXX</u>ARA LEALLTDAGELRGPPLQLDTGQLVKIAKRG-GVTAMEAVHASRNALTGAP (SEQ ID NO: 131). In various embodiments, XXXXX of SEQ ID NO: 131 is KRPAG (SEQ ID NO: 132) or KRPSG (SEQ ID NO: 133). Additionally, the protein may include, a E40G mutation (with reference to SEQ ID NO: 131) that exhibits enhanced activity.

In another embodiment, the TALE protein includes a repeat domain having an amino acid sequence set forth as follows: LTPDVVAI SNNGGKQALETVQRLLPVLCQDGH (SEQ ID NO: 134). In various embodiments, the TALE protein includes a mutated variant in which SNNG (SEQ ID NO: 135) of SEQ ID NO: 134 is selected from RGGG (SEQ ID NO: 136), RGGR (SEQ ID NO: 137), RGVR (SEQ ID NO: 138), KGGG (SEQ ID NO: 139), SGGG (SEQ ID NO: 140), GGRG (SEQ ID NO: 141), LGGS (SEQ ID NO: 142), MDNI (SEQ ID NO: 143), RVMA (SEQ ID NO: 144), LASV (SEQ ID NO: 145), VGTG (SEQ ID NO: 146) and QGGG (SEQ ID NO: 147).

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Chimeric Tale Recombinases

Experimental Summary.

This study provides the first example of a TALE recombinase (TALER). Using a library of incrementally truncated TALE domains, an optimized TALER architecture was identified that can be used to recombine DNA in bacterial and mammalian cells. Any customized TALE repeat array can be inserted into the TALER architecture described herein, thus dramatically expanding the targeting capacity of engineered recombinases for applications in biotechnology and medicine.

The following Material and Methods were utilized in this Example.

Reagents.

All enzymes were purchased from New England BioLabs unless otherwise indicated. Primer sequences are provided in Table 4.

TABLE 4

Primers.

Primers used in this study
Primers for pBLA substrate construction

| | | |
|---|---|---|
| AvrXa7 lac target F | SEQ ID NO: 148 | TTAATTAAGAGTCTAGAAATATAAACCCCCTC CAACCAGGTGCTAACTGTAAACCATGGTTTTG GATTAGCACCTGGTTGGAGGGGGTTTATAAGA TCTAGGAGGAATTTAAAATGAG |
| AvrXa7 lac target R | SEQ ID NO: 149 | ACTGACCTAGAGAAGCTTATATAAACCCCCTC CAACCAGGTGCTAATCCAAAACCATGGTTTAC AGTTAGCACCTGGTTGGAGGGGGTTTATACTG CAGTTATTTGTACAGTTCATC |
| AvrXa7 N F | SEQ ID NO: 150 | TTAATTAAGAGTCTAGATTAGCACCTGGTTGG AGGGGGTTTATAAGGTTTTGGTACCAAATGTC TATAAACCCCCTCCAACCAGGTGCTAAAGATC TAGGAGGAATTTAAAATGAG |
| AvrXa7 N R | SEQ ID NO: 152 | ACTGACCTAGAGAAGCTTTTAGCACCTGGTTG GAGGGGGTTTATAGACATTTGGTACCAAAACC TTATAAACCCCCTCCAACCAGGTGCTAACTGC AGTTATTTGTACAGTTCATC |

TABLE 4-continued

Primers.

| | | |
|---|---|---|
| AvrXa7 N RC F | SEQ ID NO: 153 | TTAATTAAGAGTCTAGATTAGCACCTGGTTGG AGGGGGTTTATATCCAAAACCATGGTTTACAG TATAAACCCCCTCCAACCAGGTGCTAAAGATC TAGGAGGAATTTAAAATGAG |
| AvrXa7 N RC R | SEQ ID NO: 154 | ACTGACCTAGAGAAGCTTTTAGCACCTGGTTG GAGGGGGTTTATATCCAAAACCATGGTTTACA GTATAAACCCCCTCCAACCAGGTGCTAACTGC AGTTATTTGTACAGTTCATC |
| AvrXa7 N RC + 3 F | SEQ ID NO: 155 | TTAATTAAGAGTCTAGATTAGCACCTGGTTGG AGGGGGTTTATAGCTTCCAAAACCATGGTTTA CAGGGTTATAAACCCCCTCCAACCAGGTGCTA AAGATCTAGGAGGAATTTAAAATGAG |
| AvrXa7 N RC + 3 R | SEQ ID NO: 277 | ACTGACCTAGAGAAGCTTTTAGCACCTGGTTG GAGGGGGTTTATAACCCTGTAAACCATGGTTT TGGAAGCTATAAACCCCCTCCAACCAGGTGCT AACTGCAGTTATTTGTACAGTTCATC |
| AvrXa7 N RC + 6 F | SEQ ID NO: 156 | TTAATTAAGAGTCTAGATTAGCACCTGGTTGG AGGGGGTTTATAGCTTCATCCAAAACCATGGT TTACAGGGTTCCTATAAACCCCCTCCAACCAG GTGCTAAAGATCTAGGAGGAATTTAAAATGAG |
| AvrXa7 N RC + 6 R | SEQ ID NO: 157 | ACTGACCTAGAGAAGCTTTTAGCACCTGGTTG GAGGGGGTTTATAGCAACCCTGTAAACCATGG TTTTGGATGAAGCTATAAACCCCCTCCAACCA GGTGCTAACTGCAGTTATTTGTACAGTTCATC |
| AvrXa7 N RC + 12 F | SEQ ID NO: 158 | TTAATTAAGAGTCTAGATTAGCACCTGGTTGG AGGGGGTTTATAGCTTCAGCTTCATCCAAAAC CATGGTTTACAGGGTTCCGGTTCCTATAAACC CCTCCAACCAGGTGCTAAAGATCTAGGAGGA ATTTAAAATGAG |
| AvrXa7 N RC + 12 R | SEQ ID NO: 278 | ACTGACCTAGAGAAGCTTTTAGCACCTGGTTG GAGGGGGTTTATAGCAACCGCAACCCTGTAAA CCATGGTTTTGGATGAAGCTGAAGCTATAAAC CCCTCCAACCAGGTGCTAACTGCAGTTATTT GTACAGTTCATC |
| AvrXa7 N RC - 3 F | SEQ ID NO: 160 | TTAATTAAGAGTCTAGATTAGCACCTGGTTGG AGGGGGTTTATAAAAACCATGGTTTATATAAA CCCCCTCCAACCAGGTGCTAAAGATCTAGGAG GAATTTAAAATGAG |
| AvrXa7 N RC - 3 R | SEQ ID NO: 161 | ACTGACCTAGAGAAGCTTTTAGCACCTGGTTG GAGGGGGTTTATATAAACCATGGTTTTTATAA ACCCCCTCCAACCAGGTGCTAACTGCAGTTAT TTGTACAGTTCATC |
| AvrXa7 N RC GG F | SEQ ID NO: 162 | TTAATTAAGAGTCTAGATTAGCACCTGGTTGG AGGGGGTTTATATCCAAAACCGGGGTTTACAG TATAAACCCCCTCCAACCAGGTGCTAAAGATC TAGGAGGAATTTAAAATGAG |
| AvrXa7 N RC GG R | SEQ ID NO: 163 | ACTGACCTAGAGAAGCTTTTAGCACCTGGTTG GAGGGGGTTTATACTGTAAACCCCGGTTTTGG ATATAAACCCCCTCCAACCAGGTGCTAACTGC AGTTATTTGTACAGTTCATC |
| AvrXa7 N 20t F | SEQ ID NO: 164 | TTAATTAAGAGTCTAGATTAGCACCTGGTTGG AGGGGGTTTATACGAAATATTATAAATTATCA TATAAACCCCCTCCAACCAGGTGCTAAAGATC TAGGAGGAATTTAAAATGAG |
| AvrXa7 N RC 20t R | SEQ ID NO: 165 | ACTGACCTAGAGAAGCTTTTAGCACCTGGTTG GAGGGGGTTTATATGATAATTTATAATATTTC GTATAAACCCCCTCCAACCAGGTGCTAACTGC AGTTATTTGTACAGTTCATC |
| AvrXa7 32 GG F | SEQ ID NO: 166 | TTAATTAAGAGTCTAGATTAGCACCTGGTTGG AGGGGGTTTATAGCTTCATCCAAAACCGGGGT TTACAGGGTTCCTATAAACCCCCTCCAACCAG GTGCTAAAGATCTAGGAGGAATTTAAAATGAG |

TABLE 4-continued

Primers.

| Name | SEQ ID | Sequence |
|---|---|---|
| AvrXa7 32 GG R | SEQ ID NO: 167 | ACTGACCTAGAGAAGCTTTTAGCACCTGGTTG GAGGGGGTTTATAGCAACCCTGTAAACCGGGG TTTTGGATGAAGCTATAAACCCCCTCCAACCA GGTGCTAACTGCAGTTATTTGTACAGTTCATC |
| AvrXa7 32t F | SEQ ID NO: 168 | TTAATTAAGAGTCTAGATTAGCACCTGGTTGG AGGGGGTTTATAGCTTCACGAAATATTATAAA TTATCAGGTTCCTATAAACCCCCTCCAACCAG GTGCTAAAGATCTAGGAGGAATTTAAAATGAG |
| AvrXa7 32t R | SEQ ID NO: 169 | ACTGACCTAGAGAAGCTTTTAGCACCTGGTTG GAGGGGGTTTATAGCAACCTGATAATTTATAA TATTTCGTGAAGCTATAAACCCCCTCCAACCA GGTGCTAACTGCAGTTATTTGTACAGTTCATC |

Primers for pGL3Pro target site construction.

| Name | SEQ ID | Sequence |
|---|---|---|
| 5' pGL3 SV40 Avr.32G BglII | SEQ ID NO: 170 | TTAATTAAGAGAGATCTTTAGCACCTGGTTGG AGGGGGTTTATAGCTTCATCCAAAACCATGGT TTACAGGGTTCCTATAAACCCCCTCCAACCAG GTGCTAAGCGATCTGCATCTCAATTAGTCAGC |
| 3' pGL3 SV40 Avr.20G HindIII | SEQ ID NO: 171 | ACT GAC CTA GAG AAG CTT TTA GCA CCT GGT TGG AGG GGG TTT ATAGCAACC CTG TAA ACC ATG GTT TTG GATGAAGCT ATA AAC CCC CTC CAA CCA GGT GCT AAT TTG CAA AAG CCT AGG CCT CCA AA |
| 5' pGL3 SV40 PH4.20G6Avr BglII | SEQ ID NO: 172 | TTAATTAAGAGAGATCTGCGGGAGGCGTGTCC AAAACCATGGTTTACAGGGTTCCTATAAACCC CCTCCAACCAGGTGCTAAGCGATCTGCATCTC AATTAGTCAGC |
| 3' pGL3 SV40 PH4.20G6Avr HindIII | SEQ ID NO: 173 | ACT GAC CTA GAG AAG CTT TTA GCA CCT GGT TGG AGG GGG TTT ATAGCAAC CCTGTAAACCATGGTTTTGGACACGCCTCCCG CTTTGCAAAAGCCTAGGCCTCCAAA |
| 5' pGL3 SV40 Avr.44G BglII | SEQ ID NO: 174 | TTAATTAAGAGAGATCTTTAGCACCTGGTTGG AGGGGGTTTATAGCTTCAGCTTCATCCAAAAC CATGGTTTACAGGGTTCCGGTTCCTATAAACC CCCTCCAACCAGGTGCTAAGCGATCTGCATCT CAATTAGTCAGC |
| 3' pGL3 SV40 Avr.44G HindIII | SEQ ID NO: 175 | ACT GAC CTA GAG AAG CTT TTA GCA CCT GGT TGG AGG GGG TTTATAGCAACC GCAACCCTG TAA ACC ATG GTT TTG GA TGAAGCTGAAGCT ATA AAC CCC CTC CAA CCA GGT GCT AAT TTG CAA AAG CCT AGG CCT CCA AA |

Primers for BamHI fusions

| Name | SEQ ID | Sequence |
|---|---|---|
| Gin_N-term F | SEQ ID NO: 176 | AGTCAGTCGAGAGCTCATGGATCCCGGCTCTA TGCTGATTGGCTATGTAAGG |
| Gin_N-term R | SEQ ID NO: 177 | ATGCTGATATCTAGACTATCCCGATTTAGGTG GGCGACC |
| Gin_C-term F | SEQ ID NO: 178 | AGTCAGTCGAGAGCTCATGCTGATTGGCTATG TAAGG |
| Gin_C-term R | SEQ ID NO: 179 | TCTAGACTACGGATCCACCGATTTACGCGGGC |

Primers for designed truncations

| Name | SEQ ID | Sequence |
|---|---|---|
| TalR + 28 Xba | SEQ ID NO: 180 | ATCGCGTATCTAGACTAGCCGAGGCAGGCCAA GGCGACG |
| TalR + 95 Xba AvrX | SEQ ID NO: 181 | ATCGCGTATCTAGACTAGCTCATCTCGAACTG CGTCATG |
| avr n 1 | SEQ ID NO: 182 | GTCGCCCGCGTAAATCGGGATCCACTGCAGAT CGGGGGGGGC |

TABLE 4-continued

Primers.

| | | |
|---|---|---|
| avr n 2 | SEQ ID NO: 183 | GTCGCCCGCGTAAATCGGGATCCCCCTCGCCT GCGTTCTCGGC |
| avr n 3 | SEQ ID NO: 184 | GTCGCCCGCGTAAATCGGGATCCGATTCGATG CCTGCCGTCGG |
| avr n 4 | SEQ ID NO: 185 | GTCGCCCGCGTAAATCGGGATCCACCGTGCGT GTCGCTGTCACTG |
| avr n 5 | SEQ ID NO: 186 | GTCGCCCGCGTAAATCGGGATCCGTGGATCTA CGCACGCTCGGC |
| avr n 6 | SEQ ID NO: 187 | GTCGCCCGCGTAAATCGGGATCCACACACGCG CACATCGTTGC |
| avr n 7 | SEQ ID NO: 188 | GTCGCCCGCGTAAATCGGGATCCCACGAAGAC ATCGTTGGCGTCG |
| avr n 8 | SEQ ID NO: 189 | GTCGCCCGCGTAAATCGGGATCCAGCGCTCTG GAGGCCTTGCTC |
| avr n 9 | SEQ ID NO: 190 | GTCGCCCGCGTAAATCGGGATCCTTGGACACA GGCCAACTTCTC |
| avr n 10 | SEQ ID NO: 191 | GTCGCCCGCGTAAATCGGGATCCAGCGGCGTG ACCGCAgTGGA |
| GinNTALPCRfusR | SEQ ID NO: 192 | GGATCCCGATTTACGCGGGC |
| Primers used for pcDNA cloning | | |
| Nhe-SD-Gin F | SEQ ID NO: 193 | ATCGTAGCAGCTAGCGCCACCATGCTGATTGG CTATGTAAG |
| GinGS R | SEQ ID NO: 194 | GGATCCAGACCCCGATTTACGCGGGC |

Plasmid Construction.

In order to introduce a BamH1 restriction site either 5' or 3' to the Gin coding sequence, the Gin catalytic domain was PCR amplified with primers 5' Gin_N-term and 3' Gin_N-term or 5' Gin_C-term and 3' Gin_C-term, respectively. PCR products were ligated into the SacI and XbaI restriction sites of pBluescriptII (Fermentas) to generate pB-Bam-Gin and pB-Gin-Bam. To generate the C-terminal and N-terminal TALER fusions, the AvrXa7 gene (kindly provided by Dr. B. Yang, Iowa State University) was released from pWAvrXa7 with BamH1 and ligated into BamH1 sites of pB-Bam-Gin and pB-Gin-Bam (41) to establish pB-Avr-Bam-Gin and pB-Gin-Bam-Avr, respectively. Correct construction of each TALER was verified by sequence analysis (FIGS. 6-16).

To generate N-terminal truncations of AvrXa7, AvrXa7 was PCR amplified using the Expand High Fidelity PCR System (Roche) with 5' Avr-n-(1-10) and 3' Avr+28 or 3' Avr+95 primers with the following program: 1 cycle of 3 min at 94° C., 16 cycles of 1 min at 94° C., 1 min at 52° C., 6 min at 68° C.; and a final cycle of 1 hr at 68° C. The Gin catalytic domain was PCR amplified under standard PCR conditions with 5' Gin_C-term and 3' GinNTalPCRFus and fused to truncated AvrXa7 variants by overlap PCR using the PCR conditions described above. Purified Gin-Avr PCR products were mixed in an equimolar ratio and digested with SacI and XbaI.

To generate designer TALEs, we used a TALEN kit (Addgene) with the following modification: pTAL1 was modified to include truncations at Δ120, Δ128, or +28. To achieve this, AvrXa7Δ120 and AvrXa7Δ128 fragments were PCR amplified with 5' Avr n4 or Avr n128 and 3' TalR Xba+28 and ligated into the BamH1 restriction site of pTAL1 to generate pTALΔ120 and pTALΔ128. The plasmids pTALΔ120 and pTALΔ128 retained the Esp3I restriction sites for Golden Gate cloning. TALE arrays cloned into pTALΔ120 and pTALΔ128 were digested with BamH1 and XbaI for ligation into pB-Gin-Bam.

To generate mammalian TALER expression vectors, the Gin catalytic domain was PCR amplified from pB-Gin-Avr with 5' Nhe-SD-Gin F and 3' GinGS R and ligated into the NheI and BamHI restriction sites of pcDNA 3.1 (Invitrogen). Avr15 was digested from pTALΔ120 or pTALΔ128 with BamH1 and XbaI and ligated into pcDNA-Gin-Bam to generate pcDNA-Gin-Avr expression vectors.

The pBLA substrate plasmids were constructed as previously described.

To generate pGL3 reporter plasmids, the SV40 promoter was PCR amplified from pGL3-Promoter (Promega) with the recombination site-containing primers 5' pGL3 SV40 BglII and 3' pGL3 SV40 HindIII and ligated into the BglII and HindIII restriction sites of pGL3-Promoter.

Bacterial Recombination Assays.

Bacterial recombination assays were performed as previously described.

Incremental Truncation Library.

The incremental truncation library was generated using a modified protocol previously described. Briefly, in order to protect the Gin coding sequence from exonuclease digestion, a stuffer fragment with a SmaI restriction site was inserted into BamH1 to generate pB-Gin-SmaI-Bam-Avr. This plasmid was linearized with NheI and incubated with Exonuclease III for 2.5 min at 37° C. followed by heat inactivation at 75° C. for 25 min. pB-Gin-Bam-Avr was then incubated with Klenow Fragment (3' to 5' Exo) with 200 μM dNTPs and 5 µM [α]-S-dNTPs for 30 min at 37° C. followed by heat inactivation at 80° C. for 25 min. To generate the truncation library, pB-Gin-Bam-Avr was incubated with Exonuclease III for 2.5 min at 37° C. followed by heat inactivation and subsequent blunt-ending with Mung Bean Nuclease for 1 hr at 30° C. After digestion with SmaI, the blunt 3' end of the recombinase coding sequence was ligated to the blunt-ended library of TALE fragments. After transformation and purification, the plasmids were digested with SacI and XbaI to release Gin-ΔAvr.

Mammalian Reporter Assays.

HEK293T cells were seeded onto 96-well plates at a density of 4×10⁴ cells per well and grown in a humidified 5% $CO_2$ atmosphere at 37° C. At 24 hr after seeding, cells were transfected with 150 ng pcDNA TALER expression vector, 2.5 ng pGL3 reporter plasmid, and 1 ng pRL-CMV for expression of *Renilla* luciferase using Lipofectamine 2000 (Invitrogen) according to the manufacturer's instructions. At 48 hr after transfection, cells were lysed with Passive Lysis Buffer (Promega) and luciferase expression was determined using the Dual-Luciferase Reporter Assay System (Promega) according to the manufacturer's instructions. Luminescence was measured using a Veritas Microplate Luminometer (Turner Biosystems).

Results.

TALER Architecture.

A quantitative system for the evaluation and directed evolution of recombinase activity has been described. In this system (FIG. 1A), a GFPuv transgene flanked by recombination sites is inserted into the gene encoding TEM-1β-lactamase. This alteration disrupts β-lactamase expression and renders *Escherichia coli* cells that harbor this plasmid (pBLA) susceptible to ampicillin. Expression of an active recombinase from the substrate-containing plasmid, however, leads to recombination between target sites and restoration of the β-lactamase reading frame. This modification establishes host-cell resistance to ampicillin and enables the isolation of active recombinase variants from the substrate-containing plasmid. By measuring the number of ampicillin-resistant transformants following plasmid purification and re-transformation, recombinase activity can be also directly assessed. Because the activity of a chimeric recombinase is dependent upon both the catalytic domain and the DBD, this split gene reassembly selection system can also be used to evaluate the effectiveness of individual DBDs. Thus, the system was adapted to determine an optimal TALER architecture.

Figure 1:
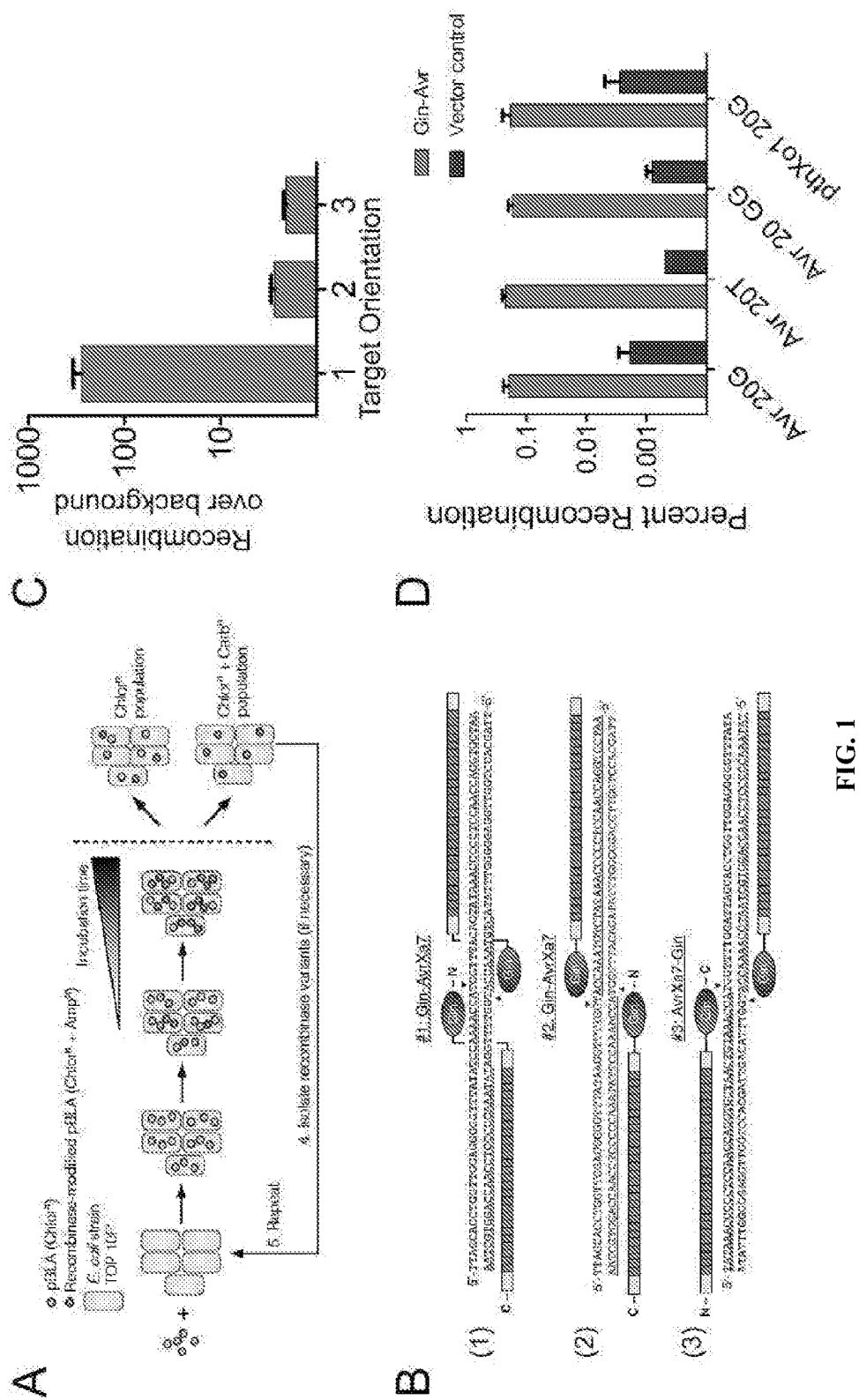
FIG. 1 is a series of graphical and diagrammatic representations regarding TALER fusion orientation and activity. A) Cartoon illustrating the split β-lactamase system used to evaluate TALER activity. B) Schematic showing the fusion orientation of each TALER and its corresponding target site (1=SEQ ID NO: 288; 2=SEQ ID NO: 289; 3=SEQ ID NO: 290). C) Activity of each designed TALER fusion against its intended DNA target. Recombination was normalized to background (vector only control). D) Gin-Avr activity against cognate (Avr-20G) and non-cognate (Avr-20T, Avr-20GG, PthXo1-20G) DNA targets. Error bars indicate standard deviation (s.d.) (n=3).

Importantly, because the catalytic domain of the DNA invertase Gin and related serine recombinases have predefined catalytic specificities, TALER fusion proteins cannot be constructed using the design described for TALENs. Structural and functional studies with the γδ resolvase and designed enzymes have indicated that the C-terminal E-helix mediates serine recombinase DNA recognition. In ZFRs, this helix binds DNA from the C to the N-terminus, 5' to 3'. Thus, because TALEs bind DNA in the 5' to 3' direction, it was anticipated that recombination could only occur when the TALE binding site is positioned on the opposite strand of the 20-bp core (FIG. 1B).

It was chosen to generate TALERs using AvrXa7, as this TALE protein has been previously used to generate TALE nucleases and transcription factors. Conveniently, BamHI restriction sites flank many TALEs, including AvrXa7 and multiple groups have used this restriction site to generate synthetic TALE fusions. Notably, this BamHI fragment leaves the N-terminus of the TALE intact but removes the native effector domain from the C-terminus. This strategy was adopted and generated a Gin-AvrXa7 fusion by BamH1 restriction digestion.

Gin-AvrXa7 was cloned into a pBLA selection vector containing recombination sites composed of a central 20-bp core sequence, which is recognized by the Gin catalytic domain, and two flanking 26-bp AvrXa7 binding sites. As anticipated, the Gin-AvrXa7 fusion was unable to recombine DNA when AvrXa7 binding sites were positioned adjacent to the 20-bp core (FIG. 1C). However, when AvrXa7 binding sites were positioned on the opposite strand of the 20-bp core, recombination was evident (FIG. 1C), indicating that recombination site orientation is a critical component for catalytic domain fusion to the TALE N-terminus. In order to further establish that N-terminal fusion is necessary for recombination, a C-terminal AvrXa7-Gin variant was constructed that contained a non-canonical fusion orientation predicted to constrain catalytic domain activity (FIG. 1B and Table 5). As expected, it was determined that this C-terminal AvrXa7 fusion demonstrated negligible activity in bacterial cells (FIG. 1C).

TABLE 5

| Variant | SEQ ID NO: | Sequence |
|---|---|---|
| Gin-Avr (#1)/ Avr20G | 195 | TTAGCACCTGGTTGGAGGGGGTTTATA TCCAAAACCATGGTTTACAGTATAAAC CCCCTCCAACCAGGTGCTAA |
| Gin-Avr (#2) | 196 | TTAGCACCTGGTTGGAGGGGGTTTATA AGGTTTTGGTACCAAATGTCTATAAAC CCCCTCCAACCAGGTGCTAA |
| Avr-Gin (#3) | 197 | TATAAACCCCCTCCAACCAGGTGCTAA CTGTAAACCATGGTTTTGGATTAGCAC CTGGTTGGAGGGGGTTTATA |
| Avr14G | 198 | TTAGCACCTGGTTGGAGGGGGTTTATA AAAACCATGGTTTATATAAACCCCCTC CAACCAGGTGCTAA |
| Avr26G | 199 | TTAGCACCTGGTTGGAGGGGGTTTATA GCTTCCAAAACCATGGTTTACAGGGTT ATAAACCCCCTCCAACCAGGTGCTAA |
| Avr32G | 200 | TTAGCACCTGGTTGGAGGGGGTTTATA GCTTCATCCAAAACCATGGTTTACAGG GTTCCTATAAACCCCCTCCAACCAGGT GCTAA |
| Avr44G | 201 | TTAGCACCTGGTTGGAGGGGGTTTATA GCTTCAGCTTCATCCAAAACCATGGTT TACAGGGTTCCGGTTCCTATAAACCCC CTCCAACCAGGTGCTAA |
| Avr20GG | 202 | TTAGCACCTGGTTGGAGGGGGTTTATA TCCAAAACCGGGGTTTACAGTATAAAC CCCCTCCAACCAGGTGCTAA |
| Avr20T | 203 | TTAGCACCTGGTTGGAGGGGGTTTATA CGAAATATTATAAATTATCATATAAAC CCCCTCCAACCAGGTGCTAA |
| Avr32GG | 204 | TTAGCACCTGGTTGGAGGGGGTTTATA GCTTCATCCAAAACCGGGGTTTACAGG GTTCCTATAAACCCCCTCCAACCAGGT GCTAA |
| Avr32T | 205 | TTAGCACCTGGTTGGAGGGGGTTTATA GCTTCACGAAATATTATAAATTATCAG GTTCCTATAAACCCCCTCCAACCAGGT GCTAA |

TABLE 5-continued

| Variant | SEQ ID NO: | Sequence |
|---|---|---|
| Avr-G-ZF | 206 | GCGGGAGGCGTGTCCAAAACCATGGTT TACAGGGTTCCTATAAACCCCCTCCAA CCAGGTGCTAA |
| PthXo1-20G | 207 | GTGGTGTACAGTAGGGGGAGATGCATC CAAAACCATGGTTTACAGTGCATCTCC CCCTACTGTACACCAC |
| PthXo1-32G | 208 | GTGGTGTACAGTAGGGGGAGATGCAGC TGCTTCCAAAACCATGGTTTACAGGGT GGTTGCATCTCCCCCTACTGTACACCA C |

Designed Truncations.

Figure 2:
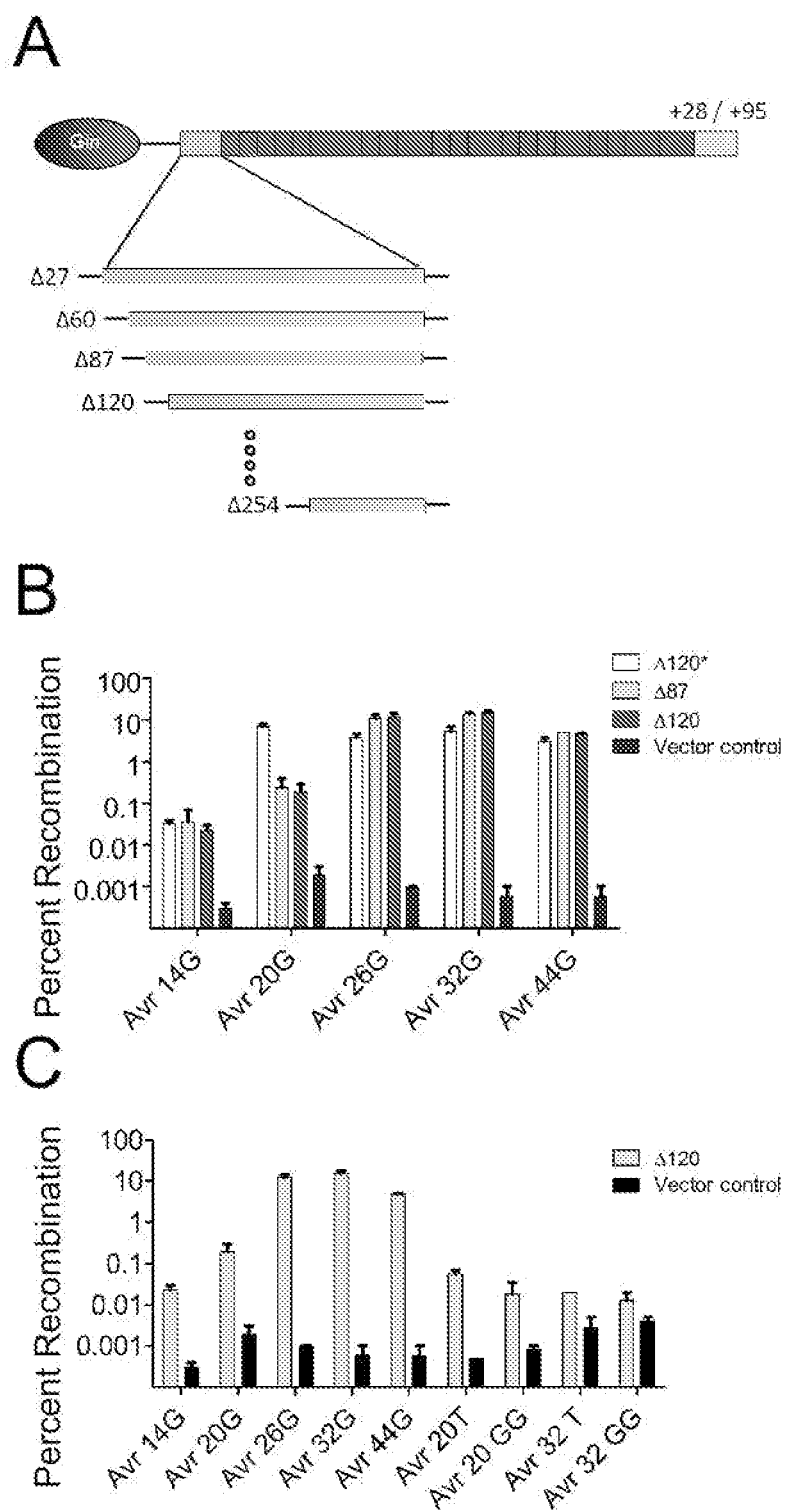
FIG. 2 is a series of graphical and diagrammatic representations regarding recombination profiles of selected TALER truncations. A) Schematic illustrating the design of the 20-member TALER truncation library. B) Activity of selected TALER variants against DNA targets containing core sequences of increasing length (14, 20, 26, 32 and 44-bp). C) Gin-AvrXa7Δ120 activity against a diverse panel of substrates containing non-cognate cores sequences or core sites of increasing length. Error bars indicate s.d. (n=3).

Although the Gin-AvrXa7 fusion described above catalyzed recombination, the activity of this variant was considerably lower than that of engineered ZFRs. Further, specificity analysis revealed that the Gin-AvrXa7 fusion was unable to faithfully discriminate between recognition sites containing non-cognate DBD sites and non-native 20-bp core sequences, indicating that recombination might not be Gin-mediated (FIG. 1D). Recent reports have shown that TALEN activity can be enhanced when the TALE portion of the fusion protein is truncated. Thus, in order to attempt to improve TALER activity, a series of N and C-terminal AvrXa7 truncations were generated (FIG. 2A).

Figure 6:
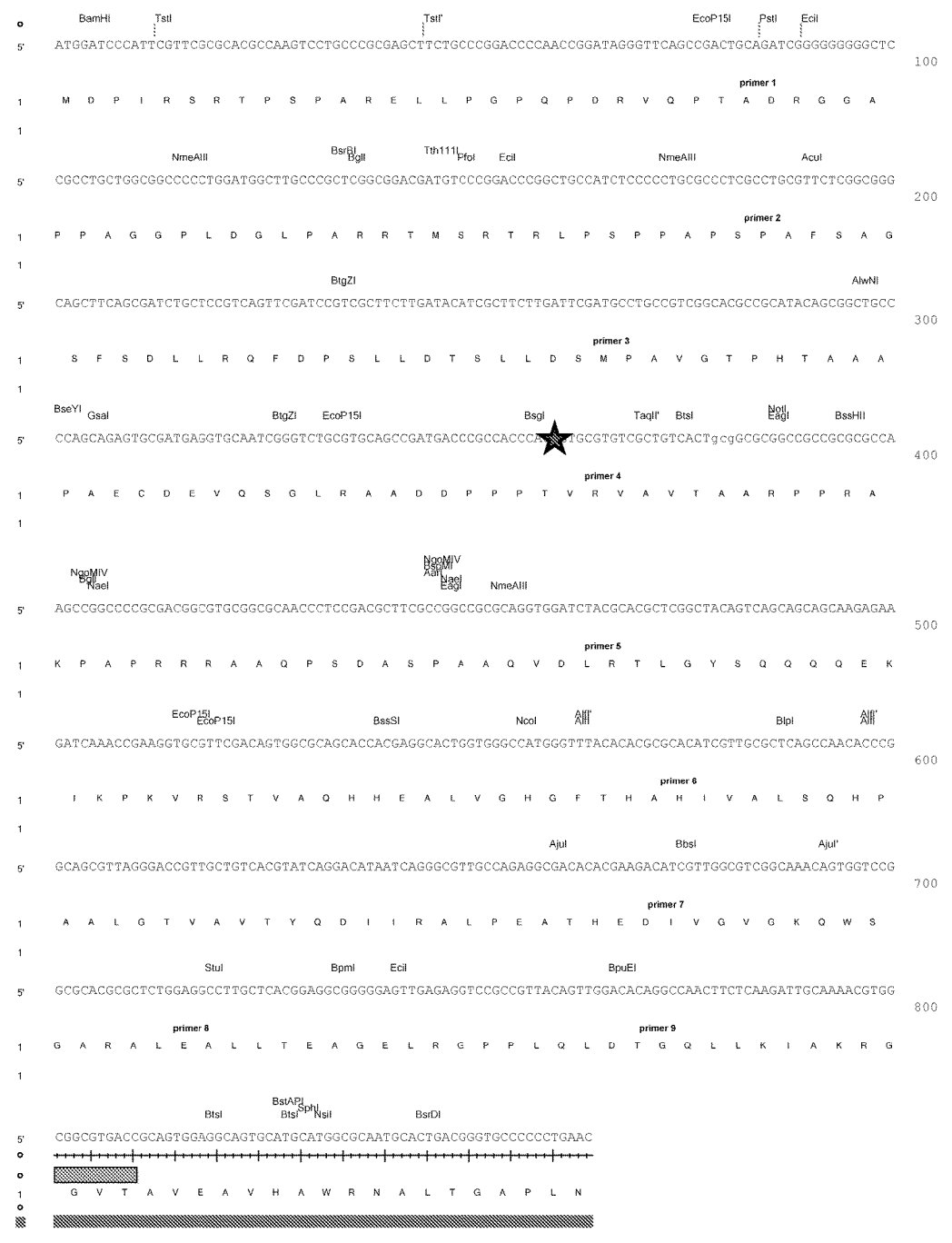

Ten N-terminal truncations were assembled at roughly equal intervals beginning at AvrXa7 Thr 27 (Δ27) and ending at AvrXa7 Gly 268 (Δ268) (FIG. 6). AvrXa7 Δ150, which has been reported as an N-terminal truncation variant for TALENs, was also generated. Two C-terminal AvrXa7 truncations were generated at positions 28 (+28) and 95 (+95). Both +28 and +95 have been reported as stable fusion points in TALENs. Each TALE truncation variant was fused to the Gin catalytic domain and this 20-member TALER library was cloned into a pBLA selection vector containing Avr-20G recognition sites. Following one round of selection in bacterial cells (Materials and Methods), individual ampicillin-resistant clones were sequences and it was found that all selected TALERs contained either one of two N-terminal truncations: Δ87 and Δ120. Each selected clone was also +28 on the C-terminus. With the exception of a single Δ120 clone with a spontaneous 12 amino acid deletion near the fusion point (Δ120*), the activity of these clones was quite low (FIG. 2B). In this assay, Gin-based ZFRs routinely show 20-40% recombination, however, the highest activity observed amongst the selected TALER fusions was ~7% recombination (Gin-AvrXa7Δ120*). Because the TALE DBD is three times larger than a ZF domain (not including the required flanking peptide sequence), we reasoned that the 20-bp spacer used for these TALER constructs might not be the optimal length for recombination.

Core Sequence Length.

Next the effect core sequence length has on recombination was investigated by evaluating whether DNA targets containing 14 (Avr-14G), 26 (Avr-26G) and 32-bp (Avr-32G) core sites could be recombined by selected TALERs. In order to maintain the reading frame of the β-lactamase gene following recombinase-mediated reassembly, core half-sites were modified by ±3-bps (Table 1). The 20-member TALER library described above was subjected to one round of selection against each target site variant. Although identification of TALER variants capable of recombining the shortest target was not possible, Avr-14G (data not shown), two Gin-ΔAvrXa7 variants were identified (based on the N-terminal TALE truncations Δ87 and Δ120 and the C-terminal truncation +28) that recombined Avr-26G and Avr-32G. In particular, clonal analysis revealed that the selected TALERs (Gin-AvrXa7Δ87 and Gin-AvrXa7Δ120) recombined DNA with longer cores (e.g., 26 and 32-bps) at least 100-fold more efficiently than shorter cores (e.g., 14 and 20-bps) (FIG. 2B). Further, it was found that Gin-AvrXa7Δ120 recombined targets containing a cognate core sequence (Avr-26G and Avr-32G)>100-fold more efficiently than a non-cognate core (Avr-20T, Avr-20GG, Avr-32T and Avr-32GG) (FIG. 2C). Interestingly, the Gin-AvrXa7Δ120 fusion was not as active on 44-bp cores (Avr-44G) (recombination was ~3-fold lower than Avr-32G) (FIG. 2C), indicating that core lengths between 26 and 44-bp are likely optimal for recombination by Gin-AvrXa7Δ120 in E. coli.

Incremental Truncation Library.

Although Gin-AvrXa7Δ120 showed increased recombination in comparison to Gin-AvrXa7, it was suspected that Gin-AvrXa7Δ120 might not be an optimal TALE fusion architecture because: (i) ZFRs containing the Gin catalytic domain recombined DNA >2-fold more efficiently than Gin-AvrXa7Δ120 and (ii) Gin-AvrXa7Δ120 was not identified from a comprehensive library of TALE truncation variants. Thus, in order to identify better fusion architectures, a screen was devised based on the generation of a library of incrementally truncated TALE DBDs.

To achieve this, a protocol was adapted as previously described to enable fusion of an unmodified N-terminal domain (Gin) to a library of truncated C-terminal fragments (AvrXa7) (Materials and Methods). N-terminal AvrXa7 truncations that spanned the region between the AvrXa7 N-terminus (Met 1) and the first AvrXa7 repeat (Leu 298) were generated by exonuclease digestion and fused to an unmodified copy of the Gin catalytic domain (theoretical number of protein variants: ~300). Because previous results indicated that +28 is the optimal C-terminal truncation, we incorporated this architecture into the truncation library. TALERs were cloned into a pBLA selection vector containing Avr-32G target sites and transformed into E. coli (>1× $10^5$ transformants). Sequence analysis confirmed an equal distribution of truncations spanning the region of interest (data not shown).

Figure 3:
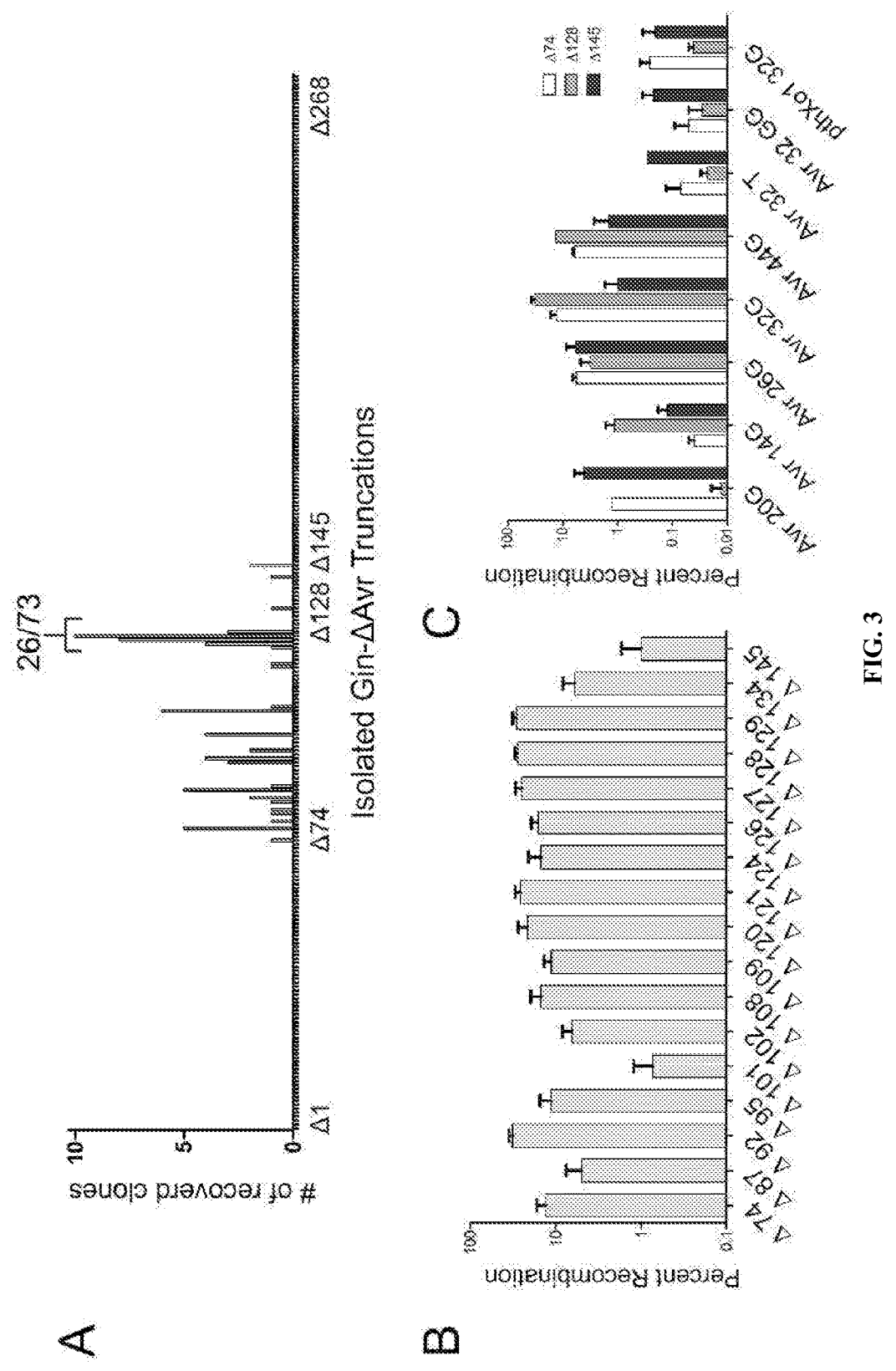

Following three rounds of selection, individual ampicillin-resistant clones were sequences and a number of unique truncation variants were identified (FIG. 3A). Consistent with the selections performed using the 20-member TALE truncation library, which suggested that the optimal N-terminal TALER fusion points were likely located in proximity to positions 87 and 120, all selected Gin-AvrXa7 variants were found to contain a truncation between positions 74 (Δ74) and 147 (Δ147). In particular, 26 of 73 (35.6%, p<0.001) clones contained truncations between positions 124 (Δ124) and 129 (Δ129). From this population, truncations at position 128 (Δ128) were among the most represented.

In order to systematically determine whether selected AvrXa7 domains increased TALER activity, we evaluated the performance of isolated Gin-AvrXa7 variants against DNA substrates containing Avr-32G target sites in E. coli. We focused our analysis on clones containing N-terminal deletions between AvrXa7 position 92 (Δ92) and 134 (Δ134). Consistent with sequence analysis, it was found that TALERs containing N-terminal truncations between Δ120 and Δ129 recombined DNA more efficiently than variants based on comparatively longer or shorter truncations, although the Δ92 fusion was also quite active (FIG. 3B). Three clones further characterized: Δ74 and Δ145 were chosen because they represented the boundaries of possible fusion points, and Δ128 was assayed because it was the most prevalent clone found in the selections. Five targets with spacer lengths from 14 to 44-bp were assayed along with three negative controls (Avr32T, Avr32GG, and PthXo1-32G). It was determined that Gin-Avr32GΔ74 and Gin-Avr32GΔ145 had modest activity on spacers longer than 20-bp, whereas Gin-Avr32GΔ128 recombined DNA with efficiencies comparable to the ZFR GinC4 (FIG. 3C). Furthermore, specificity analysis revealed that Gin-Avr32GΔ74, Gin-Avr32GΔ128, and Gin-Avr32GΔ145 could recombine substrates harboring cognate cores >100-fold more efficiently than non-cognate cores (Avr-32T, Avr-32GG and PthXo1-32G) (FIG. 3C). Together, these results suggest that TALE proteins containing N-terminal deletions between Δ120 and Δ129 represent an optimal truncation for fusion to a recombinase.

Incorporation of Synthetic TALE Repeat Arrays.

The studies described above used the native DBDs of the naturally occurring AvrXa7 TALE protein. In order to determine whether designed TALE repeat arrays can be incorporated into the selected Gin-ΔAvrXa7 frameworks, a series of synthetic TALE proteins (15 to 20 repeats in length) were generated designed to target the AvrXa7 binding site (FIG. 7). TALE proteins were constructed using a publicly available TALEN plasmid set (Addgene). The cloning plasmid was modified to include the +28 C-terminal truncation and either the Δ120 or Δ128 N-terminal truncation. Designed TALEs were fused to the Gin catalytic domain (denoted as Gin-Avr15Δ120 and Gin-Avr15Δ128) and cloned into a pBLA selection vector containing Avr-32G or Avr-32T target sites.

Figure 4:
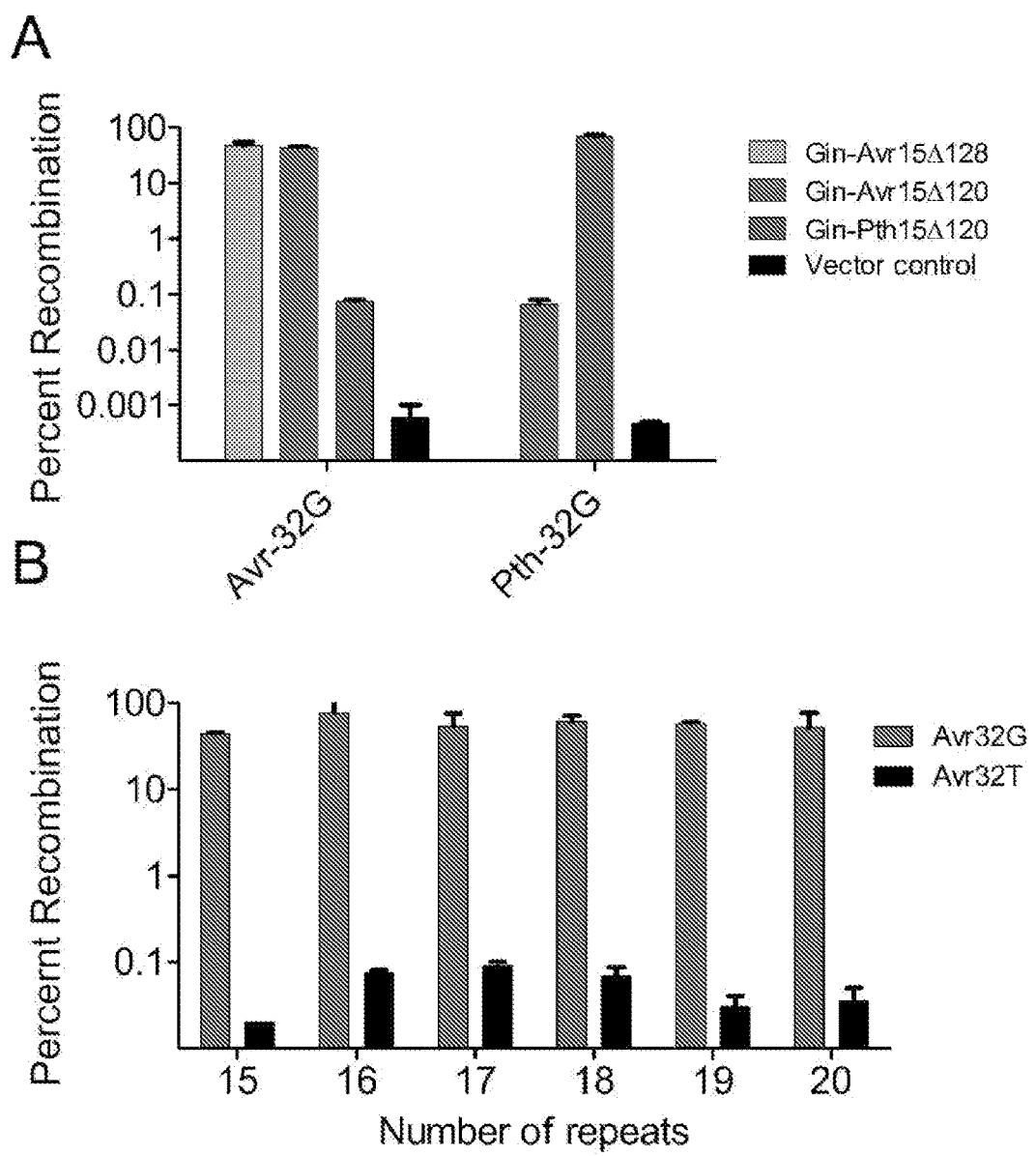
FIG. 4 is a series graphical representations regarding activity of synthetic TALERs. A) Activity of synthetic Gin-Avr15Δ128, Gin-Avr15Δ120 and Gin-Pht15Δ120 variants against the DNA targets Avr-32G or Pth-32G. B) Activity of synthetic TALERs with DBDs between 15 and 20 repeats in length based on Gin-AvrΔ120 against Avr-32G and Avr-32T. Error bars indicate s.d. (n=3).

Activity analysis in *E. coli* revealed that both Gin-Avr15Δ120 and Gin-Avr15Δ128 could be used to recombine DNA when fused to an active catalytic domain and that incorporation of synthetic repeats provided an increase in activity (FIG. 4A). Importantly, each TALER displayed stringent selectivity, recombining target sites that contained cognate cores >1,000-fold more efficiently than non-cognate cores (FIG. 4B). Surprisingly, TALERs based on the Δ120 truncation were also found to recombine DNA as effectively as TALEs based on the Δ128 architecture (FIG. 4A), indicating that designed TALEs may be less sensitive to N-terminal truncation than those containing the native AvrXa7 DBD.

To further demonstrate that the TALER architecture described herein can be reprogrammed to target any DNA sequence, a synthetic enzyme was created designed to target the sequence recognized by the naturally occurring TALE protein PthXo1 (Gin-Pth15Δ120). It was found that Gin-Pth15Δ120 was highly active on its cognate substrate and that both Gin-Pth15Δ120 and Gin-Avr15Δ120 showed a >600 fold increase in recombination for targets with their cognate binding sites (FIG. 4A). The activity of a series of designed TALERs containing DBDs between 15 and 20 repeats in length was also assessed and found that each fusion catalyzed recombination with similarly high efficiency and specificity (FIG. 4B), demonstrating that chimeric recombinases that incorporate synthetic TALE repeat arrays can be used for site-specific recombination.

TALER Activity in Mammalian Cells.

It was also determined whether TALERs could modify DNA in mammalian cells. To achieve this, we used an episomal reporter assay that enables rapid assessment of recombinase activity in cell culture. In this assay, human embryonic kidney (HEK) 293T cells are co-transfected with a recombinase expression vector and a reporter plasmid (pGL3) that contains a luciferase gene under the control of a SV40 promoter flanked by recombination sites. Transient expression of the appropriate recombinase leads to excision of the SV40 promoter and reduced luciferase expression in cells. Recombinase activity is thus directly proportional to the fold-reduction in luciferase expression.

Figure 5:
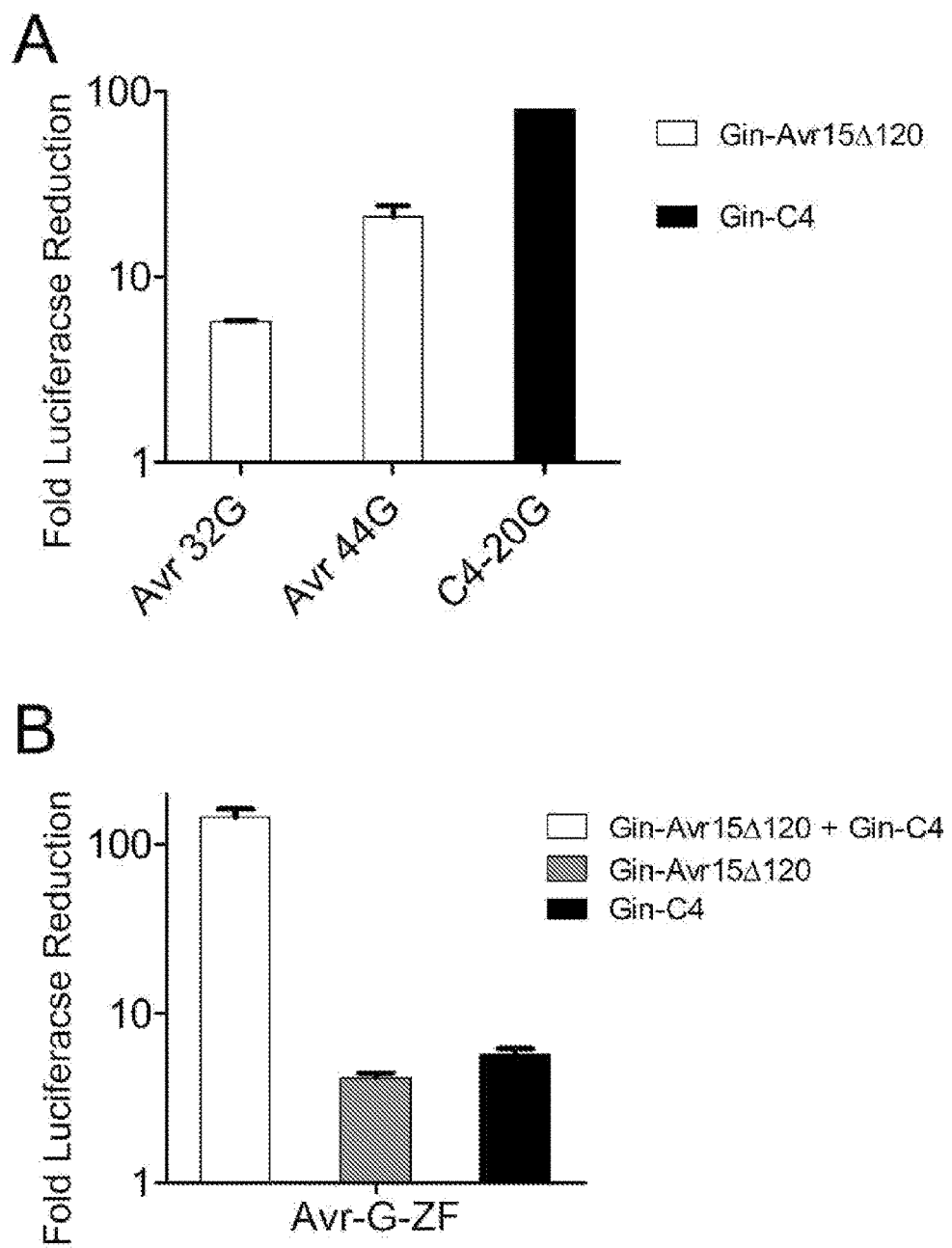
FIG. 5 is a series of graphical representations regarding TALER activity in mammalian cells. (A, B) Fold-reduction of luciferase expression in HEK293T cells co-transfected with (A) TALER or ZFR expression vectors (Gin-AvrΔ120 and GinC4) in the presence of reporter plasmid (Avr-32G, Avr-44G and C4-20G) or (B) TALER and ZFR expression vector in combination (Gin-AvrΔ120+GinC4) with reporter plasmid (Avr-G-ZF). Error bars indicate s.d. (n=3).

Co-transfection of Gin-Avr15Δ120 with a reporter plasmid harboring Avr-44G recognition sites (pGL3-Avr-44G) led to a ~20-fold reduction in luciferase expression as compared to transfection of pGL3-Avr-44G alone (FIG. 5A). Despite the fact that Gin-Avr15Δ120 showed similar activity to the ZFR GinC4 in *E. coli*, we found that GinC4 reduced luciferase expression by >80-fold after co-transfection with its cognate target plasmid, pGL3-C4-20G (FIG. 5A). This discrepancy may be due to the comparatively shorter intervening DNA sequence between recombinase target sites in pGL3 than pBLA or differential expression between TALERs and ZFRs in mammalian cells. The underlying cause for this disparity, however, remains unclear. Finally, although 32-bp was determined to be the optimal core sequence length for TALERs in *E. coli*, it was determined that co-transfection of Gin-Avr15Δ120 with pGL3-Avr-32G led to only a 6-fold reduction in luciferase expression (FIG. 5A). The underlying cause behind this disparity also remains unclear.

Next whether a ZFR (GinC4) and a TALER (Gin-Avr15Δ120) could form a compatible heterodimer in mammalian cells was investigated. To evaluate this possibility, a hybrid recombination site was generated in which the AvrXa7 binding site and the C4 zinc-finger binding site (GCG GGA GGC GTG; SEQ ID NO: 279) flank the core sequence recognized by the Gin catalytic domain (pGL3-Avr-G-ZF) (see Table 2). Surprisingly, co-transfection of pGL3-Avr-G-ZF with GinC4 and Gin-Avr15Δ120 led to a >140-fold reduction in luciferase expression as compared to pGL3-Avr-G-ZF (FIG. 5B), whereas transfection with either GinC4 or Gin-Avr15Δ120 with pGL3-Avr-G-ZF led to a negligible decrease in reporter gene expression. These results demonstrate that generating ZF-TALE heterodimers represents a potentially effective approach for improving the targeting capacity of chimeric recombinases.

Discussion.

Unlike ZFPs, which contain a very minimal fusion architecture, TALE DBDs require native protein framework on either side of the DBD array to function. The so-called $0^{th}$ and $1^{st}$ repeats, which mediate binding of the thymidine residue at position 0 and are found in almost all known TALE recognition sites, represent such an N-terminal framework. A recent crystal structure provided a description of the binding of the position 0 thymine, yet there remains insufficient data to determine a minimal TALE architecture. Indeed, all studies to date have used an N-terminal truncation containing considerably more residues than those required to mediate binding at position 0. It remains uncertain what role this part of the protein has in enabling the proper DNA binding conformation or what might constitute a minimal TALE domain. Although initial attempts to generate functional TALE chimeras were based on fusion to full-length TALE proteins, more recent studies have focused on the identification of unique C-terminal truncations that improve effector domain function in the context of the Δ150 N-terminal architecture. A previous report indicated that deletion of N-terminal residues 2-153 (Δ150) of the AvrBs3 TALE removes the domain required for translocation of the TALE from its native bacteria to the target plant cell but does not compromise transcription factor activity.

Developing an active TALER, however, necessitated that unique N-terminal TALE variants be identified. A broad, systematic survey was initially conducted of N-terminal TALEs with the C-terminal truncations +28 and +95 and found that only two domains (Δ87 with +28 and Δ120 with +28) demonstrated sufficiently high activity for further analysis. A secondary analysis based on incremental truncation of the AvrXa7 N-terminus led to the identification of a broad cluster of truncation variants centered between AvrXa7 position 74 (Δ74) and position 145 (Δ145). Of the clones recovered in this experiment, 38% contained truncations between positions Δ119 and Δ128, and a survey of data obtained on TALERs with fusions in this region showed high activity. In particular, it was determined that TALERs based on N-terminal truncations from this region (Δ128 and Δ120) could be used to recombine DNA in bacteria and mammalian cells. The clustering of truncation variants between Δ119 and Δ128 may also be indicative of the intrinsic stability of this region.

ZFRs typically catalyze recombination between target sites 44 to 50-bp in length. Each target site contains a central 20-bp core sequence, which is recognized by the recombinase catalytic domain, and two adjacent ZFP binding sites. The fusion orientation of TALERs, however, necessitates that TALE binding sites are on the opposite strand relative to the central core sequence. This unique geometry led us to investigate the minimum core sequence requirements for recombination. Because of the length of TALE DBDs (TALE repeats are 3 to 4 times longer than ZFPs) and the extended N-terminal linker between the catalytic domain and the TALE domain, we reasoned that longer core sequences (32 or 44-bp) would be necessary for recombination. Indeed, with the exception of a TALE variant harboring a spontaneous deletion (Δ120*), most N-terminal truncation variants identified in this study demonstrated optimal performance against 32-bp cores. These results are consistent with those reported with TALENs, which unlike ZFNs require significantly longer spacer sequences (e.g. TALENs: 17 to 20-bp, ZFNs: 5 to 6-bp) to efficiently cleave DNA. In support of these observations, it was found that selection for unique N-terminal truncation variants against a short core sequence (14-bp) did not yield any clones.

Gin-AvrXa7Δ128 was identified as an optimal TALE fusion, but subsequent studies using synthetic TALE proteins generated using a publicly available TALE assembly kit indicated that Δ128 and Δ120-based TALERs showed similar activity in E. coli. These designed TALEs were based on a chimeric protein derived from the closely related and naturally occurring Tal1c and PthXo1 TALE proteins. Although TALEs share high homology, they are not identical. While polymorphisms in RVD repeats outside of residues 12 and 13 have been shown to have no affect on TALE fusion activities, to our knowledge no systematic evaluation of differences in TALE framework outside the DBDs has been reported. As demonstrated by the analysis of the incremental truncation library, minor amino acid alterations can significantly influence the activity of a particular fusion. Thus, some of the discrepancy in activity we observed between Gin-AvrXa7Δ120 and the synthetic Gin-Avr15Δ120 may be attributable to the sequence variations between AvrXa7 framework and the TALE framework architecture used previously.

The four RVDs (NI: A, HD: C, NG: T, and NN: G) favored for construction of synthetic TALEs are the most prevalent in nature; however, it remains to be determined whether these repeats represent the most specific RVD modules. For the 26-repeat AvrXa7 TALE, a synthetic version targeting the same sequence would have 16 changes in RVD composition (FIG. 7). It was hypothesized that because they are more commonly found in nature, the four RVDs selected for synthetic use might have a higher affinity for their cognate bases than other RVDs. If this were the case, it would be reasonable to assume that a TALE created with the synthetic RVD repeats could have higher DNA-binding affinity than a TALE using the native domains. Although the issue of RVD affinity was not directly addressed, it was determined that that TALERs containing synthetic repeat arrays were more active than constructs, which contained the native AvrXa7 DBD. TALERs with synthetic DBDs showed approximately two-fold higher activities than constructs containing the native repeats, despite containing significantly fewer DBDs. Additionally, the gain in activity observed with the synthetic arrays was not correlated with any increase in off-target recombination.

Several studies have shown that TALEs can tolerate some mismatches in their target sequence. These findings are unsurprising, as RVDs that are positively associated with particular bases have been shown to tolerate non-cognate bases in nature. The cooperative specificity afforded by TALERs could be used to circumvent potential limitations, however. Because the catalytic domain contributes specificity to recombination, it is envisioned that designer TALERs capable of selectively modifying highly homologous genomic sequences could be generated as well. Indeed, it has been recently demonstrated that recombinase catalytic specificity can be effectively reprogrammed to target unnatural core sites.

Example 2

Selection of Novel $0^{th}$ Residue Specificity

A new class of Tal-based DNA binding proteins was engineered. TAL (transcription activator-like) effectors constitute a novel class of DNA-binding proteins with predictable specificity. Tal effectors are employed by Gram-negative plant-pathogenic bacteria of the genus *Xanthomonas* which translocate a cocktail of different effector proteins via a type III secretion system (T3SS) into plant cells where they serve as virulence determinants. DNA-binding specificity of TALs is determined by a central domain of tandem repeats. Each repeat confers recognition of one base pair (bp) in the DNA. Rearrangement of repeat modules allows design of proteins with desired DNA-binding specificities with certain important limitations. For example, the most constraining feature of targeting a DNA sequence with a Tal domain is the requirement that the Tal DNA site start with the base T and sometimes C. Targeting a binding site starting with a G or A base has not been possible at the −1 position. Tal-recombinase activity selections were used to select for Tal DNA binding domains that lack this restriction by targeting mutations to the −1 and $0^{th}$ RVD regions. The practical consequences of this discovery are vast since now every DNA sequence can be targeted with new Tal domains facilitating new unrestricted approaches to TAL transcription factors to turn transcription on/up or off/down, to target TAL nucleases to knock out gene function or to direct homologous recombination or to target our own TAL recombinases or other TAL enzymes.

For G specificity at the (−1) position, the amino acids QWSG (SEQ ID NO: 209) were first randomized using an NNK codon strategy within the (−1) domain of the GinAvr15Δ128-synthetic protein. Following 3 rounds of tal recombinase activity selection of the resulting library, novel tal binding domains with the selected sequences RSNG (SEQ ID NO: 210) and SRSG (SEQ ID NO: 211) in the targeted region were selected. These were then shown to bind G at the 0th position of the target sequence over the parental T recognized by the starting clone. The selection was repeated randomizing the KQW region shown below in red that overlaps with the QWSG (SEQ ID NO: 212) selected initially. Now clones with selected SSR, SRA, SRC, and KRC sequences were selected. All selected Tal binding domains were assayed in binding studies to defined oligos bearing the G substitution and shown to now preferentially bind the sequence G-ATAAACCCCCTCCAA (SEQ ID NO: 213). Note that the Tal recombinase activity selection was performed using this same sequence. The starting Tal binding protein the GinAvr15Δ128 binds T-ATAAACCCCCTC-CAA (SEQ ID NO: 214). Subsequence testing of Tal nucleases bearing the selected mutations verify the G specify of these sequences allowing for this novel class of Tals to be developed for the first time. Selected sequences are portable to Tals derived from other species.

TABLE 6

Selections

SEQ ID NO: 215    ATHEDIVGVGKQWSGARALEALLTDAGELRG
                  PPLQ (-1 domain)

SEQ ID NO: 216    ATHEDIVGVGKQWSGARALEALLTDAGELRG
                  PPLQ (randomized AA in bold)

SEQ ID NO: 217    KQWSG-starting clone sequence

SEQ ID NO: 218    K*RSNG*-selected to bind G

SEQ ID NO: 219    K*SRSG*-selected to bind G

SEQ ID NO: 220    ATHEDIVGVGKQWSGARALEALLTDAGELRG
                  PPLQ

SEQ ID NO: 221    KQWSG-WT
                  SSR-selected to bind G
                  SRA-selected to bind G
                  SRC-selected to bind G
                  KRC-selected to bind G Selections were also performed using this same library to target A. In this study, sequences PRG, PTR, and PKD were selected. All selected Tal binding domains were assayed in binding studies to defined oligos bearing the A substitution and shown to now preferentially bind the sequence A-ATAAACCCCCTCCAA (SEQ ID NO: 222). Note that the Tal recombinase activity selection was performed using this same sequence. The starting Tal binding protein the GinAvr15Δ128 binds T-ATAAACCCCCTCCAA (SEQ ID NO: 223). Subsequence testing of Tal nucleases bearing the selected mutations verify the A specify of these sequences allowing for this novel class of Tals to be developed for the first time. Subsequent refinements in binding activities can be achieved by random mutagenesis of the N-terminal domain or target mutagenesis of the KRGG (SEQ ID NO: 224) sequence within the 0th domain and reselection in the recombinase system.

Example 3

Selections

For context dependent RVD selections and selections of RVDs with new specificities, libraries were created that randomize the HD sequence emboldened below.

(prototype RVD sequence; SEQ ID NO: 225)
LTPDQVVAIASHDGGKQALETVQRLLPVLCQDHG

Typically the library allows all amino acids at these two positions, though libraries limited to N, D, H, K, and Q amino acids are often successful substitutes for the H residue. Alternatively larger libraries that randomized the SHDG (SEQ ID NO: 226) and ASHDGG (SEQ ID NO: 227) regions allow for the selection of unique RVD specificities with context dependent characteristics.

Tal recombinase activity selections then rapidly allow for the selection of new specificities within the targeted RVD domain. The resulting RVDs can be highly modular or context dependent in their sequence recognition and can be then used to create Tal nucleases and transcription factors.

Utility of this technology includes unrestricted approaches to TAL transcription factors to turn transcription on/up or off/down, to target TAL nucleases to knock out gene function or to direct homologous recombination or to target our own TAL recombinases or other TAL enzymes for use as tools and therapeutics.

Advantages and the practical consequences of this discovery are vast since now every DNA sequence can be targeted with our new Tal domains and their specificities can be readily optimized.

Example 4

Directed Evolution of Tale N-Terminal Domain to Accommodate 5' Bases Other than Thymine Transcription activator-like effector (TALE) proteins can be designed to bind virtually any DNA sequence of interest. The DNA binding sites for natural TALE transcription factors (TALE-TFs) that target plant avirulence genes have a 5' thymidine. Synthetic TALE-TFs also have this requirement. Recent structural data indicate that there is an interaction between the N-terminal domain (NTD) and a 5' T of the target sequence. A survey of the recent TALE nuclease (TALEN) literature yielded conflicting data regarding the importance of the first base of the target sequence, the $N_0$ residue. Additionally, there have been no studies regarding the impact of the $N_0$ base on the activities of TALE recombinases (TALE-Rs). Here, the impact of the $N_0$ base is quantified in the binding regions of TALE-Rs, TALE-TFs, TALE DNA-binding domains expressed as fusions with maltose binding protein (MBP-TALEs) and TALENs. Each of these TALE platforms have distinct N- and C-terminal architectures, but all demonstrated highest activity when the $N_0$ residue was a thymidine. To simplify the rules for constructing effective TALEs in these platforms, and allow precision genome engineering applications at any arbitrary DNA sequence, we devised a structure-guided activity selection using our recently developed TALE-R system. Novel NTD sequences were identified that provided highly active and selective TALE-R activity on TALE binding sites with 5' G, and additional domain sequences were selected that permitted general targeting of any 5' $N_0$ residue. These domains were imported into TALE-TF, MBP-TALE and TALEN architectures and consistently exhibited greater activity than did the wild-type NTD on target sequences with non-T 5' residues. The novel NTDs are compatible with the golden gate TALEN assembly protocol and now make possible the efficient construction of TALE transcription factors, recombinases, nucleases and DNA-binding proteins that recognize any DNA sequence allowing for precise and unconstrained positioning of TALE-based proteins on DNA without regard to the 5' T rule that limits most natural TALE proteins.

The following Material and Methods were utilized in this Example.

Oligonucleotides.

Primers and other oligonucleotides (Table 4 below) were ordered from Integrated DNA Technologies (San Diego, Calif.).

TABLE 7

Primers.

| Primer | SEQ ID NO: | Sequence |
|---|---|---|
| KXXG Lib Rev | 228 | TCTCAACTCCCCCGCCTCCGTG AGCAAGGCCTCCAGAGCGCGTG CCCCMNNMNNTTTGCCGACGCC AACGATGTCTTCGTG |
| KXXXX Lib Rev | 229 | TCT CAA CTC CCC CGC CTC CGT GAG CAA GGC CTC CAG AGC GCG TGC MNN MNN MNN MNN TTT GCC GAC GCC AAC GAT GTC TTC GTG |
| XXXSG Lib Rev | 230 | CCCGCCTCCGTGAGCAAGGCCT CCAGGGCGCGTGCGCCGGAMNN MNNMNNGCCGACGCCAACGATG TCTTCGTGTGTCGC |
| KRGG Lib Rev | 231 | GGC ACC CGT CAG TGC ATT GCG CCA TGC ATG CAC TGC CTC CAC TGC GGT CAC MNN MNN MNN MNN TGC AAT CTT GAG AAG TTG GCC TGT GTC |
| Goldy TALEN fwd | 232 | AGAGAGAGAAGAAAATGAGATC TCCTAAGAAAAAGAGGAAGGTG CAGGTGGATCTACGCACGCTCG GCTAC |
| NTD-dHax3 Fwd | 233 | AGGAAGAAGAGAAGCATGAGAT CTCCTAAGAAAAAGAGGAAGGT GATGGTGGACTTGAGGACACTC GGTTA |
| NTD-dHax3 Rev | 234 | AAGAGAAGAAGAAGAAGCATTG CGCCATGCATGCACTGCCTCTA |
| pTal127 Not1 fwd | 235 | CCC GCC ACC CAC CGT GC |
| N-Term Sph1 | 236 | TGC TCT ATG CAT GCA CTG CCT CC |
| pTAL127-SFI Fwd | 237 | AGA GAA GAG AAG AGA AGG CGC CCG CGG CCC AGG CGG CCT CGG GAT CCC CTC GGC CTC CGC GCG CCA AG |
| pTAL127-SFI + 95 Rev | 238 | AGA GAG AGA GAG AGA GTC TAG AGG CCG GCC TGG CCG CTC ATC CGG AAC TGC GTC ATG GCC TCA TC |
| pTAL127 Xba + 28 Rev | 239 | GCC CCA GAT CCT GGT ACG CTC TAG AGG |
| Avr 5' A biotin hairpin | 240 | 5'BiosgATC TTA GCA CCT GGT TGG AGG GGG TTT ATTGG GTT TTC CCAAT AAA CCC CCT CCA ACC AGG TGC TAA GAT |
| Avr 5' T biotin hairpin | 241 | 5'Biosg/ATC TTA GCA CCT GGT TGG AGG GGG TTT ATAGG GTT TTC CCTAT AAA CCC CCT CCA ACC AGG TGC TAA GAT |

TABLE 7-continued

Primers.

| Primer | SEQ ID NO: | Sequence |
|---|---|---|
| Avr 5' G biotin hairpin | 242 | 5'BiosgATC TTA GCA CCT GGT TGG AGG GGG TTT ATCGG GTT TTC CCGAT AAA CCC CCT CCA ACC AGG TGC TAA GAT |
| Avr 5' C biotin hairpin | 243 | 5'BiosgATC TTA GCA CCT GGT TGG AGG GGG TTT ATGGG GTT TTC CCCAT AAA CCC CCT CCA ACC AGG TGC TAA GAT |
| CCR5-inner fwd | 244 | TTAAAAGCCAGGACGGTCAC |
| CCR5-inner rev | 245 | TGTAGGGAGCCCAGAAGAGA |
| CCR5-outer fwd | 246 | ACAGTTTGCATTCATGGAGGGC |
| CCR5-outer rev | 247 | CCGAGCGAGCAAGCTCAGTT |
| CCR5-indel fwd | 248 | CGCGGATCCCCGCCCAGTGGGA CTTTG |
| CCR5-indel rev2 | 249 | CCGGAATTCACCTGTTAGAGCT ACTGC |
| pGL3 NTD stuffer fwd | 250 | AGA GAG AGA GAG AGG CGG CCG CCC TAC CAG GGA TTT CAG TCG ATG TAC ACG TTC |
| pGL3 NTD stuffer rev | 251 | AAG AAG AAG AAG GAA GAG AAG TAG GCC TGT CAT CGT CGG GAA GAC CTG CGA CAC CTG C |
| pgl3 5X Avr Xho1 | 252 | ACTGCTATCCGAGTATAAACCC CCTCCAACCAGGTATAAACCCC CTCCAACCAGGTATAAACCCCC TCCAACCAGGTATAAACCCCCT CCAACCAGGTATAAACCCCCTC CAACCAGGATCTGCGATCTAAG TAAGCT |
| AvrXa7 32G A F | 253 | TTAATTAAGAGTCTAGAttagc acctggttggagggggtttatT gcttcaTCCAAAACCATGGTTT ACAGgttccAATAAACCCCCT CCAACCAGGTGCTAAAGATCTA GGAGGAATTTAAAATGAG |
| AvrXa7 32G A R | 254 | ACTGACCTAGAGAAGCTTTTAG CACCTGGTTGGAGGGGGTTTAT TgcaaccCTGTAAACCATGGTT TTGGAtgaagcAATAAACCCCC TCCAACCAGGTGCTAACTGCAG TTATTTGTACAGTTCATC |
| AvrXa7 32G G F | 255 | TTAATTAAGAGTCTAGAttagc acctggttggagggggtttatC gcttcaTCCAAAACCATGGTTT ACAGggttccGATAAACCCCCT CCAACCAGGTGCTAAAGATCTA GGAGGAATTTAAAATGAG |
| AvrXa7 32G G R | 256 | ACTGACCTAGAGAAGCTTTTAG CACCTGGTTGGAGGGGGTTTAT CgcaaccCTGTAAACCATGGTT TTGGAtgaagcGATAAACCCCC TCCAACCAGGTGCTAACTGCAG TTATTTGTACAGTTCATC |
| AvrXa7 32G C F | 257 | TTAATTAAGAGTCTAGAttagc acctggttggagggggtttatG gcttcaTCCAAAACCATGGTTT ACAGggttccCATAAACCCCCT |

TABLE 7-continued

Primers.

| | | |
|---|---|---|
| | | CCAACCAGGTGCTAAAGATCTA GGAGGAATTTAAAATGAG |
| AvrXa7 32G C R | 258 | ACTGACCTAGAGAAGCTTTTAG CACCTGGTTGGAGGGGGTTTAT GgcaaccCTGTAAACCATGGTT TTGGAtgaagcCATAAACCCCC TCCAACCAGGTGCTAACTGCAG TTATTTGTACAGTTCATC |

Luciferase. Vector = pgl3 basic. XhoI/SphI

| Forward target containing: | | SEQ ID NO: |
|---|---|---|
| 5x Avr15 n-1c xhoF: | 259 | actgctatctcgagcTATAAAC CCCCTCCAACCAGGcTATAAAC CCCCTCCAACCAGGcTATAAAC CCCCTCCAACCAGGcTATAAAC CCCCTCCAACCAGGcTATAAAC CCCCTCCAACCAGGATCTGCGA TCTAAGTAAGCT |
| 5x Avr150 = A n-1c | 260 | actgctatctcgagcAATAAAC CCCCTCCAACCAGGcAATAAAC CCCCTCCAACCAGGcAATAAAC CCCCTCCAACCAGGcAATAAAC CCCCTCCAACCAGGcAATAAAC CCCCTCCAACCAGGATCTGCGA TCTAAGTAAGCT |
| 5x Avr150 = C n-1c | 261 | actgctatctcgagcCATAAAC CCCCTCCAACCAGGcCATAAAC CCCCTCCAACCAGGcCATAAAC CCCCTCCAACCAGGcCATAAAC CCCCTCCAACCAGGcCATAAAC CCCCTCCAACCAGGATCTGCGA TCTAAGTAAGCT |
| 5x Avr150 = G n-1c | 262 | actgctatctcgagcGATAAAC CCCCTCCAACCAGGcGATAAAC CCCCTCCAACCAGGcGATAAAC CCCCTCCAACCAGGcGATAAAC CCCCTCCAACCAGGcGATAAAC CCCCTCCAACCAGGATCTGCGA TCTAAGTAAGCT |
| Luciferase Reverse Primer: | 263 | TCAGAAACAGCTCTTCTTCAAA TCT |

Generation of TALE-R NTD Evolution Plasmids.

The TALE-R system previously reported was adapted for this study. Briefly, pBCS (containing chloramphenicol and carbenicillin resistance genes) was digested with HindIII/Spe1. The stuffer (Avr X, where X is the NO base), containing twin recombinase sites, was digested with HindIII/Xba1 and ligated into the vector to create a split beta-lactamase gene. pBCS AvrX was then digested with BamH1/Sac1, and Gin127-N-stuffer-Avr15 was digested with BamH1/Sac1 and ligated into the vector to create Gin127-N-stuffer-Avr15-X. The stuffer was digested with Not1/Stu1 for evolutions at the $N_{-1}$ TALE hairpin and Not1/Sph1 for evolutions at the $N_0$ TALE hairpin.

Generation of TALE NTD Evolution Libraries.

Primer ptal127 Not1 fwd and reverse primers KXXG lib rev or KXXXX lib rev were used to generate N-terminal variants at the $N_{-1}$ TALE hairpin and were subsequently digested with Not1/Stu1 then ligated into digested Gin127-AvrX. Forward primer ptal127 Not1 fwd and reverse primer KRGG Lib Rev were used to PCR amplify a library with mutations in the $N_0$ TALE hairpin. This was subsequently digested with Not1/Sph1 and ligated into Not1/Sph1-digested Gin127-AvrX.

TALE-R NTD Evolution Assay.

Round 1 ligations were ethanol precipitated and transformed into electrocompetent Top10 F' cells then recovered in SOC for 1 h. The cells were grown overnight in 100 ml Super Broth (SB) media containing 100 mg/ml chloramphenicol. DNA was isolated via standard procedures. The resulting plasmid DNA (Rd 1 input) was transformed into electrocompetent Top10F' cells; cells were grown overnight in 100 ml of SB containing 100 mg/ml carbenicillin and 100 mg/ml chloramphenicol. Plasmid DNA was isolated via standard procedures. Round 1 output was digested with Not1/Xba1 and ligated into the Gin127-AvrX vector with complementary sticky ends. This protocol was repeated three to four times when a consensus sequence was observed and clones were characterized.

Measurement of N-Terminal TALEN Activity.

Four TALEN pairs containing each possible base were generated using the golden gate protocol. Fusion A and B plasmids were directly ligated via second golden gate reaction into the Goldy TALEN (N Δ152/C+63) framework. The NTD was modified by digesting the pCAG vector with BglII/Nsi1 and ligating with PCR amplified NTD digested with BglII/Nsi1. TALEN pairs (50-75 ng each TALEN/well) were transfected into HeLa cells in wells of 96-well plates at a density of $1.5 \times 10^4$ cells/well. After transfection, cells were placed in a 37° C. incubator for 24 h, then were moved to 30° C. for 2 days and then moved to 37° C. for 24 h. Genomic DNA was isolated according to a published protocol, and DNA mutation rates were quantified with the Cell Surveyor assay and by sequencing. For Cell assays, genomic DNA was amplified by nested PCR, first with primers CCR5 outer fwd/CCR5 outer rev and then with CCR5 inner fwd/CCR5 inner rev. For sequencing of indels, the second PCR was performed with CCR5 indel fwd/CCR5 indel rev. Fragments were then digested with BamH1/EcoR1 and ligated into pUC19 with complementary digestion.

TALE-TFs and Luciferase Assay.

Variant NTDs from the recombinase selection were PCR amplified with primers ptal127 SFI fwd and N-Term Sph1. The PCR product was amplified and digested with Not1/Stu1 and ligated into pTAL127-SFI Avr15, which contains twin SFI-1 digestion sites facilitating transfer of the N-terminal-modified TALE from pTAL127-SFI Avr15 into pcDNA 3.0 VP64. Corresponding TALE binding sites were cloned into the pGL3 Basic vector (Promega) upstream of the luciferase gene. For each assay, 100 ng of pcDNA was co-transfected with 5 ng of pGL3 vector and 1 ng of pRL Renilla luciferase control vector into HEK293t cells in a well of a 96-well plate using Lipofectimine 2000 (Life Technology) according to manufacturer's specifications. After 48 h, cells were washed, lysed and luciferase activity assessed with the Dual-Luciferase reporter system (Promega) on a Veritas Microplate luminometer (Turner Biosystems). Transfections were done in triplicate and results averaged.

MBP-TALE Assay.

Affinity assays of MBP-TALE binding to biotinylated oligonucleotides were performed using a protocol previously described. Briefly, AvrXa7 TALE domains were expressed from pMAL MBP-AvrXa7 plasmid in XL1-Blue cells and purified on amylose resin. Biotinylated oligonucleotides containing the target AvrXa7 target site with modified residues were used to determine TALE-binding activity in sandwich enzyme-linked immunosorbent assay format. Antibodies targeting the MBP substituent were used for assay development.

Results.

Preliminary Analysis of the 5' T Rule.

Figure 18:
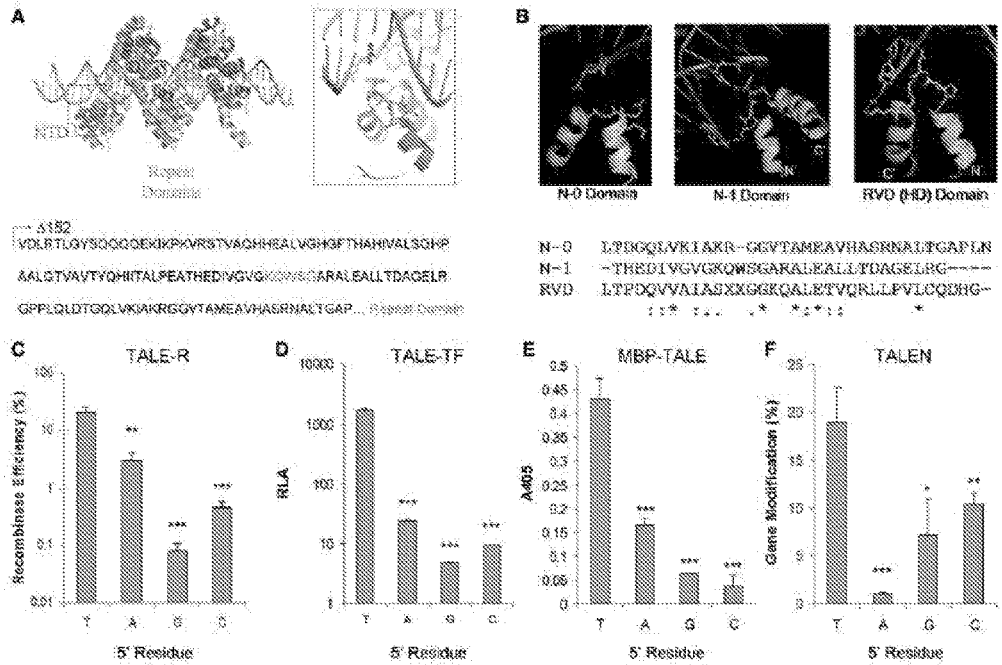
FIG. 18 is a series of pictorial and graphical representations pertaining to the specificity of the TALE N-terminal domain. A) Illustration of a TALE (SEQ ID NO: 29) bound to its target DNA. B) Structural analysis suggests contact of the 5' T by W232 of the N-1 hairpin (N-0—SEQ ID NO: 30; N-1—SEQ ID NO: 31; and RVD—SEQ ID NO: 32). This hairpin shares significant sequence homology with RVD hairpins. C-F) Analyses of NT-T (wt) NTD in the context of C) AvrXa7 TALE-R, D) AvrXa7 TALE-TF, E) AvrXa7 MBPTALE, and F) a CCR5 targeting TALEN. (*=p<0.05, =p<0.01, *=p<0.001 compared to 5'T).

A recent crystal structure of a TALE protein bound to PthXo7 DNA sequence revealed a unique interaction between W232 in the N-1 hairpin with a thymidine at the 5' end of the contacted region of the DNA substrate (the $N_0$ base). This study provided a structural basis for the previously established 5' T rule reported when the TALE code was first deciphered (FIGS. 18A and B). There are conflicting data regarding the importance of the first base of the target sequence of TALENs. The requirement for a 5' T in the target DNA was initially assesses in the context of TALE-Rs using four split beta lactamase TALE recombinase selection vectors containing four AvrXa7 binding sites with all possible 5' residues flanking a Gin32G core (FIG. 18C). Recognition of the $N_0$ residue by TALE-TFs was then evaluated using four luciferase reporter vectors containing a pentamer AvrXa7 promoter region with recognition sites containing each possible 5' residue (FIG. 18D). With bases other than a 5' T, we observed decreases in activity up to >100-fold in TALE-Rs and 1000-fold in TALE-TFs relative to the sequence with a 5' T (FIGS. 18C and D). These reductions were observed despite variations in the C-terminal architectures of these chimeras that reportedly remove the 5' T bias, especially in the presence of a greatly shortened C-terminal domain (CTD). Enzyme-linked immunosorbent assay also indicated decreased affinity of MBP-TALE DNA-binding proteins toward target oligonucleotides with non-T 5' residues (FIG. 18E). Finally, examination of the activity of designed TALENs with wild-type NTDs on targets with non-T 5' nucleotides showed up to 10-fold decrease in activity versus those with a 5' T (FIG. 18F). The results indicate that a 5' T is an important design parameter for maximally effective TALE domains in the context of recombinases, transcription factors, nucleases and simple DNA-binding proteins.

Evolution of the TALE NTD to Accommodate Non-T 5' Residues.

Figure 19:
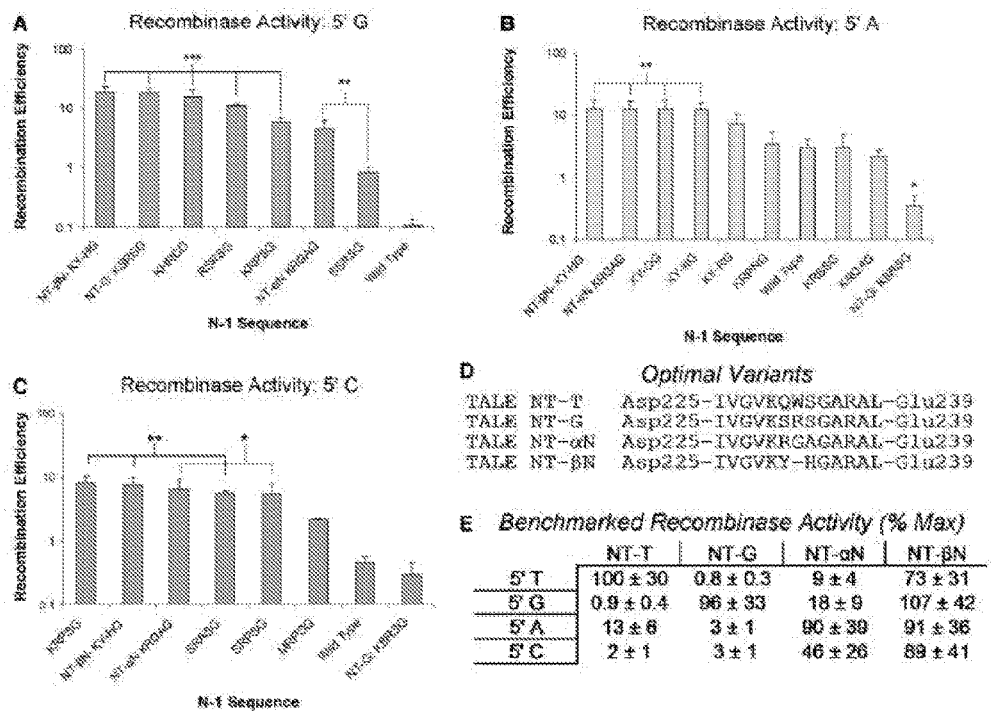
FIG. 19 is a series of graphical and diagrammatic representations pertaining to recombinase variants. A-C) Activities of recombinase selection variants against substrates with A) 5' G, B) 5' A, and C) 5' C.
Figures 22, 23:
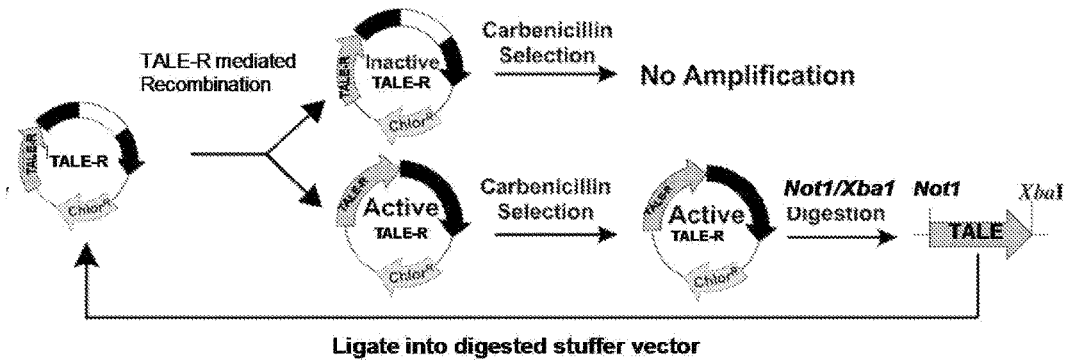
FIG. 22 is a diagrammatic representation showing alignment of N- and C-terminal domains SEQ ID NOs: 48-53).
FIG. 23 is a schematic representation illustrating TALE-Recombinase selection protocol. A library of NTD was cloned into Avr15 TALE-R using Not1/Stu1 restriction enzymes and complementary ligation. Active TALE-R's result in more frequent recombination events that can be selected and amplified with antibiotics (carbenecillin). The resulting output plasmid was the digested Not1/Xba1 and ligated into the TALE-R backbone vector for further selection and amplification.
Figures 24, 25:
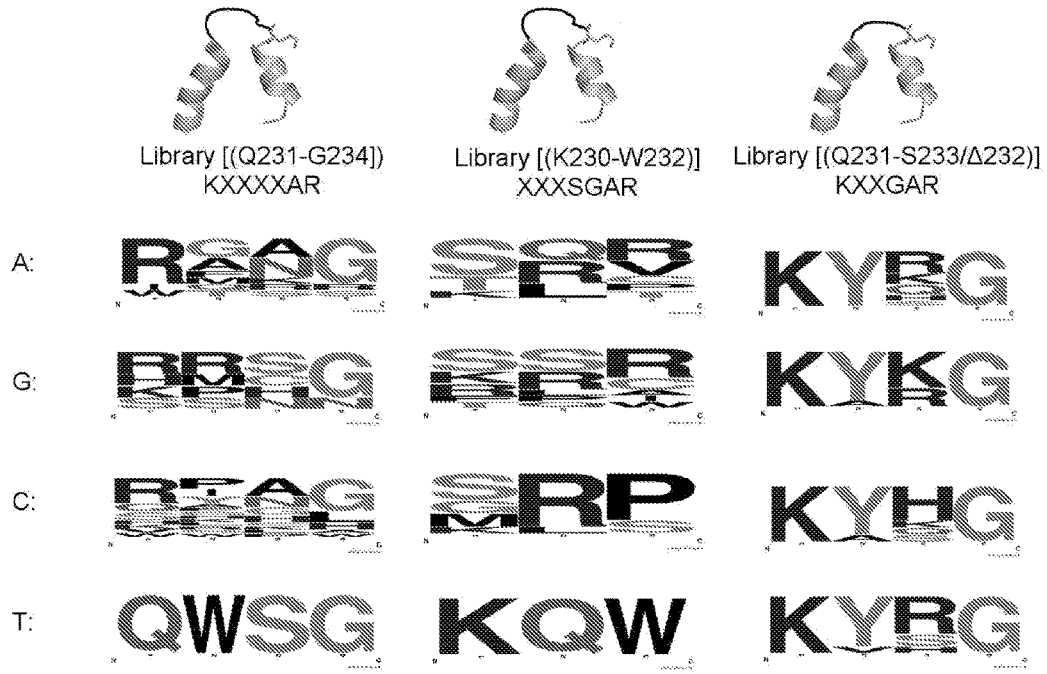
FIG. 24 is a diagrammatic representation of a summary of variant populations discovered from library selections (Library XXXSGAR (SEQ ID NO: 39) and Library KXXGAR (SEQ ID NO: 291)).
FIG. 25 is a diagrammatic representation showing alignment of NT-G (SEQ ID NO: 54) with NTD-Brg11 (SEQ ID NO: 55), a *Ralstonia* TALE domain. Alignment indicates Brg11 could exhibit specificity for 5' G bases.

To create a more flexible system for DNA recognition, it was hypothesized that the recently developed TALE-R selection system could be utilized to evolve the NTD of the TALE to remove the 5' T constraint (FIG. 23). Libraries were generated with residues K230 through G234 randomized, and TALE-Rs with activity against each possible 5' base were isolated after several rounds of selection (FIG. 19A-C). The most active selected clones exhibited strong conservation of K230 and G234; the former may contact the DNA phosphate backbone, and the latter may influence hairpin loop formation (FIG. 24). In the case of library K230-W232, K230S was frequently observed but had much lower activity than K230R or K230 variants in nearly all variants assayed individually. One clone (NT-G) of several observed with a W232 to S232 mutation demonstrated a significant shift of selectivity from 5' T to 5' G; the sequence resembles that of the NTD of a recently described *Ralstonia* TALE protein in this region. The *Ralstonia* NTD, in the context of plant transcription factor reporter gene regulation, has been reported to prefer a 5' G in its substrate (see FIG. 25 for a protein alignment). Residue R232 may contact the G base specifically, as indicated by the stringency of NT-G for 5' G. The preference of NT-G for a 5' G was comparable with the specificity of the wild-type domain for 5' T. NTD variants specific for 5' A or 5' C were not able to be derived, but a permissive NTD, NT-αN, was obtained that resembles the K265-G268 $N_0$ hairpin that accepts substrates with any 5' residue and maintains high activity. It was hypothesized that this variant makes enhanced non-specific contacts with the DNA phosphate backbone compared with the wild-type NTD, enhancing the overall binding of the TALE-DNA complex without contacting a specific 5' residue. It was hypothesized that a shortened hairpin structure would allow selection of variants with specificity for 5' A or 5' C residues. A library with randomization at Q231-W232 and with residue 233 deleted was designed to shorten the putative DNA-binding loop. Recombinase selection revealed a highly conserved Q231Y mutation that had high activity in a number of clones (FIG. 19D). In particular, NT-βN demonstrated improved activity on substrates with 5' A, C and G but diminished activity on 5' T substrates compared with TALEs with the wild-type NTD (FIG. 19E).

Applications of Evolved TALE NTDs.

Figure 20:
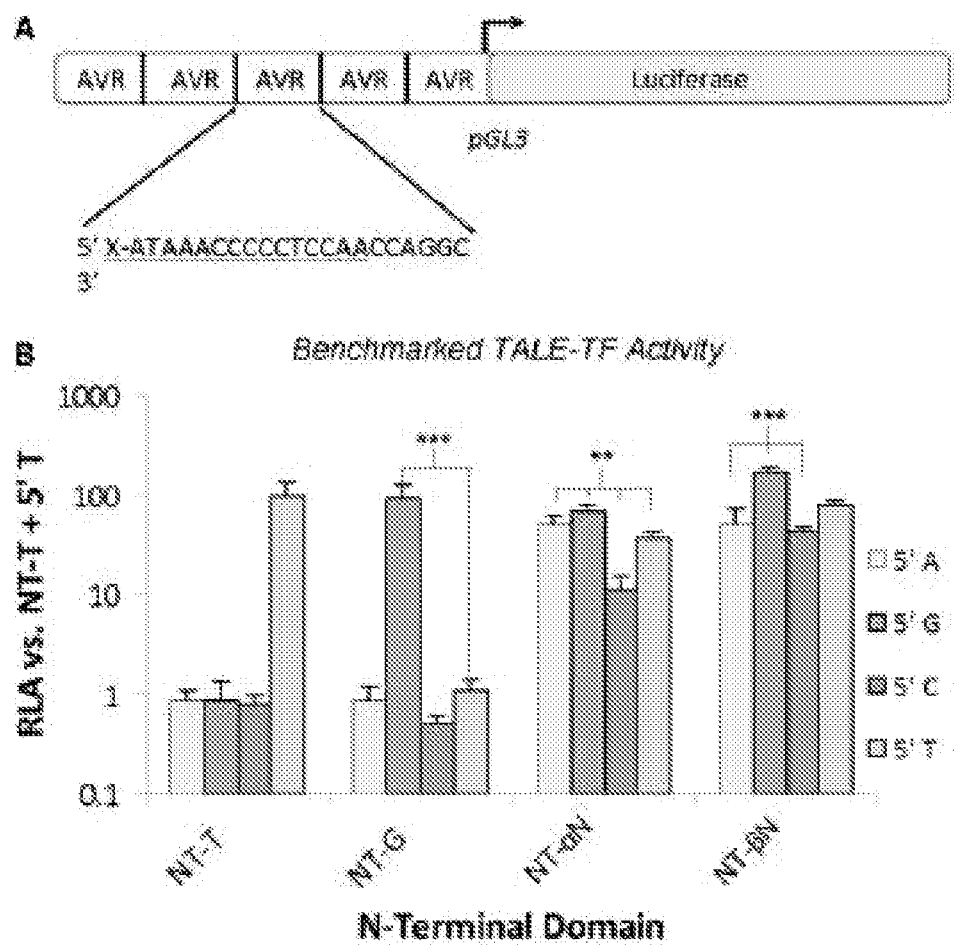
FIG. 20 is a series of diagrammatic and graphical representations of analysis of selected NTDs in the context of TALE-TFs. A) Illustration of 5×Avr promoter region (SEQ ID NO: 37) on the luciferase reporter plasmid used for transcription activation experiments. B) Relative luciferase activation of substrates with indicated 5' residues by TALE-TFs with NT-T, NT-G, NT-áN, and NT-âN domains. (*=p<0.05, =p<0.01, *=p<0.001, compared to NT-T and respective 5'A/G/C/T).
Figure 26:
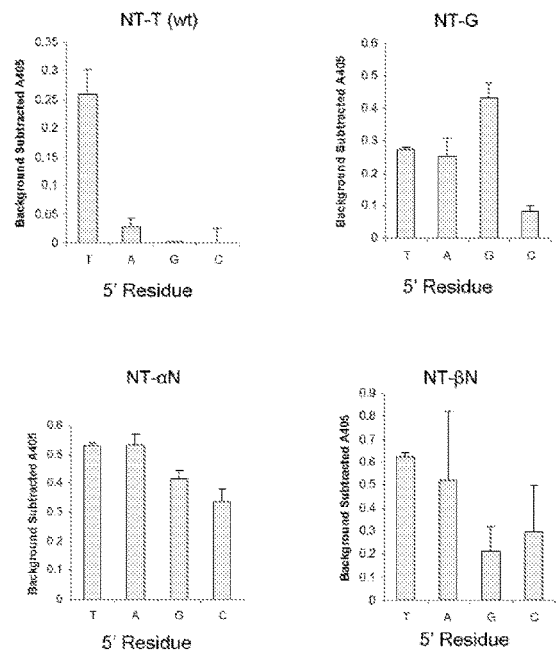
FIG. 26 is a series of graphical representations of relative binding affinity of MBP-TALE proteins to target 5' A/G/C/T Avr15 hairpin oligonucleotides as assayed by ELISA. Protein concentrations were ~75 nM and plates were developed for 120 minutes.

To assess the portability of the evolved NTDs in designer TALE fusion protein applications, optimized NTDs were incorporated into TALE-TFs, MBP-TALEs and TALENs. TALE-TFs with NT-G, NT-αN and NT-βN domains demonstrated 400-1500-fold increases in transcriptional activation of a luciferase target gene bearing operator sites without a 5' T residue when compared with the TALE-TF with the NT-T domain. The NT-G-based TF retained the 5' G selectivity as observed in the TALE-R selection system. The activities of NT-αN- and NT-βN-based TFs against all 5' nucleotides tracked the relative activity observed in the recombinase format (FIG. 20). MBP-TALEs also exhibited greater relative binding affinity for target oligonucleotides with sites that did not have a 5' T than did the wild-type MBP-TALE (FIG. 26), providing further evidence that the selected domains enhanced recognition of or tolerance for non-thymine 5' bases.

Four of the optimized NTDs were then imported into the Goldy TALEN framework. For these experiments, four substrates were constructed within the context of the A32 locus of the CCR5 gene (FIG. 21A). Each substrate contained a different 5' residue. Experiments included TALENs with wild-type (NT-T) and dHax3 NTDs (dHax3 is commonly used NTD variant isolated from *Xanthomonas campestris*) with specificity for 5' T, to benchmark gene editing activity. The substrate TALEN pairs were designed to retain as much RVD homology (50-90%) as possible to determine the activity enhancing contributions of the variant NTDs (FIG. 21A).

Figure 21:
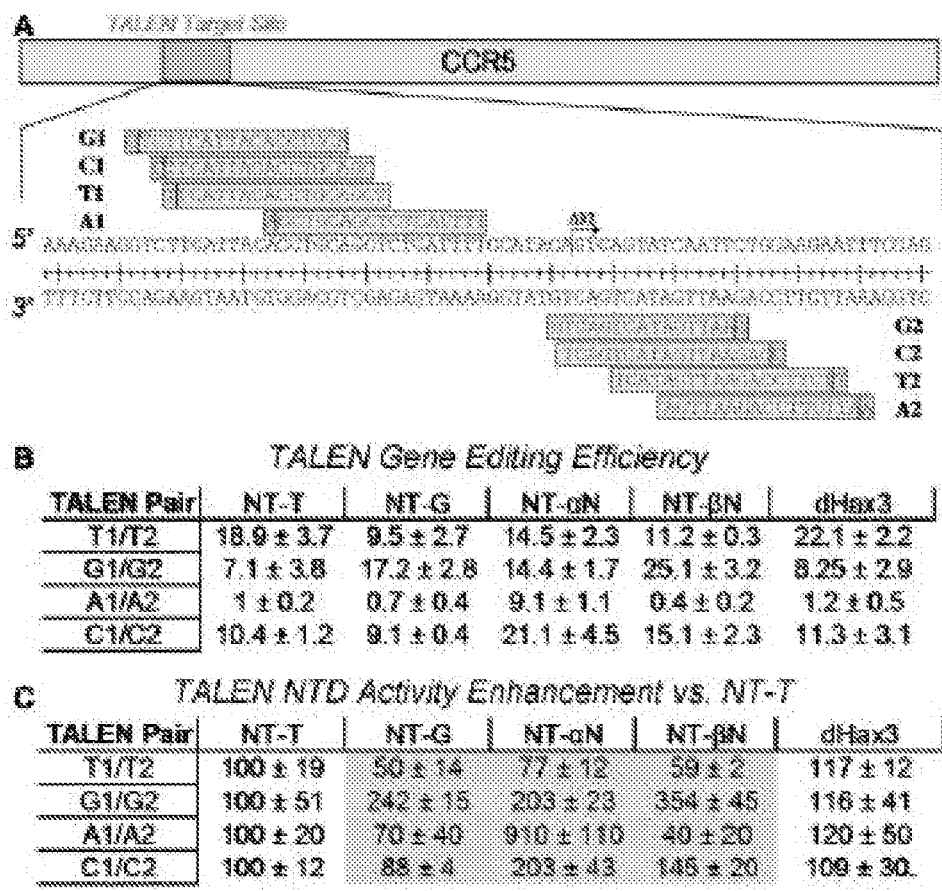
FIG. 21 is a series of diagrammatic and graphical representations of design and activity of TALEN pairs with wild-type and evolved NTD's with varying 5' bases. A) The CCR5 gene (SEQ ID NOs: 38-39) expanded to highlight the target site (SEQ ID NOs: 40-47) for induction of the H32 mutation. B) Gene editing efficiency of the wild type (NT-T) TALEN, TALENs with domains optimized for non-T 5' residues, and dHax3 NTD. C) Fold enhancement of the TALEN pairs with optimized NTD vs. TALENs with 5' T specificity. The activity of each NTD is shown on each TALEN pair substrate.
Figure 27:
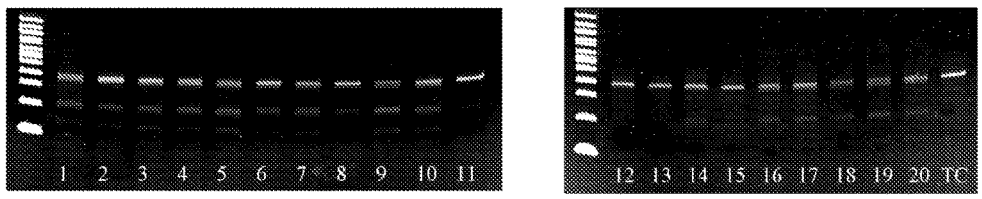
FIG. 27 is a series of pictorial and graphical representations of a cell assay of PCR amplified CCR5 after TALEN editing with % indels and indel populations shown on the right.

Activities of the TALENs were analyzed both by sequencing and by using the Cell assay. The selected domains exhibited increases in gene editing activity between 2- and 9-fold for the non-T 5' residues when compared with activities of the TALEN containing the wild-type domain (FIG. 21 and FIG. 27). Activity was highest on TALEN pair T1/T2 with wild-type or dHax3 NTD. The TALEN pair substrate G1/G2 was processed most effectively by TALENs with NT-αN, NT-βN and NT-G, with 2.0-3.5-fold enhancement versus NT-T. NT-αN had activity 9- and 2-fold higher than the wild-type NT-T on TALEN pairs A1/A2 and C1/C2, respectively. Although the impact of a mismatch at the 5' residue is more modest in TALENs than in TALE-TF and TALE-R frameworks, the optimized NTDs greatly improved TALEN activity when used in gene editing experiments.

Discussion.

Most, but not all, previous studies have suggested that a thymidine is required as the 5'-most residue in design of optimal TALE DNA-binding domains. The analyses described here indicate that a thymidine is optimal, and in some cases critical, for building functional TALE fusion proteins. This requirement therefore imposes limitations on the sequences that can be effectively targeted with TALE transcription factor, nuclease and recombinase chimeras. Although this requirement theoretically imposes minor limitations on the use of TALENs for inducing gene knockout, given their broad spacer region tolerance, NTD's that can accommodate any 5' residue would further simplify the rules for effective TALE construction and greatly enhance applications requiring precise TALE placement for genome engineering and interrogation (e.g. precise cleavage of DNA at a defined base pair using TALENs, seamless gene insertion and exchange via TALE-Recombinases, displacement of natural DNA-binding proteins from specific endogenous DNA sequences to interrogate their functional role, the development of orthogonal transcription factors for pathway engineering, the synergistic activation of natural and synthetic genes wherein transcription factor placement is key and many other applications). Other uses in DNA-based nanotechnology include decorating DNA nanostructures/origami with specific DNA-binding proteins. Here, targeting to specific sites is constrained based on DNA folding/structure and thus being able to bind any site is critical. Elaboration of these structures and devices with DNA-binding proteins could be a fascinating approach to expanding function. Indeed, it is not difficult to imagine many applications for DNA binding proteins and their fusions when all targeting constraints are removed. Encouraged by these potential applications, we aimed to develop NTDs that enable targeting of sites initiated at any base.

The recently developed TALE-R system was used to evolve the NTD of the TALE to remove the 5'-T constraint. In three rounds of selection, an NTD was obtained with specificity for a 5' G. Numerous selections were performed in attempts to obtain variants that recognized either 5' A or 5' C. The G230-K234 hairpin was inverted, the K230-G234/ins232 hairpin extended, modification of the K265-G268 $N_0$ hairpin attempted, and random mutagenesis libraries evaluated. None of these strategies yielded NTDs with affinity for target sequences with 5' A or 5' C, although we did identify an NTD, NT-βN, with a deletion that recognized substrates with both 5' A and 5' C residues with acceptable affinity. The strong selection preference exhibited by the NTDs NT-T and NT-G and the importance of W232 in NT-T and R232 in NT-G are likely due to specific interactions of these amino acids with the 5' terminal residue of the DNA recognition sequence. It was recently reported that the *Ralstonia solanacearum* TALE stringently requires a 5' G, and a sequence alignment with NT-G shows what appears to be a comparable N-1 hairpin containing an arginine at the position analogous to 232 in NT-G (FIG. 25). Owing to the high structural homology between the NTDs Brg11 and NT-T, it may be possible to modify the preference of the *Ralstonia* TALE NTD to thymine by a simple arginine to tryptophan mutation or to eliminate specificity by grafting NT-αN or NT-βN domains into this related protein. It is also interesting to note that arginine-guanine interactions are common in evolved zinc finger domains.

The variant NTDs selected were successfully imported into TALE-TFs, MBP-TALEs and TALENs and generally conferred the activity and specificity expected based on data from the recombinase evolution system. TALE-TFs with optimized NTDs enhanced TALE activation between 400- and 1500-fold relative to the activity of NT-T against AvrXa7 promoter sites with non-T 5' residues. When incorporated into TALENs, our NTD with non-selectivity enhanced activity 2-9-fold relative to that of the NT-T domain on substrates with 5' A, C or G. The increases in TALEN gene editing generally correlated with increases in activity observed in TALE-R and TALE-TF constructs. The specificity and high activity of NT-G was maintained, as evidenced by the lower activity in assays with TALEN pairs A1/A2, C1/C2, and T1/T2, and the generally high activity of NT-αN and NT-βN was also imparted into the TALEN Δ152/+63 architecture.

Figure 29:
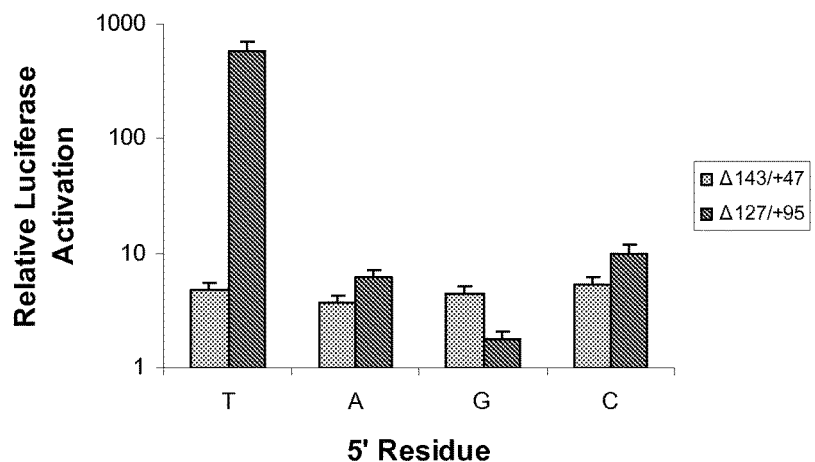
FIG. 29 is a graphical representation of a comparison of the activity of two separate Goldy TALE-Transcription factor architectures, each targeting identical 5× AvrXa7 promoters varying only in the 5' residue.
Figure 30:
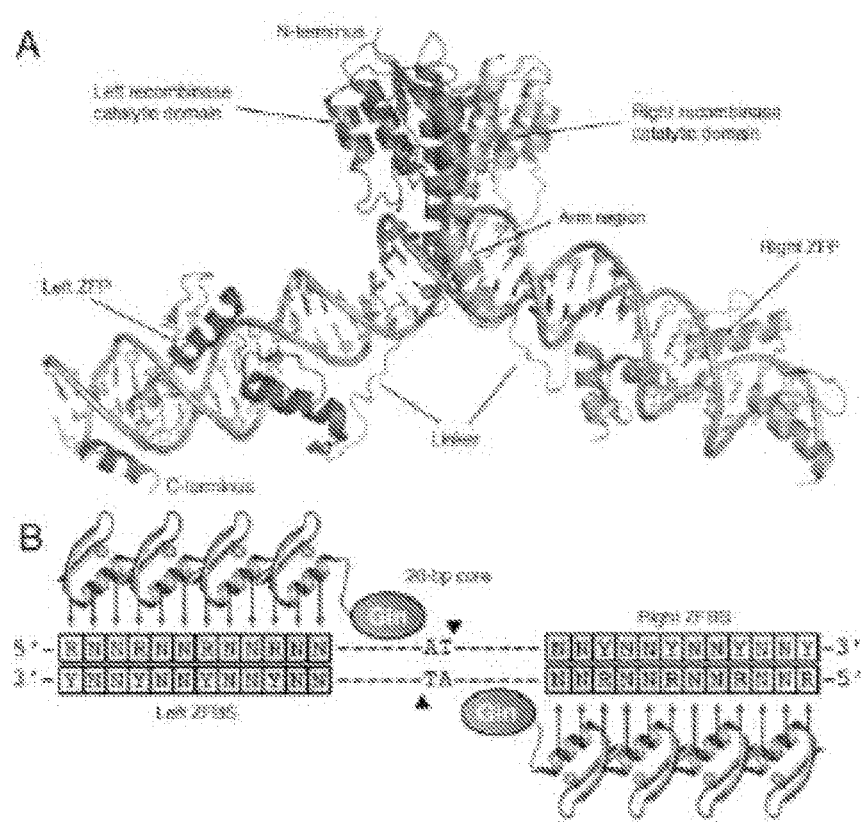
FIG. 30 is a series of diagrammatic representations relating to the structure of the zinc-finger recombinase dimer bound to DNA. A) Each zinc-finger recombinase (ZFR) monomer (blue or orange) consists of an activated serine recombinase catalytic domain linked to a custom-designed zinc-finger DNA-binding domain. Model was generated from crystal structures of the γδ resolvase and Aart zinc-finger protein (PDB IDs: 1GDT and 2I13, respectively). B) Cartoon of the ZFR dimer bound to DNA (SEQ ID NOs: 333-334). ZFR target sites consist of two-inverted zinc-finger binding sites (ZFBS) flanking a central 20-bp core sequence recognized by the ZFR catalytic domain. Zinc-finger proteins (ZFPs) can be designed to recognize 'left' or 'right' half-sites (blue and orange boxes, respectively). Abbreviations are as follows: N indicates A, T, C, or G; R indicates G or A; and Y indicates C or T.

It was recently reported that alternatively truncated TALEs with synthetic TALE RVD domains do not require a 5' T in the DNA substrate. The reported Δ143, +47 truncation was constructed as a Goldy TALE-TF and substantially lower activity on the AvrXa7 substrate was observed than for the Δ127, +95 truncation, which has been most commonly used by others and which is the truncation set used in our study (FIG. 29). Thus, the difference in reported outcomes could be due to the truncated architectures used.

In summary, the importance of a 5' thymidine in the DNA substrate for binding and activity of designed TALEs was determined in the context of TALE-R, TALE-TF, MBP-TALEs and TALEN chimeras. Targeted mutagenesis and TALE-R selection were applied to engineer TALE NTDs that recognize bases other than thymine as the 5' most base of the substrate DNA. The engineered TALE domains developed here demonstrated modularity and were highly active in TALE-TF and TALEN architectures. These novel NTDs expand by 15-fold the number of sites that can be targeted by current TALE-Rs, which have strict geometric requirements on their binding sites and which are highly sensitive to the identity of the $N_0$ base. Furthermore, they now allow for the precise placement of TALE DBDs and TALE-TFs at any DNA sequence to facilitate gene regulation, displacement of endogenous DNA-binding proteins and synthetic biology applications where precise binding might be key. Although TALENs based on the native NTD show varying degrees of tolerance of $N_0$ base substitutions, the data indicate that the novel NTDs reported here also facilitate higher efficiency gene editing with any $N_0$ base as compared with natural NTD-based TALENs.

Example 5

Chimeric Zinc Finger Recombinases

The following materials and method were utilized.

The split gene reassembly vector (pBLA) was derived from pBluescriptII SK (−) (Stratagene) and modified to contain a chloramphenicol resistance gene and an interrupted TEM-1 β lactamase gene under the control of a lac promoter. ZFR target sites were introduced as previously described. Briefly, GFPuv (Clontech) was PCR amplified with the primers GFP-ZFR-XbaI-Fwd and GFP-ZFR-HindIII-Rev and cloned into the SpeI and HindIII restriction sites of pBLA to generate pBLA-ZFR substrates. All primer sequences are provided in Table 8.

TABLE 8

Primer Sequences.

| Primer | SEQ ID NO: | Sequence |
|---|---|---|
| GFP-ZFR-20G-XbaI-Fwd | 264 | TTAATTAAGAGTCTAGAGGAGGCGTGTC CAAAACCATGGTTTACAGCACGCCTCCA GATCTAGGAGGAATTTAAAATGAG |

TABLE 8-continued

Primer Sequences.

| Primer | SEQ ID NO: | Sequence |
|---|---|---|
| GFP-ZFR-20G-HindIII-Rev | 265 | ACTGACCTAGAGAAGCTTGGAGGCGTGCTGTAAACCATGGTTTTGGACACGCCTCCCTGCAGTTATTTGTACAGTTCATC |
| SV40-ZFR-1-BglII-Fwd | 266 | TTAATTAAGAGAGATCTGCTGATGCAGATACAGAAACCAAGGTTTTCTTACTTGCTGCTGCGCGATCTGCATCTCAATTAGTCAGC |
| CMV-PstI-ZFR-1 Rev | 267 | CACCACCACGGATCCGCAGCAGCAAGTAAGAAAACCTTGGTTTCTGTATCTGCATCAGCAATTTCGATAAGCCAGTAAGCAG |
| 5' Gin-HBS-Koz | 268 | CACCACCACGCGCGCAAGCTTAGATCTGGCCCAGGCGGCCACCATGCTGATTGGCTATGTAAGGG |
| 3' Gin-AgeI-Rev | 269 | CACCACCACACCGGTTCCCGATTTAGGTGGGCGAC |
| ZFR-Target-1-Fwd | 270 | GTTCCTGCCAGGATCCACTAG |
| ZFR-Target-1-Rev | 271 | GCATGTGTCCAGATGCATAGG |
| ZFR-Target-2-Fwd | 272 | CACCTTCTCCCAGGATAAGG |
| ZFR-Target-2-Rev | 273 | GTTGGCCTGTATTCCTCTGG |
| ZFR-Target-3-Fwd | 274 | AATGAAGTTCCCTTGGCACTTC |
| ZFR-Target-3-Rev | 275 | CTGAAGGGTTTTAAGTGCAGAAG |
| CMV-Mid Prim-1 | 276 | TGACGTCAATGACGGTAAATGG |

ZFR targets are underlined.

To generate luciferase reporter plasmids, the SV40 promoter was PCR amplified from pGL3-Prm (Promega) with the primers SV40-ZFR-BglIII-Fwd and SV40-ZFR-HindIII-Rev. PCR products were digested with BglII and HindIII and ligated into the same restriction sites of pGL3-Prm to generate pGL3-ZFR-1, 2, 3 . . . 18. The pBPS-ZFR donor plasmid was constructed as previously described with the following exception: the ZFR-1, 2 and 3 recombination sites were encoded by primers 3' CMV-PstI-ZFR-1, 2 or 3-Rev. Correct construction of each plasmid was verified by sequence analysis.

Recombination Assays.

ZFRs were assembled by PCR as previously described. PCR products were digested with SacI and XbaI and ligated into the same restrictions sites of pBLA. Ligations were transformed by electroporation into Escherichia coli TOP10F' (Invitrogen). After 1 hr recovery in SOC medium, cells were incubated with 5 mL SB medium with 30 ˆg mL$^{-1}$ chloramphenicol and cultured at 37° C. At 16 hr, cells were harvested; plasmid DNA was isolated by Mini-prep (Invitrogen) and 200 ng pBLA was used to transform E. coli TOP10F'. After 1 hr recovery in SOC, cells were plated on solid LB media with 30 ˆg mL$^{-1}$ chloramphenicol or 30 ˆg mL$^{-1}$ chloramphenicol and 100 ˆg mL$^{-1}$ carbenicillin, an ampicillin analogue. Recombination was determined as the number of colonies on LB media containing chloramphenicol and carbenicillin divided by the number of colonies on LB media containing chloramphenicol. Colony number was determined by automated counting using the GelDoc XR Imaging System (Bio-Rad).

Selections.

The ZFR library was constructed by overlap extension PCR as previously described. Mutations were introduced at positions 120, 123, 127, 136 and 137 with the degenerate codon NNK (N: A, T, C or G and K: G or T), which encodes all 20 amino acids. PCR products were digested with SacI and XbaI and ligated into the same restriction sites of pBLA. Ligations were ethanol precipitated and used to transform E. coli TOP10F'. Library size was routinely determined to be ~5×10$^7$. After 1 hr recovery in SOC medium, cells were incubated in 100 mL SB medium with 30 ˆg mL$^{-1}$ chloramphenicol at 37° C. At 16 hr, 30 mL of cells were harvested; plasmid DNA was isolated by Mini-prep and 3 ˆg plasmid DNA was used to transform E. coli TOP10F'. After 1 hr recovery in SOC, cells were incubated with 100 mL SB medium with 30 ˆg mL$^{-1}$ chloramphenicol and 100 ˆg mL$^{-1}$ carbenicillin at 37° C. At 16 hr, cells were harvested and plasmid DNA was isolated by Maxi-prep (Invitrogen). Enriched ZFRs were isolated by SacI and XbaI digestion and ligated into fresh pBLA for further selection. After 4 rounds of selection, sequence analysis was performed on individual carbenicillin-resistant clones. Recombination assays were performed as described above.

ZFR Construction.

Recombinase catalytic domains were PCR amplified from their respective pBLA selection vector with the primers 5' Gin-HBS-Koz and 3' Gin-AgeI-Rev. PCR products were digested with HindIII and AgeI and ligated into the same restriction sites of pBH to generate the SuperZiF-compitable subcloning plasmids: pBH-Gin-α, β, γ, δ, ε or ζ. Zinc-fingers were assembled by SuperZiF and ligated into the AgeI and SpeI restriction sites of pBH-Gin-α, β, γ, δ, ε or ζ to generate pBH-ZFR-L/R-1, 2, 3..18 (L: left ZFR; R: right ZFR). ZFR genes were released from pBH by SfiI digestion and ligated into pcDNA 3.1 (Invitrogen) to generate pcDNA-ZFR-L/R-1, 2, 3..18. Correct construction of each ZFR was verified by sequence analysis (Table 9).

TABLE 9

Catalytic domain substitutions and intended DNA targets.

| | | Positions | | | | |
|---|---|---|---|---|---|---|
| Catalytic domain | Target | 120 | 123 | 127 | 136 | 137 |
| A | CC$^a$ | Ile | Thr | Leu | Ile | Gly |
| B | GC | Ile | Thr | Leu | Arg | Phe |
| Γ | GT | Leu | Val | Ile | Arg | Trp |
| Δ | CA | Ile | Val | Leu | Arg | Phe |
| ε$^b$ | AC | Leu | Pro | His | Arg | Phe |
| ζ$^c$ | TT | Ile | Thr | Arg | Ile | Phe |

$^a$Indicates wild-type DNA target.
$^b$The ε catalytic domain also contains the substitutions E117L and L118S.
$^c$The ζ catalytic domain also contains the substitutions M124S, R131I and P141R.

Luciferase Assays.

Human embryonic kidney (HEK) 293 and 293T cells (ATCC) were maintained in DMEM containing 10% (vol/vol) FBS and 1% (vol/vol) Antibiotic-Antimycotic (Anti-Anti; Gibco). HEK293 cells were seeded onto 96-well plates at a density of 4×10$^4$ cells per well and established in a humidified 5% CO$_2$ atmosphere at 37° C. At 24 hr after seeding, cells were transfected with 150 ng pcDNA-ZFR-L 1-18, 150 ng pcDNA-ZFR-R 1-18, 2.5 ng pGL3-ZFR-1, 2, 3. or 18 and 1 ng pRL-CMV using Lipofectamine 2000 (Invitrogen) according to the manufacturer's instructions. At 48 hr after transfection, cells were lysed with Passive Lysis Buffer (Promega) and luciferase expression was determined with the Dual-Luciferase Reporter Assay System (Promega) using a Veritas Microplate Luminometer (Turner Biosystems).

Integration Assays.

HEK293 cells were seeded onto 6-well plates at a density of $5\times10^5$ cells per well and maintained in serum-containing media in a humidified 5% $CO_2$ atmosphere at 37° C. At 24 hr after seeding, cells were transfected with 1 ^g pcDNA-ZFR-L-1, 2 or 3 and 1 ^g pcDNA-ZFR-R-1, 2 or 3 and 200 ng pBPS-ZFR-1, 2 or 3 using Lipofectamine 2000 according to the manufacturer's instructions. At 48 hr after transfection, cells were split onto 6-well plates at a density of $5\times10^4$ cells per well and maintained in serum-containing media with 2 ^g mL" puromycin. Cells were harvested upon reaching 100% confluence and genomic DNA was isolated with the Quick Extract DNA Extraction Solution (Epicentre). ZFR targets were PCR amplified with the following primer combinations: ZFR-Target-1, 2 or 3-Fwd and ZFR-Target-1, 2 or 3-Rev (Unmodified target); ZFR-Target-1, 2 or 3-Fwd and CMV-Mid-Prim-1 (Forward integration); and CMV-Mid-Prim-1 and ZFR-Target-1, 2 or 3-Rev (Reverse integration) using the Expand High Fidelity Taq System (Roche). For clonal analysis, at 2 days post-transfection $1\times10^5$ cells were split onto a 100 mm dish and maintained in serum-containing media with 2 ^g $mL^{-1}$ puromycin. Individual colonies were isolated with 10 mm×10 mm open-ended cloning cylinders with sterile silicone grease (Millipore) and expanded in culture. Cells were harvested upon reaching 100% confluence and genomic DNA was isolated and used as template for PCR, as described above. For colony counting assays, at 2 days post-transfection cells were split into 6-well plates at a density of $1\times10^4$ cells per well and maintained in serum-containing media with or without 2 ^g $mL^{-1}$ puromycin. At 16 days, cells were stained with a 0.2% crystal violet solution and integration efficiency was determined by counting the number of colonies formed in puromycin-containing media divided by the number of colonies formed in the absence of puromycin. Colony number was determined by automated counting using the GelDoc XR Imaging System (Bio-Rad).

Results.

Specificity Profile of the Gin Recombinase.

In order to re-engineer serine recombinase catalytic specificity, a detailed understanding was developed of the factors underlying substrate recognition by this family of enzymes. To accomplish this, the ability of an activated mutant of the catalytic domain of the DNA invertase Gin to recombine a comprehensive set of symmetrically substituted target sites was evaluated. The Gin catalytic domain recombines a pseudo-symmetric 20-bp core that consists of two 10-bp half-site regions. This collection of recombination sites therefore contained each possible single-base substitution at positions 10, 9, 8, 7, 6, 5, and 4 and each possible two-base combination at positions 3 and 2 and in the dinucleotide core. Recombination was determined by split gene reassembly, a previously described method that links recombinase activity to antibiotic resistance.

Figure 31:
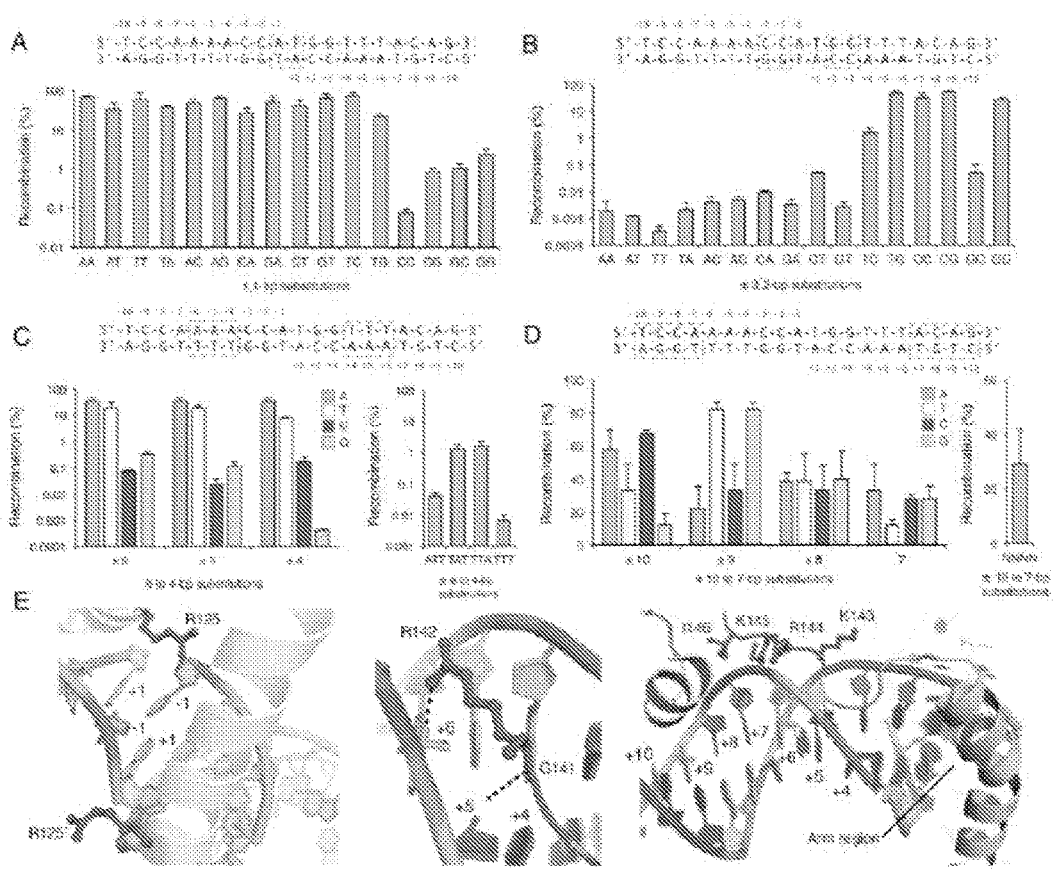
FIG. 31 is a series of graphical and diagrammatic representations of specificity of the Gin recombinase catalytic domain. A-D) Recombination was measured on DNA targets that contained (A, SEQ ID NO: 335) each possible two-base combination at the dinucleotide core, (B, SEQ ID NO: 336) each possible two-base combination at positions 3 and 2, (C, SEQ ID NO: 337) each possible single-base substitution at positions 6, 5, and 4, and (D, SEQ ID NO: 338) each possible single-base substitution at positions 10, 9, 8, and 7. Substituted bases are boxed above each panel. Recombination was evaluated by split gene reassembly and measured as the ratio of carbenicillin-resistant to chloramphenicol-resistant transformants (Materials and Methods). Error bars indicate standard deviation (n=3). (E) Interactions between the γδ resolvase dimer and DNA at (left) the dinucleotide core, (middle) positions 6, 5, and 4, and (right) positions 10, 9, 8, and 7 (PDB ID: 1GDT). Interacting residues are shown as purple sticks. Bases are colored as follows: A, yellow; T, blue; C, brown; and G, pink.

In general, it was found that Gin tolerates (i) 12 of the 16 possible two-base combinations at the dinucleotide core (AA, AT, AC, AG, TA, TT, TC, TG, CA, CT, GA, GT); (ii) 4 of the 16 possible two-base combinations at positions 3 and 2 (CC, CG, GG and TG); (iii) a single A to T substitution at positions 6, 5, or 4; and (iv) all 12 possible single-base substitutions at positions 10, 9, 8, and 7 (FIG. 31A-D). Further, it was found that Gin could recombine a target site library containing at least $10^6$ (of a possible $4.29\times10^9$) unique base combinations at positions 10, 9, 8, and 7 (FIG. 31D).

These findings are consistent with observations made from crystal structures of the yδ resolvase, which indicate that (i) the interactions made by the recombinase dimer across the dinucleotide core are asymmetric and predominately non-specific; (ii) the interactions between an evolutionarily conserved Gly-Arg motif in the recombinase arm region and the DNA minor groove imposes a requirement for adenine or thymine at positions 6, 5, and 4; and (iii) there are no sequence-specific interactions between the arm region and the minor groove at positions 10, 9, 8, or 7 (FIG. 31E). These results are also consistent with studies that focused on determining the DNA-binding properties of the closely related Hin recombinase.

Re-Engineering Gin Recombinase Catalytic Specificity.

Figure 32:
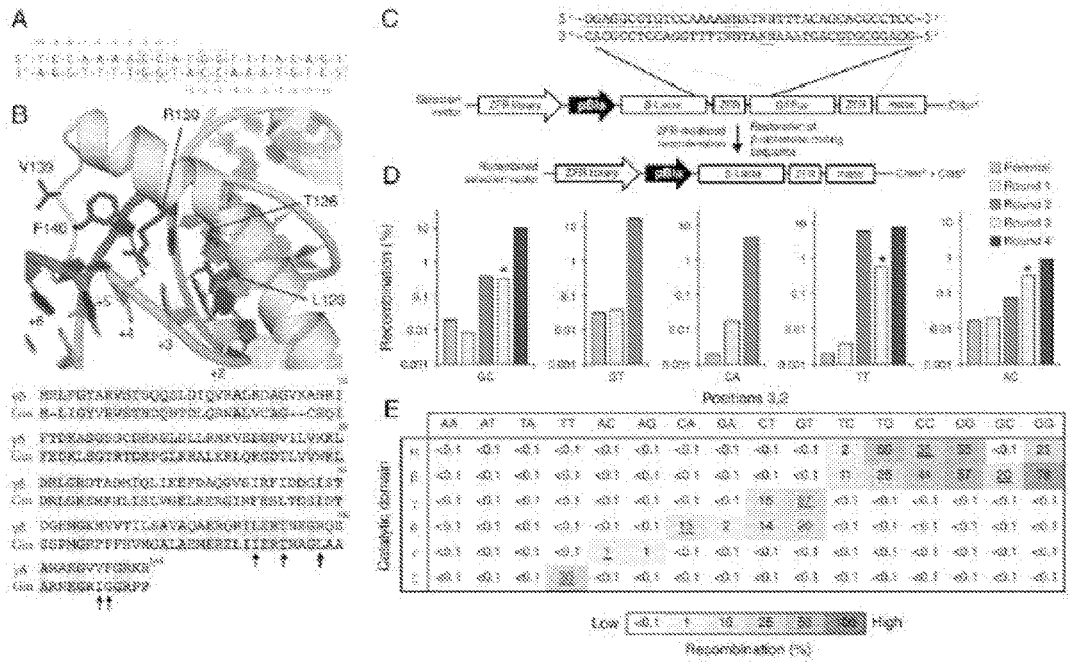
FIG. 32 is a series of graphical and diagrammatic representations of re-engineering Gin recombinase catalytic specificity. A) The canonical 20-bp core recognized by the Gin catalytic domain. Positions 3 and 2 are boxed (SEQ ID NO: 339). B) (Top) Structure of the γδ resolvase in complex with DNA (PDB ID: 1GDT). Arm region residues selected for mutagenesis are shown as purple sticks. (Bottom) Sequence alignment of the γδ resolvase (SEQ ID NO: 341) and Gin recombinase (SEQ ID NO: 342) catalytic domains. Conserved residues are shaded orange. Black arrows indicate arm region positions selected for mutagenesis. C) Schematic representation of the split gene reassembly selection system. Expression of active ZFR variants leads to restoration of the β-lactamase reading frame and host-cell resistance to ampicillin. Solid lines indicate the locations and identity of the ZFR target sites. Positions 3 and 2 are underlined (SEQ ID NO: 340). D) Selection of Gin mutants that recombine core sites containing GC, GT, CA, TT, and AC base combinations at positions 3 and 2. Asterisks indicate selection steps in which incubation time was decreased from 16 hr to 6 hr (Materials and Methods, Example 5). E) Recombination specificity of the selected catalytic domains (β, γ, δ, ε, and ζ, wild-type Gin indicated by α) for each possible two-base combination at positions 3 and 2. Intended DNA targets are underlined. Recombination was determined by split gene reassembly and performed in triplicate.

Based on the finding that Gin tolerates conservative substitutions at positions 3 and 2 (i.e., CC, CG, GG, and TG), whether Gin catalytic specificity could be re-engineered to specifically recognize core sequences containing each of the 12 base combinations not tolerated by the native enzyme (FIG. 32A) was investigated. In order to identify the specific amino acid residues involved in DNA recognition by Gin, the crystal structures of two related serine recombinases, the yδ resolvase and Sin recombinase, in complex with their respective DNA targets were examined. Based on these models, five residues were identified that contact DNA at positions 3 and 2: Leu 123, Thr 126, Arg 130, Val 139, and Phe 140 (numbered according to the yδ resolvase) (FIG. 32B). Random mutagenesis was performed on the equivalent residues in the Gin catalytic domain (Ile 120, Thr 123, Leu 127, Ile 136, and Gly 137) by overlap extension PCR and constructed a library of ZFR mutants by fusing these catalytic domain variants to an unmodified copy of the 'H1' ZFP. The theoretical size of this library was $3.3\times10^7$ variants.

The ZFR library was cloned into substrate plasmids containing one of the five base combinations not tolerated by the native enzyme (GC, GT, CA, AC, or TT) and enriched for active ZFRs by split gene reassembly (FIG. 32C). After 4 rounds of selection, it was found that the activity of each ZFR population increased >1,000-fold on DNA targets containing GC, GT, CA, and TT substitutions and >100-fold on a DNA target containing AC substitutions (FIG. 32D).

Figure 36:
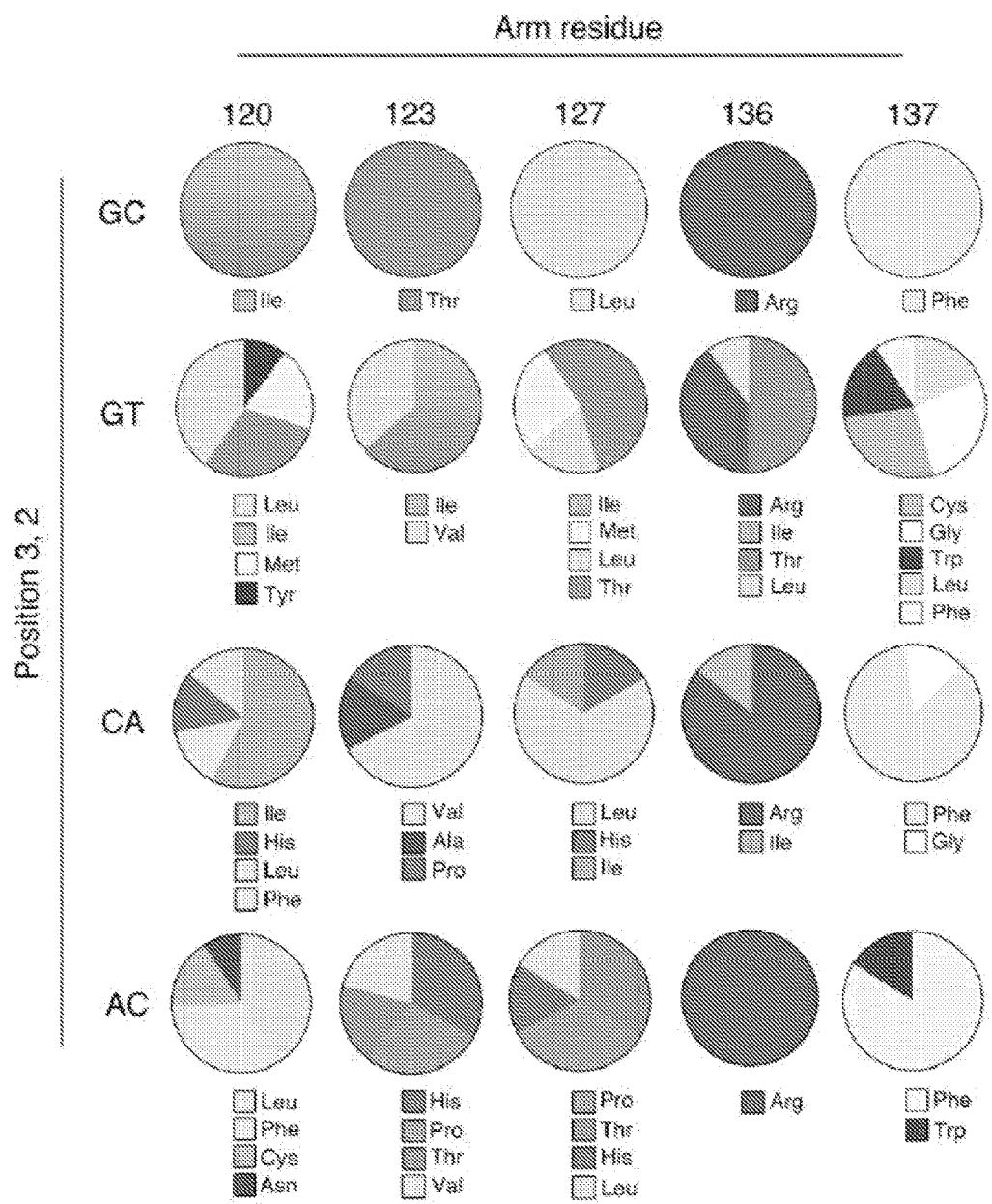
FIG. 36 is a diagrammatic representation of sequence analysis of selected recombinases. Pie charts showing the percentage of amino acid substitutions at each targeted arm position. After the 4$^{th}$ round of selection, >20 clones were sequenced from each library. Sequence analysis of clones that recombine TT are described elsewhere(1).
Figure 37:
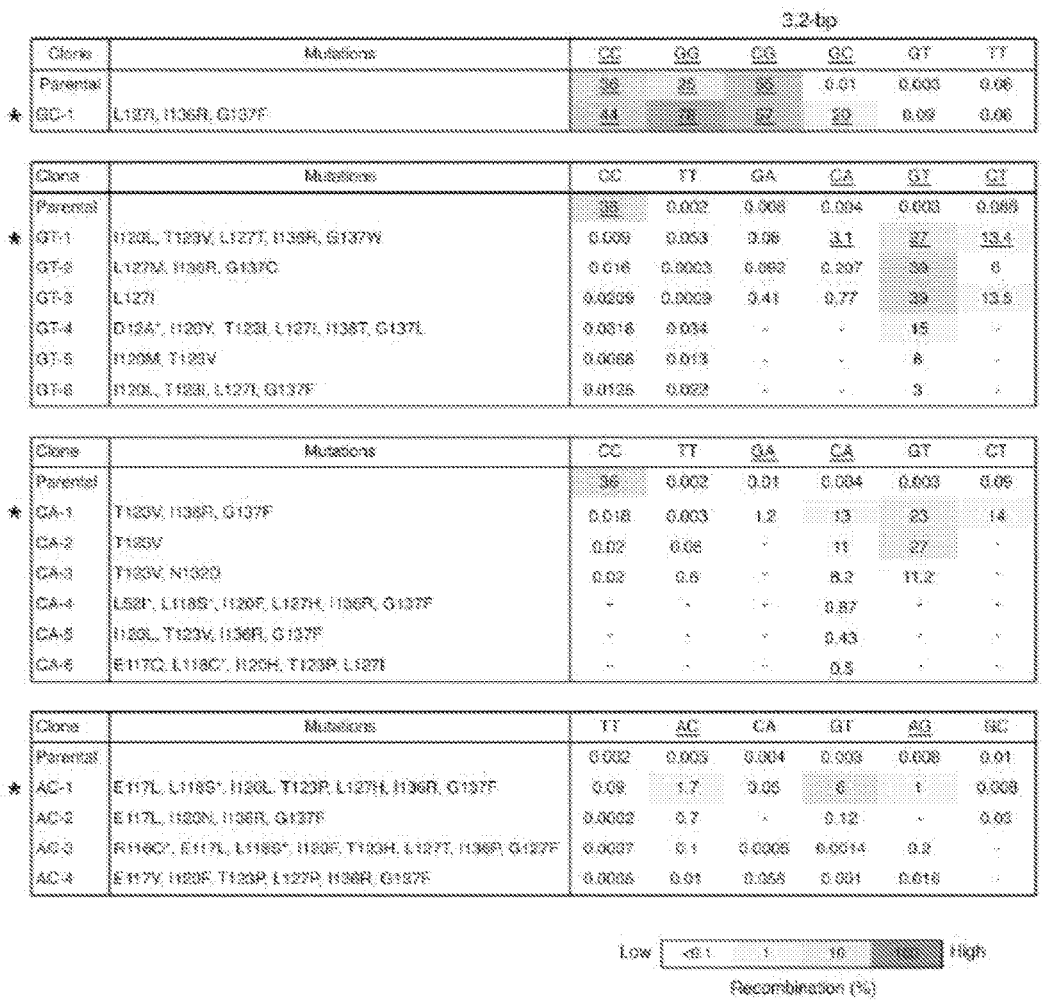
FIG. 37 is a table showing core specificity of isolated catalytic domains. After 4 rounds of selection, the ability of selected catalytic domains to recombine core sequences with substitutions at positions 3 and 2 was evaluated. Assigned DNA targets are underlined. Recombinase mutations are shown. Asterisks indicate catalytic domains selected for further analysis. Wild-type base combination at positions 3 and 2 is CC. Recombination was determined by split gene reassembly(2) and performed in triplicate. Catalytic domains that recombine TT substitutions are described elsewhere(1).

Individual recombinase variants were sequenced from each population and found that a high level of amino acid diversity was present at positions 120, 123, and 127 and that >80% of selected clones contained Arg at position 136 and Trp or Phe at position 137 (FIG. 36). These results suggest that positions 136 and 137 play critical roles in the recognition of unnatural core sequences. The ability of each selected enzyme to recombine its target DNA was evaluated and it was found that nearly all recombinases showed activity (>10% recombination) and displayed a >1,000-fold shift in specificity toward their intended core sequence (FIG. 37). As with the parental Gin, it was found that several recombinases tolerated conservative substitutions at positions 3 and 2 (i.e., cross-reactivity against GT and CT or AC and AG), indicating that a single re-engineered catalytic domain could be used to target multiple core sites (FIG. 37).

Figure 38:
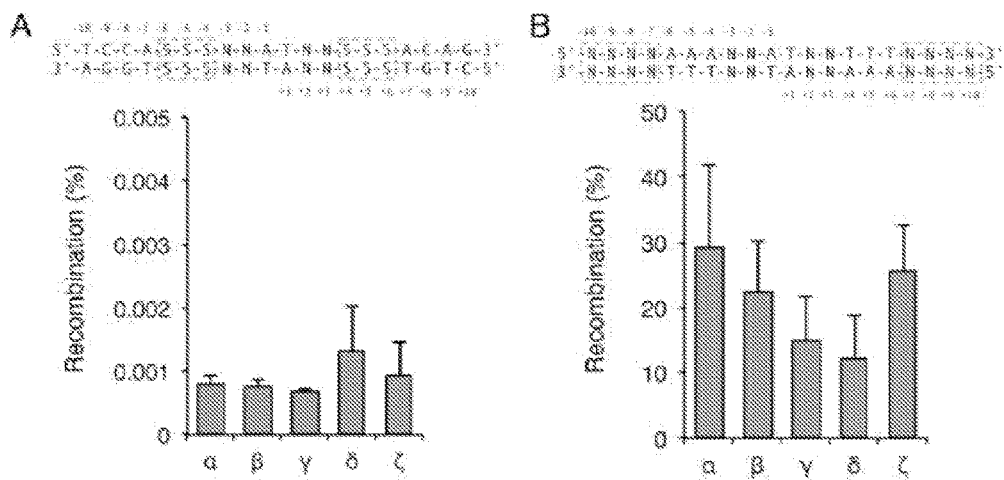
FIG. 38 is a series of graphical representations of position specificity of selected catalytic domains. Recombination assays between the α, β, γ, δ and ζ catalytic domains and symmetrically substituted target sites. Recombination was measured on a library DNA targets that contained (A (SEQ ID NO: 368))>4,000 random strong base (S: G or C) substitutions at positions 6, 5 and 4 and (B (SEQ ID NO: 369))>$10^6$ (of a possible 4.29×$10^9$) unique base combinations at positions 10, 9, 8 and 7 (N: A, T, C or G). Recombination was measured by split gene reassembly(2) (n=3).

In order to further investigate recombinase specificity, the recombination profiles were determined of five Gin variants (hereafter designated Gin p, y, 6, e and Z) shown to recognize nine of the 12 possible two-base combinations not tolerated by the parental enzyme (GC, TC, GT, CT, GA, CA, AG, AC, and TT) (Table 1). Gin p, δ, and ε recombined their intended core sequences with activity and specificity comparable to that of the parental enzyme (hereafter referred to as Gin α) and that Gin γ and Z were able to recombine their intended core sequences with specificity exceeding that of Gin α (FIG. 32E). Each recombinase displayed >1,000-fold preference for adenine or thymine at positions 6, 5, and 4 and showed no base preference at positions 10, 9, 8, and 7 (FIG. 38). These results indicate that mutagenesis of the DNA-binding arm did not compromise recombinase specificity. It was not possible to select for Gin variants capable of tolerating AA, AT, or TA substitutions at positions 3 and 2. One possibility for this result is that DNA targets containing >4 consecutive A-T bps might exhibit bent DNA conformations that interfere with recombinase binding and/or catalysis.

Engineering ZFRs to Recombine User-Defined Sequences

Figure 33:
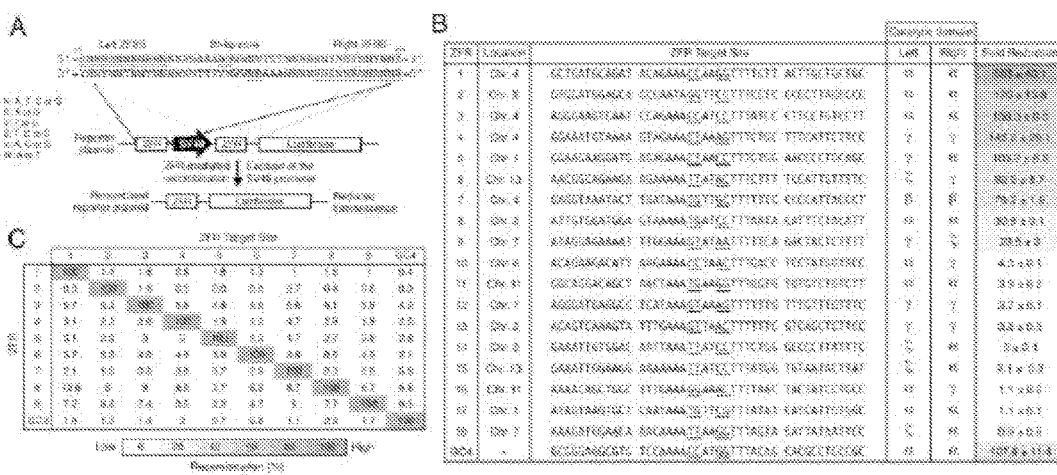
FIG. 33 is a series of graphical and diagrammatic representations illustrating the ability of ZFRs to recombine user-defined sequences in mammalian cells. A) Schematic representation of the luciferase reporter system used to evaluate ZFR activity in mammalian cells. ZFR target sites flank an SV40 promoter that drives luciferase expression. Solid lines denote the 44-bp consensus target sequence used to identify potential ZFR target sites. Underlined bases indicate zinc-finger targets and positions 3 and 2 (SEQ ID NO: 343). B) Fold-reduction of luciferase expression in HEK293T cells co-transfected with designed ZFR pairs and their cognate reporter plasmid. Fold-reduction was normalized to transfection with empty vector and reporter plasmid. The sequence identity and chromosomal location of each ZFR target site (SEQ ID NOs: 344-362 top to bottom) and the catalytic domain composition of each ZFR pair are shown. Underlined bases indicate positions 3 and 2. Standard errors were calculated from three independent experiments. ZFR amino acid sequences are provided in Table 2. C) Specificity of ZFR pairs. Fold-reduction of luciferase expression was measured for ZFR pairs 1 through 9 and GinC4 for each non-cognate reporter plasmid. Recombination was normalized to the fold-reduction of each ZFR pair with its cognate reporter plasmid. Assays were performed in triplicate.

Whether ZFRs composed of the re-engineered catalytic domains could recombine pre-determined sequences was investigated. To test this possibility, the human genome (GRCh37 primary reference assembly) was searched for potential ZFR target sites using a 44-bp consensus recombination site predicted to occur approximately once every 400,000 bp of random DNA (FIG. 4A). This ZFR consensus target site, which was derived from the core sequence profiles of the selected Gin variants, includes approximately $7 \times 10^8$ (of a possible $1.0955 \times 10^{12}$) unique 20-bp core combinations predicted to be tolerated by the 21 possible catalytic domain combinations and a conservative selection of modular zinc finger domains that excludes 5'-CNN-3' and 5'-TNN-3' triplets within each ZFBS. Using ZFP specificity as the primary determinant for selection, 18 possible ZFR target sites across 8 human chromosomes (Chr. 1, 2, 4, 6, 7, 11, 13 and X) at non-protein coding loci were identified. On average, each 20-bp core showed ~46% sequence identity to the core sequence recognized by the native Gin catalytic domain (FIG. 33B). Each corresponding ZFR was constructed by modular assembly (see Materials and Methods).

Figure 39:
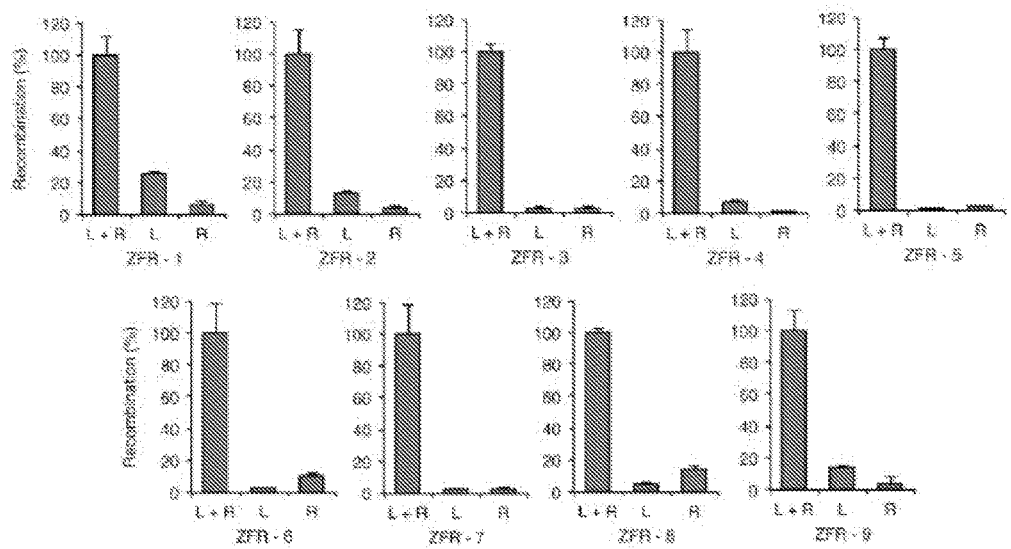
FIG. 39 is a series of graphical representations of ZFR homodimer activity. HEK293T cells were co-transfected with 150 ng ZFR-L or 150 ng ZFR-R with 2.5 ng of corresponding pGL3 ZFR reporter plasmid. Recombination was normalized to co-transfection with 150 ng ZFR-L and 150 ng ZFR-R with 2.5 ng pGL3 ZFR reporter plasmid.
Figure 40:
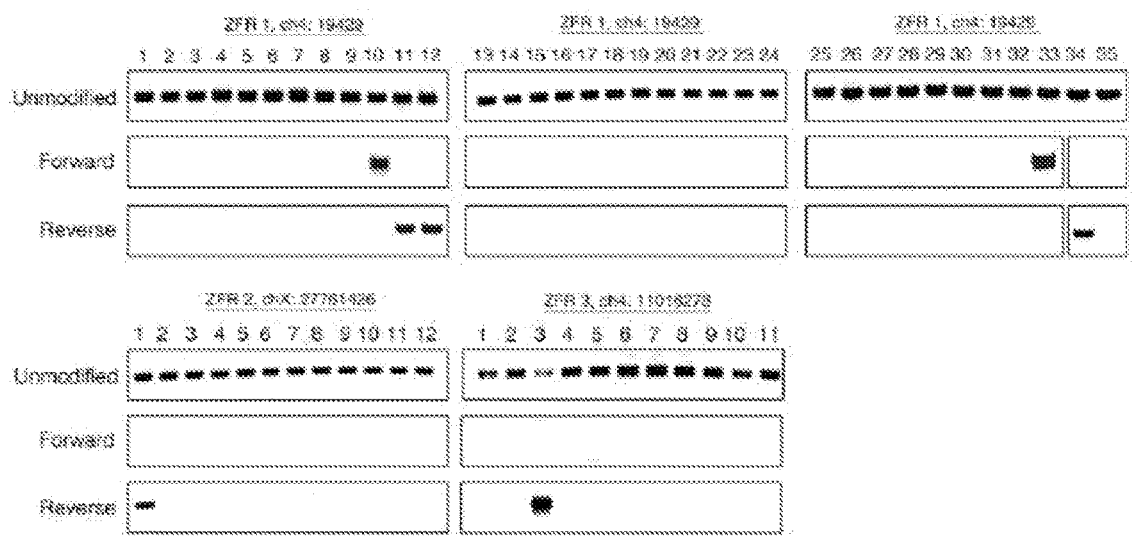
FIG. 40 is a series of pictorial representations depicting clonal analysis of ZFR-modified cells. PCR primer combinations amplified either unmodified genomic target or integrated plasmid in the forward or reverse orientation.

To determine whether each ZFR pair could recombine its intended DNA target, a transient reporter assay was developed that correlates ZFR-mediated recombination to reduced luciferase expression (FIGS. 33A and 39). To accomplish this, ZFR target sites were introduced upstream and downstream an SV40 promoter that drives expression of a luciferase reporter gene. Human embryonic kidney (HEK) 293T cells were co-transfected with expression vectors for each ZFR pair and its corresponding reporter plasmid. Luciferase expression was measured 48 hr after transfection. Of the 18 ZFR pairs analyzed, 38% (7 of 18) reduced luciferase expression by >75-fold and 22% (4 of 18) decreased luciferase expression by >140-fold (FIG. 33B). In comparison, GinC4, a positive ZFR control designed to target the core sequence recognized by the native Gin catalytic domain, reduced luciferase expression by 107 fold. Overall, it was found that 50% (9 of 18) of the evaluated ZFR pairs decreased luciferase expression by at least 20-fold. Importantly, virtually every catalytic domain that displayed significant activity in bacterial cells (>20% recombination) was successfully used to recombine at least one naturally occurring sequence in mammalian cells.

In order to evaluate ZFR specificity, separately HEK293T cells were co-transfected with expression plasmids for the nine most active ZFRs with each non-cognate reporter plasmid. Each ZFR pair demonstrated high specificity for its intended DNA target and 77% (7 of 9) of the evaluated ZFRs showed an overall recombination specificity nearly identical to that of the positive control GinC4 (FIG. 4C). To establish that reduced luciferase expression is the product of the intended ZFR heterodimer and not the byproduct of recombination-competent ZFR homodimers, the contribution of each ZFR monomer to recombination was measured. Co-transfection of the ZFR 1 'left' monomer with its corresponding reporter plasmid led to a modest reduction in luciferase expression (total contribution to recombination: ~22%), but the vast majority of individual ZFR monomers (16 of 18) did not significantly contribute to recombination (<10% recombination), and many (7 of 18) showed no activity (FIG. 39). Taken together, these studies indicate that ZFRs can be engineered to recombine user-defined sequences with high specificity.

Engineered ZFRs mediate targeted integration into the human genome.

Figure 34:
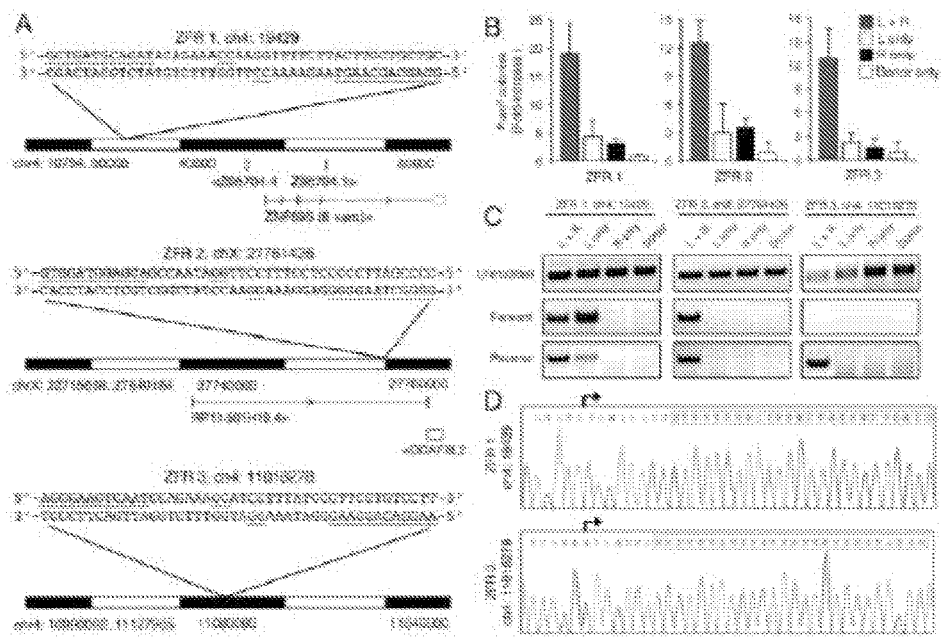
FIG. 34 is a series of graphical and diagrammatic representations illustrating ZFRs ability to target integration into the human genome. A) Schematic representation of the donor plasmid (top) and the genomic loci targeted by ZFRs 1 (SEQ ID NO: 363), 2 (SEQ ID NO: 364), and 3 (SEQ ID NO: 365). Open boxes indicate neighboring exons. Arrows indicate transcript direction. The sequence and location of each ZFR target are shown. Underlined bases indicate zinc-finger targets and positions 3 and 2. B) Efficiency of ZFR-mediated integration. Data were normalized to data from cells transfected with donor plasmid only. Error bars indicate standard deviation (n=3). C) PCR analysis of ZFR-mediated integration. PCR primer combinations amplified (top) unmodified locus or integrated plasmid in (middle) the forward or (bottom) the reverse orientation. D) Representative chromatograms of PCR-amplified integrated donor for ZFRs 1 (SEQ ID NO: 366) and 3 (SEQ ID NO: 367). Arrows indicate sequencing primer orientation. Shaded boxes denote genomic target sequences.

Whether ZFRs could integrate DNA into endogenous loci in human cells was evaluated next. To accomplish this, HEK293 cells were co-transfected with ZFR expression vectors and a corresponding DNA donor plasmid that contained a specific ZFR target site and a puromycin-resistance gene under the control of an SV40 promoter. For this analysis, ZFR pairs 1, 2, and 3, were used which were designed to target non-protein coding loci on human chromosomes 4, X, and 4, respectively (FIG. 34A). At 2 days post-transfection, cells were incubated with puromycin-containing media and measured integration efficiency by determining the number of puromycin-resistant (puro$^R$) colonies. It was found that (i) co-transfection of the donor plasmid and the corresponding ZFR pair led to a >12-fold increase in puro$^R$ colonies in comparison to transfection with donor plasmid only and that (ii) co-transfection with both ZFRs led to a 6- to 9 fold increase in puro$^R$ colonies in comparison to transfection with individual ZFR monomers (FIG. 34B). In order to evaluate whether ZFR pairs correctly targeted integration, genomic DNA was isolated from puro$^R$ populations and amplified each targeted locus by PCR. The PCR products corresponding to integration in the forward and/or reverse orientations were observed at each locus targeted by these ZFR pairs (FIG. 34C). Next, to determine the overall specificity of ZFR-mediated integration, genomic DNA was isolated from clonal cell populations and evaluated plasmid insertion by PCR. This analysis revealed targeting efficiencies of 8.3% (1 of 12 clones), 14.2% (5 of 35 clones), and 9.1% (1 of 11 clones) for ZFR pairs 1, 2, and 3, respectively (FIG. S6). Sequence analysis of each PCR product confirmed ZFR-mediated integration (FIG. 34D). Taken together, these results indicate that ZFRs can be designed to accurately integrate DNA into endogenous loci.

Finally, it is noted that the ZFR-1 'left' monomer was found to target integration into the ZFR-1 locus (FIG. 34C). This result, which is consistent with the luciferase reporter studies described above (FIG. 39) indicates that recombination-competent ZFR homodimers have the capacity to mediate off-target integration. Future development of an optimized heterodimeric ZFR architecture and a comprehensive evaluation of off-target integration should lead to the design of ZFRs that demonstrate greater targeting efficiency.

It is herein shown that ZFRs can be designed to recombine user-defined sequences with high specificity and that ZFRs can integrate DNA into pre-determined endogenous loci in human cells. By combining substrate specificity analysis and directed evolution, virtually all sequence requirements imposed by the ZFR catalytic domain were eliminated. Using the archive of 45 pre-selected zinc-finger modules, it is estimated that ZFRs can be designed to recognize $>1 \times 10^{22}$ unique 44-bp DNA sequences, which corresponds to approximately one potential ZFR target site for every 4,000 bp of random sequence. Construction of customized zinc-finger domains by selection would further extend targeting. The re-engineered catalytic domains described herein will be compatible with recently described TAL effector recombinases. This work demonstrates the feasibility of generating ZFRs with custom specificity and illustrates the potential utility of ZFRs for a wide range of applications, including genome engineering, synthetic biology, and gene therapy.

Although the invention has been described with reference to the above example, it will be understood that modifications and variations are encompassed within the spirit and scope of the invention. Accordingly, the invention is limited only by the following claims.

What is claimed is:

1. An isolated polypeptide comprising a *Xanthamonus* derived transcription activator-like effector (TALE) protein, the TALE protein having an N-terminal domain (NTD) comprising the amino acid sequence as set forth in SEQ ID NO: 3 (VGKQWSGARAL) having one or more mutations selected from: Q is Y, Q is S, Q is R, W is G, W is deleted, S is R, S is H, S is A, S is N, and S is T.

2. The polypeptide of claim 1, wherein the NTD comprises an amino acid sequence selected from: VGKYRGARAL (SEQ ID NO: 4), VGKYHGARAL (SEQ ID NO: 6), and VGKRGAGARAL (SEQ ID NO: 7).

3. The polypeptide of claim 1 further comprising a recombinase domain or a nuclease domain.

4. The polypeptide of claim 1, comprising a C-terminal or N-terminal truncation relative to the wildtype TALE protein.

5. The polypeptide of claim 1, wherein the TALE protein is derived from AvrXa7, Tal1c, or PthXo1.

6. The polypeptide of claim 1, wherein the TALE protein is derived from AvrXa7 and is truncated at amino acid residue 28, 74, 87, 92, 95, 120, 124, 128, 129, 147 or 150.

7. An isolated nucleic acid molecule encoding the polypeptide of claim 1.

8. The polypeptide of claim 3, wherein the recombinase domain is selected from the group consisting of Gin, Hin, Tn3, Sin, Beta, Pin, Min, Din, and Cin, muteins of Gin, muteins of Hin, muteins of Tn3, muteins of Sin, muteins of Beta, muteins of Pin, muteins of Min, muteins of Din, and muteins of Cin.

9. The polypeptide of claim 1, wherein the TALE protein further comprises a synthetic repeat variable di-residues (RVD) domain.

* * * * *

UNITED STATES PATENT AND TRADEMARK OFFICE
CERTIFICATE OF CORRECTION

PATENT NO. : 9,902,962 B2
APPLICATION NO. : 14/425944
DATED : February 27, 2018
INVENTOR(S) : Barbas, III et al.

It is certified that error appears in the above-identified patent and that said Letters Patent is hereby corrected as shown below:

In the Specification

Column 3, Line 25:
AcrXa7
Should be changed to:
--AvrXa7--

Column 3, Line 46:
Xanthamonus
Should be changed to:
--Xanthomonas--

In the Claims

Column 301, Line 46:
Xanthamonus
Should be changed to:
--Xanthomonas--

Signed and Sealed this
Fifteenth Day of May, 2018

Andrei Iancu
*Director of the United States Patent and Trademark Office*

UNITED STATES PATENT AND TRADEMARK OFFICE
CERTIFICATE OF CORRECTION

PATENT NO. : 9,902,962 B2
APPLICATION NO. : 14/425944
DATED : February 27, 2018
INVENTOR(S) : Barbas et al.

Page 1 of 1

It is certified that error appears in the above-identified patent and that said Letters Patent is hereby corrected as shown below:

In the Specification

Column 1, Line 13, insert the paragraph below:
-- STATEMENT OF GOVERNMENT LICENSE RIGHTS
This invention was made with government support under grant numbers OD006990, CA174426, and GM065059 awarded by The National Institutes of Health. The government has certain rights in the invention. --

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 369

<210> SEQ ID NO 1
<211> LENGTH: 864
<212> TYPE: DNA
<213> ORGANISM: Artificial Sequence
<220> FEATURE:
<223> OTHER INFORMATION: Synthetic construct

<400> SEQUENCE: 1
atggatccca ttcgttcgcg cacgccaagt cctgcccgcg agcttctgcc cggaccccaa      60
ccggataggg ttcagccgac tgcagatcgg ggggggctc cgcctgctgg cggcccctg     120 gatggcttgc ccgctcggcg gacgatgtcc cggacccggt tgccatctcc ccctgcgccc     180
tcgcctgcgt tctcggcggg cagcttcagc gatctgctcc gtcagttcga tccgtcgctt     240
cttgatacat cgcttcttga ttcgatgcct gccgtcggca cgccgcatac agcggctgcc     300
ccagcagagt gcgatgaggt gcaatcgggt ctgcgtgcag ccgatgaccc gccacccacc     360
gtgcgtgtcg ctgtcactgc ggcgcggccg ccgcgcgcca agccggcccc gcgacggcgt     420
gcggcgcaac cctccgacgc ttcgccggcc gcgcaggtgg atctacgcac gctcggctac     480
agtcagcagc agcaagagaa gatcaaaccg aaggtgcgtt cgacagtggc gcagcaccac     540
gaggcactgg tgggccatgg gtttacacac gcgcacatcg ttgcgctcag ccaacacccg     600
gcagcgttag ggaccgttgc tgtcacgtat caggacataa tcagggcgtt gccagaggcg     660
acacacgaag acatcgttgg cgtcggcaaa cagtggtccg gcgcacgcgc tctggaggcc     720
ttgctcacgg aggcggggga gttgagaggt ccgccgttac agttggacac aggccaactt     780
ctcaagattg caaaacgtgg cggcgtgacc gcagtggagg cagtgcatgc atggcgcaat     840
gcactgacgg gtgcccccct gaac                                          864

<210> SEQ ID NO 2
<211> LENGTH: 288
<212> TYPE: PRT
<213> ORGANISM: Artificial Sequence
<220> FEATURE:
<223> OTHER INFORMATION: Synthetic construct

<400> SEQUENCE: 2

Met Asp Pro Ile Arg Ser Arg Thr Pro Ser Pro Ala Arg Glu Leu Leu
1               5                   10                  15

Pro Gly Pro Gln Pro Asp Arg Val Gln Pro Thr Ala Asp Arg Gly Gly
            20                  25                  30

Ala Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Gly Ser Phe Ser Asp Leu Leu Arg Gln Phe Asp Pro Ser Leu
65                  70                  75                  80

Leu Asp Thr Ser Leu Leu Asp Ser Met Pro Ala Val Gly Thr Pro His
```

```
                    85                  90                  95
Thr Ala Ala Ala Pro Ala Glu Cys Asp Glu Val Gln Ser Gly Leu Arg
                100                 105                 110
Ala Ala Asp Asp Pro Pro Thr Val Arg Val Ala Val Thr Ala Ala
            115                 120                 125
Arg Pro Pro Arg Ala Lys Pro Ala Arg Arg Ala Ala Gln Pro
        130                 135                 140
Ser Asp Ala Ser Pro Ala Ala Gln Val Asp Leu Arg Thr Leu Gly Tyr
145                 150                 155                 160
Ser Gln Gln Gln Gln Glu Lys Ile Lys Pro Lys Val Arg Ser Thr Val
                165                 170                 175
Ala Gln His His Glu Ala Leu Val Gly His Gly Phe Thr His Ala His
                180                 185                 190
Ile Val Ala Leu Ser Gln His Pro Ala Ala Leu Gly Thr Val Ala Val
                195                 200                 205
Thr Tyr Gln Asp Ile Ile Arg Ala Leu Pro Glu Ala Thr His Glu Asp
210                 215                 220
Ile Val Gly Val Gly Lys Gln Trp Ser Gly Ala Arg Ala Leu Glu Ala
225                 230                 235                 240
Leu Leu Thr Glu Ala Gly Glu Leu Arg Gly Pro Pro Leu Gln Leu Asp
                245                 250                 255
Thr Gly Gln Leu Leu Lys Ile Ala Lys Arg Gly Gly Val Thr Ala Val
                260                 265                 270
Glu Ala Val His Ala Trp Arg Asn Ala Leu Thr Gly Ala Pro Leu Asn
                275                 280                 285

<210> SEQ ID NO 3
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Y, S or R
<220> FEATURE:
<221> NAME/KEY: MISC_FEATURE
<222> LOCATION: (5)..(5)
<223> OTHER INFORMATION: Xaa is R or G
<220> FEATURE:
<221> NAME/KEY: MISC_FEATURE
<222> LOCATION: (6)..(6)
<223> OTHER INFORMATION: Xaa is R, H, A, N or T

<400> SEQUENCE: 3

Val Gly Lys Xaa Xaa Xaa Gly Ala Arg Ala Leu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic construct

<400> SEQUENCE: 4

Val Gly Lys Tyr Arg Gly Ala Arg Ala Leu
1               5                   10

<210> SEQ ID NO 5
<211> LENGTH: 11
```

```
<212> TYPE: PRT
<213> ORGANISM: Artificial Sequence
<220> FEATURE:
<223> OTHER INFORMATION: Synthetic construct

<400> SEQUENCE: 5

Val Gly Lys Ser Arg Ser Gly Ala Arg Ala Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic construct

<400> SEQUENCE: 6

Val Gly Lys Tyr His Gly Ala Arg Ala Leu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic construct

<400> SEQUENCE: 7

Val Gly Lys Arg Gly Ala Gly Ala Arg Ala Leu
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa is Y, S or R
<220> FEATURE:
<221> NAME/KEY: MISC_FEATURE
<222> LOCATION: (8)..(8)
<223> OTHER INFORMATION: Xaa is W or G
<220> FEATURE:
<221> NAME/KEY: MISC_FEATURE
<222> LOCATION: (9)..(9)
<223> OTHER INFORMATION: Xaa is R, H, A, N or T

<400> SEQUENCE: 8

Ile Val Asp Ile Ala Lys Xaa Xaa Xaa Gly Asp Leu Ala
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic construct

<400> SEQUENCE: 9

Ile Val Asp Ile Ala Arg Gln Trp Ser Gly Asp Leu Ala
1               5                   10

<210> SEQ ID NO 10
<211> LENGTH: 12
<212> TYPE: PRT
<213> ORGANISM: Artificial Sequence
```

```
<220> FEATURE:
<223> OTHER INFORMATION: Synthetic construct

<400> SEQUENCE: 10

Ile Val Asp Ile Ala Arg Tyr Arg Gly Asp Leu Ala
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic construct

<400> SEQUENCE: 11

Ile Val Asp Ile Ala Arg Ser Arg Ser Gly Asp Leu Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic construct

<400> SEQUENCE: 12

Ile Val Asp Ile Ala Arg Tyr His Gly Asp Leu Ala
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic construct

<400> SEQUENCE: 13

Ile Val Asp Ile Ala Arg Arg Gly Ala Gly Asp Leu Ala
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(6)
<223> OTHER INFORMATION: Xaa can be any naturally occurring amino acid

<400> SEQUENCE: 14

Val Gly Lys Xaa Xaa Xaa Gly Ala Arg
1               5

<210> SEQ ID NO 15
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(8)
<223> OTHER INFORMATION: Xaa can be any naturally occurring amino acid

<400> SEQUENCE: 15

Val Asp Ile Ala Xaa Xaa Xaa Xaa Gly Asp Leu Ala
```

<210> SEQ ID NO 16
<211> LENGTH: 48
<212> TYPE: PRT
<213> ORGANISM: Artificial Sequence
<220> FEATURE:
<223> OTHER INFORMATION: Synthetic construct

<400> SEQUENCE: 16

Asn Ile His Gly Asn Ile Asn Ile Asn Ser His Asp Asn Asn His Asp
1               5                   10                  15

His Asp His Asp Asn Ser Asn Asn His Asp His Asp Asn Ser Asn Ser
            20                  25                  30

Asn Asn Asn Asn Asn Ile Asn Gly Asn Asn Asn Ile Asn Asn Ser Asn
        35                  40                  45

<210> SEQ ID NO 17
<211> LENGTH: 26
<212> TYPE: DNA
<213> ORGANISM: Artificial Sequence
<220> FEATURE:
<223> OTHER INFORMATION: Synthetic construct

<400> SEQUENCE: 17
ataaaccccc tccaaccagg tgctaa                                          26

<210> SEQ ID NO 18
<211> LENGTH: 52
<212> TYPE: PRT
<213> ORGANISM: Artificial Sequence
<220> FEATURE:
<223> OTHER INFORMATION: Synthetic construct

<400> SEQUENCE: 18

Asn Ile Asn Gly Asn Ile Asn Ile Asn Ile His Asp His Asp His Asp
1               5                   10                  15

His Asp His Asp Asn Gly His Asp His Asp Asn Ile Asn Ile His Asp
            20                  25                  30

His Asp Asn Ile Asn Asn Asn Asn Gly Asn Asn His Asp Asn Gly
        35                  40                  45

Asn Ile Asn Ile
    50

<210> SEQ ID NO 19
<211> LENGTH: 1446
<212> TYPE: PRT
<213> ORGANISM: Artificial Sequence
<220> FEATURE:
<223> OTHER INFORMATION: Synthetic construct

<400> SEQUENCE: 19

Met Asp Pro Ile Arg Ser Arg Thr Pro Ser Pro Ala Arg Glu Leu Leu
1               5                   10                  15

Pro Gly Pro Gln Pro Asp Arg Val Gln Pro Thr Ala Asp Arg Gly Gly
            20                  25                  30

Ala Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Gly Ser Phe Ser Asp Leu Leu Arg Gln Phe Asp Pro Ser Leu
65                  70                  75                  80

```
Leu Asp Thr Ser Leu Leu Asp Ser Met Pro Ala Val Gly Thr Pro His
            85                  90                  95
Thr Ala Ala Ala Pro Ala Glu Cys Asp Glu Val Gln Ser Gly Leu Arg
           100                 105                 110
Ala Ala Asp Asp Pro Pro Thr Val Arg Val Ala Val Thr Ala Ala
           115                 120                 125
Arg Pro Pro Arg Ala Lys Pro Ala Pro Arg Arg Ala Ala Gln Pro
130                 135                 140
Ser Asp Ala Ser Pro Ala Ala Gln Val Asp Leu Arg Thr Leu Gly Tyr
145                 150                 155                 160
Ser Gln Gln Gln Gln Glu Lys Ile Lys Pro Lys Val Arg Ser Thr Val
                165                 170                 175
Ala Gln His His Glu Ala Leu Val Gly His Gly Phe Thr His Ala His
                180                 185                 190
Ile Val Ala Leu Ser Gln His Pro Ala Ala Leu Gly Thr Val Ala Val
                195                 200                 205
Thr Tyr Gln Asp Ile Ile Arg Ala Leu Pro Glu Ala Thr His Glu Asp
        210                 215                 220
Ile Val Gly Val Gly Lys Gln Trp Ser Gly Ala Arg Ala Leu Glu Ala
225                 230                 235                 240
Leu Leu Thr Glu Ala Gly Glu Leu Arg Gly Pro Pro Leu Gln Leu Asp
                245                 250                 255
Thr Gly Gln Leu Leu Lys Ile Ala Lys Arg Gly Gly Val Thr Ala Val
                260                 265                 270
Glu Ala Val His Ala Trp Arg Asn Ala Leu Thr Gly Ala Pro Leu Asn
                275                 280                 285
Leu Thr Pro Asp Gln Val Val Ala Ile Ala Ser Asn Ile Gly Gly Lys
        290                 295                 300
Gln Ala Leu Glu Thr Val Gln Arg Leu Leu Pro Val Leu Cys Gln Asp
305                 310                 315                 320
His Gly Leu Thr Pro Asp Gln Val Val Ala Ile Ala Ser His Gly Gly
                325                 330                 335
Gly Lys Gln Ala Leu Glu Thr Val Gln Arg Leu Leu Pro Val Leu Cys
                340                 345                 350
Gln Asp His Gly Leu Thr Pro Asp Gln Val Val Ala Ile Ala Ser Asn
                355                 360                 365
Ile Gly Gly Lys Gln Ala Leu Glu Thr Val Gln Arg Leu Leu Pro Val
        370                 375                 380
Leu Cys Gln Ala His Gly Leu Thr Pro Asp Gln Val Val Ala Ile Ala
385                 390                 395                 400
Ser Asn Ile Gly Gly Lys Gln Ala Leu Glu Thr Val Gln Arg Leu Leu
                405                 410                 415
Pro Val Leu Cys Gln Asp His Gly Leu Thr Pro Ala Gln Val Val Ala
                420                 425                 430
Ile Ala Ser Asn Ser Gly Gly Lys Gln Ala Leu Glu Thr Val Gln Arg
                435                 440                 445
Leu Leu Pro Val Leu Cys Gln Asp His Gly Leu Thr Pro Asp Gln Val
        450                 455                 460
Val Ala Ile Ala Ser His Asp Gly Gly Lys Gln Ala Leu Glu Thr Leu
465                 470                 475                 480
Gln Arg Leu Leu Pro Val Leu Cys Gln Asp His Gly Leu Thr Pro Asp
                485                 490                 495
```

-continued

```
Gln Val Val Ala Ile Ala Asn Asn Asn Gly Gly Lys Gln Ala Leu Glu
            500                 505                 510
Thr Leu Gln Arg Leu Leu Pro Val Leu Cys Gln Asp His Gly Leu Thr
        515                 520                 525
Pro Asp Gln Val Val Ala Ile Ala Ser His Asp Gly Gly Lys Gln Ala
    530                 535                 540
Leu Glu Thr Val Gln Arg Leu Leu Pro Val Leu Cys Gln Asp His Gly
545                 550                 555                 560
Leu Thr Pro Asp Gln Val Val Ala Ile Ala Ser His Asp Gly Gly Lys
                565                 570                 575
Gln Ala Leu Glu Thr Val Gln Arg Leu Leu Pro Val Leu Cys Gln Asp
            580                 585                 590
His Gly Leu Thr Pro Ala Gln Val Val Ala Ile Ala Ser His Asp Gly
        595                 600                 605
Gly Lys Gln Ala Leu Glu Thr Val Gln Arg Leu Leu Pro Val Leu Cys
    610                 615                 620
Gln Asp His Gly Leu Thr Pro Asp Gln Val Val Ala Ile Ala Ser Asn
625                 630                 635                 640
Ser Gly Gly Lys Gln Ala Leu Glu Thr Val Gln Arg Leu Leu Pro Val
                645                 650                 655
Leu Cys Gln Asp His Gly Leu Thr Pro Asp Gln Val Val Ala Ile Ala
            660                 665                 670
Ser Asn Gly Gly Lys Gln Ala Leu Glu Thr Val Gln Arg Leu Leu Pro
        675                 680                 685
Val Leu Cys Gln Asp His Gly Leu Thr Pro Asp Gln Val Val Ala Ile
    690                 695                 700
Ala Ser Asn Gly Gly Lys Gln Ala Leu Glu Thr Val Gln Arg Leu Leu
705                 710                 715                 720
Pro Val Gln Arg Leu Leu Pro Val Leu Cys Gln Asp His Gly Leu Thr
                725                 730                 735
Gln Asp Gln Val Val Ala Ile Ala Ser His Asp Gly Gly Lys Gln Ala
            740                 745                 750
Leu Glu Thr Val Gln Arg Leu Leu Pro Val Leu Cys Gln Asp His Gly
        755                 760                 765
Leu Thr Pro Asp Gln Val Val Ala Ile Ala Ser His Asp Gly Gly Lys
    770                 775                 780
Gln Ala Leu Glu Thr Val Gln Arg Leu Leu Pro Val Leu Cys Gln Asp
785                 790                 795                 800
His Gly Leu Thr Pro Asp Gln Val Val Ala Ile Ala Ser Asn Ser Gly
                805                 810                 815
Gly Lys Gln Ala Leu Glu Thr Val Gln Arg Leu Leu Pro Val Leu Cys
            820                 825                 830
Gln Asp His Gly Leu Thr Pro Asp Gln Val Val Ala Ile Ala Ser Asn
        835                 840                 845
Ser Gly Gly Lys Gln Ala Leu Glu Thr Val Gln Arg Leu Leu Pro Val
    850                 855                 860
Leu Cys Gln Asp His Gly Leu Thr Pro Asp Gln Val Val Ala Ile Ala
865                 870                 875                 880
Ser Asn Asn Gly Gly Lys Gln Ala Leu Glu Thr Val Gln Arg Leu Leu
                885                 890                 895
Pro Val Leu Cys Gln Asp His Gly Leu Thr Pro Asp Gln Val Val Ala
            900                 905                 910
Ile Ala Asn Asn Asn Gly Gly Lys Gln Ala Leu Glu Thr Val Gln Arg
```

-continued

```
            915                 920                925
Leu Leu Pro Val Leu Cys Gln Asp His Gly Leu Thr Pro Ala Gln Val
        930                935                 940
Val Ala Ile Ala Ser Asn Ile Gly Gly Lys Gln Ala Leu Glu Thr Val
945                 950                 955                 960
Gln Arg Leu Leu Pro Val Leu Cys Gln Asp His Gly Leu Thr Leu Asp
                965                 970                 975
Gln Val Val Ala Ile Ala Ser Asn Gly Gly Ser Lys Gln Ala Leu Glu
            980                 985                 990
Thr Val Gln Arg Leu Leu Pro Val Leu Cys Gln Asp His Gly Leu Thr
                995                1000                1005
Pro Asp Gln Val Val Ala Ile Ala Asn Asn Asn Gly Gly Lys Gln
    1010                1015                1020
Ala Leu Glu Thr Val Gln Arg Leu Leu Pro Val Leu Cys Gln Asp
    1025                1030                1035
His Gly Leu Thr Pro Asp Gln Val Val Ala Ile Ala Ser Asn Ile
    1040                1045                1050
Gly Gly Lys Gln Ala Leu Glu Thr Val Gln Arg Leu Leu Pro Val
    1055                1060                1065
Leu Cys Gln Asp His Gly Leu Thr Leu Asp Gln Val Val Ala Ile
    1070                1075                1080
Ala Ser Asn Gly Gly Lys Ala Leu Glu Thr Val Gln Arg Leu
    1085                1090                1095
Leu Pro Val Leu Cys Gln Asp His Gly Leu Thr Pro Asn Gln Val
    1100                1105                1110
Val Ala Ile Ala Ser Asn Ser Gly Gly Lys Gln Ala Leu Glu Thr
    1115                1120                1125
Val Gln Arg Leu Leu Pro Val Leu Cys Gln Asp His Gly Leu Thr
    1130                1135                1140
Pro Asn Gln Val Val Ala Ile Ala Ser Asn Gly Gly Lys Gln Ala
    1145                1150                1155
Leu Glu Ser Ile Val Ala Gln Leu Ser Arg Pro Asp Pro Ala Leu
    1160                1165                1170
Ala Ala Leu Thr Asn Asp His Leu Val Ala Leu Ala Cys Leu Gly
    1175                1180                1185
Gly Arg Pro Ala Leu Asp Ala Val Lys Lys Gly Leu Pro His Ala
    1190                1195                1200
Pro Glu Leu Ile Arg Arg Ile Asn Arg Arg Ile Pro Glu Arg Thr
    1205                1210                1215
Ser His Arg Val Pro Asp Leu Ala His Val Val Arg Val Leu Gly
    1220                1225                1230
Phe Phe Gln Ser His Ser His Pro Ala Gln Ala Phe Asp Asp Ala
    1235                1240                1245
Met Thr Gln Phe Glu Met Ser Arg His Gly Leu Val Gln Leu Phe
    1250                1255                1260
Arg Arg Val Gly Val Thr Glu Phe Glu Ala Arg Tyr Gly Thr Leu
    1265                1270                1275
Pro Pro Ala Ser Gln Arg Trp Asp Arg Ile Leu Gln Ala Ser Gly
    1280                1285                1290
Met Lys Arg Ala Lys Pro Ser Pro Thr Ser Ala Gln Thr Pro Asp
    1295                1300                1305
Gln Ala Ser Leu His Ala Phe Ala Asp Ser Leu Glu Arg Asp Leu
    1310                1315                1320
```

```
Asp Ala Pro Ser Pro Met His Glu Gly Asp Gln Thr Arg Ala Ser
        1325                1330                1335

Ser Arg Lys Arg Ser Arg Ser Asp Arg Ala Val Thr Gly Pro Ser
    1340                1345                1350

Thr Gln Gln Ser Phe Glu Val Arg Val Pro Glu Gln Gln Asp Ala
    1355                1360                1365

Leu His Leu Pro Leu Ser Trp Arg Val Lys Arg Pro Arg Thr Arg
    1370                1375                1380

Ile Gly Gly Gly Leu Pro Asp Pro Gly Thr Pro Ile Ala Ala Asp
1385                1390                1395

Leu Ala Ala Ser Ser Thr Val Met Trp Glu Gln Asp Ala Ala Pro
    1400                1405                1410

Phe Ala Gly Ala Ala Asp Asp Phe Pro Ala Phe Asn Glu Glu Glu
    1415                1420                1425

Leu Ala Trp Leu Met Glu Leu Leu Pro Gln Ser Gly Ser Val Gly
    1430                1435                1440

Gly Thr Ile
    1445

<210> SEQ ID NO 20
<211> LENGTH: 4341
<212> TYPE: DNA
<213> ORGANISM: Artificial Sequence
<220> FEATURE:
<223> OTHER INFORMATION: Synthetic construct

<400> SEQUENCE: 20
atggatccca ttcgttcgcg cacgccaagt cctgcccgcg agcttctgcc cggaccccaa      60
ccggataggg ttcagccgac tgcagatcgg gggggggctc cgcctgctgg cggcccccctg    120 gatggcttgc ccgctcggcg gacgatgtcc cggacccggc tgccatctcc ccctgcgccc    180
tcgcctgcgt tctcggcggg cagcttcagc gatctgctcc gtcagttcga tccgtcgctt    240
cttgatacat cgcttcttga ttcgatgcct gccgtcggca cgccgcatac agcggctgcc    300
ccagcagagt gcgatgaggt gcaatcgggt ctgcgtgcag ccgatgaccc gccacccacc    360
gtgcgtgtcg ctgtcactgc ggcgcggccg ccgcgcgcca agccggcccc gcgacggcgt    420
gcggcgcaac cctccgacgc ttcgccggcc gcgcaggtgg atctacgcac gctcggctac    480
agtcagcagc agcaagagaa gatcaaaccg aaggtgcgtt cgacagtggc gcagcaccac    540
gaggcactgg tgggccatgg gtttacacac gcgcacatcg ttgcgctcag ccaacacccg    600
gcagcgttag ggaccgttgc tgtcacgtat caggacataa tcagggcgtt gccagaggcg    660
acacacgaag acatcgttgg cgtcggcaaa cagtggtccg gcgcacgcgc tctggaggcc    720
ttgctcacgg aggcggggga gttgagaggt ccgccgttac agttggacac aggccaactt    780
ctcaagattg caaaacgtgg cggcgtgacc gcagtggagg cagtgcatgc atggcgcaat    840
gcactgacgg gtgccccccct gaacctgacc ccggaccaag tggtggccat cgccagcaat    900
attggcggca agcaggcgct ggagacggta cagcggctgt tgccggtgct gtgccaggac    960
catggcctga ccccggacca ggtcgtggcc atcgccagcc atggcggcgg caagcaggcg   1020
ctggagacgg tgcagcggct gttgccggtg ctgtgccagg accatggcct gaccccggac   1080
caggtggtgg ccatcgccag caatattggc ggcaagcagg cgctagagac ggtgcagcgg   1140
ctgttgccgg tgctgtgcca ggcccatggc ctgaccccgg accaggtcgt ggccatcgcc   1200
agcaatattg gcggcaagca ggcgctggag acggtgcagc ggctgttgcc ggtgctgtgc   1260
```

```
caggaccatg gcctgacccc ggcccaggtg gtggccatcg ccagcaatag tggcggcaag    1320
caggcgctgg agacggtgca gcggctgttg ccggtgctgt gccaggacca tggcctgacc    1380
ccggaccaag tcgtggccat cgccagccac gatggcggca agcaggcgct ggagacgctg    1440
cagcggctgt tgccggtgct gtgccaggac catggcctga ccccggacca ggtcgtggcc    1500
atcgccaaca taacggcgg caagcaggcg ctggagacgc tgcagcggct gttgccggtg    1560
ctgtgccagg accatggcct gaccccggac caagtggtgg ccatcgccag ccacgatggc    1620
ggcaagcagg cgctggagac ggtgcagcgg ctgttgccgg tgctgtgcca ggaccatggc    1680
ctgaccccgg accaggtggt ggccatcgcc agccacgatg gcggcaagca ggcgctggag    1740
acggtgcagc ggctgttgcc ggtgctgtgc caggaccatg gcctgacccc ggcccaagtg    1800
gtggccatcg ccagccacga tggcggcaag caggcgctgg agacggtgca gcggctgttg    1860
ccggtgctgt gccaggacca tggcctgacc ccggaccagg tggtggccat cgccagcaat    1920
agcggcggca agcaggcgct ggagacggta gcggctgt tgccggtgct gtgccaggac    1980
catggactga ccccggacca ggtcgtggcc atcgccagca atggcggcaa gcaggcgctg    2040
gagacggtac agcggctgtt gccggtgctg tgccaggacc atggcctgac cccggaccag    2100
gtcgtggcca tcgccagcaa tggcggcaag caggcgctgg agacggtgca gcggctgttg    2160
ccggtacagc ggctgttgcc ggtgctgtgc caggaccatg gcctgaccca ggaccaggtg    2220
gtggccatcg ccagccacga tggcggcaag caggcgctgg agacggtgca gcggctgttg    2280
ccggtgctgt gccaggacca tggcctgacc ccggaccaag tggtggccat cgccagccac    2340
gatgcggca aacaggcgct ggagacggtg cagcggctgt tgccggtgct gtgccaggac    2400
catggcctga ccccggacca ggtggtggcc atcgccagca atagtggcgg caagcaggcg    2460
ctggagacgg tgcagcggct gttgccggtg ctgtgccagg accatggcct gaccccggac    2520
caagtggtgg ccatcgccag caatagtggc ggcaagcagg cgctggagac ggtgcagcgg    2580
ctgttgccgg tgctgtgcca ggaccatggc ctgaccccgg accaggtggt ggccatcgcc    2640
agcaataacg gcggcaagca ggcgctggag acggtcagc ggctgttgcc ggtgctgtgc    2700
caggaccatg gcctgacccc ggaccaggtc gtggccatcg ccaacaataa cggcggcaag    2760
caggcgctgg agacggtgca gcggctgttg ccggtgctgt gccaggacca tggcctgacc    2820
ccggcgcagg tggtggccat cgccagcaat attggcggca agcaggcgct ggagacggtg    2880
cagcggctgt tgccggtgct gtgccaggac catggcctga ccctggacca ggtggtggcc    2940
attgccagca atggcggcag caaacaggcg ctagagacgg tgcagcggct gttgccggtg    3000
ctgtgccagg accatggcct gaccccggac caagtggtgg ccatcgccaa caataacggc    3060
ggcaagcagg cgctggagac ggtgcagcgg ctgttgccgg tgctgtgcca ggaccatggc    3120
ctgaccccgg accaggtcgt ggccatcgcc agcaatattg gcggcaagca ggcgctggag    3180
acggtgcagc ggctgttgcc ggtgctgtgc caggaccatg gcctgaccct ggaccaggtg    3240
gtggccatcg ccagcaatgg cggcaagcag gcgctggaga cggtgcagcg gctgttgccg    3300
gtgctgtgcc aggaccatgg cctgaccccg aaccaggtgg tggccatcgc cagcaatagt    3360
ggcggcaagc aggcgctgga gacggtgcag cggctgttgc cggtgctgtg ccaggaccat    3420
ggcctgaccc cgaaccaggt ggtggccatc gccagcaatg gcggcaagca ggcgctggag    3480
agcattgttg cccagttatc tcgccctgat ccggcgttgg ccgcgttgac caacgaccac    3540
ctcgtcgcct tggcctgcct cggcggacgt cctgccctga tgcagtgaa aaagggattg    3600
```

-continued

```
ccgcacgcgc cggaattgat cagaagaatc aatcgccgca ttcccgaacg cacgtcccat    3660
cgcgttcccg acctcgcgca cgtggttcgc gtgcttggtt ttttccagag ccactcccac    3720
ccagcgcaag cattcgatga cgccatgacg cagttcgaga tgagcaggca cggcttggta    3780
cagctctttc gcagagtggg cgtcaccgaa ttcgaagccc gctacggaac gctcccccca    3840
gcctcgcagc gttgggaccg tatcctccag gcatcaggga tgaaaagggc caaaccgtcc    3900
cctacttcag ctcaaacacc ggatcaggcg tctttgcatg cattcgccga ttcgctggag    3960
cgtgaccttg atgcgcccag cccaatgcac gagggagatc agacgcgggc aagcagccgt    4020
aaacggtccc gatcggatcg tgctgtcacc ggcccctcca cacagcaatc tttcgaggtg    4080
cgcgttcccg aacagcaaga tgcgctgcat ttgcccctca gctggagggt aaaacgcccg    4140
cgtaccagga tcggggggcgg cctcccggat cctggtacgc ccatcgctgc cgacctggca    4200
gcgtccagca ccgtgatgtg ggaacaagat gcggcccccct tcgcaggggc agcggatgat    4260
ttcccggcat caacgaaga ggagctcgca tggttgatgg agctattgcc tcagtcaggc    4320
tcagtcggag ggacgatctg a                                              4341
```

<210> SEQ ID NO 21
<211> LENGTH: 1263
<212> TYPE: PRT
<213> ORGANISM: Artificial Sequence
<220> FEATURE:
<223> OTHER INFORMATION: Synthetic construct

<400> SEQUENCE: 21

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Arg Lys Ser Gly
    130                 135                 140

Ser Gly Ser Pro Arg Gln Phe Asp Pro Ser Leu Leu Asp Thr Ser Leu
145                 150                 155                 160

Leu Asp Ser Met Pro Ala Val Gly Thr Pro His Thr Ala Ala Ala Pro
                165                 170                 175

Ala Glu Cys Asp Glu Val Gln Ser Gly Leu Arg Ala Ala Asp Asp Pro
            180                 185                 190

Pro Pro Thr Val Arg Val Ala Val Thr Ala Ala Arg Pro Pro Arg Ala
        195                 200                 205

Lys Pro Ala Pro Arg Arg Ala Ala Gln Pro Ser Asp Ala Ser Pro
    210                 215                 220

Ala Ala Gln Val Asp Leu Arg Thr Leu Gly Tyr Ser Gln Gln Gln Gln
```

```
                225                 230                 235                 240
Glu Lys Ile Lys Pro Lys Val Arg Ser Thr Val Ala Gln His His Glu
                    245                 250                 255

Ala Leu Val Gly His Gly Phe Thr His Ala His Ile Val Ala Leu Ser
                260                 265                 270

Gln His Pro Ala Ala Leu Gly Thr Val Ala Val Thr Tyr Gln Asp Ile
            275                 280                 285

Ile Arg Ala Leu Pro Glu Ala Thr His Glu Asp Ile Val Gly Val Gly
        290                 295                 300

Lys Gln Trp Ser Gly Ala Arg Ala Leu Glu Ala Leu Leu Thr Glu Ala
305                 310                 315                 320

Gly Glu Leu Arg Gly Pro Leu Gln Leu Asp Thr Gly Gln Leu Leu
                325                 330                 335

Lys Ile Ala Lys Arg Gly Gly Val Thr Ala Val Glu Ala Val His Ala
                340                 345                 350

Trp Arg Asn Ala Leu Thr Gly Ala Pro Leu Asn Leu Thr Pro Asp Gln
                355                 360                 365

Val Val Ala Ile Ala Ser Asn Ile Gly Gly Lys Gln Ala Leu Glu Thr
            370                 375                 380

Val Gln Arg Leu Leu Pro Val Leu Cys Gln Asp His Gly Leu Thr Pro
385                 390                 395                 400

Asp Gln Val Val Ala Ile Ala Ser His Gly Gly Gly Lys Gln Ala Leu
                    405                 410                 415

Glu Thr Val Gln Arg Leu Leu Pro Val Leu Cys Gln Asp His Gly Leu
                420                 425                 430

Thr Pro Asp Gln Val Val Ala Ile Ala Ser Asn Ile Gly Gly Lys Gln
            435                 440                 445

Ala Leu Glu Thr Val Gln Arg Leu Leu Pro Val Leu Cys Gln Ala His
        450                 455                 460

Gly Leu Thr Pro Asp Gln Val Val Ala Ile Ala Ser Asn Ile Gly Gly
465                 470                 475                 480

Lys Gln Ala Leu Glu Thr Val Gln Arg Leu Leu Pro Val Leu Cys Gln
                485                 490                 495

Asp His Gly Leu Thr Pro Ala Gln Val Val Ala Ile Ala Ser Asn Ser
                500                 505                 510

Gly Gly Lys Gln Ala Leu Glu Thr Val Gln Arg Leu Leu Pro Val Leu
            515                 520                 525

Cys Gln Asp His Gly Leu Thr Pro Asp Gln Val Val Ala Ile Ala Ser
        530                 535                 540

His Asp Gly Gly Lys Gln Ala Leu Glu Thr Leu Gln Arg Leu Leu Pro
545                 550                 555                 560

Val Leu Cys Gln Asp His Gly Leu Thr Pro Asp Gln Val Val Ala Ile
                565                 570                 575

Ala Asn Asn Asn Gly Gly Lys Gln Ala Leu Glu Thr Leu Gln Arg Leu
                580                 585                 590

Leu Pro Val Leu Cys Gln Asp His Gly Leu Thr Pro Asp Gln Val Val
            595                 600                 605

Ala Ile Ala Ser His Asp Gly Gly Lys Gln Ala Leu Glu Thr Val Gln
        610                 615                 620

Arg Leu Leu Pro Val Leu Cys Gln Asp His Gly Leu Thr Pro Asp Gln
625                 630                 635                 640

Val Val Ala Ile Ala Ser His Asp Gly Gly Lys Gln Ala Leu Glu Thr
                645                 650                 655
```

Val Gln Arg Leu Leu Pro Val Leu Cys Gln Asp His Gly Leu Thr Pro
                660                 665                 670

Ala Gln Val Val Ala Ile Ala Ser His Asp Gly Gly Lys Gln Ala Leu
            675                 680                 685

Glu Thr Val Gln Arg Leu Leu Pro Val Leu Cys Gln Asp His Gly Leu
        690                 695                 700

Thr Pro Asp Gln Val Val Ala Ile Ala Ser Asn Ser Gly Gly Lys Gln
705                 710                 715                 720

Ala Leu Glu Thr Val Gln Arg Leu Leu Pro Val Leu Cys Gln Asp His
                725                 730                 735

Gly Leu Thr Pro Asp Gln Val Val Ala Ile Ala Ser Asn Gly Gly Lys
            740                 745                 750

Gln Ala Leu Glu Thr Val Gln Arg Leu Leu Pro Val Leu Cys Gln Asp
        755                 760                 765

His Gly Leu Thr Pro Asp Gln Val Val Ala Ile Ala Ser Asn Gly Gly
    770                 775                 780

Lys Gln Ala Leu Glu Thr Val Gln Arg Leu Leu Pro Val Gln Arg Leu
785                 790                 795                 800

Leu Pro Val Leu Cys Gln Asp His Gly Leu Thr Gln Asp Gln Val Val
                805                 810                 815

Ala Ile Ala Ser His Asp Gly Gly Lys Gln Ala Leu Glu Thr Val Gln
            820                 825                 830

Arg Leu Leu Pro Val Leu Cys Gln Asp His Gly Leu Thr Pro Asp Gln
        835                 840                 845

Val Val Ala Ile Ala Ser His Asp Gly Gly Lys Gln Ala Leu Glu Thr
    850                 855                 860

Val Gln Arg Leu Leu Pro Val Leu Cys Gln Asp His Gly Leu Thr Pro
865                 870                 875                 880

Asp Gln Val Val Ala Ile Ala Ser Asn Ser Gly Gly Lys Gln Ala Leu
                885                 890                 895

Glu Thr Val Gln Arg Leu Leu Pro Val Leu Cys Gln Asp His Gly Leu
            900                 905                 910

Thr Pro Asp Gln Val Val Ala Ile Ala Ser Asn Ser Gly Gly Lys Gln
        915                 920                 925

Ala Leu Glu Thr Val Gln Arg Leu Leu Pro Val Leu Cys Gln Asp His
    930                 935                 940

Gly Leu Thr Pro Asp Gln Val Val Ala Ile Ala Ser Asn Asn Gly Gly
945                 950                 955                 960

Lys Gln Ala Leu Glu Thr Val Gln Arg Leu Leu Pro Val Leu Cys Gln
                965                 970                 975

Asp His Gly Leu Thr Pro Asp Gln Val Val Ala Ile Ala Asn Asn Asn
            980                 985                 990

Gly Gly Lys Gln Ala Leu Glu Thr  Val Gln Arg Leu Leu  Pro Val Leu
        995                 1000                1005

Cys Gln  Asp His Gly Leu Thr  Pro Ala Gln Val Val  Ala Ile Ala
    1010                 1015                1020

Ser Asn  Ile Gly Gly Lys Gln  Ala Leu Glu Thr Val  Gln Arg Leu
    1025                 1030                1035

Leu Pro  Val Leu Cys Gln Asp  His Gly Leu Thr Leu  Asp Gln Val
    1040                 1045                1050

Val Ala  Ile Ala Ser Asn Gly  Gly Ser Lys Gln Ala  Leu Glu Thr
    1055                 1060                1065

-continued

Val Gln Arg Leu Leu Pro Val Leu Cys Gln Asp His Gly Leu Thr
1070            1075                1080

Pro Asp Gln Val Val Ala Ile Ala Asn Asn Asn Gly Gly Lys Gln
1085            1090                1095

Ala Leu Glu Thr Val Gln Arg Leu Leu Pro Val Leu Cys Gln Asp
1100            1105                1110

His Gly Leu Thr Pro Asp Gln Val Val Ala Ile Ala Ser Asn Ile
1115            1120                1125

Gly Gly Lys Gln Ala Leu Glu Thr Val Gln Arg Leu Leu Pro Val
1130            1135                1140

Leu Cys Gln Asp His Gly Leu Thr Leu Asp Gln Val Val Ala Ile
1145            1150                1155

Ala Ser Asn Gly Gly Lys Gln Ala Leu Glu Thr Val Gln Arg Leu
1160            1165                1170

Leu Pro Val Leu Cys Gln Asp His Gly Leu Thr Pro Asn Gln Val
1175            1180                1185

Val Ala Ile Ala Ser Asn Ser Gly Gly Lys Gln Ala Leu Glu Thr
1190            1195                1200

Val Gln Arg Leu Leu Pro Val Leu Cys Gln Asp His Gly Leu Thr
1205            1210                1215

Pro Asn Gln Val Val Ala Ile Ala Ser Asn Gly Gly Lys Gln Ala
1220            1225                1230

Leu Glu Ser Ile Val Ala Gln Leu Ser Arg Pro Asp Pro Ala Leu
1235            1240                1245

Ala Ala Leu Thr Asn Asp His Leu Val Ala Leu Ala Cys Leu Gly
1250            1255                1260

<210> SEQ ID NO 22
<211> LENGTH: 1250
<212> TYPE: PRT
<213> ORGANISM: Artificial Sequence
<220> FEATURE:
<223> OTHER INFORMATION: Synthetic construct

<400> SEQUENCE: 22

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
        50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Arg Lys Ser Gly
    130                 135                 140

Ser Gly Ser Pro Asp Ser Met Pro Ala Val Gly Thr Pro His Thr Ala
145                 150                 155                 160

Ala Ala Pro Ala Glu Cys Asp Glu Val Gln Ser Gly Leu Arg Ala Ala
                165                 170                 175

Asp Asp Pro Pro Pro Thr Val Arg Val Ala Val Thr Ala Ala Arg Pro
            180                 185                 190

Pro Arg Ala Lys Pro Ala Pro Arg Arg Ala Ala Gln Pro Ser Asp
        195                 200                 205

Ala Ser Pro Ala Ala Gln Val Asp Leu Arg Thr Leu Gly Tyr Ser Gln
    210                 215                 220

Gln Gln Gln Glu Lys Ile Lys Pro Lys Val Arg Ser Thr Val Ala Gln
225                 230                 235                 240

His His Glu Ala Leu Val Gly His Gly Phe Thr His Ala His Ile Val
                245                 250                 255

Ala Leu Ser Gln His Pro Ala Ala Leu Gly Thr Val Ala Val Thr Tyr
            260                 265                 270

Gln Asp Ile Ile Arg Ala Leu Pro Glu Ala Thr His Glu Asp Ile Val
        275                 280                 285

Gly Val Gly Lys Gln Trp Ser Gly Ala Arg Ala Leu Glu Ala Leu Leu
    290                 295                 300

Thr Glu Ala Gly Glu Leu Arg Gly Pro Pro Leu Gln Leu Asp Thr Gly
305                 310                 315                 320

Gln Leu Leu Lys Ile Ala Lys Arg Gly Gly Val Thr Ala Val Glu Ala
                325                 330                 335

Val His Ala Trp Arg Asn Ala Leu Thr Gly Ala Pro Leu Asn Leu Thr
            340                 345                 350

Pro Asp Gln Val Val Ala Ile Ala Ser Asn Ile Gly Gly Lys Gln Ala
        355                 360                 365

Leu Glu Thr Val Gln Arg Leu Leu Pro Val Leu Cys Gln Asp His Gly
    370                 375                 380

Leu Thr Pro Asp Gln Val Val Ala Ile Ala Ser His Gly Gly Gly Lys
385                 390                 395                 400

Gln Ala Leu Glu Thr Val Gln Arg Leu Leu Pro Val Leu Cys Gln Asp
                405                 410                 415

His Gly Leu Thr Pro Asp Gln Val Val Ala Ile Ala Ser Asn Ile Gly
            420                 425                 430

Gly Lys Gln Ala Leu Glu Thr Val Gln Arg Leu Leu Pro Val Leu Cys
        435                 440                 445

Gln Ala His Gly Leu Thr Pro Asp Gln Val Val Ala Ile Ala Ser Asn
    450                 455                 460

Ile Gly Gly Lys Gln Ala Leu Glu Thr Val Gln Arg Leu Leu Pro Val
465                 470                 475                 480

Leu Cys Gln Asp His Gly Leu Thr Pro Ala Gln Val Val Ala Ile Ala
                485                 490                 495

Ser Asn Ser Gly Gly Lys Gln Ala Leu Glu Thr Val Gln Arg Leu Leu
            500                 505                 510

Pro Val Leu Cys Gln Asp His Gly Leu Thr Pro Asp Gln Val Val Ala
        515                 520                 525

Ile Ala Ser His Asp Gly Gly Lys Gln Ala Leu Glu Thr Leu Gln Arg
    530                 535                 540

Leu Leu Pro Val Leu Cys Gln Asp His Gly Leu Thr Pro Asp Gln Val
545                 550                 555                 560

Val Ala Ile Ala Asn Asn Asn Gly Gly Lys Gln Ala Leu Glu Thr Leu
                565                 570                 575

Gln Arg Leu Leu Pro Val Leu Cys Gln Asp His Gly Leu Thr Pro Asp

-continued

```
                580                 585                 590
Gln Val Val Ala Ile Ala Ser His Asp Gly Gly Lys Gln Ala Leu Glu
                595                 600                 605
Thr Val Gln Arg Leu Leu Pro Val Leu Cys Gln Asp His Gly Leu Thr
            610                 615                 620
Pro Asp Gln Val Val Ala Ile Ala Ser His Asp Gly Gly Lys Gln Ala
625                 630                 635                 640
Leu Glu Thr Val Gln Arg Leu Leu Pro Val Leu Cys Gln Asp His Gly
                645                 650                 655
Leu Thr Pro Ala Gln Val Val Ala Ile Ala Ser His Asp Gly Gly Lys
            660                 665                 670
Gln Ala Leu Glu Thr Val Gln Arg Leu Leu Pro Val Leu Cys Gln Asp
        675                 680                 685
His Gly Leu Thr Pro Asp Gln Val Val Ala Ile Ala Ser Asn Ser Gly
                690                 695                 700
Gly Lys Gln Ala Leu Glu Thr Val Gln Arg Leu Leu Pro Val Leu Cys
705                 710                 715                 720
Gln Asp His Gly Leu Thr Pro Asp Gln Val Val Ala Ile Ala Ser Asn
                725                 730                 735
Gly Gly Lys Gln Ala Leu Glu Thr Val Gln Arg Leu Leu Pro Val Leu
            740                 745                 750
Cys Gln Asp His Gly Leu Thr Pro Asp Gln Val Val Ala Ile Ala Ser
        755                 760                 765
Asn Gly Gly Lys Gln Ala Leu Glu Thr Val Gln Arg Leu Leu Pro Val
    770                 775                 780
Gln Arg Leu Leu Pro Val Leu Cys Gln Asp His Gly Leu Thr Gln Asp
785                 790                 795                 800
Gln Val Val Ala Ile Ala Ser His Asp Gly Gly Lys Gln Ala Leu Glu
                805                 810                 815
Thr Val Gln Arg Leu Leu Pro Val Leu Cys Gln Asp His Gly Leu Thr
            820                 825                 830
Pro Asp Gln Val Val Ala Ile Ala Ser His Asp Gly Gly Lys Gln Ala
        835                 840                 845
Leu Glu Thr Val Gln Arg Leu Leu Pro Val Leu Cys Gln Asp His Gly
    850                 855                 860
Leu Thr Pro Asp Gln Val Val Ala Ile Ala Ser Asn Ser Gly Gly Lys
865                 870                 875                 880
Gln Ala Leu Glu Thr Val Gln Arg Leu Leu Pro Val Leu Cys Gln Asp
                885                 890                 895
His Gly Leu Thr Pro Asp Gln Val Val Ala Ile Ala Ser Asn Ser Gly
            900                 905                 910
Gly Lys Gln Ala Leu Glu Thr Val Gln Arg Leu Leu Pro Val Leu Cys
        915                 920                 925
Gln Asp His Gly Leu Thr Pro Asp Gln Val Val Ala Ile Ala Ser Asn
    930                 935                 940
Asn Gly Gly Lys Gln Ala Leu Glu Thr Val Gln Arg Leu Leu Pro Val
945                 950                 955                 960
Leu Cys Gln Asp His Gly Leu Thr Pro Asp Gln Val Val Ala Ile Ala
                965                 970                 975
Asn Asn Asn Gly Gly Lys Gln Ala Leu Glu Thr Val Gln Arg Leu Leu
            980                 985                 990
Pro Val Leu Cys Gln Asp His Gly  Leu Thr Pro Ala Gln  Val Val Ala
        995                 1000                 1005
```

```
Ile Ala Ser Asn Ile Gly Gly Lys Gln Ala Leu Glu Thr Val Gln
    1010                1015                1020

Arg Leu Leu Pro Val Leu Cys Gln Asp His Gly Leu Thr Leu Asp
    1025                1030                1035

Gln Val Val Ala Ile Ala Ser Asn Gly Gly Ser Lys Gln Ala Leu
    1040                1045                1050

Glu Thr Val Gln Arg Leu Leu Pro Val Leu Cys Gln Asp His Gly
    1055                1060                1065

Leu Thr Pro Asp Gln Val Val Ala Ile Ala Asn Asn Asn Gly Gly
    1070                1075                1080

Lys Gln Ala Leu Glu Thr Val Gln Arg Leu Leu Pro Val Leu Cys
    1085                1090                1095

Gln Asp His Gly Leu Thr Pro Asp Gln Val Val Ala Ile Ala Ser
    1100                1105                1110

Asn Ile Gly Gly Lys Gln Ala Leu Glu Thr Val Gln Arg Leu Leu
    1115                1120                1125

Pro Val Leu Cys Gln Asp His Gly Leu Thr Leu Asp Gln Val Val
    1130                1135                1140

Ala Ile Ala Ser Asn Gly Gly Lys Gln Ala Leu Glu Thr Val Gln
    1145                1150                1155

Arg Leu Leu Pro Val Leu Cys Gln Asp His Gly Leu Thr Pro Asn
    1160                1165                1170

Gln Val Val Ala Ile Ala Ser Asn Ser Gly Gly Lys Gln Ala Leu
    1175                1180                1185

Glu Thr Val Gln Arg Leu Leu Pro Val Leu Cys Gln Asp His Gly
    1190                1195                1200

Leu Thr Pro Asn Gln Val Val Ala Ile Ala Ser Asn Gly Gly Lys
    1205                1210                1215

Gln Ala Leu Glu Ser Ile Val Ala Gln Leu Ser Arg Pro Asp Pro
    1220                1225                1230

Ala Leu Ala Ala Leu Thr Asn Asp His Leu Val Ala Leu Ala Cys
    1235                1240                1245

Leu Gly
    1250

<210> SEQ ID NO 23
<211> LENGTH: 1216
<212> TYPE: PRT
<213> ORGANISM: Artificial Sequence
<220> FEATURE:
<223> OTHER INFORMATION: Synthetic construct

<400> SEQUENCE: 23

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
        50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95
```

```
Ser Ser Pro Met Gly Arg Phe Phe Tyr Val Met Gly Leu Ala
            100                 105                 110

Glu Met Glu Arg Glu Leu Ile Ile Glu Arg Thr Met Ala Gly Leu Ala
            115                 120                 125

Ala Ala Arg Asn Lys Gly Arg Ile Gly Gly Arg Pro Arg Lys Ser Gly
130                 135                 140

Ser Gly Ser Thr Val Arg Val Ala Val Thr Ala Ala Arg Pro Pro Arg
145                 150                 155                 160

Ala Lys Pro Ala Pro Arg Arg Ala Ala Gln Pro Ser Asp Ala Ser
                165                 170                 175

Pro Ala Ala Gln Val Asp Leu Arg Thr Leu Gly Tyr Ser Gln Gln Gln
            180                 185                 190

Gln Glu Lys Ile Lys Pro Lys Val Arg Ser Thr Val Ala Gln His His
            195                 200                 205

Glu Ala Leu Val Gly His Gly Phe Thr His Ala His Ile Val Ala Leu
            210                 215                 220

Ser Gln His Pro Ala Ala Leu Gly Thr Val Ala Val Thr Tyr Gln Asp
225                 230                 235                 240

Ile Ile Arg Ala Leu Pro Glu Ala Thr His Glu Asp Ile Val Gly Val
                245                 250                 255

Gly Lys Gln Trp Ser Gly Ala Arg Ala Leu Glu Ala Leu Leu Thr Glu
            260                 265                 270

Ala Gly Glu Leu Arg Gly Pro Pro Leu Gln Leu Asp Thr Gly Gln Leu
            275                 280                 285

Leu Lys Ile Ala Lys Arg Gly Gly Val Thr Ala Val Glu Ala Val His
290                 295                 300

Ala Trp Arg Asn Ala Leu Thr Gly Ala Pro Leu Asn Leu Thr Pro Asp
305                 310                 315                 320

Gln Val Val Ala Ile Ala Ser Asn Ile Gly Gly Lys Gln Ala Leu Glu
                325                 330                 335

Thr Val Gln Arg Leu Leu Pro Val Leu Cys Gln Asp His Gly Leu Thr
            340                 345                 350

Pro Asp Gln Val Val Ala Ile Ala Ser His Gly Gly Lys Gln Ala
            355                 360                 365

Leu Glu Thr Val Gln Arg Leu Leu Pro Val Leu Cys Gln Asp His Gly
370                 375                 380

Leu Thr Pro Asp Gln Val Val Ala Ile Ala Ser Asn Ile Gly Gly Lys
385                 390                 395                 400

Gln Ala Leu Glu Thr Val Gln Arg Leu Leu Pro Val Leu Cys Gln Ala
                405                 410                 415

His Gly Leu Thr Pro Asp Gln Val Val Ala Ile Ala Ser Asn Ile Gly
            420                 425                 430

Gly Lys Gln Ala Leu Glu Thr Val Gln Arg Leu Leu Pro Val Leu Cys
            435                 440                 445

Gln Asp His Gly Leu Thr Pro Ala Gln Val Val Ala Ile Ala Ser Asn
450                 455                 460

Ser Gly Gly Lys Gln Ala Leu Glu Thr Val Gln Arg Leu Leu Pro Val
465                 470                 475                 480

Leu Cys Gln Asp His Gly Leu Thr Pro Asp Gln Val Val Ala Ile Ala
                485                 490                 495

Ser His Asp Gly Gly Lys Gln Ala Leu Glu Thr Leu Gln Arg Leu Leu
            500                 505                 510
```

```
Pro Val Leu Cys Gln Asp His Gly Leu Thr Pro Asp Gln Val Val Ala
            515                 520                 525

Ile Ala Asn Asn Asn Gly Gly Lys Gln Ala Leu Glu Thr Leu Gln Arg
530                 535                 540

Leu Leu Pro Val Leu Cys Gln Asp His Gly Leu Thr Pro Asp Gln Val
545                 550                 555                 560

Val Ala Ile Ala Ser His Asp Gly Gly Lys Gln Ala Leu Glu Thr Val
                565                 570                 575

Gln Arg Leu Leu Pro Val Leu Cys Gln Asp His Gly Leu Thr Pro Asp
            580                 585                 590

Gln Val Val Ala Ile Ala Ser His Asp Gly Gly Lys Gln Ala Leu Glu
            595                 600                 605

Thr Val Gln Arg Leu Leu Pro Val Leu Cys Gln Asp His Gly Leu Thr
610                 615                 620

Pro Asp Gln Val Val Ala Ile Ala Ser His Asp Gly Gly Lys Gln Ala
625                 630                 635                 640

Leu Glu Thr Val Gln Arg Leu Leu Pro Val Leu Cys Gln Asp His Gly
                645                 650                 655

Leu Thr Pro Asp Gln Val Val Ala Ile Ala Ser Asn Ser Gly Gly Lys
            660                 665                 670

Gln Ala Leu Glu Thr Val Gln Arg Leu Leu Pro Val Leu Cys Gln Asp
            675                 680                 685

His Gly Leu Thr Pro Asp Gln Val Val Ala Ile Ala Ser Asn Gly Gly
            690                 695                 700

Lys Gln Ala Leu Glu Thr Val Gln Arg Leu Leu Pro Val Leu Cys Gln
705                 710                 715                 720

Asp His Gly Leu Thr Pro Asp Gln Val Val Ala Ile Ala Ser Asn Gly
                725                 730                 735

Gly Lys Gln Ala Leu Glu Thr Val Gln Arg Leu Leu Pro Val Gln Arg
            740                 745                 750

Leu Leu Pro Val Leu Cys Gln Asp His Gly Leu Thr Gln Asp Gln Val
            755                 760                 765

Val Ala Ile Ala Ser His Asp Gly Gly Lys Gln Ala Leu Glu Thr Val
            770                 775                 780

Gln Arg Leu Leu Pro Val Leu Cys Gln Asp His Gly Leu Thr Pro Asp
785                 790                 795                 800

Gln Val Val Ala Ile Ala Ser His Asp Gly Gly Lys Gln Ala Leu Glu
                805                 810                 815

Thr Val Gln Arg Leu Leu Pro Val Leu Cys Gln Asp His Gly Leu Thr
            820                 825                 830

Pro Asp Gln Val Val Ala Ile Ala Ser Asn Ser Gly Gly Lys Gln Ala
            835                 840                 845

Leu Glu Thr Val Gln Arg Leu Leu Pro Val Leu Cys Gln Asp His Gly
850                 855                 860

Leu Thr Pro Asp Gln Val Val Ala Ile Ala Ser Asn Ser Gly Gly Lys
865                 870                 875                 880

Gln Ala Leu Glu Thr Val Gln Arg Leu Leu Pro Val Leu Cys Gln Asp
                885                 890                 895

His Gly Leu Thr Pro Asp Gln Val Val Ala Ile Ala Ser Asn Asn Gly
            900                 905                 910

Gly Lys Gln Ala Leu Glu Thr Val Gln Arg Leu Leu Pro Val Leu Cys
            915                 920                 925

Gln Asp His Gly Leu Thr Pro Asp Gln Val Val Ala Ile Ala Asn Asn
```

-continued

```
            930                 935                 940
Asn Gly Gly Lys Gln Ala Leu Glu Thr Val Gln Arg Leu Leu Pro Val
945                 950                 955                 960

Leu Cys Gln Asp His Gly Leu Thr Pro Ala Gln Val Val Ala Ile Ala
                965                 970                 975

Ser Asn Ile Gly Gly Lys Gln Ala Leu Glu Thr Val Gln Arg Leu Leu
            980                 985                 990

Pro Val Leu Cys Gln Asp His Gly Leu Thr Leu Asp Gln Val Val Ala
        995                 1000                1005

Ile Ala Ser Asn Gly Gly Ser Lys Gln Ala Leu Glu Thr Val Gln
    1010                1015                1020

Arg Leu Leu Pro Val Leu Cys Gln Asp His Gly Leu Thr Pro Asp
    1025                1030                1035

Gln Val Val Ala Ile Ala Asn Asn Gly Gly Lys Gln Ala Leu
    1040                1045                1050

Glu Thr Val Gln Arg Leu Leu Pro Val Leu Cys Gln Asp His Gly
    1055                1060                1065

Leu Thr Pro Asp Gln Val Val Ala Ile Ala Ser Asn Ile Gly Gly
    1070                1075                1080

Lys Gln Ala Leu Glu Thr Val Gln Arg Leu Leu Pro Val Leu Cys
    1085                1090                1095

Gln Asp His Gly Leu Thr Leu Asp Gln Val Val Ala Ile Ala Ser
    1100                1105                1110

Asn Gly Gly Lys Gln Ala Leu Glu Thr Val Gln Arg Leu Leu Pro
    1115                1120                1125

Val Leu Cys Gln Asp His Gly Leu Thr Pro Asn Gln Val Val Ala
    1130                1135                1140

Ile Ala Ser Asn Ser Gly Gly Lys Gln Ala Leu Glu Thr Val Gln
    1145                1150                1155

Arg Leu Leu Pro Val Leu Cys Gln Asp His Gly Leu Thr Pro Asn
    1160                1165                1170

Gln Val Val Ala Ile Ala Ser Asn Gly Gly Lys Gln Ala Leu Glu
    1175                1180                1185

Ser Ile Val Ala Gln Leu Ser Arg Pro Asp Pro Ala Leu Ala Ala
    1190                1195                1200

Leu Thr Asn Asp His Leu Val Ala Leu Ala Cys Leu Gly
    1205                1210                1215

<210> SEQ ID NO 24
<211> LENGTH: 1204
<212> TYPE: PRT
<213> ORGANISM: Artificial Sequence
<220> FEATURE:
<223> OTHER INFORMATION: Synthetic construct

<400> SEQUENCE: 24

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
```

```
                65                  70                  75                  80
        Arg Glu Arg Gly Ile Asn Phe Arg Ser Leu Thr Asp Ser Ile Asp Thr
                        85                  90                  95

Ser Ser Pro Met Gly Arg Phe Phe Phe Tyr Val Met Gly Ala Leu Ala
                        100                 105                 110

Glu Met Glu Arg Glu Leu Ile Ile Glu Arg Thr Met Ala Gly Leu Ala
                        115                 120                 125

Ala Ala Arg Asn Lys Gly Arg Ile Gly Gly Arg Pro Arg Lys Ser Gly
                130                 135                 140

Ser Gly Ser Thr Val Arg Val Ala Val Thr Ala Ala Arg Pro Pro His
        145                 150                 155                 160

Ala Val Ala Gly Pro Ala Ala Gln Val Asp Leu Arg Thr Leu Gly Tyr
                        165                 170                 175

Ser Gln Gln Gln Gln Glu Lys Ile Lys Pro Lys Val Arg Ser Thr Val
                        180                 185                 190

Ala Gln His His Glu Ala Leu Val Gly His Gly Phe Thr His Ala His
                        195                 200                 205

Ile Val Ala Leu Ser Gln His Pro Ala Ala Leu Gly Thr Val Ala Val
                210                 215                 220

Thr Tyr Gln Asp Ile Ile Arg Ala Leu Pro Glu Ala Thr His Glu Asp
        225                 230                 235                 240

Ile Val Gly Val Gly Lys Gln Trp Ser Gly Ala Arg Ala Leu Glu Ala
                        245                 250                 255

Leu Leu Thr Glu Ala Gly Glu Leu Arg Gly Pro Pro Leu Gln Leu Asp
                        260                 265                 270

Thr Gly Gln Leu Leu Lys Ile Ala Lys Arg Gly Gly Val Thr Ala Val
                        275                 280                 285

Glu Ala Val His Ala Trp Arg Asn Ala Leu Thr Gly Ala Pro Leu Asn
                290                 295                 300

Leu Thr Pro Asp Gln Val Val Ala Ile Ala Ser Asn Ile Gly Gly Lys
        305                 310                 315                 320

Gln Ala Leu Glu Thr Val Gln Arg Leu Leu Pro Val Leu Cys Gln Asp
                        325                 330                 335

His Gly Leu Thr Pro Asp Gln Val Val Ala Ile Ala Ser His Gly Gly
                        340                 345                 350

Gly Lys Gln Ala Leu Glu Thr Val Gln Arg Leu Leu Pro Val Leu Cys
                        355                 360                 365

Gln Asp His Gly Leu Thr Pro Asp Gln Val Val Ala Ile Ala Ser Asn
                370                 375                 380

Ile Gly Gly Lys Gln Ala Leu Glu Thr Val Gln Arg Leu Leu Pro Val
        385                 390                 395                 400

Leu Cys Gln Ala His Gly Leu Thr Pro Asp Gln Val Val Ala Ile Ala
                        405                 410                 415

Ser Asn Ile Gly Gly Lys Gln Ala Leu Glu Thr Val Gln Arg Leu Leu
                        420                 425                 430

Pro Val Leu Cys Gln Asp His Gly Leu Thr Pro Ala Gln Val Val Ala
                        435                 440                 445

Ile Ala Ser Asn Ser Gly Gly Lys Gln Ala Leu Glu Thr Val Gln Arg
                450                 455                 460

Leu Leu Pro Val Leu Cys Gln Asp His Gly Leu Thr Pro Asp Gln Val
        465                 470                 475                 480

Val Ala Ile Ala Ser His Asp Gly Gly Lys Gln Ala Leu Glu Thr Leu
                        485                 490                 495
```

```
Gln Arg Leu Leu Pro Val Leu Cys Gln Asp His Gly Leu Thr Pro Asp
            500                 505                 510
Gln Val Val Ala Ile Ala Asn Asn Gly Gly Lys Gln Ala Leu Glu
        515                 520                 525
Thr Leu Gln Arg Leu Leu Pro Val Leu Cys Gln Asp His Gly Leu Thr
530                 535                 540
Pro Asp Gln Val Val Ala Ile Ala Ser His Asp Gly Lys Gln Ala
545                 550                 555                 560
Leu Glu Thr Val Gln Arg Leu Leu Pro Val Leu Cys Gln Asp His Gly
                565                 570                 575
Leu Thr Pro Asp Gln Val Val Ala Ile Ala Ser His Asp Gly Lys
                580                 585                 590
Gln Ala Leu Glu Thr Val Gln Arg Leu Leu Pro Val Leu Cys Gln Asp
        595                 600                 605
His Gly Leu Thr Pro Ala Gln Val Val Ala Ile Ala Ser His Asp Gly
        610                 615                 620
Gly Lys Gln Ala Leu Glu Thr Val Gln Arg Leu Leu Pro Val Leu Cys
625                 630                 635                 640
Gln Asp His Gly Leu Thr Pro Asp Gln Val Val Ala Ile Ala Ser Asn
                645                 650                 655
Ser Gly Gly Lys Gln Ala Leu Glu Thr Val Gln Arg Leu Leu Pro Val
                660                 665                 670
Leu Cys Gln Asp His Gly Leu Thr Pro Asp Gln Val Val Ala Ile Ala
        675                 680                 685
Ser Asn Gly Gly Lys Gln Ala Leu Glu Thr Val Gln Arg Leu Leu Pro
        690                 695                 700
Val Leu Cys Gln Asp His Gly Leu Thr Pro Asp Gln Val Val Ala Ile
705                 710                 715                 720
Ala Ser Asn Gly Gly Lys Gln Ala Leu Glu Thr Val Gln Arg Leu Leu
                725                 730                 735
Pro Val Gln Arg Leu Leu Pro Val Leu Cys Gln Asp His Gly Leu Thr
                740                 745                 750
Gln Asp Gln Val Val Ala Ile Ala Ser His Asp Gly Gly Lys Gln Ala
        755                 760                 765
Leu Glu Thr Val Gln Arg Leu Leu Pro Val Leu Cys Gln Asp His Gly
770                 775                 780
Leu Thr Pro Asp Gln Val Val Ala Ile Ala Ser His Asp Gly Gly Lys
785                 790                 795                 800
Gln Ala Leu Glu Thr Val Gln Arg Leu Leu Pro Val Leu Cys Gln Asp
                805                 810                 815
His Gly Leu Thr Pro Asp Gln Val Val Ala Ile Ala Ser Asn Ser Gly
                820                 825                 830
Gly Lys Gln Ala Leu Glu Thr Val Gln Arg Leu Leu Pro Val Leu Cys
        835                 840                 845
Gln Asp His Gly Leu Thr Pro Asp Gln Val Val Ala Ile Ala Ser Asn
        850                 855                 860
Ser Gly Gly Lys Gln Ala Leu Glu Thr Val Gln Arg Leu Leu Pro Val
865                 870                 875                 880
Leu Cys Gln Asp His Gly Leu Thr Pro Asp Gln Val Val Ala Ile Ala
                885                 890                 895
Ser Asn Asn Gly Gly Lys Gln Ala Leu Glu Thr Val Gln Arg Leu Leu
                900                 905                 910
```

```
Pro Val Leu Cys Gln Asp His Gly Leu Thr Pro Asp Gln Val Val Ala
            915                 920                 925

Ile Ala Asn Asn Asn Gly Gly Lys Gln Ala Leu Glu Thr Val Gln Arg
            930                 935                 940

Leu Leu Pro Val Leu Cys Gln Asp His Gly Leu Thr Pro Ala Gln Val
945                 950                 955                 960

Val Ala Ile Ala Ser Asn Ile Gly Gly Lys Gln Ala Leu Glu Thr Val
                965                 970                 975

Gln Arg Leu Leu Pro Val Leu Cys Gln Asp His Gly Leu Thr Leu Asp
            980                 985                 990

Gln Val Val Ala Ile Ala Ser Asn Gly Gly Ser Lys Gln Ala Leu Glu
            995                1000                1005

Thr Val Gln Arg Leu Leu Pro Val Leu Cys Gln Asp His Gly Leu
       1010                1015                1020

Thr Pro Asp Gln Val Val Ala Ile Ala Asn Asn Asn Gly Gly Lys
       1025                1030                1035

Gln Ala Leu Glu Thr Val Gln Arg Leu Leu Pro Val Leu Cys Gln
       1040                1045                1050

Asp His Gly Leu Thr Pro Asp Gln Val Val Ala Ile Ala Ser Asn
       1055                1060                1065

Ile Gly Gly Lys Gln Ala Leu Glu Thr Val Gln Arg Leu Leu Pro
       1070                1075                1080

Val Leu Cys Gln Asp His Gly Leu Thr Leu Asp Gln Val Val Ala
       1085                1090                1095

Ile Ala Ser Asn Gly Gly Lys Gln Ala Leu Glu Thr Val Gln Arg
       1100                1105                1110

Leu Leu Pro Val Leu Cys Gln Asp His Gly Leu Thr Pro Asn Gln
       1115                1120                1125

Val Val Ala Ile Ala Ser Asn Ser Gly Gly Lys Gln Ala Leu Glu
       1130                1135                1140

Thr Val Gln Arg Leu Leu Pro Val Leu Cys Gln Asp His Gly Leu
       1145                1150                1155

Thr Pro Asn Gln Val Val Ala Ile Ala Ser Asn Gly Gly Lys Gln
       1160                1165                1170

Ala Leu Glu Ser Ile Val Ala Gln Leu Ser Arg Pro Asp Pro Ala
       1175                1180                1185

Leu Ala Ala Leu Thr Asn Asp His Leu Val Ala Leu Ala Cys Leu
       1190                1195                1200

Gly

<210> SEQ ID NO 25
<211> LENGTH: 1190
<212> TYPE: PRT
<213> ORGANISM: Artificial Sequence
<220> FEATURE:
<223> OTHER INFORMATION: Synthetic construct

<400> SEQUENCE: 25

Met Leu Ile Gly Tyr Val Arg Val Ser Thr Asn Asp Gln Asn Thr Asp
1               5                  10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
```

```
            50                  55                  60
Arg Leu Gly Arg Ser Met Lys His Leu Ile Ser Leu Val Gly Glu Leu
 65                  70                  75                  80

Arg Glu Arg Gly Ile Asn Phe Arg Ser Leu Thr Asp Ser Ile Asp Thr
                     85                  90                  95

Ser Ser Pro Met Gly Arg Phe Phe Phe Tyr Val Met Gly Ala Leu Ala
                    100                 105                 110

Glu Met Glu Arg Glu Leu Ile Ile Glu Arg Thr Met Ala Gly Leu Ala
                    115                 120                 125

Ala Ala Arg Asn Lys Gly Arg Ile Gly Gly Arg Pro Arg Lys Ser Gly
                130                 135                 140

Ser Gly Ser Pro Ala Ser Pro Ala Ala Gln Val Asp Leu Arg Thr Leu
145                 150                 155                 160

Gly Tyr Ser Gln Gln Gln Gln Glu Lys Ile Lys Pro Lys Val Arg Ser
                    165                 170                 175

Thr Val Ala Gln His His Glu Ala Leu Val Gly His Gly Phe Thr His
                    180                 185                 190

Ala His Ile Val Ala Leu Ser Gln His Pro Ala Ala Leu Gly Thr Val
                195                 200                 205

Ala Val Thr Tyr Gln Asp Ile Ile Arg Ala Leu Pro Glu Ala Thr His
                210                 215                 220

Glu Asp Ile Val Gly Val Gly Lys Gln Trp Ser Gly Ala Arg Ala Leu
225                 230                 235                 240

Glu Ala Leu Leu Thr Glu Ala Gly Glu Leu Arg Gly Pro Pro Leu Gln
                    245                 250                 255

Leu Asp Thr Gly Gln Leu Leu Lys Ile Ala Lys Arg Gly Gly Val Thr
                    260                 265                 270

Ala Val Glu Ala Val His Ala Trp Arg Asn Ala Leu Thr Gly Ala Pro
                275                 280                 285

Leu Asn Leu Thr Pro Asp Gln Val Val Ala Ile Ala Ser Asn Ile Gly
                290                 295                 300

Gly Lys Gln Ala Leu Glu Thr Val Gln Arg Leu Leu Pro Val Leu Cys
305                 310                 315                 320

Gln Asp His Gly Leu Thr Pro Asp Gln Val Val Ala Ile Ala Ser His
                    325                 330                 335

Gly Gly Gly Lys Gln Ala Leu Glu Thr Val Gln Arg Leu Leu Pro Val
                340                 345                 350

Leu Cys Gln Asp His Gly Leu Thr Pro Asp Gln Val Val Ala Ile Ala
                355                 360                 365

Ser Asn Ile Gly Gly Lys Gln Ala Leu Glu Thr Val Gln Arg Leu Leu
                370                 375                 380

Pro Val Leu Cys Gln His Gly Leu Thr Pro Asp Gln Val Val Ala
385                 390                 395                 400

Ile Ala Ser Asn Ile Gly Gly Lys Gln Ala Leu Glu Thr Val Gln Arg
                    405                 410                 415

Leu Leu Pro Val Leu Cys Gln Asp His Gly Leu Thr Pro Ala Gln Val
                    420                 425                 430

Val Ala Ile Ala Ser Asn Ser Gly Gly Lys Gln Ala Leu Glu Thr Val
                435                 440                 445

Gln Arg Leu Leu Pro Val Leu Cys Gln Asp His Gly Leu Thr Pro Asp
                450                 455                 460

Gln Val Val Ala Ile Ala Ser His Asp Gly Gly Lys Gln Ala Leu Glu
465                 470                 475                 480
```

```
Thr Leu Gln Arg Leu Leu Pro Val Leu Cys Gln Asp His Gly Leu Thr
            485                 490                 495

Pro Asp Gln Val Val Ala Ile Ala Asn Asn Gly Gly Lys Gln Ala
        500                 505                 510

Leu Glu Thr Leu Gln Arg Leu Leu Pro Val Leu Cys Gln Asp His Gly
            515                 520                 525

Leu Thr Pro Asp Gln Val Val Ala Ile Ala Ser His Asp Gly Gly Lys
    530                 535                 540

Gln Ala Leu Glu Thr Val Gln Arg Leu Leu Pro Val Leu Cys Gln Asp
545                 550                 555                 560

His Gly Leu Thr Pro Asp Gln Val Val Ala Ile Ala Ser His Asp Gly
                565                 570                 575

Gly Lys Gln Ala Leu Glu Thr Val Gln Arg Leu Leu Pro Val Leu Cys
            580                 585                 590

Gln Asp His Gly Leu Thr Pro Ala Gln Val Val Ala Ile Ala Ser His
        595                 600                 605

Asp Gly Gly Lys Gln Ala Leu Glu Thr Val Gln Arg Leu Leu Pro Val
610                 615                 620

Leu Cys Gln Asp His Gly Leu Thr Pro Asp Gln Val Val Ala Ile Ala
625                 630                 635                 640

Ser Asn Ser Gly Gly Lys Gln Ala Leu Glu Thr Val Gln Arg Leu Leu
                645                 650                 655

Pro Val Leu Cys Gln Asp His Gly Leu Thr Pro Asp Gln Val Val Ala
            660                 665                 670

Ile Ala Ser Asn Gly Gly Lys Gln Ala Leu Glu Thr Val Gln Arg Leu
        675                 680                 685

Leu Pro Val Leu Cys Gln Asp His Gly Leu Thr Pro Asp Gln Val Val
    690                 695                 700

Ala Ile Ala Ser Asn Gly Gly Lys Gln Ala Leu Glu Thr Val Gln Arg
705                 710                 715                 720

Leu Leu Pro Val Gln Arg Leu Leu Pro Val Leu Cys Gln Asp His Gly
                725                 730                 735

Leu Thr Gln Asp Gln Val Val Ala Ile Ala Ser His Asp Gly Gly Lys
            740                 745                 750

Gln Ala Leu Glu Thr Val Gln Arg Leu Leu Pro Val Leu Cys Gln Asp
        755                 760                 765

His Gly Leu Thr Pro Asp Gln Val Val Ala Ile Ala Ser His Asp Gly
    770                 775                 780

Gly Lys Gln Ala Leu Glu Thr Val Gln Arg Leu Leu Pro Val Leu Cys
785                 790                 795                 800

Gln Asp His Gly Leu Thr Pro Asp Gln Val Val Ala Ile Ala Ser Asn
                805                 810                 815

Ser Gly Gly Lys Gln Ala Leu Glu Thr Val Gln Arg Leu Leu Pro Val
            820                 825                 830

Leu Cys Gln Asp His Gly Leu Thr Pro Asp Gln Val Val Ala Ile Ala
        835                 840                 845

Ser Asn Ser Gly Gly Lys Gln Ala Leu Glu Thr Val Gln Arg Leu Leu
    850                 855                 860

Pro Val Leu Cys Gln Asp His Gly Leu Thr Pro Asp Gln Val Val Ala
865                 870                 875                 880

Ile Ala Ser Asn Asn Gly Gly Lys Gln Ala Leu Glu Thr Val Gln Arg
                885                 890                 895
```

```
Leu Leu Pro Val Leu Cys Gln Asp His Gly Leu Thr Pro Asp Gln Val
                900                 905                 910

Val Ala Ile Ala Asn Asn Asn Gly Gly Lys Gln Ala Leu Glu Thr Val
        915                 920                 925

Gln Arg Leu Leu Pro Val Leu Cys Gln Asp His Gly Leu Thr Pro Ala
930                 935                 940

Gln Val Val Ala Ile Ala Ser Asn Ile Gly Gly Lys Gln Ala Leu Glu
945                 950                 955                 960

Thr Val Gln Arg Leu Leu Pro Val Leu Cys Gln Asp His Gly Leu Thr
                965                 970                 975

Leu Asp Gln Val Val Ala Ile Ala Ser Asn Gly Gly Ser Lys Gln Ala
        980                 985                 990

Leu Glu Thr Val Gln Arg Leu Leu Pro Val Leu Cys Gln Asp His Gly
                995                 1000                1005

Leu Thr Pro Asp Gln Val Val Ala Ile Ala Asn Asn Asn Gly Gly
        1010                1015                1020

Lys Gln Ala Leu Glu Thr Val Gln Arg Leu Leu Pro Val Leu Cys
    1025                1030                1035

Gln Asp His Gly Leu Thr Pro Asp Gln Val Val Ala Ile Ala Ser
    1040                1045                1050

Asn Ile Gly Gly Lys Gln Ala Leu Glu Thr Val Gln Arg Leu Leu
    1055                1060                1065

Pro Val Leu Cys Gln Asp His Gly Leu Thr Leu Asp Gln Val Val
    1070                1075                1080

Ala Ile Ala Ser Asn Gly Gly Lys Gln Ala Leu Glu Thr Val Gln
    1085                1090                1095

Arg Leu Leu Pro Val Leu Cys Gln Asp His Gly Leu Thr Pro Asn
    1100                1105                1110

Gln Val Val Ala Ile Ala Ser Asn Ser Gly Gly Lys Gln Ala Leu
    1115                1120                1125

Glu Thr Val Gln Arg Leu Leu Pro Val Leu Cys Gln Asp His Gly
    1130                1135                1140

Leu Thr Pro Asn Gln Val Val Ala Ile Ala Ser Asn Gly Gly Lys
    1145                1150                1155

Gln Ala Leu Glu Ser Ile Val Ala Gln Leu Ser Arg Pro Asp Pro
    1160                1165                1170

Ala Leu Ala Ala Leu Thr Asn Asp His Leu Val Ala Leu Ala Cys
    1175                1180                1185

Leu Gly
    1190

<210> SEQ ID NO 26
<211> LENGTH: 841
<212> TYPE: PRT
<213> ORGANISM: Artificial Sequence
<220> FEATURE:
<223> OTHER INFORMATION: Synthetic construct

<400> SEQUENCE: 26

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45
```

-continued

```
Leu Lys Arg Leu Gln Lys Gly Asp Thr Leu Val Val Trp Lys Leu Asp
 50                  55                  60
Arg Leu Gly Arg Ser Met Lys His Leu Ile Ser Leu Val Gly Glu Leu
 65                  70                  75                  80
Arg Glu Arg Gly Ile Asn Phe Arg Ser Leu Thr Asp Ser Ile Asp Thr
                 85                  90                  95
Ser Ser Pro Met Gly Arg Phe Phe Tyr Val Met Gly Ala Leu Ala
             100                 105                 110
Glu Met Glu Arg Glu Leu Ile Ile Glu Arg Thr Met Ala Gly Leu Ala
             115                 120                 125
Ala Ala Arg Asn Lys Gly Arg Ile Gly Gly Arg Pro Arg Lys Ser Gly
130                 135                 140
Ser Gly Ser Pro Ala Leu Arg Pro Pro Arg Ala Lys Pro Ala Pro Arg
145                 150                 155                 160
Arg Arg Ala Ala Gln Pro Ser Asp Ala Ser Pro Ala Ala Gln Val Asp
                165                 170                 175
Leu Arg Thr Leu Gly Tyr Ser Gln Gln Gln Glu Lys Ile Lys Pro
             180                 185                 190
Lys Val Arg Ser Thr Val Ala Gln His His Glu Ala Leu Val Gly His
             195                 200                 205
Gly Phe Thr His Ala His Ile Val Ala Leu Ser Gln His Pro Ala Ala
             210                 215                 220
Leu Gly Thr Val Ala Val Thr Tyr Gln His Ile Ile Thr Ala Leu Pro
225                 230                 235                 240
Glu Ala Thr His Glu Asp Ile Val Gly Val Gly Lys Gln Trp Ser Gly
                245                 250                 255
Ala Arg Ala Leu Glu Ala Leu Leu Thr Asp Ala Gly Glu Leu Arg Gly
             260                 265                 270
Pro Pro Leu Gln Leu Asp Thr Gly Gln Leu Val Lys Ile Ala Lys Arg
             275                 280                 285
Gly Gly Val Thr Ala Met Glu Ala Val His Ala Ser Arg Asn Ala Leu
             290                 295                 300
Thr Gly Ala Pro Leu Asn Leu Thr Pro Asp Gln Val Val Ala Ile Ala
305                 310                 315                 320
Ser Asn Ile Gly Gly Lys Gln Ala Leu Glu Thr Val Gln Arg Leu Leu
                325                 330                 335
Pro Val Leu Cys Gln Asp His Gly Leu Thr Pro Asp Gln Val Val Ala
             340                 345                 350
Ile Ala Ser Asn Gly Gly Gly Lys Gln Ala Leu Glu Thr Val Gln Arg
             355                 360                 365
Leu Leu Pro Val Leu Cys Gln Asp His Gly Leu Thr Pro Asp Gln Val
             370                 375                 380
Val Ala Ile Ala Ser Asn Ile Gly Gly Lys Gln Ala Leu Glu Thr Val
385                 390                 395                 400
Gln Arg Leu Leu Pro Val Leu Cys Gln Asp His Gly Leu Thr Pro Asp
                405                 410                 415
Gln Val Val Ala Ile Ala Ser Asn Ile Gly Gly Lys Gln Ala Leu Glu
             420                 425                 430
Thr Val Gln Arg Leu Leu Pro Val Leu Cys Gln Asp His Gly Leu Thr
             435                 440                 445
Pro Asp Gln Val Val Ala Ile Ala Ser Asn Ile Gly Gly Lys Gln Ala
450                 455                 460
Leu Glu Thr Val Gln Arg Leu Leu Pro Val Leu Cys Gln Asp His Gly
```

```
            465                 470                 475                 480
Leu Thr Pro Asp Gln Val Val Ala Ile Ala Ser His Asp Gly Gly Lys
                485                 490                 495
Gln Ala Leu Glu Thr Val Gln Arg Leu Leu Pro Val Leu Cys Gln Asp
                500                 505                 510
His Gly Leu Thr Pro Asp Gln Val Val Ala Ile Ala Ser His Asp Gly
                515                 520                 525
Gly Lys Gln Ala Leu Glu Thr Val Gln Arg Leu Leu Pro Val Leu Cys
            530                 535                 540
Gln Asp His Gly Leu Thr Pro Asp Gln Val Val Ala Ile Ala Ser His
545                 550                 555                 560
Asp Gly Gly Lys Gln Ala Leu Glu Thr Val Gln Arg Leu Leu Pro Val
                565                 570                 575
Leu Cys Gln Asp His Gly Leu Thr Pro Asp Gln Val Val Ala Ile Ala
                580                 585                 590
Ser His Asp Gly Gly Lys Gln Ala Leu Glu Thr Val Gln Arg Leu Leu
            595                 600                 605
Pro Val Leu Cys Gln Asp His Gly Leu Thr Pro Asp Gln Val Val Ala
        610                 615                 620
Ile Ala Ser His Asp Gly Gly Lys Gln Ala Leu Glu Thr Val Gln Arg
625                 630                 635                 640
Leu Leu Pro Val Leu Cys Gln Asp His Gly Leu Thr Pro Asp Gln Val
                645                 650                 655
Val Ala Ile Ala Ser Asn Gly Gly Lys Gln Ala Leu Glu Thr Val
                660                 665                 670
Gln Arg Leu Leu Pro Val Leu Cys Gln Asp His Gly Leu Thr Pro Asp
            675                 680                 685
Gln Val Val Ala Ile Ala Ser His Asp Gly Gly Lys Gln Ala Leu Glu
        690                 695                 700
Thr Val Gln Arg Leu Leu Pro Val Leu Cys Gln Asp His Gly Leu Thr
705                 710                 715                 720
Pro Asp Gln Val Val Ala Ile Ala Ser His Asp Gly Gly Lys Gln Ala
                725                 730                 735
Leu Glu Thr Val Gln Arg Leu Leu Pro Val Leu Cys Gln Asp His Gly
            740                 745                 750
Leu Thr Pro Asp Gln Val Val Ala Ile Ala Ser Asn Ile Gly Gly Lys
            755                 760                 765
Gln Ala Leu Glu Thr Val Gln Arg Leu Leu Pro Val Leu Cys Gln Asp
        770                 775                 780
His Gly Leu Thr Pro Asp Gln Val Val Ala Ile Ala Ser Asn Ile Gly
785                 790                 795                 800
Gly Lys Gln Ala Leu Glu Ser Ile Val Ala Gln Leu Ser Arg Pro Asp
                805                 810                 815
Pro Ala Leu Ala Ala Leu Thr Asn Asp His Leu Val Ala Leu Ala Cys
                820                 825                 830
Leu Gly Pro Lys Lys Lys Arg Lys Val
            835                 840

<210> SEQ ID NO 27
<211> LENGTH: 2523
<212> TYPE: DNA
<213> ORGANISM: Artificial Sequence
<220> FEATURE:
<223> OTHER INFORMATION: Synthetic construct
```

<400> SEQUENCE: 27

```
atgctgattg gctatgtaag ggtatcaaca aatgaccaga atacagacct gcaacgaaac    60
gctcttgttt gtgcaggatg tgaacaaata tttgaagata aattaagcgg aacaaggaca   120
gaccgaccgg gattaaaacg cgctttaaag cgccttcaaa aaggtgacac actggttgtc   180
tggaaactgg atcgcctcgg gcgaagcatg aaacatttga tttctctcgt aggggaatta   240
cgagagcgag ggattaattt tcgcagtctt actgacagta ttgatacgtc atctccaatg   300
gggcgttttt tcttctacgt tatgggtgcc ctggctgaaa tggaacgaga actaattatc   360
gagcgaacga tggctggact tgctgccgcc agaaataaag gccgtattgg aggtcgcccg   420
cgtaaatcgg ggtctggatc ccccgcgcgg ccgccgcgcg ccaagccggc cccgcgacgg   480
cgtgctgcgc aaccctccga cgcttcgccg gccgcgcagg tggatctacg cacgctcggc   540
tacagtcagc agcagcaaga gaagatcaaa ccgaaggtgc gttcgacagt ggcgcagcac   600
cacgaggcac tggtgggcca tgggtttaca cacgcgcaca tcgttgcgct cagccaacac   660
ccggcagcgt tagggaccgt cgctgtcacg tatcagcaca taatcacggc gttgccagag   720
gcgacacacg aagacatcgt tggcgtcggc aaacagtggt ccggcgcacg cgccctggag   780
gccttgctca cggatgcggg ggagttgaga ggtccgccgt tacagttgga cacaggccaa   840
cttgtgaaga ttgcaaaacg tggcggcgtg accgcaatgg aggcagtgca tgcatcgcgc   900
aatgcactga cgggtgcccc cctggagctg actccggacc aagtggtggc tatcgccagc   960
aacattggcg gcaagcaagc gctcgaaacg gtgcagcggc tgttgccggt gctgtgccag  1020
gaccatggcc tgactccgga ccaagtggtg gctatcgcca gcaacggtgg cggcaagcaa  1080
gcgctcgaaa cggtgcagcg gctgttgccg gtgctgtgcc aggaccatgg cctgactccg  1140
gaccaagtgg tggctatcgc cagcaacatt ggcggcaagc aagcgctcga acggtgcag   1200
cggctgttgc cggtgctgtg ccaggaccat ggcctgactc cggaccaagt ggtggctatc  1260
gccagcaaca ttggcggcaa gcaagcgctc gaaacggtgc agcggctgtt gccggtgctg  1320
tgccaggacc atggcctgac tccggaccaa gtggtggcta tcgccagcaa cattggcggc  1380
aagcaagcgc tcgaaacggt gcagcggctg ttgccggtgc tgtgccagga ccatggcctg  1440
actccggacc aagtggtggc tatcgccagc acgatggcg gcaagcaagc gctcgaaacg  1500
gtgcagcggc tgttgccggt gctgtgccag gaccatggcc tgactccgga ccaagtggtg  1560
gctatcgcca gccacgatgg cggcaagcaa gcgctcgaaa cggtgcagcg gctgttgccg  1620
gtgctgtgcc aggaccatgg cctgactccg gaccaagtgg tggctatcgc cagccacgat  1680
ggcggcaagc aagcgctcga acggtgcag cggctgttgc cggtgctgtg ccaggaccat  1740
ggcctgactc cggaccaagt ggtggctatc gccagccacg atggcggcaa gcaagcgctc  1800
gaaacggtgc agcggctgtt gccggtgctg tgccaggacc atggcctgac tccggaccaa  1860
gtggtggcta tcgccagcca cgatggcggc aagcaagcgc tcgaaacggt gcagcggctg  1920
ttgccggtgc tgtgccagga ccatggcctg acccgacc aagtggtggc tatcgccagc  1980
aacggtggcg gcaagcaagc gctcgaaacg gtgcagcggc tgttgccggt gctgtgccag  2040
gaccatggcc tgactccgga ccaagtggtg gctatcgcca gccacgatgg cggcaagcaa  2100
gcgctcgaaa cggtgcagcg gctgttgccg gtgctgtgcc aggaccatgg cctgactccg  2160
gaccaagtgg tggctatcgc cagccacgat ggcggcaagc aagcgctcga acggtgcag  2220
cggctgttgc cggtgctgtg ccaggaccat ggcctgaccc ggaccaagt ggtggctatc   2280
gccagcaaca ttggcggcaa gcaagcgctc gaaacggtgc agcggctgtt gccggtgctg  2340
```

```
tgccaggacc atggcctgac cccggaccaa gtggtggcta tcgccagcaa cattggcggc    2400
aagcaagcgc tcgaaagcat tgtggcccag ctgagccggc tgatccggc gttggccgcg     2460 ttgaccaacg accacctcgt cgccttggcc tgcctcggcc ccaagaagaa gcgcaaggtg    2520
tag                                                                  2523
```

<210> SEQ ID NO 28
<211> LENGTH: 841
<212> TYPE: PRT
<213> ORGANISM: Artificial Sequence
<220> FEATURE:
<223> OTHER INFORMATION: Synthetic construct

<400> SEQUENCE: 28

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Arg Lys Ser Gly
    130                 135                 140

Ser Gly Ser Pro Ala Leu Arg Pro Pro Arg Ala Lys Pro Ala Pro Arg
145                 150                 155                 160

Arg Arg Ala Ala Gln Pro Ser Asp Ala Ser Pro Ala Ala Gln Val Asp
                165                 170                 175

Leu Arg Thr Leu Gly Tyr Ser Gln Gln Gln Gln Glu Lys Ile Lys Pro
            180                 185                 190

Lys Val Arg Ser Thr Val Ala Gln His His Glu Ala Leu Val Gly His
        195                 200                 205

Gly Phe Thr His Ala His Ile Val Ala Leu Ser Gln His Pro Ala Ala
    210                 215                 220

Leu Gly Thr Val Ala Val Thr Tyr Gln His Ile Ile Thr Ala Leu Pro
225                 230                 235                 240

Glu Ala Thr His Glu Asp Ile Val Gly Val Gly Lys Gln Trp Ser Gly
                245                 250                 255

Ala Arg Ala Leu Glu Ala Leu Leu Thr Asp Ala Gly Glu Leu Arg Gly
            260                 265                 270

Pro Pro Leu Gln Leu Asp Thr Gly Gln Leu Val Lys Ile Ala Lys Arg
        275                 280                 285

Gly Gly Val Thr Ala Met Glu Ala Val His Ala Ser Arg Asn Ala Leu
    290                 295                 300

Thr Gly Ala Pro Leu Asn Leu Thr Pro Asp Gln Val Val Ala Ile Ala
305                 310                 315                 320
```

Ser Asn Ile Gly Gly Lys Gln Ala Leu Glu Thr Val Gln Arg Leu Leu
            325                 330                 335

Pro Val Leu Cys Gln Asp His Gly Leu Thr Pro Asp Gln Val Val Ala
        340                 345                 350

Ile Ala Ser Asn Gly Gly Lys Gln Ala Leu Glu Thr Val Gln Arg
            355                 360                 365

Leu Leu Pro Val Leu Cys Gln Asp His Gly Leu Thr Pro Asp Gln Val
    370                 375                 380

Val Ala Ile Ala Ser Asn Ile Gly Gly Lys Gln Ala Leu Glu Thr Val
385                 390                 395                 400

Gln Arg Leu Leu Pro Val Leu Cys Gln Asp His Gly Leu Thr Pro Asp
            405                 410                 415

Gln Val Val Ala Ile Ala Ser Asn Ile Gly Gly Lys Gln Ala Leu Glu
        420                 425                 430

Thr Val Gln Arg Leu Leu Pro Val Leu Cys Gln Asp His Gly Leu Thr
            435                 440                 445

Pro Asp Gln Val Val Ala Ile Ala Ser Asn Ile Gly Gly Lys Gln Ala
    450                 455                 460

Leu Glu Thr Val Gln Arg Leu Leu Pro Val Leu Cys Gln Asp His Gly
465                 470                 475                 480

Leu Thr Pro Asp Gln Val Val Ala Ile Ala Ser His Asp Gly Gly Lys
            485                 490                 495

Gln Ala Leu Glu Thr Val Gln Arg Leu Leu Pro Val Leu Cys Gln Asp
        500                 505                 510

His Gly Leu Thr Pro Asp Gln Val Val Ala Ile Ala Ser His Asp Gly
            515                 520                 525

Gly Lys Gln Ala Leu Glu Thr Val Gln Arg Leu Leu Pro Val Leu Cys
    530                 535                 540

Gln Asp His Gly Leu Thr Pro Asp Gln Val Val Ala Ile Ala Ser His
545                 550                 555                 560

Asp Gly Gly Lys Gln Ala Leu Glu Thr Val Gln Arg Leu Leu Pro Val
            565                 570                 575

Leu Cys Gln Asp His Gly Leu Thr Pro Asp Gln Val Val Ala Ile Ala
        580                 585                 590

Ser His Asp Gly Gly Lys Gln Ala Leu Glu Thr Val Gln Arg Leu Leu
            595                 600                 605

Pro Val Leu Cys Gln Asp His Gly Leu Thr Pro Asp Gln Val Val Ala
    610                 615                 620

Ile Ala Ser His Asp Gly Gly Lys Gln Ala Leu Glu Thr Val Gln Arg
625                 630                 635                 640

Leu Leu Pro Val Leu Cys Gln Asp His Gly Leu Thr Pro Asp Gln Val
            645                 650                 655

Val Ala Ile Ala Ser Asn Gly Gly Lys Gln Ala Leu Glu Thr Val
        660                 665                 670

Gln Arg Leu Leu Pro Val Leu Cys Gln Asp His Gly Leu Thr Pro Asp
            675                 680                 685

Gln Val Val Ala Ile Ala Ser His Asp Gly Gly Lys Gln Ala Leu Glu
        690                 695                 700

Thr Val Gln Arg Leu Leu Pro Val Leu Cys Gln Asp His Gly Leu Thr
705                 710                 715                 720

Pro Asp Gln Val Val Ala Ile Ala Ser His Asp Gly Gly Lys Gln Ala
            725                 730                 735

Leu Glu Thr Val Gln Arg Leu Leu Pro Val Leu Cys Gln Asp His Gly

```
                    740                 745                 750
Leu Thr Pro Asp Gln Val Val Ala Ile Ala Ser Asn Ile Gly Gly Lys
            755                 760                 765

Gln Ala Leu Glu Thr Val Gln Arg Leu Leu Pro Val Leu Cys Gln Asp
            770                 775                 780

His Gly Leu Thr Pro Asp Gln Val Val Ala Ile Ala Ser Asn Ile Gly
785                 790                 795                 800

Gly Lys Gln Ala Leu Glu Ser Ile Val Ala Gln Leu Ser Arg Pro Asp
                805                 810                 815

Pro Ala Leu Ala Ala Leu Thr Asn Asp His Leu Val Ala Leu Ala Cys
                820                 825                 830

Leu Gly Pro Lys Lys Arg Lys Val
                835                 840

<210> SEQ ID NO 29
<211> LENGTH: 134
<212> TYPE: PRT
<213> ORGANISM: Artificial Sequence
<220> FEATURE:
<223> OTHER INFORMATION: Synthetic construct

<400> SEQUENCE: 29

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
                20                  25                  30

Gly His Gly Phe Thr His Ala His Ile Val Ala Leu Ser Gln His Pro
            35                  40                  45

Ala Ala Leu Gly Thr Val Ala Val Thr Tyr Gln His Ile Ile Thr Ala
        50                  55                  60

Leu Pro Glu Ala Thr His Glu Asp Ile Val Gly Val Gly Lys Gln Trp
65                  70                  75                  80

Ser Gly Ala Arg Ala Leu Glu Ala Leu Leu Thr Asp Ala Gly Glu Leu
                85                  90                  95

Arg Gly Pro Pro Leu Gln Leu Asp Thr Gly Gln Leu Val Lys Ile Ala
            100                 105                 110

Lys Arg Gly Gly Val Thr Ala Met Glu Ala Val His Ala Ser Arg Asn
        115                 120                 125

Ala Leu Thr Gly Ala Pro
    130

<210> SEQ ID NO 30
<211> LENGTH: 34
<212> TYPE: PRT
<213> ORGANISM: Artificial Sequence
<220> FEATURE:
<223> OTHER INFORMATION: Synthetic construct

<400> SEQUENCE: 30

Leu Thr Asp Gly Gln Leu Val Lys Ile Ala Lys Arg Gly Gly Val Thr
1               5                   10                  15

Ala Met Glu Ala Val His Ala Ser Arg Asn Ala Leu Thr Gly Ala Pro
                20                  25                  30

Leu Asn

<210> SEQ ID NO 31
<211> LENGTH: 30
<212> TYPE: PRT
```

```
<213> ORGANISM: Artificial Sequence
<220> FEATURE:
<223> OTHER INFORMATION: Synthetic construct

<400> SEQUENCE: 31

Thr His Glu Asp Ile Val Gly Val Gly Lys Gln Trp Ser Gly Ala Arg
1               5                   10                  15

Ala Leu Glu Ala Leu Leu Thr Asp Ala Gly Glu Leu Arg Gly
            20                  25                  30

<210> SEQ ID NO 32
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (12)..(13)
<223> OTHER INFORMATION: Xaa can be any naturally occurring amino acid

<400> SEQUENCE: 32

Leu Thr Pro Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 33
<211> LENGTH: 15
<212> TYPE: PRT
<213> ORGANISM: Artificial Sequence
<220> FEATURE:
<223> OTHER INFORMATION: Synthetic construct

<400> SEQUENCE: 33

Asp Ile Val Gly Val Lys Gln Trp Ser Gly Ala Arg Ala Leu Glu
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic construct

<400> SEQUENCE: 34

Asp Ile Val Gly Val Lys Ser Arg Ser Gly Ala Arg Ala Leu Glu
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic construct

<400> SEQUENCE: 35

Asp Ile Val Gly Val Lys Arg Gly Ala Gly Ala Arg Ala Leu Glu
1               5                   10                  15

<210> SEQ ID NO 36
<211> LENGTH: 14
<212> TYPE: PRT
<213> ORGANISM: Artificial Sequence
<220> FEATURE:
```

```
<223> OTHER INFORMATION: Synthetic construct

<400> SEQUENCE: 36

Asp Ile Val Gly Val Lys Tyr His Gly Ala Arg Ala Leu Glu
1               5                   10

<210> SEQ ID NO 37
<211> LENGTH: 21
<212> TYPE: DNA
<213> ORGANISM: Artificial Sequence
<220> FEATURE:
<223> OTHER INFORMATION: Synthetic construct

<400> SEQUENCE: 37
ataaaccccc tccaaccagg c                                             21

<210> SEQ ID NO 38
<211> LENGTH: 71
<212> TYPE: DNA
<213> ORGANISM: Artificial Sequence
<220> FEATURE:
<223> OTHER INFORMATION: Synthetic construct

<400> SEQUENCE: 38
aagaaggtct tcattacacc tgcagctctc attttccata cagtcagtat caattctgga   60
agaatttcca g                                                        71

<210> SEQ ID NO 39
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid

<400> SEQUENCE: 39

Xaa Xaa Xaa Ser Gly Ala Arg
1               5

<210> SEQ ID NO 40
<211> LENGTH: 18
<212> TYPE: DNA
<213> ORGANISM: Artificial Sequence
<220> FEATURE:
<223> OTHER INFORMATION: Synthetic construct

<400> SEQUENCE: 40
gtcttcatta cacctgca                                                 18

<210> SEQ ID NO 41
<211> LENGTH: 18
<212> TYPE: DNA
<213> ORGANISM: Artificial Sequence
<220> FEATURE:
<223> OTHER INFORMATION: Synthetic construct

<400> SEQUENCE: 41
cttcattaca cctgcagc                                                 18

<210> SEQ ID NO 42
<211> LENGTH: 18
<212> TYPE: DNA
<213> ORGANISM: Artificial Sequence
```

```
<220> FEATURE:
<223> OTHER INFORMATION: Synthetic construct

<400> SEQUENCE: 42
ttcattacac ctgcagct                                                        18

<210> SEQ ID NO 43
<211> LENGTH: 18
<212> TYPE: DNA
<213> ORGANISM: Artificial Sequence
<220> FEATURE:
<223> OTHER INFORMATION: Synthetic construct

<400> SEQUENCE: 43
acctgcagct ctcatttt                                                        18

<210> SEQ ID NO 44
<211> LENGTH: 16
<212> TYPE: DNA
<213> ORGANISM: Artificial Sequence
<220> FEATURE:
<223> OTHER INFORMATION: Synthetic construct

<400> SEQUENCE: 44
gtcagtcata gttaag                                                          16

<210> SEQ ID NO 45
<211> LENGTH: 18
<212> TYPE: DNA
<213> ORGANISM: Artificial Sequence
<220> FEATURE:
<223> OTHER INFORMATION: Synthetic construct

<400> SEQUENCE: 45
tcagtcatag ttaagacc                                                        18

<210> SEQ ID NO 46
<211> LENGTH: 19
<212> TYPE: DNA
<213> ORGANISM: Artificial Sequence
<220> FEATURE:
<223> OTHER INFORMATION: Synthetic construct

<400> SEQUENCE: 46
tcatagttaa gaccttctt                                                       19

<210> SEQ ID NO 47
<211> LENGTH: 17
<212> TYPE: DNA
<213> ORGANISM: Artificial Sequence
<220> FEATURE:
<223> OTHER INFORMATION: Synthetic construct

<400> SEQUENCE: 47
agttaagacc ttcttaa                                                         17

<210> SEQ ID NO 48
<211> LENGTH: 159
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (104)..(107)
<223> OTHER INFORMATION: Xaa can be any naturally occurring amino acid
```

```
<400> SEQUENCE: 48

Pro Arg Pro Pro Arg Ala Lys Pro Ala Pro Arg Arg Ala Ala Gln
1               5                   10                  15

Pro Ser Asp Ala Ser Pro Ala Ala Gln Val Asp Leu Arg Thr Leu Gly
            20                  25                  30

Tyr Ser Gln Gln Gln Glu Lys Ile Lys Pro Lys Val Arg Ser Thr
        35                  40                  45

Val Ala Gln His His Glu Ala Leu Val Gly His Gly Phe Thr His Ala
    50                  55                  60

His Ile Val Ala Leu Ser Gln His Pro Ala Ala Leu Gly Thr Val Ala
65                  70                  75                  80

Val Thr Tyr Gln His Ile Ile Thr Ala Leu Pro Glu Ala Thr His Glu
                85                  90                  95

Asp Ile Val Gly Val Gly Lys Xaa Xaa Xaa Xaa Ala Arg Ala Leu Glu
            100                 105                 110

Ala Leu Leu Thr Asp Ala Gly Glu Leu Arg Gly Pro Pro Leu Gln Leu
        115                 120                 125

Asp Thr Gly Gln Leu Val Lys Ile Ala Lys Arg Gly Gly Val Thr Ala
    130                 135                 140

Met Glu Ala Val His Ala Ser Arg Asn Ala Leu Thr Gly Ala Pro
145                 150                 155

<210> SEQ ID NO 49
<211> LENGTH: 134
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (79)..(82)
<223> OTHER INFORMATION: Xaa can be any naturally occurring amino acid

<400> SEQUENCE: 49

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Thr Tyr Gln His Ile Ile Thr Ala
    50                  55                  60

Leu Pro Glu Ala Thr His Glu Asp Ile Val Gly Val Gly Lys Xaa Xaa
65                  70                  75                  80

Xaa Xaa Ala Arg Ala Leu Glu Ala Leu Leu Thr Asp Ala Gly Glu Leu
                85                  90                  95

Arg Gly Pro Pro Leu Gln Leu Asp Thr Gly Gln Leu Val Lys Ile Ala
            100                 105                 110

Lys Arg Gly Gly Val Thr Ala Met Glu Ala Val His Ala Ser Arg Asn
        115                 120                 125

Ala Leu Thr Gly Ala Pro
    130

<210> SEQ ID NO 50
<211> LENGTH: 134
<212> TYPE: PRT
<213> ORGANISM: Artificial Sequence
<220> FEATURE:
```

<223> OTHER INFORMATION: Synthetic construct

<400> SEQUENCE: 50

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro
    130

<210> SEQ ID NO 51
<211> LENGTH: 80
<212> TYPE: PRT
<213> ORGANISM: Artificial Sequence
<220> FEATURE:
<223> OTHER INFORMATION: Synthetic construct

<400> SEQUENCE: 51

Asn Asp His Leu Val Ala Leu Ala Cys Leu Gly Gly Arg Pro Ala Met
1               5                   10                  15

Asp Ala Val Lys Lys Gly Leu Pro His Ala Pro Glu Leu Ile Arg Arg
            20                  25                  30

Val Asn Arg Arg Ile Gly Glu Arg Thr Ser His Arg Val Ala Asp Tyr
        35                  40                  45

Ala Gln Val Val Arg Val Leu Glu Phe Phe Gln Cys His Ser His Pro
    50                  55                  60

Ala Tyr Ala Phe Asp Glu Ala Met Thr Gln Phe Gly Met Ser Gly Gln
65                  70                  75                  80

<210> SEQ ID NO 52
<211> LENGTH: 46
<212> TYPE: PRT
<213> ORGANISM: Artificial Sequence
<220> FEATURE:
<223> OTHER INFORMATION: Synthetic construct

<400> SEQUENCE: 52

Asn Asp His Leu Val Ala Leu Ala Cys Leu Gly Gly Arg Pro Ala Met
1               5                   10                  15

Asp Ala Val Lys Lys Gly Leu Pro His Ala Pro Glu Leu Ile Arg Arg
            20                  25                  30

Val Asn Arg Arg Ile Gly Glu Arg Thr Ser His Arg Val Ala
        35                  40                  45

<210> SEQ ID NO 53
<211> LENGTH: 10
<212> TYPE: PRT

```
<213> ORGANISM: Artificial Sequence
<220> FEATURE:
<223> OTHER INFORMATION: Synthetic construct

<400> SEQUENCE: 53

Asn Asp His Leu Val Ala Leu Ala Cys Leu
1               5                   10

<210> SEQ ID NO 54
<211> LENGTH: 135
<212> TYPE: PRT
<213> ORGANISM: Artificial Sequence
<220> FEATURE:
<223> OTHER INFORMATION: Synthetic construct

<400> SEQUENCE: 54

Gln Val Asp Leu Arg Thr Leu Gly Tyr Ser Gln Gln Gln Glu Lys
1               5                   10                  15

Ile Lys Pro Lys Val Arg Ser Thr Val Ala Gln His His Glu Ala Leu
                20                  25                  30

Val Gly His Gly Phe Thr His Ala His Ile Val Ala Leu Ser Gln His
            35                  40                  45

Pro Ala Ala Leu Gly Thr Val Ala Val Thr Tyr Gln His Ile Ile Thr
    50                  55                  60

Ala Leu Pro Glu Ala Thr His Glu Asp Ile Val Gly Val Gly Lys Ser
65                  70                  75                  80

Arg Ser Gly Ala Arg Ala Leu Glu Ala Leu Leu Thr Asp Ala Gly Glu
                85                  90                  95

Leu Arg Gly Pro Pro Leu Gln Leu Asp Thr Gly Gln Leu Val Lys Ile
            100                 105                 110

Ala Lys Arg Gly Gly Val Thr Ala Met Glu Ala Val His Ala Ser Arg
        115                 120                 125

Asn Ala Leu Thr Gly Ala Pro
    130                 135

<210> SEQ ID NO 55
<211> LENGTH: 132
<212> TYPE: PRT
<213> ORGANISM: Artificial Sequence
<220> FEATURE:
<223> OTHER INFORMATION: Synthetic construct

<400> SEQUENCE: 55

Met Ala Ala Leu Gly Tyr Ser Arg Glu Gln Ile Arg Lys Leu Lys Gln
1               5                   10                  15

Glu Ser Leu Ser Gly Val Ala Lys Tyr His Ala Pro Leu Thr Arg His
                20                  25                  30

Gly Phe Thr His Thr Asp Ile Cys Arg Ile Ser Arg Arg Trp Gln Ser
            35                  40                  45

Leu Arg Met Val Ala Lys Asn Tyr Pro Lys Leu Ile Ala Ala Leu Pro
        50                  55                  60

Asp Leu Thr Arg Thr His Ile Val Asp Ile Ala Arg Gln Arg Ser Gly
65                  70                  75                  80

Asp Leu Ala Leu Glu Ala Leu Pro Val Ala Thr Ala Leu Ala Ala
                85                  90                  95

Ala Pro Leu Arg Leu Arg Ala Ser Gln Ile Ala Ile Ile Ala Gln Cys
            100                 105                 110

Gly Glu Arg Pro Ala Ile Leu Ala Leu His Arg Leu Arg Arg Lys Leu
        115                 120                 125
```

Thr Gly Ala Pro
    130

<210> SEQ ID NO 56
<211> LENGTH: 180
<212> TYPE: PRT
<213> ORGANISM: Artificial Sequence
<220> FEATURE:
<223> OTHER INFORMATION: Synthetic construct

<400> SEQUENCE: 56

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Pro Lys Leu Thr
    130                 135                 140

Lys Ala Glu Trp Glu Gln Ala Gly Arg Leu Leu Ala Gln Gly Ile Pro
145                 150                 155                 160

Arg Lys Gln Val Ala Leu Ile Tyr Asp Val Ala Leu Ser Thr Leu Tyr
                165                 170                 175

Lys Lys His Pro
            180

<210> SEQ ID NO 57
<211> LENGTH: 144
<212> TYPE: PRT
<213> ORGANISM: Artificial Sequence
<220> FEATURE:
<223> OTHER INFORMATION: Synthetic construct

<400> SEQUENCE: 57

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala

```
                100                 105                 110
Glu Met Glu Arg Glu Leu Ile Ile Glu Arg Thr Met Ala Gly Leu Ala
            115                 120                 125

Ala Ala Arg Asn Lys Gly Arg Ile Gly Gly Arg Pro Pro Lys Ser Gly
        130                 135                 140

<210> SEQ ID NO 58
<211> LENGTH: 143
<212> TYPE: PRT
<213> ORGANISM: Artificial Sequence
<220> FEATURE:
<223> OTHER INFORMATION: Synthetic construct

<400> SEQUENCE: 58

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Ile Ala
            115                 120                 125

Ala Ala Arg Asn Lys Gly Arg Phe Gly Arg Pro Pro Lys Ser
        130                 135                 140

<210> SEQ ID NO 59
<211> LENGTH: 144
<212> TYPE: PRT
<213> ORGANISM: Artificial Sequence
<220> FEATURE:
<223> OTHER INFORMATION: Synthetic construct

<400> SEQUENCE: 59

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Leu Glu Arg Val Met Ala Gly Ile Ala
            115                 120                 125
```

```
Ala Ala Arg Asn Lys Gly Arg Arg Trp Gly Arg Pro Pro Lys Ser Gly
        130                 135                 140

<210> SEQ ID NO 60
<211> LENGTH: 144
<212> TYPE: PRT
<213> ORGANISM: Artificial Sequence
<220> FEATURE:
<223> OTHER INFORMATION: Synthetic construct

<400> SEQUENCE: 60

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Val Met Ala Gly Leu Ala
        115                 120                 125

Ala Ala Arg Asn Lys Gly Arg Arg Phe Gly Arg Pro Pro Lys Ser Gly
    130                 135                 140

<210> SEQ ID NO 61
<211> LENGTH: 144
<212> TYPE: PRT
<213> ORGANISM: Artificial Sequence
<220> FEATURE:
<223> OTHER INFORMATION: Synthetic construct

<400> SEQUENCE: 61

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Leu Ser Ile Leu Glu Arg Pro Met Ala Gly His Ala
        115                 120                 125

Ala Ala Arg Asn Lys Gly Arg Arg Phe Gly Arg Pro Pro Lys Ser Gly
    130                 135                 140

<210> SEQ ID NO 62
```

<211> LENGTH: 144
<212> TYPE: PRT
<213> ORGANISM: Artificial Sequence
<220> FEATURE:
<223> OTHER INFORMATION: Synthetic construct

<400> SEQUENCE: 62

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Tyr Val Met Gly Ala Leu Ala
            100                 105                 110

Glu Met Glu Arg Glu Leu Ile Ile Glu Arg Thr Ser Ala Gly Arg Ala
        115                 120                 125

Ala Ala Ile Asn Lys Gly Arg Ile Met Gly Arg Pro Arg Lys Ser Gly
    130                 135                 140
```

<210> SEQ ID NO 63
<211> LENGTH: 267
<212> TYPE: PRT
<213> ORGANISM: Artificial Sequence
<220> FEATURE:
<223> OTHER INFORMATION: Synthetic construct

<400> SEQUENCE: 63

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Pro Lys Ser Gly
    130                 135                 140

Thr Gly Glu Lys Pro Tyr Lys Cys Pro Glu Cys Gly Lys Ser Phe Ser
145                 150                 155                 160

Thr Ser Gly Asn Leu Val Arg His Gln Arg Thr His Thr Gly Glu Lys
                165                 170                 175

Pro Tyr Lys Cys Pro Glu Cys Gly Lys Ser Phe Ser Gln Ser Gly Asp
```

```
              180                 185                 190
Leu Arg Arg His Gln Arg Thr His Thr Gly Glu Lys Pro Tyr Lys Cys
            195                 200                 205

Pro Glu Cys Gly Lys Ser Phe Ser Thr Ser Gly Asn Leu Val Arg His
        210                 215                 220

Gln Arg Thr His Thr Gly Glu Lys Pro Tyr Lys Cys Pro Glu Cys Gly
225                 230                 235                 240

Lys Ser Phe Ser Thr Ser Gly Glu Leu Val Arg His Gln Arg Thr His
            245                 250                 255

Thr Gly Lys Lys Thr Ser Gly Gln Ala Gly Gln
        260                 265

<210> SEQ ID NO 64
<211> LENGTH: 267
<212> TYPE: PRT
<213> ORGANISM: Artificial Sequence
<220> FEATURE:
<223> OTHER INFORMATION: Synthetic construct

<400> SEQUENCE: 64

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Pro Lys Ser Gly
130                 135                 140

Thr Gly Glu Lys Pro Tyr Lys Cys Pro Glu Cys Gly Lys Ser Phe Ser
145                 150                 155                 160

His Arg Thr Thr Leu Thr Asn His Gln Arg Thr His Thr Gly Glu Lys
                165                 170                 175

Pro Tyr Lys Cys Pro Glu Cys Gly Lys Ser Phe Ser Gln Ser Gly Asp
            180                 185                 190

Leu Arg Arg His Gln Arg Thr His Thr Gly Glu Lys Pro Tyr Lys Cys
        195                 200                 205

Pro Glu Cys Gly Lys Ser Phe Ser Gln Ser Gly Asp Leu Arg Arg His
    210                 215                 220

Gln Arg Thr His Thr Gly Glu Lys Pro Tyr Lys Cys Pro Glu Cys Gly
225                 230                 235                 240

Lys Ser Phe Ser Gln Ser Gly Asp Leu Arg Arg His Gln Arg Thr His
                245                 250                 255

Thr Gly Lys Lys Thr Ser Gly Gln Ala Gly Gln
            260                 265
```

```
<210> SEQ ID NO 65
<211> LENGTH: 267
<212> TYPE: PRT
<213> ORGANISM: Artificial Sequence
<220> FEATURE:
<223> OTHER INFORMATION: Synthetic construct

<400> SEQUENCE: 65

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
        50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Pro Lys Ser Gly
    130                 135                 140

Thr Gly Glu Lys Pro Tyr Lys Cys Pro Glu Cys Gly Lys Ser Phe Ser
145                 150                 155                 160

Gln Ser Gly Asp Leu Arg Arg His Gln Arg Thr His Thr Gly Glu Lys
                165                 170                 175

Pro Tyr Lys Cys Pro Glu Cys Gly Lys Ser Phe Ser Gln Arg Ala His
            180                 185                 190

Leu Glu Arg His Gln Arg Thr His Thr Gly Glu Lys Pro Tyr Lys Cys
        195                 200                 205

Pro Glu Cys Gly Lys Ser Phe Ser Thr Ser Gly Asn Leu Val Arg His
    210                 215                 220

Gln Arg Thr His Thr Gly Glu Lys Pro Tyr Lys Cys Pro Glu Cys Gly
225                 230                 235                 240

Lys Ser Phe Ser Arg Ser Asp Glu Leu Val Arg His Gln Arg Thr His
                245                 250                 255

Thr Gly Lys Thr Ser Gly Gln Ala Gly Gln
            260                 265

<210> SEQ ID NO 66
<211> LENGTH: 267
<212> TYPE: PRT
<213> ORGANISM: Artificial Sequence
<220> FEATURE:
<223> OTHER INFORMATION: Synthetic construct

<400> SEQUENCE: 66

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45
```

```
Leu Lys Arg Leu Gln Lys Gly Asp Thr Leu Val Val Trp Lys Leu Asp
     50                  55                  60

Arg Leu Gly Arg Ser Met Lys His Leu Ile Ser Leu Val Gly Glu Leu
 65                  70                  75                  80

Arg Glu Arg Gly Ile Asn Phe Arg Ser Leu Thr Asp Ser Ile Asp Thr
                 85                  90                  95

Ser Ser Pro Met Gly Arg Phe Phe Tyr Val Met Gly Ala Leu Ala
                100                 105                 110

Glu Met Glu Arg Glu Leu Ile Ile Glu Arg Thr Met Ala Gly Leu Ala
                115                 120                 125

Ala Ala Arg Asn Lys Gly Arg Ile Gly Gly Arg Pro Pro Lys Ser Gly
    130                 135                 140

Thr Gly Glu Lys Pro Tyr Lys Cys Pro Glu Cys Gly Lys Ser Phe Ser
145                 150                 155                 160

Arg Ser Asp Lys Leu Val Arg His Gln Arg Thr His Thr Gly Glu Lys
                165                 170                 175

Pro Tyr Lys Cys Pro Glu Cys Gly Lys Ser Phe Ser Arg Lys Asp Asn
                180                 185                 190

Leu Lys Asn His Gln Arg Thr His Thr Gly Glu Lys Pro Tyr Lys Cys
    195                 200                 205

Pro Glu Cys Gly Lys Ser Phe Ser Thr Ser Gly Glu Leu Val Arg His
    210                 215                 220

Gln Arg Thr His Thr Gly Glu Lys Pro Tyr Lys Cys Pro Glu Cys Gly
225                 230                 235                 240

Lys Ser Phe Ser Arg Ser Asp Lys Leu Val Arg His Gln Arg Thr His
                245                 250                 255

Thr Gly Lys Lys Thr Ser Gly Gln Ala Gly Gln
                260                 265

<210> SEQ ID NO 67
<211> LENGTH: 267
<212> TYPE: PRT
<213> ORGANISM: Artificial Sequence
<220> FEATURE:
<223> OTHER INFORMATION: Synthetic construct

<400> SEQUENCE: 67

Met Leu Ile Gly Tyr Val Arg Val Ser Thr Asn Asp Gln Asn Thr Asp
 1               5                  10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
     50                  55                  60

Arg Leu Gly Arg Ser Met Lys His Leu Ile Ser Leu Val Gly Glu Leu
 65                  70                  75                  80

Arg Glu Arg Gly Ile Asn Phe Arg Ser Leu Thr Asp Ser Ile Asp Thr
                 85                  90                  95

Ser Ser Pro Met Gly Arg Phe Phe Tyr Val Met Gly Ala Leu Ala
                100                 105                 110

Glu Met Glu Arg Glu Leu Ile Ile Glu Arg Thr Met Ala Gly Leu Ala
                115                 120                 125

Ala Ala Arg Asn Lys Gly Arg Ile Gly Gly Arg Pro Pro Lys Ser Gly
    130                 135                 140
```

```
Thr Gly Glu Lys Pro Tyr Lys Cys Pro Glu Cys Gly Lys Ser Phe Ser
145                 150                 155                 160

Thr Thr Gly Asn Leu Thr Val His Gln Arg Thr His Thr Gly Glu Lys
                165                 170                 175

Pro Tyr Lys Cys Pro Glu Cys Gly Lys Ser Phe Ser Asp Pro Gly Ala
            180                 185                 190

Leu Val Arg His Gln Arg Thr His Thr Gly Glu Lys Pro Tyr Lys Cys
        195                 200                 205

Pro Glu Cys Gly Lys Ser Phe Ser Gln Ser Ser Asn Leu Val Arg His
    210                 215                 220

Gln Arg Thr His Thr Gly Glu Lys Pro Tyr Lys Cys Pro Glu Cys Gly
225                 230                 235                 240

Lys Ser Phe Ser Arg Ser Asp His Leu Thr Asn His Gln Arg Thr His
                245                 250                 255

Thr Gly Lys Lys Thr Ser Gly Gln Ala Gly Gln
            260                 265
```

<210> SEQ ID NO 68
<211> LENGTH: 267
<212> TYPE: PRT
<213> ORGANISM: Artificial Sequence
<220> FEATURE:
<223> OTHER INFORMATION: Synthetic construct

<400> SEQUENCE: 68

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
        50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Pro Lys Ser Gly
    130                 135                 140

Thr Gly Glu Lys Pro Tyr Lys Cys Pro Glu Cys Gly Lys Ser Phe Ser
145                 150                 155                 160

Arg Lys Asp Asn Leu Lys Asn His Gln Arg Thr His Thr Gly Glu Lys
                165                 170                 175

Pro Tyr Lys Cys Pro Glu Cys Gly Lys Ser Phe Ser Arg Ser Asp His
            180                 185                 190

Leu Thr Asn His Gln Arg Thr His Thr Gly Glu Lys Pro Tyr Lys Cys
        195                 200                 205

Pro Glu Cys Gly Lys Ser Phe Ser Asp Pro Gly Asn Leu Val Arg His
    210                 215                 220

Gln Arg Thr His Thr Gly Glu Lys Pro Tyr Lys Cys Pro Glu Cys Gly
225                 230                 235                 240
```

```
Lys Ser Phe Ser Arg Lys Asp Asn Leu Lys Asn His Gln Arg Thr His
            245                 250                 255

Thr Gly Lys Lys Thr Ser Gly Gln Ala Gly Gln
        260                 265

<210> SEQ ID NO 69
<211> LENGTH: 267
<212> TYPE: PRT
<213> ORGANISM: Artificial Sequence
<220> FEATURE:
<223> OTHER INFORMATION: Synthetic construct

<400> SEQUENCE: 69

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Tyr Val Met Gly Ala Leu Ala
            100                 105                 110

Glu Met Glu Arg Glu Leu Ile Leu Glu Arg Val Met Ala Gly Ile Ala
        115                 120                 125

Ala Ala Arg Asn Lys Gly Arg Arg Trp Gly Arg Pro Pro Lys Ser Gly
    130                 135                 140

Thr Gly Glu Lys Pro Tyr Lys Cys Pro Glu Cys Gly Lys Ser Phe Ser
145                 150                 155                 160

Gln Arg Ala Asn Leu Arg Ala His Gln Arg Thr His Thr Gly Glu Lys
                165                 170                 175

Pro Tyr Lys Cys Pro Glu Cys Gly Lys Ser Phe Ser Gln Ser Ser Ser
            180                 185                 190

Leu Val Arg His Gln Arg Thr His Thr Gly Glu Lys Pro Tyr Lys Cys
        195                 200                 205

Pro Glu Cys Gly Lys Ser Phe Ser Thr Thr Gly Asn Leu Thr Val His
    210                 215                 220

Gln Arg Thr His Thr Gly Glu Lys Pro Tyr Lys Cys Pro Glu Cys Gly
225                 230                 235                 240

Lys Ser Phe Ser Gln Arg Ala His Leu Glu Arg His Gln Arg Thr His
                245                 250                 255

Thr Gly Lys Lys Thr Ser Gly Gln Ala Gly Gln
        260                 265

<210> SEQ ID NO 70
<211> LENGTH: 267
<212> TYPE: PRT
<213> ORGANISM: Artificial Sequence
<220> FEATURE:
<223> OTHER INFORMATION: Synthetic construct

<400> SEQUENCE: 70

Met Leu Ile Gly Tyr Val Arg Val Ser Thr Asn Asp Gln Asn Thr Asp
1               5                   10                  15
```

```
Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Leu Glu Arg Val Met Ala Gly Ile Ala
        115                 120                 125

Ala Ala Arg Asn Lys Gly Arg Arg Trp Gly Arg Pro Pro Lys Ser Gly
130                 135                 140

Thr Gly Glu Lys Pro Tyr Lys Cys Pro Glu Cys Gly Lys Ser Phe Ser
145                 150                 155                 160

Gln Arg Ala Asn Leu Arg Ala His Gln Arg Thr His Thr Gly Glu Lys
                165                 170                 175

Pro Tyr Lys Cys Pro Glu Cys Gly Lys Ser Phe Ser Arg Arg Asp Glu
            180                 185                 190

Leu Asn Val His Gln Arg Thr His Thr Gly Glu Lys Pro Tyr Lys Cys
        195                 200                 205

Pro Glu Cys Gly Lys Ser Phe Ser Gln Leu Ala His Leu Arg Ala His
210                 215                 220

Gln Arg Thr His Thr Gly Glu Lys Pro Tyr Lys Cys Pro Glu Cys Gly
225                 230                 235                 240

Lys Ser Phe Ser Gln Arg Ala His Leu Glu Arg His Gln Arg Thr His
                245                 250                 255

Thr Gly Lys Lys Thr Ser Gly Gln Ala Gly Gln
            260                 265

<210> SEQ ID NO 71
<211> LENGTH: 267
<212> TYPE: PRT
<213> ORGANISM: Artificial Sequence
<220> FEATURE:
<223> OTHER INFORMATION: Synthetic construct

<400> SEQUENCE: 71

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110
```

```
Glu Met Glu Arg Glu Leu Ile Leu Glu Arg Val Met Ala Gly Ile Ala
            115                 120                 125

Ala Ala Arg Asn Lys Gly Arg Trp Gly Arg Pro Pro Lys Ser Gly
    130                 135                 140

Thr Gly Glu Lys Pro Tyr Lys Cys Pro Glu Cys Gly Lys Ser Phe Ser
145                 150                 155                 160

Arg Arg Asp Glu Leu Asn Val His Gln Arg Thr His Thr Gly Glu Lys
                165                 170                 175

Pro Tyr Lys Cys Pro Glu Cys Gly Lys Ser Phe Ser Arg Ser Asp His
            180                 185                 190

Leu Thr Asn His Gln Arg Thr His Thr Gly Glu Lys Pro Tyr Lys Cys
            195                 200                 205

Pro Glu Cys Gly Lys Ser Phe Ser Gln Leu Ala His Leu Arg Ala His
            210                 215                 220

Gln Arg Thr His Thr Gly Glu Lys Pro Tyr Lys Cys Pro Glu Cys Gly
225                 230                 235                 240

Lys Ser Phe Ser Gln Arg Ala His Leu Glu Arg His Gln Arg Thr His
                245                 250                 255

Thr Gly Lys Lys Thr Ser Gly Gln Ala Gly Gln
            260                 265

<210> SEQ ID NO 72
<211> LENGTH: 267
<212> TYPE: PRT
<213> ORGANISM: Artificial Sequence
<220> FEATURE:
<223> OTHER INFORMATION: Synthetic construct

<400> SEQUENCE: 72

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
            115                 120                 125

Ala Ala Arg Asn Lys Gly Arg Ile Gly Gly Arg Pro Pro Lys Ser Gly
    130                 135                 140

Thr Gly Glu Lys Pro Tyr Lys Cys Pro Glu Cys Gly Lys Ser Phe Ser
145                 150                 155                 160

Thr Ser Gly Ser Leu Val Arg His Gln Arg Thr His Thr Gly Glu Lys
                165                 170                 175

Pro Tyr Lys Cys Pro Glu Cys Gly Lys Ser Phe Ser Arg Ser Asp Lys
            180                 185                 190

Leu Val Arg His Gln Arg Thr His Thr Gly Glu Lys Pro Tyr Lys Cys
            195                 200                 205
```

```
Pro Glu Cys Gly Lys Ser Phe Ser Gln Ser Gly Asp Leu Arg Arg His
        210                 215                 220

Gln Arg Thr His Thr Gly Glu Lys Pro Tyr Lys Cys Pro Glu Cys Gly
225                 230                 235                 240

Lys Ser Phe Ser Thr Ser Gly Glu Leu Val Arg His Gln Arg Thr His
                245                 250                 255

Thr Gly Lys Lys Thr Ser Gly Gln Ala Gly Gln
        260                 265

<210> SEQ ID NO 73
<211> LENGTH: 267
<212> TYPE: PRT
<213> ORGANISM: Artificial Sequence
<220> FEATURE:
<223> OTHER INFORMATION: Synthetic construct

<400> SEQUENCE: 73

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
                100                 105                 110

Glu Met Glu Arg Glu Leu Ile Ile Glu Arg Thr Ser Ala Gly Arg Ala
            115                 120                 125

Ala Ala Ile Asn Lys Gly Arg Ile Met Gly Arg Pro Arg Lys Ser Gly
        130                 135                 140

Thr Gly Glu Lys Pro Tyr Lys Cys Pro Glu Cys Gly Lys Ser Phe Ser
145                 150                 155                 160

Gln Leu Ala His Leu Arg Ala His Gln Arg Thr His Thr Gly Glu Lys
                165                 170                 175

Pro Tyr Lys Cys Pro Glu Cys Gly Lys Ser Phe Ser Gln Leu Ala His
            180                 185                 190

Leu Arg Ala His Gln Arg Thr His Thr Gly Glu Lys Pro Tyr Lys Cys
        195                 200                 205

Pro Glu Cys Gly Lys Ser Phe Ser Asp Pro Gly His Leu Val Arg His
        210                 215                 220

Gln Arg Thr His Thr Gly Glu Lys Pro Tyr Lys Cys Pro Glu Cys Gly
225                 230                 235                 240

Lys Ser Phe Ser Asp Ser Gly Asn Leu Arg Val His Gln Arg Thr His
                245                 250                 255

Thr Gly Lys Lys Thr Ser Gly Gln Ala Gly Gln
        260                 265

<210> SEQ ID NO 74
<211> LENGTH: 267
<212> TYPE: PRT
<213> ORGANISM: Artificial Sequence
```

<220> FEATURE:
<223> OTHER INFORMATION: Synthetic construct

<400> SEQUENCE: 74

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Tyr Val Met Gly Ala Leu Ala
            100                 105                 110

Glu Met Glu Arg Glu Leu Ile Leu Glu Arg Val Met Ala Gly Ile Ala
        115                 120                 125

Ala Ala Arg Asn Lys Gly Arg Arg Trp Gly Arg Pro Lys Ser Gly
    130                 135                 140

Thr Gly Glu Lys Pro Tyr Lys Cys Pro Glu Cys Gly Lys Ser Phe Ser
145                 150                 155                 160

Gln Arg Ala His Leu Glu Arg His Gln Arg Thr His Thr Gly Glu Lys
                165                 170                 175

Pro Tyr Lys Cys Pro Glu Cys Gly Lys Ser Phe Ser Thr Thr Gly Asn
            180                 185                 190

Leu Thr Val His Gln Arg Thr His Thr Gly Glu Lys Pro Tyr Lys Cys
        195                 200                 205

Pro Glu Cys Gly Lys Ser Phe Ser Asp Ser Gly Asn Leu Arg Val His
    210                 215                 220

Gln Arg Thr His Thr Gly Glu Lys Pro Tyr Lys Cys Pro Glu Cys Gly
225                 230                 235                 240

Lys Ser Phe Ser Gln Ser Ser Asn Leu Val Arg His Gln Arg Thr His
                245                 250                 255

Thr Gly Lys Thr Ser Gly Gln Ala Gly Gln
            260                 265
```

<210> SEQ ID NO 75
<211> LENGTH: 267
<212> TYPE: PRT
<213> ORGANISM: Artificial Sequence
<220> FEATURE:
<223> OTHER INFORMATION: Synthetic construct

<400> SEQUENCE: 75

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
50                  55                  60

Arg Leu Gly Arg Ser Met Lys His Leu Ile Ser Leu Val Gly Glu Leu
```

```
                65                  70                  75                  80
Arg Glu Arg Gly Ile Asn Phe Arg Ser Leu Thr Asp Ser Ile Asp Thr
                85                  90                  95

Ser Ser Pro Met Gly Arg Phe Phe Tyr Val Met Gly Ala Leu Ala
            100                 105                 110

Glu Met Glu Arg Glu Leu Ile Ile Glu Arg Thr Met Ala Gly Ile Ala
            115                 120                 125

Ala Ala Arg Asn Lys Gly Arg Arg Phe Gly Arg Pro Lys Ser Gly
            130                 135                 140

Thr Gly Glu Lys Pro Tyr Lys Cys Pro Glu Cys Gly Lys Ser Phe Ser
145                 150                 155                 160

Thr His Leu Asp Leu Ile Arg His Gln Arg Thr His Thr Gly Glu Lys
                165                 170                 175

Pro Tyr Lys Cys Pro Glu Cys Gly Lys Ser Phe Ser Thr Gly Asn
            180                 185                 190

Leu Thr Val His Gln Arg Thr His Thr Gly Glu Lys Pro Tyr Lys Cys
            195                 200                 205

Pro Glu Cys Gly Lys Ser Phe Ser Gln Ser Ser Leu Val Arg His
            210                 215                 220

Gln Arg Thr His Thr Gly Glu Lys Pro Tyr Lys Cys Pro Glu Cys Gly
225                 230                 235                 240

Lys Ser Phe Ser Arg Ser Asp Asn Leu Val Arg His Gln Arg Thr His
                245                 250                 255

Thr Gly Lys Lys Thr Ser Gly Gln Ala Gly Gln
                260                 265

<210> SEQ ID NO 76
<211> LENGTH: 267
<212> TYPE: PRT
<213> ORGANISM: Artificial Sequence
<220> FEATURE:
<223> OTHER INFORMATION: Synthetic construct

<400> SEQUENCE: 76

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Tyr Val Met Gly Ala Leu Ala
            100                 105                 110

Glu Met Glu Arg Glu Leu Ile Ile Glu Arg Thr Met Ala Gly Ile Ala
            115                 120                 125

Ala Ala Arg Asn Lys Gly Arg Arg Phe Gly Arg Pro Lys Ser Gly
            130                 135                 140

Thr Gly Glu Lys Pro Tyr Lys Cys Pro Glu Cys Gly Lys Ser Phe Ser
145                 150                 155                 160

Arg Ser Asp Lys Leu Val Arg His Gln Arg Thr His Thr Gly Glu Lys
```

```
                165                 170                 175
Pro Tyr Lys Cys Pro Glu Cys Gly Lys Ser Phe Ser Arg Arg Asp Glu
            180                 185                 190

Leu Asn Val His Gln Arg Thr His Thr Gly Glu Lys Pro Tyr Lys Cys
        195                 200                 205

Pro Glu Cys Gly Lys Ser Phe Ser Gln Ser Ser Leu Val Arg His
    210                 215                 220

Gln Arg Thr His Thr Gly Glu Lys Pro Tyr Lys Cys Pro Glu Cys Gly
225                 230                 235                 240

Lys Ser Phe Ser Arg Ser Asp His Leu Thr Asn His Gln Arg Thr His
            245                 250                 255

Thr Gly Lys Lys Thr Ser Gly Gln Ala Gly Gln
            260                 265

<210> SEQ ID NO 77
<211> LENGTH: 267
<212> TYPE: PRT
<213> ORGANISM: Artificial Sequence
<220> FEATURE:
<223> OTHER INFORMATION: Synthetic construct

<400> SEQUENCE: 77

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Lys Ser Gly
    130                 135                 140

Thr Gly Glu Lys Pro Tyr Lys Cys Pro Glu Cys Gly Lys Ser Phe Ser
145                 150                 155                 160

Gln Arg Ala His Leu Glu Arg His Gln Arg Thr His Thr Gly Glu Lys
                165                 170                 175

Pro Tyr Lys Cys Pro Glu Cys Gly Lys Ser Phe Ser Thr Ser Gly Asn
            180                 185                 190

Leu Val Arg His Gln Arg Thr His Thr Gly Glu Lys Pro Tyr Lys Cys
        195                 200                 205

Pro Glu Cys Gly Lys Ser Phe Ser Arg Ser Asp Glu Leu Val Arg His
    210                 215                 220

Gln Arg Thr His Thr Gly Glu Lys Pro Tyr Lys Cys Pro Glu Cys Gly
225                 230                 235                 240

Lys Ser Phe Ser His Lys Asn Ala Leu Gln Asn His Gln Arg Thr His
            245                 250                 255

Thr Gly Lys Lys Thr Ser Gly Gln Ala Gly Gln
```

<210> SEQ ID NO 78
<211> LENGTH: 267
<212> TYPE: PRT
<213> ORGANISM: Artificial Sequence
<220> FEATURE:
<223> OTHER INFORMATION: Synthetic construct

<400> SEQUENCE: 78

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Pro Lys Ser Gly
    130                 135                 140

Thr Gly Glu Lys Pro Tyr Lys Cys Pro Glu Cys Gly Lys Ser Phe Ser
145                 150                 155                 160

Arg Arg Asp Glu Leu Asn Val His Gln Arg Thr His Thr Gly Glu Lys
                165                 170                 175

Pro Tyr Lys Cys Pro Glu Cys Gly Lys Ser Phe Ser Gln Ser Ser Asn
            180                 185                 190

Leu Val Arg His Gln Arg Thr His Thr Gly Glu Lys Pro Tyr Lys Cys
        195                 200                 205

Pro Glu Cys Gly Lys Ser Phe Ser Gln Ser Ser Ser Leu Val Arg His
    210                 215                 220

Gln Arg Thr His Thr Gly Glu Lys Pro Tyr Lys Cys Pro Glu Cys Gly
225                 230                 235                 240

Lys Ser Phe Ser Thr Thr Gly Asn Leu Thr Val His Gln Arg Thr His
                245                 250                 255

Thr Gly Lys Lys Thr Ser Gly Gln Ala Gly Gln
            260                 265
```

<210> SEQ ID NO 79
<211> LENGTH: 267
<212> TYPE: PRT
<213> ORGANISM: Artificial Sequence
<220> FEATURE:
<223> OTHER INFORMATION: Synthetic construct

<400> SEQUENCE: 79

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30
```

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
 50                  55                  60

Arg Leu Gly Arg Ser Met Lys His Leu Ile Ser Leu Val Gly Glu Leu
 65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Tyr Val Met Gly Ala Leu Ala
            100                 105                 110

Glu Met Glu Arg Glu Leu Ile Leu Glu Arg Val Met Ala Gly Ile Ala
            115                 120                 125

Ala Ala Arg Asn Lys Gly Arg Arg Trp Gly Arg Pro Pro Lys Ser Gly
    130                 135                 140

Thr Gly Glu Lys Pro Tyr Lys Cys Pro Glu Cys Gly Lys Ser Phe Ser
145                 150                 155                 160

Thr Thr Gly Asn Leu Thr Val His Gln Arg Thr His Thr Gly Glu Lys
                165                 170                 175

Pro Tyr Lys Cys Pro Glu Cys Gly Lys Ser Phe Ser Gln Ser Ser Asn
            180                 185                 190

Leu Val Arg His Gln Arg Thr His Thr Gly Glu Lys Pro Tyr Lys Cys
        195                 200                 205

Pro Glu Cys Gly Lys Ser Phe Ser Gln Arg Ala His Leu Glu Arg His
    210                 215                 220

Gln Arg Thr His Thr Gly Glu Lys Pro Tyr Lys Cys Pro Glu Cys Gly
225                 230                 235                 240

Lys Ser Phe Ser Gln Lys Ser Ser Leu Ile Ala His Gln Arg Thr His
                245                 250                 255

Thr Gly Lys Lys Thr Ser Gly Gln Ala Gly Gln
            260                 265

<210> SEQ ID NO 80
<211> LENGTH: 267
<212> TYPE: PRT
<213> ORGANISM: Artificial Sequence
<220> FEATURE:
<223> OTHER INFORMATION: Synthetic construct

<400> SEQUENCE: 80

Met Leu Ile Gly Tyr Val Arg Val Ser Thr Asn Asp Gln Asn Thr Asp
 1               5                  10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
 50                  55                  60

Arg Leu Gly Arg Ser Met Lys His Leu Ile Ser Leu Val Gly Glu Leu
 65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Tyr Val Met Gly Ala Leu Ala
            100                 105                 110

Glu Met Glu Arg Glu Leu Ile Ile Glu Arg Thr Ser Ala Gly Arg Ala
            115                 120                 125

```
Ala Ala Ile Asn Lys Gly Arg Ile Met Gly Arg Pro Arg Lys Ser Gly
    130                 135                 140

Thr Gly Glu Lys Pro Tyr Lys Cys Pro Glu Cys Gly Lys Ser Phe Ser
145                 150                 155                 160

Asp Pro Gly Ala Leu Val Arg His Gln Arg Thr His Thr Gly Glu Lys
                165                 170                 175

Pro Tyr Lys Cys Pro Glu Cys Gly Lys Ser Phe Ser Gln Ser Ser Ser
                180                 185                 190

Leu Val Arg His Gln Arg Thr His Thr Gly Glu Lys Pro Tyr Lys Cys
            195                 200                 205

Pro Glu Cys Gly Lys Ser Phe Ser Gln Leu Ala His Leu Arg Ala His
    210                 215                 220

Gln Arg Thr His Thr Gly Glu Lys Pro Tyr Lys Cys Pro Glu Cys Gly
225                 230                 235                 240

Lys Ser Phe Ser Gln Arg Ala Asn Leu Arg Ala His Gln Arg Thr His
                245                 250                 255

Thr Gly Lys Lys Thr Ser Gly Gln Ala Gly Gln
            260                 265

<210> SEQ ID NO 81
<211> LENGTH: 938
<212> TYPE: PRT
<213> ORGANISM: Artificial Sequence
<220> FEATURE:
<223> OTHER INFORMATION: Synthetic construct

<400> SEQUENCE: 81

Met Arg Ser Pro Lys Lys Lys Arg Lys Val Gln Val Asp Leu Arg Thr
1               5                   10                  15

Leu Gly Tyr Ser Gln Gln Gln Gln Glu Lys Ile Lys Pro Lys Val Arg
                20                  25                  30

Ser Thr Val Ala Gln His His Glu Ala Leu Val Gly His Gly Phe Thr
            35                  40                  45

His Ala His Ile Val Ala Leu Ser Gln His Pro Ala Ala Leu Gly Thr
        50                  55                  60

Val Ala Val Thr Tyr Gln His Ile Ile Thr Ala Leu Pro Glu Ala Thr
65                  70                  75                  80

His Glu Asp Ile Val Gly Val Gly Lys Gln Trp Ser Gly Ala Arg Ala
                85                  90                  95

Leu Glu Ala Leu Leu Thr Asp Ala Gly Glu Leu Arg Gly Pro Pro Leu
                100                 105                 110

Gln Leu Asp Thr Gly Gln Leu Val Lys Ile Ala Lys Arg Gly Gly Val
            115                 120                 125

Thr Ala Met Glu Ala Val His Ala Ser Arg Asn Ala Leu Thr Gly Ala
        130                 135                 140

Pro Leu Asn Leu Thr Pro Asp Gln Val Val Ala Ile Ala Ser Asn Gly
145                 150                 155                 160

Gly Gly Lys Gln Ala Leu Glu Thr Val Gln Arg Leu Leu Pro Val Leu
                165                 170                 175

Cys Gln Asp His Gly Leu Thr Pro Asp Gln Val Val Ala Ile Ala Ser
            180                 185                 190

His Asp Gly Gly Lys Gln Ala Leu Glu Thr Val Gln Arg Leu Leu Pro
        195                 200                 205

Val Leu Cys Gln Asp His Gly Leu Thr Pro Asp Gln Val Val Ala Ile
    210                 215                 220
```

-continued

```
Ala Ser Asn Ile Gly Gly Lys Gln Ala Leu Glu Thr Val Gln Arg Leu
225                 230                 235                 240

Leu Pro Val Leu Cys Gln Asp His Gly Leu Thr Pro Asp Gln Val Val
            245                 250                 255

Ala Ile Ala Ser Asn Gly Gly Lys Gln Ala Leu Glu Thr Val Gln
        260                 265                 270

Arg Leu Leu Pro Val Leu Cys Gln Asp His Gly Leu Thr Pro Asp Gln
    275                 280                 285

Val Val Ala Ile Ala Ser Asn Gly Gly Lys Gln Ala Leu Glu Thr
290                 295                 300

Val Gln Arg Leu Leu Pro Val Leu Cys Gln Asp His Gly Leu Thr Pro
305                 310                 315                 320

Asp Gln Val Val Ala Ile Ala Ser Asn Ile Gly Gly Lys Gln Ala Leu
                325                 330                 335

Glu Thr Val Gln Arg Leu Leu Pro Val Leu Cys Gln Asp His Gly Leu
            340                 345                 350

Thr Pro Asp Gln Val Val Ala Ile Ala Ser His Asp Gly Gly Lys Gln
        355                 360                 365

Ala Leu Glu Thr Val Gln Arg Leu Leu Pro Val Leu Cys Gln Asp His
    370                 375                 380

Gly Leu Thr Pro Asp Gln Val Val Ala Ile Ala Ser Asn Ile Gly Gly
385                 390                 395                 400

Lys Gln Ala Leu Glu Thr Val Gln Arg Leu Leu Pro Val Leu Cys Gln
                405                 410                 415

Asp His Gly Leu Thr Pro Asp Gln Val Val Ala Ile Val Ser His Asp
            420                 425                 430

Gly Gly Lys Gln Ala Leu Glu Thr Val Gln Arg Leu Leu Pro Val Leu
        435                 440                 445

Cys Gln Asp His Gly Leu Thr Pro Asp Gln Val Val Ala Ile Val Ser
    450                 455                 460

His Asp Gly Gly Lys Gln Ala Leu Glu Thr Val Gln Arg Leu Leu Pro
465                 470                 475                 480

Val Leu Cys Gln Asp His Gly Leu Thr Pro Asp Gln Val Val Ala Ile
                485                 490                 495

Val Ser Asn Gly Gly Gly Lys Gln Ala Leu Glu Thr Val Gln Arg Leu
            500                 505                 510

Leu Pro Val Leu Cys Gln Asp His Gly Leu Thr Pro Asp Gln Val Val
        515                 520                 525

Ala Ile Ala Ser Asn Asn Gly Gly Lys Gln Ala Leu Glu Thr Val Gln
    530                 535                 540

Arg Leu Leu Pro Val Leu Cys Gln Asp His Gly Leu Thr Pro Asp Gln
545                 550                 555                 560

Val Val Ala Ile Ala Ser His Asp Gly Gly Lys Gln Ala Leu Glu Thr
                565                 570                 575

Val Gln Arg Leu Leu Pro Val Leu Cys Gln Asp His Gly Leu Thr Pro
            580                 585                 590

Asp Gln Val Val Ala Ile Ala Ser Asn Ile Gly Gly Lys Gln Ala Leu
        595                 600                 605

Glu Thr Val Gln Arg Leu Leu Pro Val Leu Cys Gln Asp His Gly Leu
    610                 615                 620

Thr Pro Asp Gln Val Val Ala Ile Ala Ser Asn Asn Gly Gly Lys Gln
625                 630                 635                 640

Ala Leu Glu Thr Val Gln Arg Leu Leu Pro Val Leu Cys Gln Asp His
```

```
                645                 650                 655
Gly Leu Thr Pro Asp Gln Val Val Ala Ile Ala Ser His Asp Gly Gly
            660                 665                 670

Lys Gln Ala Leu Glu Ser Ile Val Ala Gln Leu Ser Arg Pro Asp Pro
            675                 680                 685

Ala Leu Ala Ala Leu Thr Asn Asp His Leu Val Ala Leu Ala Cys Leu
            690                 695                 700

Gly Gly Arg Pro Ala Met Asp Ala Val Lys Lys Gly Leu Pro His Ala
705                 710                 715                 720

Pro Glu Leu Ile Arg Arg Val Asn Arg Ile Gly Glu Arg Thr Ser
                725                 730                 735

His Arg Val Ala Gly Ser Gln Leu Val Lys Ser Glu Leu Glu Lys
            740                 745                 750

Lys Ser Glu Leu Arg His Lys Leu Lys Tyr Val Pro His Glu Tyr Ile
            755                 760                 765

Glu Leu Ile Glu Ile Ala Arg Asn Ser Thr Gln Asp Arg Ile Leu Glu
            770                 775                 780

Met Lys Val Met Glu Phe Phe Met Lys Val Tyr Gly Tyr Arg Gly Lys
785                 790                 795                 800

His Leu Gly Gly Ser Arg Lys Pro Asp Gly Ala Ile Tyr Thr Val Gly
                805                 810                 815

Ser Pro Ile Asp Tyr Gly Val Ile Val Asp Thr Lys Ala Tyr Ser Gly
            820                 825                 830

Gly Tyr Asn Leu Pro Ile Gly Gln Ala Asp Glu Met Gln Arg Tyr Val
            835                 840                 845

Glu Glu Asn Gln Thr Arg Asn Lys His Ile Asn Pro Asn Glu Trp Trp
850                 855                 860

Lys Val Tyr Pro Ser Ser Val Thr Glu Phe Lys Phe Leu Phe Val Ser
865                 870                 875                 880

Gly His Phe Lys Gly Asn Tyr Lys Ala Gln Leu Thr Arg Leu Asn His
                885                 890                 895

Ile Thr Asn Cys Asn Gly Ala Val Leu Ser Val Glu Glu Leu Leu Ile
            900                 905                 910

Gly Gly Glu Met Ile Lys Ala Gly Thr Leu Thr Leu Glu Glu Val Arg
            915                 920                 925

Arg Lys Phe Asn Asn Gly Glu Ile Asn Phe
            930                 935

<210> SEQ ID NO 82
<211> LENGTH: 34
<212> TYPE: PRT
<213> ORGANISM: Artificial Sequence
<220> FEATURE:
<223> OTHER INFORMATION: Synthetic construct

<400> SEQUENCE: 82

Asn Gly Asn Asn His Asp Asn Gly His Asp Asn Ile Asn Gly Asn Gly
1               5                  10                  15

Asn Ile His Asp Asn Ile His Asp His Asp Asn Gly Asn Asn His Asp
            20                  25                  30

Asn Ile

<210> SEQ ID NO 83
<211> LENGTH: 30
<212> TYPE: PRT
<213> ORGANISM: Artificial Sequence
```

<220> FEATURE:
<223> OTHER INFORMATION: Synthetic construct

<400> SEQUENCE: 83

His Asp Asn Ile Asn Asn Gly His Asp Asn Ile Asn Asn Gly
1               5                   10                  15

Asn Ile Asn Gly His Asp Asn Ile Asn Ile Asn Gly Asn Gly
            20                  25                  30

<210> SEQ ID NO 84
<211> LENGTH: 34
<212> TYPE: PRT
<213> ORGANISM: Artificial Sequence
<220> FEATURE:
<223> OTHER INFORMATION: Synthetic construct

<400> SEQUENCE: 84

His Asp His Asp Asn Gly Asn Asn His Asp Asn Ile Asn Asn His Asp
1               5                   10                  15

Asn Gly His Asp Asn Gly His Asp Asn Ile Asn Gly Asn Gly Asn Gly
            20                  25                  30

Asn Gly

<210> SEQ ID NO 85
<211> LENGTH: 30
<212> TYPE: PRT
<213> ORGANISM: Artificial Sequence
<220> FEATURE:
<223> OTHER INFORMATION: Synthetic construct

<400> SEQUENCE: 85

Asn Ile Asn Gly Asn Gly His Asp Asn Gly Asn Gly His Asp His Asp
1               5                   10                  15

Asn Ile Asn Asn Asn Ile Asn Gly Asn Gly Asn Asn Asn Ile
            20                  25                  30

<210> SEQ ID NO 86
<211> LENGTH: 34
<212> TYPE: PRT
<213> ORGANISM: Artificial Sequence
<220> FEATURE:
<223> OTHER INFORMATION: Synthetic construct

<400> SEQUENCE: 86

His Asp Asn Ile Asn Asn Ile Asn Ile Asn Gly Asn Gly Asn Asn
1               5                   10                  15

Asn Ile Asn Gly Asn Ile His Asp Asn Gly Asn Asn Ile His Asp
            20                  25                  30

Asn Gly

<210> SEQ ID NO 87
<211> LENGTH: 32
<212> TYPE: PRT
<213> ORGANISM: Artificial Sequence
<220> FEATURE:
<223> OTHER INFORMATION: Synthetic construct

<400> SEQUENCE: 87

Asn Gly His Asp Asn Ile Asn Gly Asn Gly Asn Ile His Asp Asn Ile
1               5                   10                  15

His Asp His Asp Asn Gly Asn Asn His Asp Asn Ile Asn Asn His Asp
            20                  25                  30

<210> SEQ ID NO 88
<211> LENGTH: 36
<212> TYPE: PRT
<213> ORGANISM: Artificial Sequence
<220> FEATURE:
<223> OTHER INFORMATION: Synthetic construct

<400> SEQUENCE: 88

His Asp Asn Gly Asn Gly His Asp His Asp Asn Ile Asn Asn Asn Ile
1               5                   10                  15

Asn Ile Asn Gly Asn Gly Asn Asn Ile Asn Gly Asn Ile His Asp
            20                  25                  30

Asn Gly Asn Asn
        35

<210> SEQ ID NO 89
<211> LENGTH: 432
<212> TYPE: DNA
<213> ORGANISM: Artificial Sequence
<220> FEATURE:
<223> OTHER INFORMATION: Synthetic construct

<400> SEQUENCE: 89
atgagatctc ctaagaaaaa gaggaagatg gtggacttga ggacactcgg ttattcgcaa      60
cagcaacagg agaaaatcaa gcctaaggtc aggagcaccg tcgcgcaaca ccacgaggcg     120
cttgtggggc atggcttcac tcatgcgcat attgtcgcgc tttcacagca ccctgcggcg     180
cttgggacgg tggctgtcaa ataccaagat atgattgcgg ccctgccgga agccacgcac     240
gaggcaattg taggggtcgg taaacagtgg tcgggagcgc gagcacttga ggcgctgctg     300
actgtggcgg gtgagcttag ggggcctccg ctccagctcg acaccgggca gctgctgaag     360
atcgcgaaga gaggggggagt aacagcggta gaggcagtgc atgcatcgcg caatgcactg     420
acgggtgccc cc                                                         432

<210> SEQ ID NO 90
<211> LENGTH: 144
<212> TYPE: PRT
<213> ORGANISM: Artificial Sequence
<220> FEATURE:
<223> OTHER INFORMATION: Synthetic construct

<400> SEQUENCE: 90

Met Arg Ser Pro Lys Lys Lys Arg Lys Met Val Asp Leu Arg Thr Leu
1               5                   10                  15

Gly Tyr Ser Gln Gln Gln Glu Lys Ile Lys Pro Lys Val Arg Ser
            20                  25                  30

Thr Val Ala Gln His His Glu Ala Leu Val Gly His Gly Phe Thr His
        35                  40                  45

Ala His Ile Val Ala Leu Ser Gln His Pro Ala Ala Leu Gly Thr Val
    50                  55                  60

Ala Val Lys Tyr Gln Asp Met Ile Ala Ala Leu Pro Glu Ala Thr His
65                  70                  75                  80

Glu Ala Ile Val Gly Val Gly Lys Gln Trp Ser Gly Ala Arg Ala Leu
                85                  90                  95

Glu Ala Leu Leu Thr Val Ala Gly Glu Leu Arg Gly Pro Pro Leu Gln
            100                 105                 110

Leu Asp Thr Gly Gln Leu Leu Lys Ile Ala Lys Arg Gly Gly Val Thr
        115                 120                 125

```
Ala Val Glu Ala Val His Ala Ser Arg Asn Ala Leu Thr Gly Ala Pro
        130                 135                 140
```

<210> SEQ ID NO 91
<211> LENGTH: 432
<212> TYPE: DNA
<213> ORGANISM: Artificial Sequence
<220> FEATURE:
<223> OTHER INFORMATION: Synthetic construct

<400> SEQUENCE: 91

```
atgagatctc ctaagaaaaa gaggaaggtg caggtggatc tacgcacgct cggctacagt      60
cagcagcagc aagagaagat caaaccgaag gtgcgttcga cagtggcgca gcaccacgag     120
gcactggtgg gccatgggtt tacacacgcg cacatcgttg cgctcagcca cacccggca     180 gcgttaggga ccgtcgctgt cacgtatcag cacataatca cggcgttgcc agaggcgaca     240
cacgaagaca tcgttggcgt cggcaaatat catggggcac gcgctctgga ggccttgctc     300
acggatgcgg gggagttgag aggtccgccg ttacagttgg acacaggcca acttgtgaag     360
attgcaaaac gtggcggcgt gaccgcaatg gaggcagtgc atgcatcgcg caatgcactg     420
acgggtgccc cc                                                         432
```

<210> SEQ ID NO 92
<211> LENGTH: 144
<212> TYPE: PRT
<213> ORGANISM: Artificial Sequence
<220> FEATURE:
<223> OTHER INFORMATION: Synthetic construct

<400> SEQUENCE: 92

```
Met Arg Ser Pro Lys Lys Arg Lys Val Gln Val Asp Leu Arg Thr
1               5                   10                  15

Leu Gly Tyr Ser Gln Gln Gln Glu Lys Ile Lys Pro Lys Val Arg
                20                  25                  30

Ser Thr Val Ala Gln His His Glu Ala Leu Val Gly His Gly Phe Thr
            35                  40                  45

His Ala His Ile Val Ala Leu Ser Gln His Pro Ala Ala Leu Gly Thr
    50                  55                  60

Val Ala Val Thr Tyr Gln His Ile Ile Thr Ala Leu Pro Glu Ala Thr
65                  70                  75                  80

His Glu Asp Ile Val Gly Val Gly Lys Tyr His Gly Ala Arg Ala Leu
                85                  90                  95

Glu Ala Leu Leu Thr Asp Ala Gly Glu Leu Arg Gly Pro Pro Leu Gln
                100                 105                 110

Leu Asp Thr Gly Gln Leu Val Lys Ile Ala Lys Arg Gly Gly Val Thr
            115                 120                 125

Ala Met Glu Ala Val His Ala Ser Arg Asn Ala Leu Thr Gly Ala Pro
        130                 135                 140
```

<210> SEQ ID NO 93
<211> LENGTH: 435
<212> TYPE: DNA
<213> ORGANISM: Artificial Sequence
<220> FEATURE:
<223> OTHER INFORMATION: Synthetic construct

<400> SEQUENCE: 93

```
atgagatctc ctaagaaaaa gaggaaggtg caggtggatc tacgcacgct cggctacagt      60
cagcagcagc aagagaagat caaaccgaag gtgcgttcga cagtggcgca gcaccacgag     120
```

```
gcactggtgg gccatgggtt tacacacgcg cacatcgttg cgctcagcca acacccggca    180
gcgttaggga ccgtcgctgt cacgtatcag cacataatca cggcgttgcc agaggcgaca    240
cacgaagaca tcgttggcgt cggcaaatcg cggtcggggg cacgcgctct ggaggccttg    300
ctcacggatg cgggggagtt gagaggtccg ccgttacagt tggacacagg ccaacttgtg    360
aagattgcaa acgtggcgg cgtgaccgca atggaggcag tgcatgcatc gcgcaatgca    420
ctgacgggtg ccccc                                                    435

<210> SEQ ID NO 94
<211> LENGTH: 145
<212> TYPE: PRT
<213> ORGANISM: Artificial Sequence
<220> FEATURE:
<223> OTHER INFORMATION: Synthetic construct

<400> SEQUENCE: 94

Met Arg Ser Pro Lys Lys Arg Lys Val Gln Val Asp Leu Arg Thr
1               5                   10                  15

Leu Gly Tyr Ser Gln Gln Gln Glu Lys Ile Lys Pro Lys Val Arg
            20                  25                  30

Ser Thr Val Ala Gln His His Glu Ala Leu Val Gly His Gly Phe Thr
        35                  40                  45

His Ala His Ile Val Ala Leu Ser Gln His Pro Ala Ala Leu Gly Thr
    50                  55                  60

Val Ala Val Thr Tyr Gln His Ile Ile Thr Ala Leu Pro Glu Ala Thr
65                  70                  75                  80

His Glu Asp Ile Val Gly Val Gly Lys Ser Arg Ser Gly Ala Arg Ala
                85                  90                  95

Leu Glu Ala Leu Leu Thr Asp Ala Gly Glu Leu Arg Gly Pro Pro Leu
            100                 105                 110

Gln Leu Asp Thr Gly Gln Leu Val Lys Ile Ala Lys Arg Gly Gly Val
        115                 120                 125

Thr Ala Met Glu Ala Val His Ala Ser Arg Asn Ala Leu Thr Gly Ala
    130                 135                 140
Pro
145

<210> SEQ ID NO 95
<211> LENGTH: 435
<212> TYPE: DNA
<213> ORGANISM: Artificial Sequence
<220> FEATURE:
<223> OTHER INFORMATION: Synthetic construct

<400> SEQUENCE: 95
atgagatctc ctaagaaaaa gaggaaggtg caggtggatc tacgcacgct cggctacagt    60
cagcagcagc aagagaagat caaaccgaag gtgcgttcga cagtggcgca gcaccacggg   120
gcactggtgg gccatgggtt tacacacgcg cacatcgttg cgctcagcca acacccggca   180
gcgttaggga ccgtcgctgt cacgtatcag cacataatca cggcgttgcc agaggcgaca   240
cacgaagaca tcgttggcgt cggcaaacg ggggctggtg cacgcgctct ggaggccttg   300
ctcacggatg cgggggagtt gagaggtccg ccgttacagt tggacacagg ccaacttgtg   360
aagattgcaa acgtggcgg cgtgaccgca atggaggcag tgcatgcatc gcgcaatgca   420
ctgacgggtg ccccc                                                   435
```

<210> SEQ ID NO 96
<211> LENGTH: 145
<212> TYPE: PRT
<213> ORGANISM: Artificial Sequence
<220> FEATURE:
<223> OTHER INFORMATION: Synthetic construct

<400> SEQUENCE: 96

```
Met Arg Ser Pro Lys Lys Arg Lys Val Gln Val Asp Leu Arg Thr
1               5                   10                  15

Leu Gly Tyr Ser Gln Gln Gln Glu Lys Ile Lys Pro Lys Val Arg
            20                  25                  30

Ser Thr Val Ala Gln His His Gly Ala Leu Val Gly His Gly Phe Thr
            35                  40                      45

His Ala His Ile Val Ala Leu Ser Gln His Pro Ala Ala Leu Gly Thr
        50                  55                      60

Val Ala Val Thr Tyr Gln His Ile Ile Thr Ala Leu Pro Glu Ala Thr
65              70                      75                  80

His Glu Asp Ile Val Gly Val Gly Lys Arg Gly Ala Gly Ala Arg Ala
                85                  90                  95

Leu Glu Ala Leu Leu Thr Asp Ala Gly Glu Leu Arg Gly Pro Pro Leu
            100                 105                 110

Gln Leu Asp Thr Gly Gln Leu Val Lys Ile Ala Lys Arg Gly Gly Val
            115                 120                 125

Thr Ala Met Glu Ala Val His Ala Ser Arg Asn Ala Leu Thr Gly Ala
        130                 135                 140

Pro
145
```

<210> SEQ ID NO 97
<211> LENGTH: 435
<212> TYPE: DNA
<213> ORGANISM: Artificial Sequence
<220> FEATURE:
<223> OTHER INFORMATION: Synthetic construct

<400> SEQUENCE: 97

```
atgagatctc ctaagaaaaa gaggaaggtg caggtggatc tacgcacgct cggctacagt    60
cagcagcagc aagagaagat caaaccgaag gtgcgttcga cagtggcgca gcaccacgag   120
gcactggtgg gccatgggtt tacacacgcg cacatcgttg cgctcagcca cacccggca   180 gcgttaggga ccgtcgctgt cacgtatcag cacataatca cggcgttgcc agaggcgaca   240
cacgaagaca tcgttggcgt cggcaaacag tggtccggcg cacgcgccct ggaggccttg   300
ctcacggatg cggggagtt gagaggtccg ccgttacagt tggacacagg ccaacttgtg   360
aagattgcaa aacgtggcgg cgtgaccgca atggaggcag tgcatgcatc gcgcaatgca   420
ctgacgggtg ccccc                                                    435
```

<210> SEQ ID NO 98
<211> LENGTH: 1080
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (498)..(498)
<223> OTHER INFORMATION: Xaa is Q, S, R or Y
<220> FEATURE:
<221> NAME/KEY: MISC_FEATURE

```
<222> LOCATION: (499)..(499)
<223> OTHER INFORMATION: Xaa is W, R or G
<220> FEATURE:
<221> NAME/KEY: MISC_FEATURE
<222> LOCATION: (500)..(500)
<223> OTHER INFORMATION: Xaa is S, A or H

<400> SEQUENCE: 98
```

| Met | Lys | Ile | Glu | Glu | Gly | Lys | Leu | Val | Ile | Trp | Ile | Asn | Gly | Asp | Lys |
|---|---|---|---|---|---|---|---|---|---|---|---|---|---|---|---|
| 1 | | | | 5 | | | | | 10 | | | | | 15 | |

| Gly | Tyr | Asn | Gly | Leu | Ala | Glu | Val | Gly | Lys | Lys | Phe | Glu | Lys | Asp | Thr |
|---|---|---|---|---|---|---|---|---|---|---|---|---|---|---|---|
| | | | 20 | | | | | 25 | | | | | 30 | | |

| Gly | Ile | Lys | Val | Thr | Val | Glu | His | Pro | Asp | Lys | Leu | Glu | Glu | Lys | Phe |
|---|---|---|---|---|---|---|---|---|---|---|---|---|---|---|---|
| | | 35 | | | | | 40 | | | | | 45 | | | |

| Pro | Gln | Val | Ala | Ala | Thr | Gly | Asp | Gly | Pro | Asp | Ile | Ile | Phe | Trp | Ala |
|---|---|---|---|---|---|---|---|---|---|---|---|---|---|---|---|
| | 50 | | | | | 55 | | | | | 60 | | | | |

| His | Asp | Arg | Phe | Gly | Gly | Tyr | Ala | Gln | Ser | Gly | Leu | Leu | Ala | Glu | Ile |
|---|---|---|---|---|---|---|---|---|---|---|---|---|---|---|---|
| 65 | | | | | 70 | | | | | 75 | | | | | 80 |

| Thr | Pro | Asp | Lys | Ala | Phe | Gln | Asp | Lys | Leu | Tyr | Pro | Phe | Thr | Trp | Asp |
|---|---|---|---|---|---|---|---|---|---|---|---|---|---|---|---|
| | | | | 85 | | | | | 90 | | | | | 95 | |

| Ala | Val | Arg | Tyr | Asn | Gly | Lys | Leu | Ile | Ala | Tyr | Pro | Ile | Ala | Val | Glu |
|---|---|---|---|---|---|---|---|---|---|---|---|---|---|---|---|
| | | | 100 | | | | | 105 | | | | | 110 | | |

| Ala | Leu | Ser | Leu | Ile | Tyr | Asn | Lys | Asp | Leu | Leu | Pro | Asn | Pro | Pro | Lys |
|---|---|---|---|---|---|---|---|---|---|---|---|---|---|---|---|
| | | 115 | | | | | 120 | | | | | 125 | | | |

| Thr | Trp | Glu | Glu | Ile | Pro | Ala | Leu | Asp | Lys | Glu | Leu | Lys | Ala | Lys | Gly |
|---|---|---|---|---|---|---|---|---|---|---|---|---|---|---|---|
| | 130 | | | | | 135 | | | | | 140 | | | | |

| Lys | Ser | Ala | Leu | Met | Phe | Asn | Leu | Gln | Glu | Pro | Tyr | Phe | Thr | Trp | Pro |
|---|---|---|---|---|---|---|---|---|---|---|---|---|---|---|---|
| 145 | | | | | 150 | | | | | 155 | | | | | 160 |

| Leu | Ile | Ala | Ala | Asp | Gly | Gly | Tyr | Ala | Phe | Lys | Tyr | Glu | Asn | Gly | Lys |
|---|---|---|---|---|---|---|---|---|---|---|---|---|---|---|---|
| | | | | 165 | | | | | 170 | | | | | 175 | |

| Tyr | Asp | Ile | Lys | Asp | Val | Gly | Val | Asp | Asn | Ala | Gly | Ala | Lys | Ala | Gly |
|---|---|---|---|---|---|---|---|---|---|---|---|---|---|---|---|
| | | | 180 | | | | | 185 | | | | | 190 | | |

| Leu | Thr | Phe | Leu | Val | Asp | Leu | Ile | Lys | Asn | Lys | His | Met | Asn | Ala | Asp |
|---|---|---|---|---|---|---|---|---|---|---|---|---|---|---|---|
| | | 195 | | | | | 200 | | | | | 205 | | | |

| Thr | Asp | Tyr | Ser | Ile | Ala | Glu | Ala | Ala | Phe | Asn | Lys | Gly | Glu | Thr | Ala |
|---|---|---|---|---|---|---|---|---|---|---|---|---|---|---|---|
| | 210 | | | | | 215 | | | | | 220 | | | | |

| Met | Thr | Ile | Asn | Gly | Pro | Trp | Ala | Trp | Ser | Asn | Ile | Asp | Thr | Ser | Lys |
|---|---|---|---|---|---|---|---|---|---|---|---|---|---|---|---|
| 225 | | | | | 230 | | | | | 235 | | | | | 240 |

| Val | Asn | Tyr | Gly | Val | Thr | Val | Leu | Pro | Thr | Phe | Lys | Gly | Gln | Pro | Ser |
|---|---|---|---|---|---|---|---|---|---|---|---|---|---|---|---|
| | | | | 245 | | | | | 250 | | | | | 255 | |

| Lys | Pro | Phe | Val | Gly | Val | Leu | Ser | Ala | Gly | Ile | Asn | Ala | Ala | Ser | Pro |
|---|---|---|---|---|---|---|---|---|---|---|---|---|---|---|---|
| | | | 260 | | | | | 265 | | | | | 270 | | |

| Asn | Lys | Glu | Leu | Ala | Lys | Glu | Phe | Leu | Glu | Asn | Tyr | Leu | Leu | Thr | Asp |
|---|---|---|---|---|---|---|---|---|---|---|---|---|---|---|---|
| | | 275 | | | | | 280 | | | | | 285 | | | |

| Glu | Gly | Leu | Glu | Ala | Val | Asn | Lys | Asp | Lys | Pro | Leu | Gly | Ala | Val | Ala |
|---|---|---|---|---|---|---|---|---|---|---|---|---|---|---|---|
| | 290 | | | | | 295 | | | | | 300 | | | | |

| Leu | Lys | Ser | Tyr | Glu | Glu | Glu | Leu | Ala | Lys | Asp | Pro | Arg | Ile | Ala | Ala |
|---|---|---|---|---|---|---|---|---|---|---|---|---|---|---|---|
| 305 | | | | | 310 | | | | | 315 | | | | | 320 |

| Thr | Met | Glu | Asn | Ala | Gln | Lys | Gly | Glu | Ile | Met | Pro | Asn | Ile | Pro | Gln |
|---|---|---|---|---|---|---|---|---|---|---|---|---|---|---|---|
| | | | | 325 | | | | | 330 | | | | | 335 | |

| Met | Ser | Ala | Phe | Trp | Tyr | Ala | Val | Arg | Thr | Ala | Val | Ile | Asn | Ala | Ala |
|---|---|---|---|---|---|---|---|---|---|---|---|---|---|---|---|
| | | | 340 | | | | | 345 | | | | | 350 | | |

| Ser | Gly | Arg | Gln | Thr | Val | Asp | Glu | Ala | Leu | Lys | Asp | Ala | Gln | Thr | Asn |
|---|---|---|---|---|---|---|---|---|---|---|---|---|---|---|---|
| | | 355 | | | | | 360 | | | | | 365 | | | |

| Ser | Ser | Ser | Asn | Asn | Asn | Asn | Asn | Asn | Asn | Asn | Asn | Asn | Leu | Gly | Ile |
|---|---|---|---|---|---|---|---|---|---|---|---|---|---|---|---|

```
                370                 375                 380
Glu Gly Arg Ile Ser Glu Phe Gly Ser Pro Ala Arg Pro Arg Ala
385                 390                 395                 400

Lys Pro Ala Pro Arg Arg Ser Ala Gln Pro Ser Asp Ala Ser Pro
                405                 410                 415

Ala Ala Gln Val Asp Leu Arg Thr Leu Gly Tyr Ser Gln Gln Gln
                420                 425                 430

Glu Lys Ile Lys Pro Lys Val Arg Ser Thr Val Ala Gln His His Glu
                435                 440                 445

Ala Leu Val Gly His Gly Phe Thr His Ala His Ile Val Ala Leu Ser
450                 455                 460

Gln His Pro Ala Ala Leu Gly Thr Val Ala Val Thr Tyr Gln His Ile
465                 470                 475                 480

Ile Thr Ala Leu Pro Glu Ala Thr His Glu Asp Ile Val Gly Val Gly
                485                 490                 495

Lys Xaa Xaa Xaa Gly Ala Arg Ala Leu Glu Ala Leu Leu Thr Asp Ala
                500                 505                 510

Gly Glu Leu Leu Arg Gly Pro Pro Leu Gln Leu Asp Thr Gly Gln Leu
                515                 520                 525

Val Lys Ile Ala Lys Arg Gly Gly Val Thr Ala Met Glu Ala Val His
                530                 535                 540

Ala Ser Arg Asn Ala Leu Thr Gly Ala Pro Leu Asn Leu Thr Pro Asp
545                 550                 555                 560

Gln Val Val Ala Ile Ala Ser Asn Ile Gly Gly Lys Gln Ala Leu Glu
                565                 570                 575

Thr Val Gln Arg Leu Leu Pro Val Leu Cys Gln Asp His Gly Leu Thr
                580                 585                 590

Pro Asp Gln Val Val Ala Ile Ala Ser Asn Gly Gly Lys Gln Ala
                595                 600                 605

Leu Glu Thr Val Gln Arg Leu Leu Pro Val Leu Cys Gln Asp His Gly
                610                 615                 620

Leu Thr Pro Asp Gln Val Val Ala Ile Ala Ser Asn Ile Gly Gly Lys
625                 630                 635                 640

Gln Ala Leu Glu Thr Val Gln Arg Leu Leu Pro Val Leu Cys Gln Asp
                645                 650                 655

His Gly Leu Thr Pro Asp Gln Val Val Ala Ile Ala Ser Asn Ile Gly
                660                 665                 670

Gly Lys Gln Ala Leu Glu Thr Val Gln Arg Leu Leu Pro Val Leu Cys
                675                 680                 685

Gln Asp His Gly Leu Thr Pro Asp Gln Val Val Ala Ile Ala Ser Asn
                690                 695                 700

Ile Gly Gly Lys Gln Ala Leu Glu Thr Val Gln Arg Leu Leu Pro Val
705                 710                 715                 720

Leu Cys Gln Asp His Gly Leu Thr Pro Asp Gln Val Val Ala Ile Ala
                725                 730                 735

Ser His Asp Gly Gly Lys Gln Ala Leu Glu Thr Val Gln Arg Leu Leu
                740                 745                 750

Pro Val Leu Cys Gln Asp His Gly Leu Thr Pro Asp Gln Val Val Ala
                755                 760                 765

Ile Ala Ser His Asp Gly Gly Lys Gln Ala Leu Glu Thr Val Gln Arg
                770                 775                 780

Leu Leu Pro Val Leu Cys Gln Asp His Gly Leu Thr Pro Asp Gln Val
785                 790                 795                 800
```

```
Val Ala Ile Ala Ser His Asp Gly Gly Lys Gln Ala Leu Glu Thr Val
                805                 810                 815

Gln Arg Leu Leu Pro Val Leu Cys Gln Asp His Gly Leu Thr Pro Asp
            820                 825                 830

Gln Val Val Ala Ile Val Ser His Asp Gly Gly Lys Gln Ala Leu Glu
        835                 840                 845

Thr Val Gln Arg Leu Leu Pro Val Leu Cys Gln Asp His Gly Leu Thr
    850                 855                 860

Pro Asp Gln Val Val Ala Ile Val Ser His Asp Gly Gly Lys Gln Ala
865                 870                 875                 880

Leu Glu Thr Val Gln Arg Leu Leu Pro Val Leu Cys Gln Asp His Gly
                885                 890                 895

Leu Thr Pro Asp Gln Val Val Ala Ile Val Ser Asn Gly Gly Gly Lys
            900                 905                 910

Gln Ala Leu Glu Thr Val Gln Arg Leu Leu Pro Val Leu Cys Gln Asp
        915                 920                 925

His Gly Leu Thr Pro Asp Gln Val Val Ala Ile Ala Ser His Asp Gly
    930                 935                 940

Gly Lys Gln Ala Leu Glu Thr Val Gln Arg Leu Leu Pro Val Leu Cys
945                 950                 955                 960

Gln Asp His Gly Leu Thr Pro Asp Gln Val Val Ala Ile Ala Ser His
                965                 970                 975

Asp Gly Gly Lys Gln Ala Leu Glu Thr Val Gln Arg Leu Leu Pro Val
            980                 985                 990

Leu Cys Gln Asp His Gly Leu Thr  Pro Asp Gln Val Val Ala Ile Ala
                995                 1000                1005

Ser Asn Ile Gly Gly Lys Gln  Ala Leu Glu Thr Val  Gln Arg Leu
        1010                1015                1020

Leu Pro Val Leu Cys Gln Asp  His Gly Leu Thr Pro  Asp Gln Val
        1025                1030                1035

Val Ala Ile Ala Ser Asn Ile  Gly Gly Lys Gln Ala  Leu Glu Ser
        1040                1045                1050

Ile Val Ala Gln Leu Ser Arg  Pro Asp Pro Ala Leu  Ala Ala Leu
        1055                1060                1065

Thr Asn Asp His Leu Val Ala  Leu Ala Cys Leu Gly
        1070                1075                1080

<210> SEQ ID NO 99
<211> LENGTH: 830
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (249)..(249)
<223> OTHER INFORMATION: Xaa is Q, S, R or Y
<220> FEATURE:
<221> NAME/KEY: MISC_FEATURE
<222> LOCATION: (250)..(250)
<223> OTHER INFORMATION: Xaa is W, R or G
<220> FEATURE:
<221> NAME/KEY: MISC_FEATURE
<222> LOCATION: (251)..(251)
<223> OTHER INFORMATION: Xaa is S, A or H

<400> SEQUENCE: 99

Met Leu Ile Gly Tyr Val Arg Val Ser Thr Asn Asp Gln Asn Thr Asp
1               5                   10                  15
```

```
Leu Gln Arg Asn Ala Leu Val Cys Ala Gly Cys Gln Ile Phe Glu
         20                  25                  30

Asp Lys Leu Ser Gly Thr Arg Thr Asp Arg Pro Gly Leu Lys Arg Ala
             35                  40                  45

Leu Lys Arg Leu Gln Lys Gly Asp Thr Leu Val Val Trp Lys Leu Asp
 50                  55                  60

Arg Leu Gly Arg Ser Met Lys His Leu Ile Ser Leu Val Gly Glu Leu
 65                  70                  75                  80

Arg Glu Arg Gly Ile Asn Phe Arg Ser Leu Thr Asp Ser Ile Asp Thr
                 85                  90                  95

Ser Ser Pro Met Gly Arg Phe Phe Phe Tyr Val Met Gly Ala Leu Ala
             100                 105                 110

Glu Met Glu Arg Glu Leu Ile Ile Glu Arg Thr Met Ala Gly Leu Ala
             115                 120                 125

Ala Ala Arg Asn Lys Gly Arg Ile Gly Gly Arg Pro Pro Lys Ser Gly
130                 135                 140

Ser Pro Arg Pro Pro Arg Ala Lys Pro Ala Pro Arg Arg Ala Ala
145                 150                 155                 160

Gln Pro Ser Asp Ala Ser Pro Ala Ala Gln Val Asp Leu Arg Thr Leu
                 165                 170                 175

Gly Tyr Ser Gln Gln Gln Glu Lys Ile Lys Pro Lys Val Arg Ser
             180                 185                 190

Thr Val Ala Gln His His Glu Ala Leu Val Gly His Gly Phe Thr His
             195                 200                 205

Ala His Ile Val Ala Leu Ser Gln His Pro Ala Ala Leu Gly Thr Val
         210                 215                 220

Ala Val Thr Tyr Gln His Ile Ile Thr Ala Leu Pro Glu Ala Thr His
225                 230                 235                 240

Glu Asp Ile Val Gly Val Gly Lys Xaa Xaa Xaa Gly Ala Arg Ala Leu
                 245                 250                 255

Glu Ala Leu Leu Thr Asp Ala Gly Glu Leu Arg Gly Pro Pro Leu Gln
             260                 265                 270

Leu Asp Thr Gly Gln Leu Val Lys Ile Ala Lys Arg Gly Gly Val Thr
         275                 280                 285

Ala Met Glu Ala Val His Ala Ser Arg Asn Ala Leu Thr Gly Ala Pro
290                 295                 300

Leu Asn Leu Thr Pro Asp Gln Val Val Ala Ile Ala Ser Asn Ile Gly
305                 310                 315                 320

Gly Lys Gln Ala Leu Glu Thr Val Gln Arg Leu Leu Pro Val Leu Cys
             325                 330                 335

Gln Asp His Gly Leu Thr Pro Asp Gln Val Val Ala Ile Ala Ser Asn
             340                 345                 350

Gly Gly Gly Lys Gln Ala Leu Glu Thr Val Gln Arg Leu Leu Pro Val
         355                 360                 365

Leu Cys Gln Asp His Gly Leu Thr Pro Asp Gln Val Val Ala Ile Ala
     370                 375                 380

Ser Asn Ile Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                 405                 410                 415

Ile Ala Ser Asn Ile Gly Gly Lys Gln Ala Leu Glu Thr Val Gln Arg
             420                 425                 430
```

Leu Leu Pro Val Leu Cys Gln Asp His Gly Leu Thr Pro Asp Gln Val
435                 440                 445

Val Ala Ile Ala Ser Asn Ile Gly Gly Lys Gln Ala Leu Glu Thr Val
        450                 455                 460

Gln Arg Leu Leu Pro Val Leu Cys Gln Asp His Gly Leu Thr Pro Asp
465                 470                 475                 480

Gln Val Val Ala Ile Ala Ser His Asp Gly Lys Gln Ala Leu Glu
                485                 490                 495

Thr Val Gln Arg Leu Leu Pro Val Leu Cys Gln Asp His Gly Leu Thr
            500                 505                 510

Pro Asp Gln Val Val Ala Ile Ala Ser His Asp Gly Lys Gln Ala
        515                 520                 525

Leu Glu Thr Val Gln Arg Leu Leu Pro Val Leu Cys Gln Asp His Gly
    530                 535                 540

Leu Thr Pro Asp Gln Val Val Ala Ile Ala Ser His Asp Gly Gly Lys
545                 550                 555                 560

Gln Ala Leu Glu Thr Val Gln Arg Leu Leu Pro Val Leu Cys Gln Asp
                565                 570                 575

His Gly Leu Thr Pro Asp Gln Val Val Ala Ile Val Ser His Asp Gly
            580                 585                 590

Gly Lys Gln Ala Leu Glu Thr Val Gln Arg Leu Leu Pro Val Leu Cys
        595                 600                 605

Gln Asp His Gly Leu Thr Pro Asp Gln Val Val Ala Ile Val Ser His
    610                 615                 620

Asp Gly Gly Lys Gln Ala Leu Glu Thr Val Gln Arg Leu Leu Pro Val
625                 630                 635                 640

Leu Cys Gln Asp His Gly Leu Thr Pro Asp Gln Val Val Ala Ile Val
                645                 650                 655

Ser Asn Gly Gly Gly Lys Gln Ala Leu Glu Thr Val Gln Arg Leu Leu
            660                 665                 670

Pro Val Leu Cys Gln Asp His Gly Leu Thr Pro Asp Gln Val Val Ala
        675                 680                 685

Ile Ala Ser His Asp Gly Gly Lys Gln Ala Leu Glu Thr Val Gln Arg
    690                 695                 700

Leu Leu Pro Val Leu Cys Gln Asp His Gly Leu Thr Pro Asp Gln Val
705                 710                 715                 720

Val Ala Ile Ala Ser His Asp Gly Gly Lys Gln Ala Leu Glu Thr Val
                725                 730                 735

Gln Arg Leu Leu Pro Val Leu Cys Gln Asp His Gly Leu Thr Pro Asp
            740                 745                 750

Gln Val Val Ala Ile Ala Ser Asn Ile Gly Gly Lys Gln Ala Leu Glu
        755                 760                 765

Thr Val Gln Arg Leu Leu Pro Val Leu Cys Gln Asp His Gly Leu Thr
    770                 775                 780

Pro Asp Gln Val Val Ala Ile Ala Ser Asn Ile Gly Gly Lys Gln Ala
785                 790                 795                 800

Leu Glu Ser Ile Val Ala Gln Leu Ser Arg Pro Asp Pro Ala Leu Ala
                805                 810                 815

Ala Leu Thr Asn Asp His Leu Val Ala Leu Ala Cys Leu Gly
            820                 825                 830

<210> SEQ ID NO 100
<211> LENGTH: 839
<212> TYPE: PRT

```
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (112)..(112)
<223> OTHER INFORMATION: Xaa is Q, S, R or Y
<220> FEATURE:
<221> NAME/KEY: MISC_FEATURE
<222> LOCATION: (113)..(113)
<223> OTHER INFORMATION: Xaa is W, R or R
<220> FEATURE:
<221> NAME/KEY: MISC_FEATURE
<222> LOCATION: (114)..(114)
<223> OTHER INFORMATION: Xaa is S, A or H

<400> SEQUENCE: 100
```

| | | | | | | | | | | | | | | |
|---|---|---|---|---|---|---|---|---|---|---|---|---|---|---|
| Met | Ala | Gln | Ala | Ala | Ser | Gly | Ser | Pro | Arg | Pro | Pro | Arg | Ala | Lys | Pro |
| 1 | | | | 5 | | | | | 10 | | | | | 15 | |

| Ala | Pro | Arg | Arg | Arg | Ala | Ala | Gln | Pro | Ser | Asp | Ala | Ser | Pro | Ala | Ala |
|---|---|---|---|---|---|---|---|---|---|---|---|---|---|---|---|
| | | | 20 | | | | | 25 | | | | | 30 | | |

| Gln | Val | Asp | Leu | Arg | Thr | Leu | Gly | Tyr | Ser | Gln | Gln | Gln | Gln | Glu | Lys |
|---|---|---|---|---|---|---|---|---|---|---|---|---|---|---|---|
| | | | 35 | | | | | 40 | | | | | 45 | | |

| Ile | Lys | Pro | Lys | Val | Arg | Ser | Thr | Val | Ala | Gln | His | His | Glu | Ala | Leu |
|---|---|---|---|---|---|---|---|---|---|---|---|---|---|---|---|
| 50 | | | | | 55 | | | | | 60 | | | | | |

| Val | Gly | His | Gly | Phe | Thr | His | Ala | His | Ile | Val | Ala | Leu | Ser | Gln | His |
|---|---|---|---|---|---|---|---|---|---|---|---|---|---|---|---|
| 65 | | | | | 70 | | | | | 75 | | | | | 80 |

| Pro | Ala | Ala | Leu | Gly | Thr | Val | Ala | Val | Thr | Tyr | Gln | His | Ile | Ile | Thr |
|---|---|---|---|---|---|---|---|---|---|---|---|---|---|---|---|
| | | | | 85 | | | | | 90 | | | | | 95 | |

| Ala | Leu | Pro | Glu | Ala | Thr | His | Glu | Asp | Ile | Val | Gly | Val | Gly | Lys | Xaa |
|---|---|---|---|---|---|---|---|---|---|---|---|---|---|---|---|
| | | | | 100 | | | | | 105 | | | | | 110 | |

| Xaa | Xaa | Gly | Ala | Arg | Ala | Leu | Glu | Ala | Leu | Leu | Thr | Asp | Ala | Gly | Glu |
|---|---|---|---|---|---|---|---|---|---|---|---|---|---|---|---|
| | | 115 | | | | | 120 | | | | | 125 | | | |

| Leu | Arg | Gly | Pro | Pro | Leu | Gln | Leu | Asp | Thr | Gly | Gln | Leu | Val | Lys | Ile |
|---|---|---|---|---|---|---|---|---|---|---|---|---|---|---|---|
| | 130 | | | | | 135 | | | | | 140 | | | | |

| Ala | Lys | Arg | Gly | Gly | Val | Thr | Ala | Met | Glu | Ala | Val | His | Ala | Ser | Arg |
|---|---|---|---|---|---|---|---|---|---|---|---|---|---|---|---|
| 145 | | | | | 150 | | | | | 155 | | | | | 160 |

| Asn | Ala | Leu | Thr | Gly | Ala | Pro | Leu | Asn | Leu | Thr | Pro | Asp | Gln | Val | Val |
|---|---|---|---|---|---|---|---|---|---|---|---|---|---|---|---|
| | | | | 165 | | | | | 170 | | | | | 175 | |

| Ala | Ile | Ala | Ser | Asn | Ile | Gly | Gly | Lys | Gln | Ala | Leu | Glu | Thr | Val | Gln |
|---|---|---|---|---|---|---|---|---|---|---|---|---|---|---|---|
| | | | 180 | | | | | 185 | | | | | 190 | | |

| Arg | Leu | Leu | Pro | Val | Leu | Cys | Gln | Asp | His | Gly | Leu | Thr | Pro | Asp | Gln |
|---|---|---|---|---|---|---|---|---|---|---|---|---|---|---|---|
| | | 195 | | | | | 200 | | | | | 205 | | | |

| Val | Val | Ala | Ile | Ala | Ser | Asn | Gly | Gly | Gly | Lys | Gln | Ala | Leu | Glu | Thr |
|---|---|---|---|---|---|---|---|---|---|---|---|---|---|---|---|
| | 210 | | | | | 215 | | | | | 220 | | | | |

| Val | Gln | Arg | Leu | Leu | Pro | Val | Leu | Cys | Gln | Asp | His | Gly | Leu | Thr | Pro |
|---|---|---|---|---|---|---|---|---|---|---|---|---|---|---|---|
| 225 | | | | | 230 | | | | | 235 | | | | | 240 |

| Asp | Gln | Val | Val | Ala | Ile | Ala | Ser | Asn | Ile | Gly | Gly | Lys | Gln | Ala | Leu |
|---|---|---|---|---|---|---|---|---|---|---|---|---|---|---|---|
| | | | | 245 | | | | | 250 | | | | | 255 | |

| Glu | Thr | Val | Gln | Arg | Leu | Leu | Pro | Val | Leu | Cys | Gln | Asp | His | Gly | Leu |
|---|---|---|---|---|---|---|---|---|---|---|---|---|---|---|---|
| | | | 260 | | | | | 265 | | | | | 270 | | |

| Thr | Pro | Asp | Gln | Val | Val | Ala | Ile | Ala | Ser | Asn | Ile | Gly | Gly | Lys | Gln |
|---|---|---|---|---|---|---|---|---|---|---|---|---|---|---|---|
| | | 275 | | | | | 280 | | | | | 285 | | | |

| Ala | Leu | Glu | Thr | Val | Gln | Arg | Leu | Leu | Pro | Val | Leu | Cys | Gln | Asp | His |
|---|---|---|---|---|---|---|---|---|---|---|---|---|---|---|---|
| | 290 | | | | | 295 | | | | | 300 | | | | |

| Gly | Leu | Thr | Pro | Asp | Gln | Val | Val | Ala | Ile | Ala | Ser | Asn | Ile | Gly | Gly |
|---|---|---|---|---|---|---|---|---|---|---|---|---|---|---|---|
| 305 | | | | | 310 | | | | | 315 | | | | | 320 |

| Lys | Gln | Ala | Leu | Glu | Thr | Val | Gln | Arg | Leu | Leu | Pro | Val | Leu | Cys | Gln |
|---|---|---|---|---|---|---|---|---|---|---|---|---|---|---|---|

```
                    325                 330                 335
Asp His Gly Leu Thr Pro Asp Gln Val Val Ala Ile Ala Ser His Asp
                340                 345                 350
Gly Gly Lys Gln Ala Leu Glu Thr Val Gln Arg Leu Leu Pro Val Leu
                355                 360                 365
Cys Gln Asp His Gly Leu Thr Pro Asp Gln Val Val Ala Ile Ala Ser
            370                 375                 380
His Asp Gly Gly Lys Gln Ala Leu Glu Thr Val Gln Arg Leu Leu Pro
385                 390                 395                 400
Val Leu Cys Gln Asp His Gly Leu Thr Pro Asp Gln Val Val Ala Ile
                405                 410                 415
Ala Ser His Asp Gly Gly Lys Gln Ala Leu Glu Thr Val Gln Arg Leu
                420                 425                 430
Leu Pro Val Leu Cys Gln Asp His Gly Leu Thr Pro Asp Gln Val Val
                435                 440                 445
Ala Ile Val Ser His Asp Gly Gly Lys Gln Ala Leu Glu Thr Val Gln
                450                 455                 460
Arg Leu Leu Pro Val Leu Cys Gln Asp His Gly Leu Thr Pro Asp Gln
465                 470                 475                 480
Val Val Ala Ile Val Ser His Asp Gly Gly Lys Gln Ala Leu Glu Thr
                    485                 490                 495
Val Gln Arg Leu Leu Pro Val Leu Cys Gln Asp His Gly Leu Thr Pro
                500                 505                 510
Asp Gln Val Val Ala Ile Val Ser Asn Gly Gly Gly Lys Gln Ala Leu
                515                 520                 525
Glu Thr Val Gln Arg Leu Leu Pro Val Leu Cys Gln Asp His Gly Leu
                530                 535                 540
Thr Pro Asp Gln Val Val Ala Ile Ala Ser His Asp Gly Gly Lys Gln
545                 550                 555                 560
Ala Leu Glu Thr Val Gln Arg Leu Leu Pro Val Leu Cys Gln Asp His
                565                 570                 575
Gly Leu Thr Pro Asp Gln Val Val Ala Ile Ala Ser His Asp Gly Gly
                580                 585                 590
Lys Gln Ala Leu Glu Thr Val Gln Arg Leu Leu Pro Val Leu Cys Gln
                595                 600                 605
Asp His Gly Leu Thr Pro Asp Gln Val Val Ala Ile Ala Ser Asn Ile
                610                 615                 620
Gly Gly Lys Gln Ala Leu Glu Thr Val Gln Arg Leu Leu Pro Val Leu
625                 630                 635                 640
Cys Gln Asp His Gly Leu Thr Pro Asp Gln Val Val Ala Ile Ala Ser
                645                 650                 655
Asn Ile Gly Gly Lys Gln Ala Leu Glu Ser Ile Val Ala Gln Leu Ser
                660                 665                 670
Arg Pro Asp Pro Ala Leu Ala Ala Leu Thr Asn Asp His Leu Val Ala
                675                 680                 685
Leu Ala Cys Leu Gly Gly Arg Pro Ala Met Asp Ala Val Lys Lys Gly
                690                 695                 700
Leu Pro His Ala Pro Glu Leu Ile Arg Arg Val Asn Arg Arg Ile Gly
705                 710                 715                 720
Glu Arg Thr Ser His Arg Val Ala Asp Tyr Ala Gln Val Val Arg Val
                    725                 730                 735
Leu Glu Phe Phe Gln Cys His Ser His Pro Ala Tyr Ala Phe Asp Glu
                740                 745                 750
```

```
Ala Met Thr Gln Phe Gly Met Ser Gly Gln Ala Gly Gln Ala Ser Pro
            755                 760                 765

Lys Lys Lys Arg Lys Val Gly Arg Ala Asp Ala Leu Asp Asp Phe Asp
        770                 775                 780

Leu Asp Met Leu Gly Ser Asp Ala Leu Asp Asp Phe Asp Leu Asp Met
785                 790                 795                 800

Leu Gly Ser Asp Ala Leu Asp Asp Phe Asp Leu Asp Met Leu Gly Ser
                805                 810                 815

Asp Ala Leu Asp Asp Phe Asp Leu Asp Met Leu Ile Asn Tyr Pro Tyr
                820                 825                 830

Asp Val Pro Asp Tyr Ala Ser
        835

<210> SEQ ID NO 101
<211> LENGTH: 30
<212> TYPE: PRT
<213> ORGANISM: Artificial Sequence
<220> FEATURE:
<223> OTHER INFORMATION: Synthetic construct

<400> SEQUENCE: 101

Asn Ile Asn Gly Asn Ile Asn Ile Asn Ile His Asp His Asp His Asp
1               5                   10                  15

His Asp His Asp Asn Ile His Asp His Asp Asn Ile Asn Ile
            20                  25                  30

<210> SEQ ID NO 102
<211> LENGTH: 33
<212> TYPE: PRT
<213> ORGANISM: Artificial Sequence
<220> FEATURE:
<223> OTHER INFORMATION: Synthetic construct

<400> SEQUENCE: 102

Leu Thr Pro Asp Gln Leu Val Lys Ile Ala Lys Arg Gly Gly Thr Ala
1               5                   10                  15

Met Glu Ala Val His Ala Ser Arg Asn Ala Leu Thr Gly Ala Pro Leu
            20                  25                  30

Asn

<210> SEQ ID NO 103
<211> LENGTH: 4
<212> TYPE: PRT
<213> ORGANISM: Artificial Sequence
<220> FEATURE:
<223> OTHER INFORMATION: Synthetic construct

<400> SEQUENCE: 103

Lys Arg Gly Gly
1

<210> SEQ ID NO 104
<211> LENGTH: 4
<212> TYPE: PRT
<213> ORGANISM: Artificial Sequence
<220> FEATURE:
<223> OTHER INFORMATION: Synthetic construct

<400> SEQUENCE: 104

Leu Asp Tyr Glu
1
```

<210> SEQ ID NO 105
<211> LENGTH: 4
<212> TYPE: PRT
<213> ORGANISM: Artificial Sequence
<220> FEATURE:
<223> OTHER INFORMATION: Synthetic construct

<400> SEQUENCE: 105

Ile Asn Leu Val
1

<210> SEQ ID NO 106
<211> LENGTH: 4
<212> TYPE: PRT
<213> ORGANISM: Artificial Sequence
<220> FEATURE:
<223> OTHER INFORMATION: Synthetic construct

<400> SEQUENCE: 106

Tyr Ser Lys Lys
1

<210> SEQ ID NO 107
<211> LENGTH: 4
<212> TYPE: PRT
<213> ORGANISM: Artificial Sequence
<220> FEATURE:
<223> OTHER INFORMATION: Synthetic construct

<400> SEQUENCE: 107

Asn Met Ala His
1

<210> SEQ ID NO 108
<211> LENGTH: 4
<212> TYPE: PRT
<213> ORGANISM: Artificial Sequence
<220> FEATURE:
<223> OTHER INFORMATION: Synthetic construct

<400> SEQUENCE: 108

Ser Pro Thr Asn
1

<210> SEQ ID NO 109
<211> LENGTH: 4
<212> TYPE: PRT
<213> ORGANISM: Artificial Sequence
<220> FEATURE:
<223> OTHER INFORMATION: Synthetic construct

<400> SEQUENCE: 109

Ser Asn Thr Arg
1

<210> SEQ ID NO 110
<211> LENGTH: 4
<212> TYPE: PRT
<213> ORGANISM: Artificial Sequence
<220> FEATURE:
<223> OTHER INFORMATION: Synthetic construct

<400> SEQUENCE: 110

Leu Thr Thr Thr
1

```
<210> SEQ ID NO 111
<211> LENGTH: 4
<212> TYPE: PRT
<213> ORGANISM: Artificial Sequence
<220> FEATURE:
<223> OTHER INFORMATION: Synthetic construct

<400> SEQUENCE: 111

Val Ala Asp Leu
1

<210> SEQ ID NO 112
<211> LENGTH: 4
<212> TYPE: PRT
<213> ORGANISM: Artificial Sequence
<220> FEATURE:
<223> OTHER INFORMATION: Synthetic construct

<400> SEQUENCE: 112

Met Val Leu Ser
1

<210> SEQ ID NO 113
<211> LENGTH: 4
<212> TYPE: PRT
<213> ORGANISM: Artificial Sequence
<220> FEATURE:
<223> OTHER INFORMATION: Synthetic construct

<400> SEQUENCE: 113

Tyr Asn Gly Arg
1

<210> SEQ ID NO 114
<211> LENGTH: 4
<212> TYPE: PRT
<213> ORGANISM: Artificial Sequence
<220> FEATURE:
<223> OTHER INFORMATION: Synthetic construct

<400> SEQUENCE: 114

Arg Ile Pro Arg
1

<210> SEQ ID NO 115
<211> LENGTH: 4
<212> TYPE: PRT
<213> ORGANISM: Artificial Sequence
<220> FEATURE:
<223> OTHER INFORMATION: Synthetic construct

<400> SEQUENCE: 115

Tyr Ser Lys Ile
1

<210> SEQ ID NO 116
<211> LENGTH: 4
<212> TYPE: PRT
<213> ORGANISM: Artificial Sequence
<220> FEATURE:
<223> OTHER INFORMATION: Synthetic construct

<400> SEQUENCE: 116

Leu Thr Gln Tyr
1

<210> SEQ ID NO 117
```

```
<211> LENGTH: 4
<212> TYPE: PRT
<213> ORGANISM: Artificial Sequence
<220> FEATURE:
<223> OTHER INFORMATION: Synthetic construct

<400> SEQUENCE: 117

Tyr Leu Ser Lys
1

<210> SEQ ID NO 118
<211> LENGTH: 4
<212> TYPE: PRT
<213> ORGANISM: Artificial Sequence
<220> FEATURE:
<223> OTHER INFORMATION: Synthetic construct

<400> SEQUENCE: 118

Leu Arg Pro Asn
1

<210> SEQ ID NO 119
<211> LENGTH: 4
<212> TYPE: PRT
<213> ORGANISM: Artificial Sequence
<220> FEATURE:
<223> OTHER INFORMATION: Synthetic construct

<400> SEQUENCE: 119

Leu Phe Thr Asn
1

<210> SEQ ID NO 120
<211> LENGTH: 4
<212> TYPE: PRT
<213> ORGANISM: Artificial Sequence
<220> FEATURE:
<223> OTHER INFORMATION: Synthetic construct

<400> SEQUENCE: 120

Leu Leu Thr Asn
1

<210> SEQ ID NO 121
<211> LENGTH: 4
<212> TYPE: PRT
<213> ORGANISM: Artificial Sequence
<220> FEATURE:
<223> OTHER INFORMATION: Synthetic construct

<400> SEQUENCE: 121

Glu Glu Asp Lys
1

<210> SEQ ID NO 122
<211> LENGTH: 4
<212> TYPE: PRT
<213> ORGANISM: Artificial Sequence
<220> FEATURE:
<223> OTHER INFORMATION: Synthetic construct

<400> SEQUENCE: 122

Val Thr Ala Met
1

<210> SEQ ID NO 123
<211> LENGTH: 4
```

```
<212> TYPE: PRT
<213> ORGANISM: Artificial Sequence
<220> FEATURE:
<223> OTHER INFORMATION: Synthetic construct

<400> SEQUENCE: 123

Cys Pro Ser Arg
1

<210> SEQ ID NO 124
<211> LENGTH: 4
<212> TYPE: PRT
<213> ORGANISM: Artificial Sequence
<220> FEATURE:
<223> OTHER INFORMATION: Synthetic construct

<400> SEQUENCE: 124

Leu Thr Arg Val
1

<210> SEQ ID NO 125
<211> LENGTH: 4
<212> TYPE: PRT
<213> ORGANISM: Artificial Sequence
<220> FEATURE:
<223> OTHER INFORMATION: Synthetic construct

<400> SEQUENCE: 125

Lys Gly Asp Leu
1

<210> SEQ ID NO 126
<211> LENGTH: 4
<212> TYPE: PRT
<213> ORGANISM: Artificial Sequence
<220> FEATURE:
<223> OTHER INFORMATION: Synthetic construct

<400> SEQUENCE: 126

Gln Lys Ala Leu
1

<210> SEQ ID NO 127
<211> LENGTH: 4
<212> TYPE: PRT
<213> ORGANISM: Artificial Sequence
<220> FEATURE:
<223> OTHER INFORMATION: Synthetic construct

<400> SEQUENCE: 127

Leu Tyr Leu Leu
1

<210> SEQ ID NO 128
<211> LENGTH: 4
<212> TYPE: PRT
<213> ORGANISM: Artificial Sequence
<220> FEATURE:
<223> OTHER INFORMATION: Synthetic construct

<400> SEQUENCE: 128

Trp Ile Ser Val
1

<210> SEQ ID NO 129
<211> LENGTH: 4
<212> TYPE: PRT
```

```
<213> ORGANISM: Artificial Sequence
<220> FEATURE:
<223> OTHER INFORMATION: Synthetic construct

<400> SEQUENCE: 129

Gly Asp Gln Val
1

<210> SEQ ID NO 130
<211> LENGTH: 4
<212> TYPE: PRT
<213> ORGANISM: Artificial Sequence
<220> FEATURE:
<223> OTHER INFORMATION: Synthetic construct

<400> SEQUENCE: 130

Cys Pro Ser Arg
1

<210> SEQ ID NO 131
<211> LENGTH: 145
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (89)..(93)
<223> OTHER INFORMATION: Xaa can be any naturally occurring amino acid

<400> SEQUENCE: 131

Met Arg Ser Pro Lys Lys Arg Lys Val Gln Val Asp Leu Arg Thr
1               5                   10                  15

Leu Gly Tyr Ser Gln Gln Gln Gln Glu Lys Ile Lys Pro Lys Val Arg
            20                  25                  30

Ser Thr Val Ala Gln His His Glu Ala Leu Val Gly His Gly Phe Thr
        35                  40                  45

His Ala His Ile Val Ala Leu Ser Gln His Pro Ala Ala Leu Gly Thr
    50                  55                  60

Val Ala Val Thr Tyr Gln His Ile Ile Thr Ala Leu Pro Glu Ala Thr
65                  70                  75                  80

His Glu Asp Ile Val Gly Val Gly Xaa Xaa Xaa Xaa Xaa Ala Arg Ala
                85                  90                  95

Leu Glu Ala Leu Leu Thr Asp Ala Gly Glu Leu Arg Gly Pro Pro Leu
            100                 105                 110

Gln Leu Asp Thr Gly Gln Leu Val Lys Ile Ala Lys Arg Gly Gly Val
        115                 120                 125

Thr Ala Met Glu Ala Val His Ala Ser Arg Asn Ala Leu Thr Gly Ala
    130                 135                 140

Pro
145

<210> SEQ ID NO 132
<211> LENGTH: 5
<212> TYPE: PRT
<213> ORGANISM: Artificial Sequence
<220> FEATURE:
<223> OTHER INFORMATION: Synthetic construct

<400> SEQUENCE: 132

Lys Arg Pro Ala Gly
1               5
```

```
<210> SEQ ID NO 133
<211> LENGTH: 5
<212> TYPE: PRT
<213> ORGANISM: Artificial Sequence
<220> FEATURE:
<223> OTHER INFORMATION: Synthetic construct

<400> SEQUENCE: 133

Lys Arg Pro Ser Gly
1               5

<210> SEQ ID NO 134
<211> LENGTH: 32
<212> TYPE: PRT
<213> ORGANISM: Artificial Sequence
<220> FEATURE:
<223> OTHER INFORMATION: Synthetic construct

<400> SEQUENCE: 134

Leu Thr Pro Asp Val Val Ala Ile Ser Asn Asn Gly Gly Lys Gln Ala
1               5                   10                  15

Leu Glu Thr Val Gln Arg Leu Leu Pro Val Leu Cys Gln Asp Gly His
            20                  25                  30

<210> SEQ ID NO 135
<211> LENGTH: 4
<212> TYPE: PRT
<213> ORGANISM: Artificial Sequence
<220> FEATURE:
<223> OTHER INFORMATION: Synthetic construct

<400> SEQUENCE: 135

Ser Asn Asn Gly
1

<210> SEQ ID NO 136
<211> LENGTH: 4
<212> TYPE: PRT
<213> ORGANISM: Artificial Sequence
<220> FEATURE:
<223> OTHER INFORMATION: Synthetic construct

<400> SEQUENCE: 136

Arg Gly Gly Gly
1

<210> SEQ ID NO 137
<211> LENGTH: 4
<212> TYPE: PRT
<213> ORGANISM: Artificial Sequence
<220> FEATURE:
<223> OTHER INFORMATION: Synthetic construct

<400> SEQUENCE: 137

Arg Gly Gly Arg
1

<210> SEQ ID NO 138
<211> LENGTH: 4
<212> TYPE: PRT
<213> ORGANISM: Artificial Sequence
<220> FEATURE:
<223> OTHER INFORMATION: Synthetic construct

<400> SEQUENCE: 138

Arg Gly Val Arg
```

```
<210> SEQ ID NO 139
<211> LENGTH: 4
<212> TYPE: PRT
<213> ORGANISM: Artificial Sequence
<220> FEATURE:
<223> OTHER INFORMATION: Synthetic construct

<400> SEQUENCE: 139

Lys Gly Gly Gly
1

<210> SEQ ID NO 140
<211> LENGTH: 4
<212> TYPE: PRT
<213> ORGANISM: Artificial Sequence
<220> FEATURE:
<223> OTHER INFORMATION: Synthetic construct

<400> SEQUENCE: 140

Ser Gly Gly Gly
1

<210> SEQ ID NO 141
<211> LENGTH: 4
<212> TYPE: PRT
<213> ORGANISM: Artificial Sequence
<220> FEATURE:
<223> OTHER INFORMATION: Synthetic construct

<400> SEQUENCE: 141

Gly Gly Arg Gly
1

<210> SEQ ID NO 142
<211> LENGTH: 4
<212> TYPE: PRT
<213> ORGANISM: Artificial Sequence
<220> FEATURE:
<223> OTHER INFORMATION: Synthetic construct

<400> SEQUENCE: 142

Leu Gly Gly Ser
1

<210> SEQ ID NO 143
<211> LENGTH: 4
<212> TYPE: PRT
<213> ORGANISM: Artificial Sequence
<220> FEATURE:
<223> OTHER INFORMATION: Synthetic construct

<400> SEQUENCE: 143

Met Asp Asn Ile
1

<210> SEQ ID NO 144
<211> LENGTH: 4
<212> TYPE: PRT
<213> ORGANISM: Artificial Sequence
<220> FEATURE:
<223> OTHER INFORMATION: Synthetic construct

<400> SEQUENCE: 144

Arg Val Met Ala
1
```

<210> SEQ ID NO 145
<211> LENGTH: 4
<212> TYPE: PRT
<213> ORGANISM: Artificial Sequence
<220> FEATURE:
<223> OTHER INFORMATION: Synthetic construct

<400> SEQUENCE: 145

Leu Ala Ser Val
1

<210> SEQ ID NO 146
<211> LENGTH: 4
<212> TYPE: PRT
<213> ORGANISM: Artificial Sequence
<220> FEATURE:
<223> OTHER INFORMATION: Synthetic construct

<400> SEQUENCE: 146

Val Gly Thr Gly
1

<210> SEQ ID NO 147
<211> LENGTH: 4
<212> TYPE: PRT
<213> ORGANISM: Artificial Sequence
<220> FEATURE:
<223> OTHER INFORMATION: Synthetic construct

<400> SEQUENCE: 147

Gln Gly Gly Gly
1

<210> SEQ ID NO 148
<211> LENGTH: 118
<212> TYPE: DNA
<213> ORGANISM: Artificial Sequence
<220> FEATURE:
<223> OTHER INFORMATION: Primer

<400> SEQUENCE: 148
ttaattaaga gtctagaaat ataaaccccc tccaaccagg tgctaactgt aaaccatggt    60
tttggattag cacctggttg gagggggttt ataagatcta ggaggaattt aaaatgag    118

<210> SEQ ID NO 149
<211> LENGTH: 117
<212> TYPE: DNA
<213> ORGANISM: Artificial Sequence
<220> FEATURE:
<223> OTHER INFORMATION: Primer

<400> SEQUENCE: 149
actgacctag agaagcttat ataaaccccc tccaaccagg tgctaatcca aaccatggt    60 ttacagttag cacctggttg gagggggttt atactgcagt tatttgtaca gttcatc      117

<210> SEQ ID NO 150
<211> LENGTH: 116
<212> TYPE: DNA
<213> ORGANISM: Artificial Sequence
<220> FEATURE:
<223> OTHER INFORMATION: Primer

<400> SEQUENCE: 150
ttaattaaga gtctagatta gcacctggtt ggagggggtt tataaggttt tggtaccaaa    60

```
tgtctataaa cccoctccaa ccaggtgcta aagatctagg aggaatttaa aatgag        116
```

<210> SEQ ID NO 151
<211> LENGTH: 116
<212> TYPE: DNA
<213> ORGANISM: Artificial Sequence
<220> FEATURE:
<223> OTHER INFORMATION: Primer

<400> SEQUENCE: 151

```
ttaattaaga gtctagatta gcacctggtt ggagggggtt tataaggttt tggtaccaaa   60
tgtctataaa cccoctccaa ccaggtgcta aagatctagg aggaatttaa aatgag       116
```

<210> SEQ ID NO 152
<211> LENGTH: 116
<212> TYPE: DNA
<213> ORGANISM: Artificial Sequence
<220> FEATURE:
<223> OTHER INFORMATION: Primer

<400> SEQUENCE: 152

```
actgacctag agaagctttt agcacctggt tggagggggt ttatagacat ttggtaccaa   60
aaccttataa acccoctcca accaggtgct aactgcagtt atttgtacag ttcatc      116
```

<210> SEQ ID NO 153
<211> LENGTH: 116
<212> TYPE: DNA
<213> ORGANISM: Artificial Sequence
<220> FEATURE:
<223> OTHER INFORMATION: Primer

<400> SEQUENCE: 153

```
ttaattaaga gtctagatta gcacctggtt ggagggggtt tatatccaaa accatggttt   60
acagtataaa cccoctccaa ccaggtgcta aagatctagg aggaatttaa aatgag       116
```

<210> SEQ ID NO 154
<211> LENGTH: 116
<212> TYPE: DNA
<213> ORGANISM: Artificial Sequence
<220> FEATURE:
<223> OTHER INFORMATION: Primer

<400> SEQUENCE: 154

```
actgacctag agaagctttt agcacctggt tggagggggt ttatatccaa aaccatggtt   60
tacagtataa acccoctcca accaggtgct aactgcagtt atttgtacag ttcatc      116
```

<210> SEQ ID NO 155
<211> LENGTH: 122
<212> TYPE: DNA
<213> ORGANISM: Artificial Sequence
<220> FEATURE:
<223> OTHER INFORMATION: Primer

<400> SEQUENCE: 155

```
ttaattaaga gtctagatta gcacctggtt ggagggggtt tatagcttcc aaaaccatgg   60
tttacagggt tataaacccc ctccaaccag gtgctaaaga tctaggagga atttaaaatg  120
ag                                                                 122
```

<210> SEQ ID NO 156
<211> LENGTH: 128
<212> TYPE: DNA

```
<213> ORGANISM: Artificial Sequence
<220> FEATURE:
<223> OTHER INFORMATION: Primer

<400> SEQUENCE: 156
ttaattaaga gtctagatta gcacctggtt ggaggggggtt tatagcttca tccaaaacca      60
tggtttacag ggttcctata aaccccctcc aaccaggtgc taaagatcta ggaggaattt     120
aaaatgag                                                              128

<210> SEQ ID NO 157
<211> LENGTH: 128
<212> TYPE: DNA
<213> ORGANISM: Artificial Sequence
<220> FEATURE:
<223> OTHER INFORMATION: Primer

<400> SEQUENCE: 157
actgacctag agaagctttt agcacctggt tggagggggt ttatagcaac cctgtaaacc      60
atggttttgg atgaagctat aaaccccctc caaccaggtg ctaactgcag ttatttgtac     120
agttcatc                                                              128

<210> SEQ ID NO 158
<211> LENGTH: 140
<212> TYPE: DNA
<213> ORGANISM: Artificial Sequence
<220> FEATURE:
<223> OTHER INFORMATION: Primer

<400> SEQUENCE: 158
ttaattaaga gtctagatta gcacctggtt ggaggggggtt tatagcttca gcttcatcca      60
aaaccatggt ttcagggtt ccggttccta taaacccccct ccaaccaggt gctaaagatc     120
taggaggaat ttaaaatgag                                                 140

<210> SEQ ID NO 159
<211> LENGTH: 140
<212> TYPE: DNA
<213> ORGANISM: Artificial Sequence
<220> FEATURE:
<223> OTHER INFORMATION: Primer

<400> SEQUENCE: 159
ttaattaaga gtctagatta gcacctggtt ggaggggggtt tatagcttca gcttcatcca      60
aaaccatggt ttcagggtt ccggttccta taaacccccct ccaaccaggt gctaaagatc     120
taggaggaat ttaaaatgag                                                 140

<210> SEQ ID NO 160
<211> LENGTH: 110
<212> TYPE: DNA
<213> ORGANISM: Artificial Sequence
<220> FEATURE:
<223> OTHER INFORMATION: Primer

<400> SEQUENCE: 160
ttaattaaga gtctagatta gcacctggtt ggaggggggtt tataaaaacc atggtttata      60
taaaccccct ccaaccaggt gctaaagatc taggaggaat ttaaaatgag                 110

<210> SEQ ID NO 161
<211> LENGTH: 110
<212> TYPE: DNA
<213> ORGANISM: Artificial Sequence
```

```
<220> FEATURE:
<223> OTHER INFORMATION: Primer

<400> SEQUENCE: 161
actgacctag agaagctttt agcacctggt tggagggggt ttatataaac catggttttt      60
ataaaccccc tccaaccagg tgctaactgc agttatttgt acagttcatc                110

<210> SEQ ID NO 162
<211> LENGTH: 116
<212> TYPE: DNA
<213> ORGANISM: Artificial Sequence
<220> FEATURE:
<223> OTHER INFORMATION: Primer

<400> SEQUENCE: 162
ttaattaaga gtctagatta gcacctggtt ggaggggggtt tatatccaaa accggggttt     60
acagtataaa cccccctccaa ccaggtgcta aagatctagg aggaatttaa aatgag        116

<210> SEQ ID NO 163
<211> LENGTH: 116
<212> TYPE: DNA
<213> ORGANISM: Artificial Sequence
<220> FEATURE:
<223> OTHER INFORMATION: Primer

<400> SEQUENCE: 163
actgacctag agaagctttt agcacctggt tggaggggggt ttatactgta aaccccggtt    60
ttggatataa accccctcca accaggtgct aactgcagtt atttgtacag ttcatc         116

<210> SEQ ID NO 164
<211> LENGTH: 116
<212> TYPE: DNA
<213> ORGANISM: Artificial Sequence
<220> FEATURE:
<223> OTHER INFORMATION: Primer

<400> SEQUENCE: 164
ttaattaaga gtctagatta gcacctggtt ggaggggggtt tatacgaaat attataaatt    60
atcatataaa cccccctccaa ccaggtgcta aagatctagg aggaatttaa aatgag        116

<210> SEQ ID NO 165
<211> LENGTH: 116
<212> TYPE: DNA
<213> ORGANISM: Artificial Sequence
<220> FEATURE:
<223> OTHER INFORMATION: Primer

<400> SEQUENCE: 165
actgacctag agaagctttt agcacctggt tggaggggggt ttatatgata atttataata    60
tttcgtataa accccctcca accaggtgct aactgcagtt atttgtacag ttcatc         116

<210> SEQ ID NO 166
<211> LENGTH: 128
<212> TYPE: DNA
<213> ORGANISM: Artificial Sequence
<220> FEATURE:
<223> OTHER INFORMATION: Primer

<400> SEQUENCE: 166
ttaattaaga gtctagatta gcacctggtt ggaggggggtt tatagcttca tccaaaaccg    60
gggtttacag ggttcctata aaccccctcc aaccaggtgc taaagatcta ggaggaattt    120
```

```
aaaatgag                                                              128

<210> SEQ ID NO 167
<211> LENGTH: 128
<212> TYPE: DNA
<213> ORGANISM: Artificial Sequence
<220> FEATURE:
<223> OTHER INFORMATION: Primer

<400> SEQUENCE: 167
actgacctag agaagctttt agcacctggt tggagggggt ttatagcaac cctgtaaacc    60
ggggttttgg atgaagctat aaacccctc caaccaggtg ctaactgcag ttatttgtac   120
agttcatc                                                            128

<210> SEQ ID NO 168
<211> LENGTH: 128
<212> TYPE: DNA
<213> ORGANISM: Artificial Sequence
<220> FEATURE:
<223> OTHER INFORMATION: Primer

<400> SEQUENCE: 168
ttaattaaga gtctagatta gcacctggtt ggaggggggtt tatagcttca cgaaatatta    60
taaattatca ggttcctata aacccctcc aaccaggtgc taaagatcta ggaggaattt   120
aaaatgag                                                            128

<210> SEQ ID NO 169
<211> LENGTH: 128
<212> TYPE: DNA
<213> ORGANISM: Artificial Sequence
<220> FEATURE:
<223> OTHER INFORMATION: Primer

<400> SEQUENCE: 169
actgacctag agaagctttt agcacctggt tggagggggt ttatagcaac ctgataattt    60
ataatatttc gtgaagctat aaacccctc caaccaggtg ctaactgcag ttatttgtac   120
agttcatc                                                            128

<210> SEQ ID NO 170
<211> LENGTH: 128
<212> TYPE: DNA
<213> ORGANISM: Artificial Sequence
<220> FEATURE:
<223> OTHER INFORMATION: Primer

<400> SEQUENCE: 170
ttaattaaga gagatcttta gcacctggtt ggaggggggtt tatagcttca tccaaaacca    60
tggtttacag ggttcctata aacccctcc aaccaggtgc taagcgatct gcatctcaat   120
tagtcagc                                                            128

<210> SEQ ID NO 171
<211> LENGTH: 128
<212> TYPE: DNA
<213> ORGANISM: Artificial Sequence
<220> FEATURE:
<223> OTHER INFORMATION: Primer

<400> SEQUENCE: 171
actgacctag agaagctttt agcacctggt tggagggggt ttatagcaac cctgtaaacc    60
atggttttgg atgaagctat aaacccctc caaccaggtg ctaatttgca aaagcctagg   120
```

```
cctccaaa                                                            128

<210> SEQ ID NO 172
<211> LENGTH: 107
<212> TYPE: DNA
<213> ORGANISM: Artificial Sequence
<220> FEATURE:
<223> OTHER INFORMATION: Primer

<400> SEQUENCE: 172
ttaattaaga gagatctgcg ggaggcgtgt ccaaaaccat ggtttacagg gttcctataa    60 acccctcca accaggtgct aagcgatctg catctcaatt agtcagc                 107

<210> SEQ ID NO 173
<211> LENGTH: 107
<212> TYPE: DNA
<213> ORGANISM: Artificial Sequence
<220> FEATURE:
<223> OTHER INFORMATION: Primer

<400> SEQUENCE: 173
actgacctag agaagctttt agcacctggt tggaggggt ttatagcaac cctgtaaacc    60
atggttttgg acacgcctcc cgctttgcaa aagcctaggc ctccaaa                107

<210> SEQ ID NO 174
<211> LENGTH: 140
<212> TYPE: DNA
<213> ORGANISM: Artificial Sequence
<220> FEATURE:
<223> OTHER INFORMATION: Primer

<400> SEQUENCE: 174
ttaattaaga gagatcttta gcacctggtt ggagggggtt tatagcttca gcttcatcca    60
aaaccatggt ttacagggtt ccggttccta taaccccct ccaaccaggt gctaagcgat   120
ctgcatctca attagtcagc                                              140

<210> SEQ ID NO 175
<211> LENGTH: 140
<212> TYPE: DNA
<213> ORGANISM: Artificial Sequence
<220> FEATURE:
<223> OTHER INFORMATION: Primer

<400> SEQUENCE: 175
actgacctag agaagctttt agcacctggt tggagggggt ttatagcaac cgcaaccctg    60
taaaccatgg ttttggatga agctgaagct ataaccccc tccaaccagg tgctaatttg   120
caaaagccta ggcctccaaa                                              140

<210> SEQ ID NO 176
<211> LENGTH: 52
<212> TYPE: DNA
<213> ORGANISM: Artificial Sequence
<220> FEATURE:
<223> OTHER INFORMATION: Primer

<400> SEQUENCE: 176
agtcagtcga gagctcatgg atcccggctc tatgctgatt ggctatgtaa gg            52

<210> SEQ ID NO 177
<211> LENGTH: 39
<212> TYPE: DNA
```

```
<213> ORGANISM: Artificial Sequence
<220> FEATURE:
<223> OTHER INFORMATION: Primer

<400> SEQUENCE: 177
atgctgatat ctagactatc ccgatttagg tgggcgacc                              39

<210> SEQ ID NO 178
<211> LENGTH: 37
<212> TYPE: DNA
<213> ORGANISM: Artificial Sequence
<220> FEATURE:
<223> OTHER INFORMATION: Primer

<400> SEQUENCE: 178
agtcagtcga gagctcatgc tgattggcta tgtaagg                                37

<210> SEQ ID NO 179
<211> LENGTH: 32
<212> TYPE: DNA
<213> ORGANISM: Artificial Sequence
<220> FEATURE:
<223> OTHER INFORMATION: Primer

<400> SEQUENCE: 179
tctagactac ggatccaccg atttacgcgg gc                                     32

<210> SEQ ID NO 180
<211> LENGTH: 39
<212> TYPE: DNA
<213> ORGANISM: Artificial Sequence
<220> FEATURE:
<223> OTHER INFORMATION: Primer

<400> SEQUENCE: 180
atcgcgtatc tagactagcc gaggcaggcc aaggcgacg                              39

<210> SEQ ID NO 181
<211> LENGTH: 39
<212> TYPE: DNA
<213> ORGANISM: Artificial Sequence
<220> FEATURE:
<223> OTHER INFORMATION: Primer

<400> SEQUENCE: 181
atcgcgtatc tagactagct catctcgaac tgcgtcatg                              39

<210> SEQ ID NO 182
<211> LENGTH: 43
<212> TYPE: DNA
<213> ORGANISM: Artificial Sequence
<220> FEATURE:
<223> OTHER INFORMATION: Primer

<400> SEQUENCE: 182
gtcgcccgcg taaatcggga tccactgcag atcgggggggg ggc                        43

<210> SEQ ID NO 183
<211> LENGTH: 43
<212> TYPE: DNA
<213> ORGANISM: Artificial Sequence
<220> FEATURE:
<223> OTHER INFORMATION: Primer

<400> SEQUENCE: 183
gtcgcccgcg taaatcggga tccccctcgc ctgcgttctc ggc                         43
```

<210> SEQ ID NO 184
<211> LENGTH: 43
<212> TYPE: DNA
<213> ORGANISM: Artificial Sequence
<220> FEATURE:
<223> OTHER INFORMATION: Primer

<400> SEQUENCE: 184
gtcgcccgcg taaatcggga tccgattcga tgcctgccgt cgg           43

<210> SEQ ID NO 185
<211> LENGTH: 45
<212> TYPE: DNA
<213> ORGANISM: Artificial Sequence
<220> FEATURE:
<223> OTHER INFORMATION: Primer

<400> SEQUENCE: 185
gtcgcccgcg taaatcggga tccaccgtgc gtgtcgctgt cactg         45

<210> SEQ ID NO 186
<211> LENGTH: 44
<212> TYPE: DNA
<213> ORGANISM: Artificial Sequence
<220> FEATURE:
<223> OTHER INFORMATION: Primer

<400> SEQUENCE: 186
gtcgcccgcg taaatcggga tccgtggatc tacgcacgct cggc          44

<210> SEQ ID NO 187
<211> LENGTH: 43
<212> TYPE: DNA
<213> ORGANISM: Artificial Sequence
<220> FEATURE:
<223> OTHER INFORMATION: Primer

<400> SEQUENCE: 187
gtcgcccgcg taaatcggga tccacacacg cgcacatcgt tgc           43

<210> SEQ ID NO 188
<211> LENGTH: 45
<212> TYPE: DNA
<213> ORGANISM: Artificial Sequence
<220> FEATURE:
<223> OTHER INFORMATION: Primer

<400> SEQUENCE: 188
gtcgcccgcg taaatcggga tcccacgaag acatcgttgg cgtcg         45

<210> SEQ ID NO 189
<211> LENGTH: 44
<212> TYPE: DNA
<213> ORGANISM: Artificial Sequence
<220> FEATURE:
<223> OTHER INFORMATION: Primer

<400> SEQUENCE: 189
gtcgcccgcg taaatcggga tccagcgctc tggaggcctt gctc          44

<210> SEQ ID NO 190
<211> LENGTH: 44
<212> TYPE: DNA
<213> ORGANISM: Artificial Sequence
<220> FEATURE:

<223> OTHER INFORMATION: Primer

<400> SEQUENCE: 190
gtcgcccgcg taaatcggga tccttggaca caggccaact tctc      44

<210> SEQ ID NO 191
<211> LENGTH: 43
<212> TYPE: DNA
<213> ORGANISM: Artificial Sequence
<220> FEATURE:
<223> OTHER INFORMATION: Primer

<400> SEQUENCE: 191
gtcgcccgcg taaatcggga tccagcggcg tgaccgcagt gga      43

<210> SEQ ID NO 192
<211> LENGTH: 20
<212> TYPE: DNA
<213> ORGANISM: Artificial Sequence
<220> FEATURE:
<223> OTHER INFORMATION: Primer

<400> SEQUENCE: 192
ggatcccgat ttacgcgggc      20

<210> SEQ ID NO 193
<211> LENGTH: 41
<212> TYPE: DNA
<213> ORGANISM: Artificial Sequence
<220> FEATURE:
<223> OTHER INFORMATION: Primer

<400> SEQUENCE: 193
atcgtagcag ctagcgccac catgctgatt ggctatgtaa g      41

<210> SEQ ID NO 194
<211> LENGTH: 26
<212> TYPE: DNA
<213> ORGANISM: Artificial Sequence
<220> FEATURE:
<223> OTHER INFORMATION: Primer

<400> SEQUENCE: 194
ggatccagac cccgatttac gcgggc      26

<210> SEQ ID NO 195
<211> LENGTH: 74
<212> TYPE: DNA
<213> ORGANISM: Artificial Sequence
<220> FEATURE:
<223> OTHER INFORMATION: Synthetic construct

<400> SEQUENCE: 195
ttagcacctg gttggagggg gtttatatcc aaaaccatgg tttacagtat aaaccccctc      60
caaccaggtg ctaa      74

<210> SEQ ID NO 196
<211> LENGTH: 74
<212> TYPE: DNA
<213> ORGANISM: Artificial Sequence
<220> FEATURE:
<223> OTHER INFORMATION: Synthetic construct

<400> SEQUENCE: 196
ttagcacctg gttggagggg gtttataagg ttttggtacc aaatgtctat aaaccccctc      60
caaccaggtg ctaa 74

<210> SEQ ID NO 197
<211> LENGTH: 74
<212> TYPE: DNA
<213> ORGANISM: Artificial Sequence
<220> FEATURE:
<223> OTHER INFORMATION: Synthetic construct

<400> SEQUENCE: 197
tataaccccc ctccaaccag gtgctaactg taaaccatgg ttttggatta gcacctggtt 60 ggaggggtt tata 74

<210> SEQ ID NO 198
<211> LENGTH: 68
<212> TYPE: DNA
<213> ORGANISM: Artificial Sequence
<220> FEATURE:
<223> OTHER INFORMATION: Synthetic construct

<400> SEQUENCE: 198
ttagcacctg gttggagggg gtttataaaa accatggttt atataaaccc cctccaacca 60
ggtgctaa 68

<210> SEQ ID NO 199
<211> LENGTH: 80
<212> TYPE: DNA
<213> ORGANISM: Artificial Sequence
<220> FEATURE:
<223> OTHER INFORMATION: Synthetic construct

<400> SEQUENCE: 199
ttagcacctg gttggagggg gtttatagct tccaaaacca tggtttacag ggttataaac 60
cccctccaac caggtgctaa 80

<210> SEQ ID NO 200
<211> LENGTH: 86
<212> TYPE: DNA
<213> ORGANISM: Artificial Sequence
<220> FEATURE:
<223> OTHER INFORMATION: Synthetic construct

<400> SEQUENCE: 200
ttagcacctg gttggagggg gtttatagct tcatccaaaa ccatggttta cagggttcct 60
ataaaccccc tccaaccagg tgctaa 86

<210> SEQ ID NO 201
<211> LENGTH: 98
<212> TYPE: DNA
<213> ORGANISM: Artificial Sequence
<220> FEATURE:
<223> OTHER INFORMATION: Synthetic construct

<400> SEQUENCE: 201
ttagcacctg gttggagggg gtttatagct tcagcttcat ccaaaaccat ggtttacagg 60
gttccggttc ctataaaccc cctccaacca ggtgctaa 98

<210> SEQ ID NO 202
<211> LENGTH: 74
<212> TYPE: DNA
<213> ORGANISM: Artificial Sequence
<220> FEATURE:

<223> OTHER INFORMATION: Synthetic construct

<400> SEQUENCE: 202
ttagcacctg gttggagggg gtttatatcc aaaaccgggg tttacagtat aaaccccctc    60
caaccaggtg ctaa                                                      74

<210> SEQ ID NO 203
<211> LENGTH: 74
<212> TYPE: DNA
<213> ORGANISM: Artificial Sequence
<220> FEATURE:
<223> OTHER INFORMATION: Synthetic construct

<400> SEQUENCE: 203
ttagcacctg gttggagggg gtttatacga aatattataa attatcatat aaaccccctc    60
caaccaggtg ctaa                                                      74

<210> SEQ ID NO 204
<211> LENGTH: 86
<212> TYPE: DNA
<213> ORGANISM: Artificial Sequence
<220> FEATURE:
<223> OTHER INFORMATION: Synthetic construct

<400> SEQUENCE: 204
ttagcacctg gttggagggg gtttatagct tcatccaaaa ccggggttta cagggttcct    60
ataaaccccc tccaaccagg tgctaa                                         86

<210> SEQ ID NO 205
<211> LENGTH: 86
<212> TYPE: DNA
<213> ORGANISM: Artificial Sequence
<220> FEATURE:
<223> OTHER INFORMATION: Synthetic construct

<400> SEQUENCE: 205
ttagcacctg gttggagggg gtttatagct tcacgaaata ttataaatta tcaggttcct    60
ataaaccccc tccaaccagg tgctaa                                         86

<210> SEQ ID NO 206
<211> LENGTH: 65
<212> TYPE: DNA
<213> ORGANISM: Artificial Sequence
<220> FEATURE:
<223> OTHER INFORMATION: Synthetic construct

<400> SEQUENCE: 206
gcgggaggcg tgtccaaaac catggtttac agggttccta taaaccccct ccaaccaggt    60
gctaa                                                                65

<210> SEQ ID NO 207
<211> LENGTH: 70
<212> TYPE: DNA
<213> ORGANISM: Artificial Sequence
<220> FEATURE:
<223> OTHER INFORMATION: Synthetic construct

<400> SEQUENCE: 207
gtggtgtaca gtaggggagg atgcatccaa aaccatggtt tacagtgcat ctccccctac    60
tgtacaccac                                                           70

```
<210> SEQ ID NO 208
<211> LENGTH: 82
<212> TYPE: DNA
<213> ORGANISM: Artificial Sequence
<220> FEATURE:
<223> OTHER INFORMATION: Synthetic construct

<400> SEQUENCE: 208
gtggtgtaca gtaggggag atgcagctgc ttccaaaacc atggtttaca gggtggttgc      60
atctccccct actgtacacc ac                                              82

<210> SEQ ID NO 209
<211> LENGTH: 4
<212> TYPE: PRT
<213> ORGANISM: Artificial Sequence
<220> FEATURE:
<223> OTHER INFORMATION: Synthetic construct

<400> SEQUENCE: 209

Gln Trp Ser Gly
1

<210> SEQ ID NO 210
<211> LENGTH: 4
<212> TYPE: PRT
<213> ORGANISM: Artificial Sequence
<220> FEATURE:
<223> OTHER INFORMATION: Synthetic construct

<400> SEQUENCE: 210

Arg Ser Asn Gly
1

<210> SEQ ID NO 211
<211> LENGTH: 4
<212> TYPE: PRT
<213> ORGANISM: Artificial Sequence
<220> FEATURE:
<223> OTHER INFORMATION: Synthetic construct

<400> SEQUENCE: 211

Ser Arg Ser Gly
1

<210> SEQ ID NO 212
<211> LENGTH: 4
<212> TYPE: PRT
<213> ORGANISM: Artificial Sequence
<220> FEATURE:
<223> OTHER INFORMATION: Synthetic construct

<400> SEQUENCE: 212

Gln Trp Ser Gly
1

<210> SEQ ID NO 213
<211> LENGTH: 16
<212> TYPE: DNA
<213> ORGANISM: Artificial Sequence
<220> FEATURE:
<223> OTHER INFORMATION: Synthetic construct

<400> SEQUENCE: 213 gataaaccc ctccaa                                                      16

<210> SEQ ID NO 214
```

```
<211> LENGTH: 15
<212> TYPE: DNA
<213> ORGANISM: Artificial Sequence
<220> FEATURE:
<223> OTHER INFORMATION: Synthetic construct

<400> SEQUENCE: 214 ataaacccccc tccaa                                                    15

<210> SEQ ID NO 215
<211> LENGTH: 35
<212> TYPE: PRT
<213> ORGANISM: Artificial Sequence
<220> FEATURE:
<223> OTHER INFORMATION: Synthetic construct

<400> SEQUENCE: 215
```

Ala Thr His Glu Asp Ile Val Gly Val Gly Lys Gln Trp Ser Gly Ala
1               5                   10                  15

Arg Ala Leu Glu Ala Leu Leu Thr Asp Ala Gly Glu Leu Arg Gly Pro
            20                  25                  30

Pro Leu Gln
        35

```
<210> SEQ ID NO 216
<211> LENGTH: 35
<212> TYPE: PRT
<213> ORGANISM: Artificial Sequence
<220> FEATURE:
<223> OTHER INFORMATION: Synthetic construct

<400> SEQUENCE: 216
```

Ala Thr His Glu Asp Ile Val Gly Val Gly Lys Gln Trp Ser Gly Ala
1               5                   10                  15

Arg Ala Leu Glu Ala Leu Leu Thr Asp Ala Gly Glu Leu Arg Gly Pro
            20                  25                  30

Pro Leu Gln
        35

```
<210> SEQ ID NO 217
<211> LENGTH: 5
<212> TYPE: PRT
<213> ORGANISM: Artificial Sequence
<220> FEATURE:
<223> OTHER INFORMATION: Synthetic construct

<400> SEQUENCE: 217
```

Lys Gln Trp Ser Gly
1               5

```
<210> SEQ ID NO 218
<211> LENGTH: 5
<212> TYPE: PRT
<213> ORGANISM: Artificial Sequence
<220> FEATURE:
<223> OTHER INFORMATION: Synthetic construct

<400> SEQUENCE: 218
```

Lys Arg Ser Asn Gly
1               5

```
<210> SEQ ID NO 219
<211> LENGTH: 5
<212> TYPE: PRT
<213> ORGANISM: Artificial Sequence
```

<220> FEATURE:
<223> OTHER INFORMATION: Synthetic construct

<400> SEQUENCE: 219

Lys Ser Arg Ser Gly
1               5

<210> SEQ ID NO 220
<211> LENGTH: 35
<212> TYPE: PRT
<213> ORGANISM: Artificial Sequence
<220> FEATURE:
<223> OTHER INFORMATION: Synthetic construct

<400> SEQUENCE: 220

Ala Thr His Glu Asp Ile Val Gly Val Gly Lys Gln Trp Ser Gly Ala
1               5                   10                  15

Arg Ala Leu Glu Ala Leu Leu Thr Asp Ala Gly Glu Leu Arg Gly Pro
            20                  25                  30

Pro Leu Gln
        35

<210> SEQ ID NO 221
<211> LENGTH: 5
<212> TYPE: PRT
<213> ORGANISM: Artificial Sequence
<220> FEATURE:
<223> OTHER INFORMATION: Synthetic construct

<400> SEQUENCE: 221

Lys Gln Trp Ser Gly
1               5

<210> SEQ ID NO 222
<211> LENGTH: 16
<212> TYPE: DNA
<213> ORGANISM: Artificial Sequence
<220> FEATURE:
<223> OTHER INFORMATION: Synthetic construct

<400> SEQUENCE: 222
aataaacccc ctccaa                                                    16

<210> SEQ ID NO 223
<211> LENGTH: 16
<212> TYPE: DNA
<213> ORGANISM: Artificial Sequence
<220> FEATURE:
<223> OTHER INFORMATION: Synthetic construct

<400> SEQUENCE: 223
tataaacccc ctccaa                                                    16

<210> SEQ ID NO 224
<211> LENGTH: 4
<212> TYPE: PRT
<213> ORGANISM: Artificial Sequence
<220> FEATURE:
<223> OTHER INFORMATION: Synthetic construct

<400> SEQUENCE: 224

Lys Arg Gly Gly
1

<210> SEQ ID NO 225

```
<211> LENGTH: 34
<212> TYPE: PRT
<213> ORGANISM: Artificial Sequence
<220> FEATURE:
<223> OTHER INFORMATION: Synthetic construct

<400> SEQUENCE: 225

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 226
<211> LENGTH: 4
<212> TYPE: PRT
<213> ORGANISM: Artificial Sequence
<220> FEATURE:
<223> OTHER INFORMATION: Synthetic construct

<400> SEQUENCE: 226

Ser His Asp Gly
1

<210> SEQ ID NO 227
<211> LENGTH: 6
<212> TYPE: PRT
<213> ORGANISM: Artificial Sequence
<220> FEATURE:
<223> OTHER INFORMATION: Synthetic construct

<400> SEQUENCE: 227

Ala Ser His Asp Gly Gly
1               5

<210> SEQ ID NO 228
<211> LENGTH: 81
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 228
tctcaactcc cccgcctccg tgagcaaggc ctccagagcg cgtgccccmn nmnntttgcc    60
gacgccaacg atgtcttcgt g                                              81

<210> SEQ ID NO 229
<211> LENGTH: 84
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
```

```
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t

<400> SEQUENCE: 229
tctcaactcc cccgcctccg tgagcaaggc ctccagagcg cgtgcmnnmn nmnnmnnttt      60
gccgacgcca acgatgtctt cgtg                                            84

<210> SEQ ID NO 230
<211> LENGTH: 80
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 230
cccgcctccg tgagcaaggc ctccagggcg cgtgcgccgg amnmnnmnn gccgacgcca      60 acgatgtctt cgtgtgtcgc                                                 80

<210> SEQ ID NO 231
<211> LENGTH: 90
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t

<400> SEQUENCE: 231
ggcacccgtc agtgcattgc gccatgcatg cactgcctcc actgcggtca cmnnmnnmnn     60
mnntgcaatc ttgagaagtt ggcctgtgtc                                      90

<210> SEQ ID NO 232
<211> LENGTH: 71
<212> TYPE: DNA
<213> ORGANISM: Artificial Sequence
<220> FEATURE:
<223> OTHER INFORMATION: Primer
```

```
<400> SEQUENCE: 232
agagagagaa gaaaatgaga tctcctaaga aaaagaggaa ggtgcaggtg gatctacgca      60
cgctcggcta c                                                          71

<210> SEQ ID NO 233
<211> LENGTH: 71
<212> TYPE: DNA
<213> ORGANISM: Artificial Sequence
<220> FEATURE:
<223> OTHER INFORMATION: Primer

<400> SEQUENCE: 233
aggaagaaga gaagcatgag atctcctaag aaaaagagga aggtgatggt ggacttgagg      60
acactcggtt a                                                          71

<210> SEQ ID NO 234
<211> LENGTH: 44
<212> TYPE: DNA
<213> ORGANISM: Artificial Sequence
<220> FEATURE:
<223> OTHER INFORMATION: Primer

<400> SEQUENCE: 234
aagagaagaa gaagaagcat tgcgccatgc atgcactgcc tcta                       44

<210> SEQ ID NO 235
<211> LENGTH: 17
<212> TYPE: DNA
<213> ORGANISM: Artificial Sequence
<220> FEATURE:
<223> OTHER INFORMATION: Primer

<400> SEQUENCE: 235
cccgccaccc accgtgc                                                    17

<210> SEQ ID NO 236
<211> LENGTH: 23
<212> TYPE: DNA
<213> ORGANISM: Artificial Sequence
<220> FEATURE:
<223> OTHER INFORMATION: Primer

<400> SEQUENCE: 236
tgctctatgc atgcactgcc tcc                                             23

<210> SEQ ID NO 237
<211> LENGTH: 68
<212> TYPE: DNA
<213> ORGANISM: Artificial Sequence
<220> FEATURE:
<223> OTHER INFORMATION: Primer

<400> SEQUENCE: 237
agagaagaga agagaaggcg cccgcggccc aggcggcctc gggatcccct cggcctccgc      60
gcgccaag                                                              68

<210> SEQ ID NO 238
<211> LENGTH: 65
<212> TYPE: DNA
<213> ORGANISM: Artificial Sequence
<220> FEATURE:
<223> OTHER INFORMATION: Primer

<400> SEQUENCE: 238
```

```
agagagagag agagagtcta gaggccggcc tggccgctca tcccgaactg cgtcatggcc    60
tcatc                                                                65

<210> SEQ ID NO 239
<211> LENGTH: 27
<212> TYPE: DNA
<213> ORGANISM: Artificial Sequence
<220> FEATURE:
<223> OTHER INFORMATION: Primer

<400> SEQUENCE: 239
gccccagatc ctggtacgct ctagagg                                        27

<210> SEQ ID NO 240
<211> LENGTH: 70
<212> TYPE: DNA
<213> ORGANISM: Artificial Sequence
<220> FEATURE:
<223> OTHER INFORMATION: Primer

<400> SEQUENCE: 240
atcttagcac ctggttggag ggggtttatt gggttttccc aataaacccc ctccaaccag    60
gtgctaagat                                                           70

<210> SEQ ID NO 241
<211> LENGTH: 70
<212> TYPE: DNA
<213> ORGANISM: Artificial Sequence
<220> FEATURE:
<223> OTHER INFORMATION: Primer

<400> SEQUENCE: 241
atcttagcac ctggttggag ggggtttata gggttttccc tataaacccc ctccaaccag    60
gtgctaagat                                                           70

<210> SEQ ID NO 242
<211> LENGTH: 70
<212> TYPE: DNA
<213> ORGANISM: Artificial Sequence
<220> FEATURE:
<223> OTHER INFORMATION: Primer

<400> SEQUENCE: 242
atcttagcac ctggttggag ggggtttatc gggttttccc gataaacccc ctccaaccag    60
gtgctaagat                                                           70

<210> SEQ ID NO 243
<211> LENGTH: 70
<212> TYPE: DNA
<213> ORGANISM: Artificial Sequence
<220> FEATURE:
<223> OTHER INFORMATION: Primer

<400> SEQUENCE: 243
atcttagcac ctggttggag ggggtttatg gggttttccc cataaacccc ctccaaccag    60
gtgctaagat                                                           70

<210> SEQ ID NO 244
<211> LENGTH: 20
<212> TYPE: DNA
<213> ORGANISM: Artificial Sequence
<220> FEATURE:
```

<223> OTHER INFORMATION: Primer

<400> SEQUENCE: 244
ttaaaagcca ggacggtcac                                                     20

<210> SEQ ID NO 245
<211> LENGTH: 20
<212> TYPE: DNA
<213> ORGANISM: Artificial Sequence
<220> FEATURE:
<223> OTHER INFORMATION: Primer

<400> SEQUENCE: 245
tgtagggagc ccagaagaga                                                     20

<210> SEQ ID NO 246
<211> LENGTH: 22
<212> TYPE: DNA
<213> ORGANISM: Artificial Sequence
<220> FEATURE:
<223> OTHER INFORMATION: Primer

<400> SEQUENCE: 246
acagtttgca ttcatggagg gc                                                  22

<210> SEQ ID NO 247
<211> LENGTH: 20
<212> TYPE: DNA
<213> ORGANISM: Artificial Sequence
<220> FEATURE:
<223> OTHER INFORMATION: Primer

<400> SEQUENCE: 247
ccgagcgagc aagctcagtt                                                     20

<210> SEQ ID NO 248
<211> LENGTH: 27
<212> TYPE: DNA
<213> ORGANISM: Artificial Sequence
<220> FEATURE:
<223> OTHER INFORMATION: Primer

<400> SEQUENCE: 248
cgcggatccc cgcccagtgg gactttg                                             27

<210> SEQ ID NO 249
<211> LENGTH: 27
<212> TYPE: DNA
<213> ORGANISM: Artificial Sequence
<220> FEATURE:
<223> OTHER INFORMATION: Primer

<400> SEQUENCE: 249
ccggaattca cctgttagag ctactgc                                             27

<210> SEQ ID NO 250
<211> LENGTH: 54
<212> TYPE: DNA
<213> ORGANISM: Artificial Sequence
<220> FEATURE:
<223> OTHER INFORMATION: Primer

<400> SEQUENCE: 250
agagagagag agaggcggcc gccctaccag ggatttcagt cgatgtacac gttc               54

```
<210> SEQ ID NO 251
<211> LENGTH: 58
<212> TYPE: DNA
<213> ORGANISM: Artificial Sequence
<220> FEATURE:
<223> OTHER INFORMATION: Primer

<400> SEQUENCE: 251
aagaagaaga aggaagagaa gtaggcctgt catcgtcggg aagacctgcg acacctgc      58

<210> SEQ ID NO 252
<211> LENGTH: 138
<212> TYPE: DNA
<213> ORGANISM: Artificial Sequence
<220> FEATURE:
<223> OTHER INFORMATION: Primer

<400> SEQUENCE: 252
actgctatcc gagtataaac cccctccaac caggtataaa cccccctccaa ccaggtataa      60 acccccctcca accaggtata aaccccctcc aaccaggtat aaaccccctc caaccaggat     120
ctgcgatcta agtaagct                                                    138

<210> SEQ ID NO 253
<211> LENGTH: 128
<212> TYPE: DNA
<213> ORGANISM: Artificial Sequence
<220> FEATURE:
<223> OTHER INFORMATION: Primer

<400> SEQUENCE: 253
ttaattaaga gtctagatta gcacctggtt ggaggggggtt tattgcttca tccaaaacca      60
tggtttacag ggttccaata aaccccctcc aaccaggtgc taaagatcta ggaggaattt     120
aaaatgag                                                               128

<210> SEQ ID NO 254
<211> LENGTH: 128
<212> TYPE: DNA
<213> ORGANISM: Artificial Sequence
<220> FEATURE:
<223> OTHER INFORMATION: Primer

<400> SEQUENCE: 254
actgacctag agaagctttt agcacctggt tggaggggggt ttattgcaac cctgtaaacc      60
atggttttgg atgaagcaat aaaccccctc caaccaggtg ctaactgcag ttatttgtac     120
agttcatc                                                               128

<210> SEQ ID NO 255
<211> LENGTH: 128
<212> TYPE: DNA
<213> ORGANISM: Artificial Sequence
<220> FEATURE:
<223> OTHER INFORMATION: Primer

<400> SEQUENCE: 255
ttaattaaga gtctagatta gcacctggtt ggaggggggtt tatcgcttca tccaaaacca      60
tggtttacag ggttccgata aaccccctcc aaccaggtgc taaagatcta ggaggaattt     120
aaaatgag                                                               128

<210> SEQ ID NO 256
<211> LENGTH: 128
<212> TYPE: DNA
```

```
<213> ORGANISM: Artificial Sequence
<220> FEATURE:
<223> OTHER INFORMATION: Primer

<400> SEQUENCE: 256
actgacctag agaagctttt agcacctggt tggagggggt ttatcgcaac cctgtaaacc    60
atggttttgg atgaagcgat aaacccctc caaccaggtg ctaactgcag ttatttgtac   120
agttcatc                                                           128

<210> SEQ ID NO 257
<211> LENGTH: 128
<212> TYPE: DNA
<213> ORGANISM: Artificial Sequence
<220> FEATURE:
<223> OTHER INFORMATION: Primer

<400> SEQUENCE: 257
ttaattaaga gtctagatta gcacctggtt ggagggggtt tatggcttca tccaaaacca    60
tggtttacag ggttcccata aaccccctcc aaccaggtgc taaagatcta ggaggaattt   120
aaaatgag                                                           128

<210> SEQ ID NO 258
<211> LENGTH: 128
<212> TYPE: DNA
<213> ORGANISM: Artificial Sequence
<220> FEATURE:
<223> OTHER INFORMATION: Primer

<400> SEQUENCE: 258
actgacctag agaagctttt agcacctggt tggagggggt ttatggcaac cctgtaaacc    60
atggttttgg atgaagccat aaacccctc caaccaggtg ctaactgcag ttatttgtac   120
agttcatc                                                           128

<210> SEQ ID NO 259
<211> LENGTH: 144
<212> TYPE: DNA
<213> ORGANISM: Artificial Sequence
<220> FEATURE:
<223> OTHER INFORMATION: Primer

<400> SEQUENCE: 259
actgctatct cgagctataa accccctcca accaggctat aaaccccctc caaccaggct    60 ataaacccc tccaaccagg ctataaaccc cctccaacca ggctataaac cccctccaac   120
caggatctgc gatctaagta agct                                         144

<210> SEQ ID NO 260
<211> LENGTH: 144
<212> TYPE: DNA
<213> ORGANISM: Artificial Sequence
<220> FEATURE:
<223> OTHER INFORMATION: Primer

<400> SEQUENCE: 260
actgctatct cgagcaataa accccctcca accaggcaat aaaccccctc caaccaggca    60 ataaacccc tccaaccagg caataaaccc cctccaacca ggcaataaac cccctccaac   120
caggatctgc gatctaagta agct                                         144

<210> SEQ ID NO 261
<211> LENGTH: 144
```

-continued

```
<212> TYPE: DNA
<213> ORGANISM: Artificial Sequence
<220> FEATURE:
<223> OTHER INFORMATION: Primer

<400> SEQUENCE: 261
actgctatct cgagccataa accccctcca accaggccat aaacccccctc caaccaggcc      60 ataaaccccc tccaaccagg ccataaaccc cctccaacca ggccataaac cccctccaac     120
caggatctgc gatctaagta agct                                             144

<210> SEQ ID NO 262
<211> LENGTH: 144
<212> TYPE: DNA
<213> ORGANISM: Artificial Sequence
<220> FEATURE:
<223> OTHER INFORMATION: Primer

<400> SEQUENCE: 262
actgctatct cgagcgataa accccctcca accaggcgat aaacccccctc caaccaggcg      60 ataaaccccc tccaaccagg cgataaaccc cctccaacca ggcgataaac cccctccaac     120
caggatctgc gatctaagta agct                                             144

<210> SEQ ID NO 263
<211> LENGTH: 25
<212> TYPE: DNA
<213> ORGANISM: Artificial Sequence
<220> FEATURE:
<223> OTHER INFORMATION: Primer

<400> SEQUENCE: 263
tcagaaacag ctcttcttca aatct                                             25

<210> SEQ ID NO 264
<211> LENGTH: 80
<212> TYPE: DNA
<213> ORGANISM: Artificial Sequence
<220> FEATURE:
<223> OTHER INFORMATION: Primer

<400> SEQUENCE: 264
ttaattaaga gtctagagga ggcgtgtcca aaaccatggt ttacagcacg cctccagatc      60
taggaggaat ttaaaatgag                                                  80

<210> SEQ ID NO 265
<211> LENGTH: 80
<212> TYPE: DNA
<213> ORGANISM: Artificial Sequence
<220> FEATURE:
<223> OTHER INFORMATION: Primer

<400> SEQUENCE: 265
actgacctag agaagcttgg aggcgtgctg taaaccatgg ttttggacac gcctccctgc      60
agttatttgt acagttcatc                                                  80

<210> SEQ ID NO 266
<211> LENGTH: 86
<212> TYPE: DNA
<213> ORGANISM: Artificial Sequence
<220> FEATURE:
<223> OTHER INFORMATION: Primer

<400> SEQUENCE: 266
```

```
ttaattaaga gagatctgct gatgcagata cagaaaccaa ggttttctta cttgctgctg    60
cgcgatctgc atctcaatta gtcagc                                        86

<210> SEQ ID NO 267
<211> LENGTH: 82
<212> TYPE: DNA
<213> ORGANISM: Artificial Sequence
<220> FEATURE:
<223> OTHER INFORMATION: Primer

<400> SEQUENCE: 267
caccaccacg gatccgcagc agcaagtaag aaaaccttgg tttctgtatc tgcatcagca    60
atttcgataa gccagtaagc ag                                            82

<210> SEQ ID NO 268
<211> LENGTH: 65
<212> TYPE: DNA
<213> ORGANISM: Artificial Sequence
<220> FEATURE:
<223> OTHER INFORMATION: Primer

<400> SEQUENCE: 268
caccaccacg cgcgcaagct tagatctggc ccaggcggcc accatgctga ttggctatgt    60
aaggg                                                               65

<210> SEQ ID NO 269
<211> LENGTH: 35
<212> TYPE: DNA
<213> ORGANISM: Artificial Sequence
<220> FEATURE:
<223> OTHER INFORMATION: Primer

<400> SEQUENCE: 269
caccaccaca ccggttcccg atttaggtgg gcgac                              35

<210> SEQ ID NO 270
<211> LENGTH: 21
<212> TYPE: DNA
<213> ORGANISM: Artificial Sequence
<220> FEATURE:
<223> OTHER INFORMATION: Primer

<400> SEQUENCE: 270
gttcctgcca ggatccacta g                                             21

<210> SEQ ID NO 271
<211> LENGTH: 21
<212> TYPE: DNA
<213> ORGANISM: Artificial Sequence
<220> FEATURE:
<223> OTHER INFORMATION: Primer

<400> SEQUENCE: 271
gcatgtgtcc agatgcatag g                                             21

<210> SEQ ID NO 272
<211> LENGTH: 20
<212> TYPE: DNA
<213> ORGANISM: Artificial Sequence
<220> FEATURE:
<223> OTHER INFORMATION: Primer

<400> SEQUENCE: 272
caccttctcc caggataagg                                               20
```

<210> SEQ ID NO 273
<211> LENGTH: 20
<212> TYPE: DNA
<213> ORGANISM: Artificial Sequence
<220> FEATURE:
<223> OTHER INFORMATION: Primer

<400> SEQUENCE: 273
gttggcctgt attcctctgg                                                20

<210> SEQ ID NO 274
<211> LENGTH: 22
<212> TYPE: DNA
<213> ORGANISM: Artificial Sequence
<220> FEATURE:
<223> OTHER INFORMATION: Primer

<400> SEQUENCE: 274
aatgaagttc ccttggcact tc                                             22

<210> SEQ ID NO 275
<211> LENGTH: 23
<212> TYPE: DNA
<213> ORGANISM: Artificial Sequence
<220> FEATURE:
<223> OTHER INFORMATION: Primer

<400> SEQUENCE: 275
ctgaagggtt ttaagtgcag aag                                            23

<210> SEQ ID NO 276
<211> LENGTH: 22
<212> TYPE: DNA
<213> ORGANISM: Artificial Sequence
<220> FEATURE:
<223> OTHER INFORMATION: Primer

<400> SEQUENCE: 276
tgacgtcaat gacggtaaat gg                                             22

<210> SEQ ID NO 277
<211> LENGTH: 122
<212> TYPE: DNA
<213> ORGANISM: Artificial Sequence
<220> FEATURE:
<223> OTHER INFORMATION: Primer

<400> SEQUENCE: 277
actgacctag agaagctttt agcacctggt tggaggggt ttataaccct gtaaaccatg     60
gttttggaag ctataaaccc cctccaacca ggtgctaact gcagttattt gtacagttca   120
tc                                                                  122

<210> SEQ ID NO 278
<211> LENGTH: 140
<212> TYPE: DNA
<213> ORGANISM: Artificial Sequence
<220> FEATURE:
<223> OTHER INFORMATION: Primer

<400> SEQUENCE: 278
actgacctag agaagctttt agcacctggt tggaggggt ttatagcaac cgcaaccctg     60
taaaccatgg ttttggatga agctgaagct ataaaccccc tccaaccagg tgctaactgc   120

```
agttatttgt acagttcatc                                               140

<210> SEQ ID NO 279
<211> LENGTH: 12
<212> TYPE: DNA
<213> ORGANISM: Artificial Sequence
<220> FEATURE:
<223> OTHER INFORMATION: Synthetic construct

<400> SEQUENCE: 279
gcgggaggcg tg                                                        12

<210> SEQ ID NO 280
<211> LENGTH: 17
<212> TYPE: DNA
<213> ORGANISM: Artificial Sequence
<220> FEATURE:
<223> OTHER INFORMATION: Synthetic construct

<400> SEQUENCE: 280
tcttcattac acctgca                                                   17

<210> SEQ ID NO 281
<211> LENGTH: 15
<212> TYPE: DNA
<213> ORGANISM: Artificial Sequence
<220> FEATURE:
<223> OTHER INFORMATION: Synthetic construct

<400> SEQUENCE: 281
cagtcagtat caatt                                                     15

<210> SEQ ID NO 282
<211> LENGTH: 17
<212> TYPE: DNA
<213> ORGANISM: Artificial Sequence
<220> FEATURE:
<223> OTHER INFORMATION: Synthetic construct

<400> SEQUENCE: 282
cctgcagctc tcatttt                                                   17

<210> SEQ ID NO 283
<211> LENGTH: 16
<212> TYPE: DNA
<213> ORGANISM: Artificial Sequence
<220> FEATURE:
<223> OTHER INFORMATION: Synthetic construct

<400> SEQUENCE: 283
attcttccag aattga                                                    16

<210> SEQ ID NO 284
<211> LENGTH: 17
<212> TYPE: DNA
<213> ORGANISM: Artificial Sequence
<220> FEATURE:
<223> OTHER INFORMATION: Synthetic construct

<400> SEQUENCE: 284
cagaattgat actgact                                                   17

<210> SEQ ID NO 285
<211> LENGTH: 16
<212> TYPE: DNA
<213> ORGANISM: Artificial Sequence
```

```
<220> FEATURE:
<223> OTHER INFORMATION: Synthetic construct

<400> SEQUENCE: 285
tcattacacc tgcagc                                                         16

<210> SEQ ID NO 286
<211> LENGTH: 18
<212> TYPE: DNA
<213> ORGANISM: Artificial Sequence
<220> FEATURE:
<223> OTHER INFORMATION: Synthetic construct

<400> SEQUENCE: 286
cttccagaat tgatactg                                                       18

<210> SEQ ID NO 287
<211> LENGTH: 15
<212> TYPE: DNA
<213> ORGANISM: Artificial Sequence
<220> FEATURE:
<223> OTHER INFORMATION: Synthetic construct

<400> SEQUENCE: 287 ataaacccc tccaa                                                           15

<210> SEQ ID NO 288
<211> LENGTH: 74
<212> TYPE: DNA
<213> ORGANISM: Artificial Sequence
<220> FEATURE:
<223> OTHER INFORMATION: Synthetic construct

<400> SEQUENCE: 288
ttagcacctg gttggagggg gtttatatcc aaaaccatgg tttacagtat aaaccccctc         60
caaccaggtg ctaa                                                           74

<210> SEQ ID NO 289
<211> LENGTH: 74
<212> TYPE: DNA
<213> ORGANISM: Artificial Sequence
<220> FEATURE:
<223> OTHER INFORMATION: Synthetic construct

<400> SEQUENCE: 289
ttagcacctg gttggagggg gtttataagg ttttggtacc aaatgtctat aaaccccctc         60
caaccaggtg ctaa                                                           74

<210> SEQ ID NO 290
<211> LENGTH: 74
<212> TYPE: DNA
<213> ORGANISM: Artificial Sequence
<220> FEATURE:
<223> OTHER INFORMATION: Synthetic construct

<400> SEQUENCE: 290
tataaacccc ctccaaccag gtgctaactg taaaccatgg ttttggatta gcacctggtt         60
ggagggggtt tata                                                           74

<210> SEQ ID NO 291
<211> LENGTH: 6
<212> TYPE: PRT
<213> ORGANISM: Artificial Sequence
<220> FEATURE:
```

<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 291

Lys Xaa Xaa Gly Ala Arg
1               5

<210> SEQ ID NO 292
<211> LENGTH: 83
<212> TYPE: DNA
<213> ORGANISM: Artificial Sequence
<220> FEATURE:
<223> OTHER INFORMATION: Synthetic construct

<400> SEQUENCE: 292
tggaaattct tccagaattg atactgactg tatggaaaat gagagctgca ggtgtaatga      60
agaccttctt tttgagatct ggt                                              83

<210> SEQ ID NO 293
<211> LENGTH: 77
<212> TYPE: DNA
<213> ORGANISM: Artificial Sequence
<220> FEATURE:
<223> OTHER INFORMATION: Synthetic construct

<400> SEQUENCE: 293
tggaaattct tccataattg atattgactg tatggaaggc tgcgggtgta atgaatacct      60 tcttttgag atctggt                                                      77

<210> SEQ ID NO 294
<211> LENGTH: 77
<212> TYPE: DNA
<213> ORGANISM: Artificial Sequence
<220> FEATURE:
<223> OTHER INFORMATION: Synthetic construct

<400> SEQUENCE: 294
tggaaattct tccagaattg atactgactg tatggaaaac tgcaggtgta atgaagacct      60 tcttttgag atctggt                                                      77

<210> SEQ ID NO 295
<211> LENGTH: 77
<212> TYPE: DNA
<213> ORGANISM: Artificial Sequence
<220> FEATURE:
<223> OTHER INFORMATION: Synthetic construct

<400> SEQUENCE: 295
tggaaattct tccagaattg atactgactg tatggaaagc tgcaggtgta atgaagacct      60 tcttttgag atctggt                                                      77

<210> SEQ ID NO 296
<211> LENGTH: 76
<212> TYPE: DNA
<213> ORGANISM: Artificial Sequence
<220> FEATURE:
<223> OTHER INFORMATION: Synthetic construct

<400> SEQUENCE: 296
tggaaattct tccagaattg atactgactg tatggaagct gcaggtgtaa tgaagacctt      60

```
cttttttgaga tctggt                                                    76

<210> SEQ ID NO 297
<211> LENGTH: 73
<212> TYPE: DNA
<213> ORGANISM: Artificial Sequence
<220> FEATURE:
<223> OTHER INFORMATION: Synthetic construct

<400> SEQUENCE: 297
tggaaattct tccagaattg atactgactg tagagctgca ggtgtaatga agaccttctt    60
tttgagatct ggt                                                       73

<210> SEQ ID NO 298
<211> LENGTH: 72
<212> TYPE: DNA
<213> ORGANISM: Artificial Sequence
<220> FEATURE:
<223> OTHER INFORMATION: Synthetic construct

<400> SEQUENCE: 298
tggaaattct tccagaattg atactgactg tatgctgcag gtgtaatgaa gaccttcttt    60
ttgagatctg gt                                                        72

<210> SEQ ID NO 299
<211> LENGTH: 70
<212> TYPE: DNA
<213> ORGANISM: Artificial Sequence
<220> FEATURE:
<223> OTHER INFORMATION: Synthetic construct

<400> SEQUENCE: 299
tggaaattct tccagaattg atactgactg tgctgcaggt gtaatgaaga ccttcttttt    60
gagatctggt                                                           70

<210> SEQ ID NO 300
<211> LENGTH: 83
<212> TYPE: DNA
<213> ORGANISM: Artificial Sequence
<220> FEATURE:
<223> OTHER INFORMATION: Synthetic construct

<400> SEQUENCE: 300
tggaaattct tccagaattg atactgactg tatggaaaat gagagctgca ggtgtaatga    60
agaccttctt tttgagatct ggt                                            83

<210> SEQ ID NO 301
<211> LENGTH: 79
<212> TYPE: DNA
<213> ORGANISM: Artificial Sequence
<220> FEATURE:
<223> OTHER INFORMATION: Synthetic construct

<400> SEQUENCE: 301
tggaaattct tccagaattg atactgactg tatggaaaga gctgcaggtg taatgaagac    60 cttcttttg agatctggt                                                  79

<210> SEQ ID NO 302
<211> LENGTH: 78
<212> TYPE: DNA
<213> ORGANISM: Artificial Sequence
<220> FEATURE:
<223> OTHER INFORMATION: Synthetic construct
```

<400> SEQUENCE: 302
tggaaattct tccagaattg atactgactg tatggaagag ctgcaggtgt aatgaagacc    60 ttcttttga gatctggt                                                  78

<210> SEQ ID NO 303
<211> LENGTH: 77
<212> TYPE: DNA
<213> ORGANISM: Artificial Sequence
<220> FEATURE:
<223> OTHER INFORMATION: Synthetic construct

<400> SEQUENCE: 303
tggaaattct tccagaattg atactgactg tatggagagc tgcaggtgta atgaagacct    60 tcttttgag atctggt                                                   77

<210> SEQ ID NO 304
<211> LENGTH: 74
<212> TYPE: DNA
<213> ORGANISM: Artificial Sequence
<220> FEATURE:
<223> OTHER INFORMATION: Synthetic construct

<400> SEQUENCE: 304
tggaaattct tccagaattg atactgacta tgagagctgc aggtgtaatg aagaccttct    60
ttttgagatc tggt                                                     74

<210> SEQ ID NO 305
<211> LENGTH: 73
<212> TYPE: DNA
<213> ORGANISM: Artificial Sequence
<220> FEATURE:
<223> OTHER INFORMATION: Synthetic construct

<400> SEQUENCE: 305
tggaaattct tccagaattg atactgactg tagagctgca ggtgtaatga agaccttctt    60
tttgagatct ggt                                                      73

<210> SEQ ID NO 306
<211> LENGTH: 72
<212> TYPE: DNA
<213> ORGANISM: Artificial Sequence
<220> FEATURE:
<223> OTHER INFORMATION: Synthetic construct

<400> SEQUENCE: 306
tggaaattct tccagaattg atactgactg agagctgcag gtgtaatgaa gaccttcttt    60
ttgagatctg gt                                                       72

<210> SEQ ID NO 307
<211> LENGTH: 72
<212> TYPE: DNA
<213> ORGANISM: Artificial Sequence
<220> FEATURE:
<223> OTHER INFORMATION: Synthetic construct

<400> SEQUENCE: 307
tggaaattct tccaggattg atactgactg agagctgcag gtgtaatgaa gaccttcttt    60
ttgagatctg gt                                                       72

<210> SEQ ID NO 308

```
<211> LENGTH: 72
<212> TYPE: DNA
<213> ORGANISM: Artificial Sequence
<220> FEATURE:
<223> OTHER INFORMATION: Synthetic construct

<400> SEQUENCE: 308
tggaaattct tccagaattg atactgactg agagctgcag gtgtaatgaa gaccttcttt    60
ttgagatctg gt                                                        72

<210> SEQ ID NO 309
<211> LENGTH: 72
<212> TYPE: DNA
<213> ORGANISM: Artificial Sequence
<220> FEATURE:
<223> OTHER INFORMATION: Synthetic construct

<400> SEQUENCE: 309
tggaaattct tccagaattg atactgacta ggagctgcag gtgtaatgaa gaccttcttt    60
ttgagatctg gt                                                        72

<210> SEQ ID NO 310
<211> LENGTH: 83
<212> TYPE: DNA
<213> ORGANISM: Artificial Sequence
<220> FEATURE:
<223> OTHER INFORMATION: Synthetic construct

<400> SEQUENCE: 310
tggaaattct tccagaattg atactgactg tatggaaaat gagagctgca ggtgtaatga    60
agaccttctt tttgagatct ggt                                            83

<210> SEQ ID NO 311
<211> LENGTH: 81
<212> TYPE: DNA
<213> ORGANISM: Artificial Sequence
<220> FEATURE:
<223> OTHER INFORMATION: Synthetic construct

<400> SEQUENCE: 311
tggaaattct tccagaattg atactgacta tggaaaatga gagctgcagg tgtaatgaag    60
accttctttt tgagatctgg t                                              81

<210> SEQ ID NO 312
<211> LENGTH: 80
<212> TYPE: DNA
<213> ORGANISM: Artificial Sequence
<220> FEATURE:
<223> OTHER INFORMATION: Synthetic construct

<400> SEQUENCE: 312
tggaaattct tcctcaattg atactgatat ggaaaatgag agctgcaggt gtaatgaaga    60
ccttcttttt gagatctggt                                                80

<210> SEQ ID NO 313
<211> LENGTH: 74
<212> TYPE: DNA
<213> ORGANISM: Artificial Sequence
<220> FEATURE:
<223> OTHER INFORMATION: Synthetic construct

<400> SEQUENCE: 313
tggaaattct tccagaattg atatggaaaa tgagagctgc aggtgtaatg aagaccttct    60
```
ttttgagatc tggt                                                        74

<210> SEQ ID NO 314
<211> LENGTH: 83
<212> TYPE: DNA
<213> ORGANISM: Artificial Sequence
<220> FEATURE:
<223> OTHER INFORMATION: Synthetic construct

<400> SEQUENCE: 314
tggaaattct tccagaattg atactgactg tatggaaaat gagagctgca ggtgtaatga      60
agaccttctt tttgagatct ggt                                              83

<210> SEQ ID NO 315
<211> LENGTH: 79
<212> TYPE: DNA
<213> ORGANISM: Artificial Sequence
<220> FEATURE:
<223> OTHER INFORMATION: Synthetic construct

<400> SEQUENCE: 315
tggaaattct tccagaattg atactgactg tatgatgaga gctgcaggtg taatgaagac      60 cttcttttg agatctggt                                                    79

<210> SEQ ID NO 316
<211> LENGTH: 79
<212> TYPE: DNA
<213> ORGANISM: Artificial Sequence
<220> FEATURE:
<223> OTHER INFORMATION: Synthetic construct

<400> SEQUENCE: 316
tggaaattct tccagaattg atactgactg tatggtgaga gctgcaggtg taatgaagac      60 cttcttttg agatctggt                                                    79

<210> SEQ ID NO 317
<211> LENGTH: 78
<212> TYPE: DNA
<213> ORGANISM: Artificial Sequence
<220> FEATURE:
<223> OTHER INFORMATION: Synthetic construct

<400> SEQUENCE: 317
tggaaattct tccagaattg atactgactg taaatgagag ctgcaggtgt aatgaagacc      60
ttctttttga gatctggt                                                    78

<210> SEQ ID NO 318
<211> LENGTH: 78
<212> TYPE: DNA
<213> ORGANISM: Artificial Sequence
<220> FEATURE:
<223> OTHER INFORMATION: Synthetic construct

<400> SEQUENCE: 318
tggaaattct tccagaattg atactgactg tatgtgagag ctgcaggtgt aatgaagacc      60
ttctttttga gatctggt                                                    78

<210> SEQ ID NO 319
<211> LENGTH: 74
<212> TYPE: DNA
<213> ORGANISM: Artificial Sequence
<220> FEATURE:

<223> OTHER INFORMATION: Synthetic construct

<400> SEQUENCE: 319
tggaaattct tccagaattg atactgaaaa tgagagctgc aggtgtaatg aagaccttct    60
ttttgagatc tggt    74

<210> SEQ ID NO 320
<211> LENGTH: 74
<212> TYPE: DNA
<213> ORGANISM: Artificial Sequence
<220> FEATURE:
<223> OTHER INFORMATION: Synthetic construct

<400> SEQUENCE: 320
tggaaattct tccagaattg atactgactg tatggactgc aggtgtaatg aagaccttct    60
ttttgagatc tggt    74

<210> SEQ ID NO 321
<211> LENGTH: 74
<212> TYPE: DNA
<213> ORGANISM: Artificial Sequence
<220> FEATURE:
<223> OTHER INFORMATION: Synthetic construct

<400> SEQUENCE: 321
tggaaattct tccagaattg atactgactg tgagagctgc aggtgtaatg aagaccttct    60
ttttgagatc tggt    74

<210> SEQ ID NO 322
<211> LENGTH: 73
<212> TYPE: DNA
<213> ORGANISM: Artificial Sequence
<220> FEATURE:
<223> OTHER INFORMATION: Synthetic construct

<400> SEQUENCE: 322
tggaaattct tccagaattg atactggtat gagagctgca ggtgtaatga agaccttctt    60
tttgagatct ggt    73

<210> SEQ ID NO 323
<211> LENGTH: 71
<212> TYPE: DNA
<213> ORGANISM: Artificial Sequence
<220> FEATURE:
<223> OTHER INFORMATION: Synthetic construct

<400> SEQUENCE: 323
tggaaattct tccagaattg atactgactg tagctgcagg tgtaatgaag accttctttt    60
tgagatctgg t    71

<210> SEQ ID NO 324
<211> LENGTH: 83
<212> TYPE: DNA
<213> ORGANISM: Artificial Sequence
<220> FEATURE:
<223> OTHER INFORMATION: Synthetic construct

<400> SEQUENCE: 324
tggaaattct tccagaattg atactgactg tatggaaaat gagagctgca ggtgtaatga    60
agaccttctt tttgagatct ggt    83

```
<210> SEQ ID NO 325
<211> LENGTH: 75
<212> TYPE: DNA
<213> ORGANISM: Artificial Sequence
<220> FEATURE:
<223> OTHER INFORMATION: Synthetic construct

<400> SEQUENCE: 325
tggaaattct tccagaattg atactgactg tatggaaact gcggtgtaat gaagaccttc    60
tttttgagat ctggt                                                    75

<210> SEQ ID NO 326
<211> LENGTH: 76
<212> TYPE: DNA
<213> ORGANISM: Artificial Sequence
<220> FEATURE:
<223> OTHER INFORMATION: Synthetic construct

<400> SEQUENCE: 326
tggaaattct tccagaattg atactgactg tatgagagct gcaggtgtaa tgaagacctt    60 cttttttgaga tctggt                                                  76

<210> SEQ ID NO 327
<211> LENGTH: 74
<212> TYPE: DNA
<213> ORGANISM: Artificial Sequence
<220> FEATURE:
<223> OTHER INFORMATION: Synthetic construct

<400> SEQUENCE: 327
tggaaattct tccagaatta atactgactg tgagagctgc aggtgtaatg aagaccttct    60
ttttgagatc tggt                                                     74

<210> SEQ ID NO 328
<211> LENGTH: 73
<212> TYPE: DNA
<213> ORGANISM: Artificial Sequence
<220> FEATURE:
<223> OTHER INFORMATION: Synthetic construct

<400> SEQUENCE: 328
tggaaattct tccagaattg atactgactg gagagctgca ggtgtaatga agaccttctt    60
tttgagatct ggt                                                      73

<210> SEQ ID NO 329
<211> LENGTH: 72
<212> TYPE: DNA
<213> ORGANISM: Artificial Sequence
<220> FEATURE:
<223> OTHER INFORMATION: Synthetic construct

<400> SEQUENCE: 329
tggaaattct tccagaattg atactgactg agagctgcag gtgtaatgaa gaccttcttt    60
ttgagatctg gt                                                       72

<210> SEQ ID NO 330
<211> LENGTH: 68
<212> TYPE: DNA
<213> ORGANISM: Artificial Sequence
<220> FEATURE:
<223> OTHER INFORMATION: Synthetic construct

<400> SEQUENCE: 330
```

```
tggaaattct tccagaattg atactgactg ctgcaggtgt aatgaagacc ttcttttga      60 gatctggt                                                              68

<210> SEQ ID NO 331
<211> LENGTH: 65
<212> TYPE: DNA
<213> ORGANISM: Artificial Sequence
<220> FEATURE:
<223> OTHER INFORMATION: Synthetic construct

<400> SEQUENCE: 331
tggaaattct tccagaattg atactgactg tatgtgtaat gaagaccttc tttttgagat      60
ctggt                                                                 65

<210> SEQ ID NO 332
<211> LENGTH: 39
<212> TYPE: DNA
<213> ORGANISM: Artificial Sequence
<220> FEATURE:
<223> OTHER INFORMATION: Synthetic construct

<400> SEQUENCE: 332
tggaaattct tccagaattg atactttttg agatctggt                            39

<210> SEQ ID NO 333
<211> LENGTH: 24
<212> TYPE: PRT
<213> ORGANISM: Artificial Sequence
<220> FEATURE:
<223> OTHER INFORMATION: Synthetic construct

<400> SEQUENCE: 333
```

Arg Asn Asn Arg Asn Asn Arg Asn Asn Arg Asn Asn Asn Asn Tyr Asn
1               5                   10                  15

Asn Tyr Asn Asn Tyr Asn Asn Tyr
            20

```
<210> SEQ ID NO 334
<211> LENGTH: 24
<212> TYPE: PRT
<213> ORGANISM: Artificial Sequence
<220> FEATURE:
<223> OTHER INFORMATION: Synthetic construct

<400> SEQUENCE: 334
```

Arg Asn Asn Arg Asn Asn Arg Asn Asn Arg Asn Asn Asn Asn Tyr Asn
1               5                   10                  15

Asn Tyr Asn Asn Tyr Asn Asn Tyr
            20

```
<210> SEQ ID NO 335
<211> LENGTH: 20
<212> TYPE: DNA
<213> ORGANISM: Artificial Sequence
<220> FEATURE:
<223> OTHER INFORMATION: Synthetic construct

<400> SEQUENCE: 335
tccaaaacca tggtttacag                                                 20

<210> SEQ ID NO 336
<211> LENGTH: 20
<212> TYPE: DNA
<213> ORGANISM: Artificial Sequence
```

```
<220> FEATURE:
<223> OTHER INFORMATION: Synthetic construct

<400> SEQUENCE: 336
tccaaaacca tggtttacag                                              20

<210> SEQ ID NO 337
<211> LENGTH: 20
<212> TYPE: DNA
<213> ORGANISM: Artificial Sequence
<220> FEATURE:
<223> OTHER INFORMATION: Synthetic construct

<400> SEQUENCE: 337
tccaaaacca tggtttacag                                              20

<210> SEQ ID NO 338
<211> LENGTH: 20
<212> TYPE: DNA
<213> ORGANISM: Artificial Sequence
<220> FEATURE:
<223> OTHER INFORMATION: Synthetic construct

<400> SEQUENCE: 338
tccaaaacca tggtttacag                                              20

<210> SEQ ID NO 339
<211> LENGTH: 20
<212> TYPE: DNA
<213> ORGANISM: Artificial Sequence
<220> FEATURE:
<223> OTHER INFORMATION: Synthetic construct

<400> SEQUENCE: 339
tccaaaacca tggtttacag                                              20

<210> SEQ ID NO 340
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t

<400> SEQUENCE: 340
ggaggcgtgt ccaaaannat nntttacagc acgcctcc                          38

<210> SEQ ID NO 341
<211> LENGTH: 144
<212> TYPE: PRT
<213> ORGANISM: Artificial Sequence
<220> FEATURE:
<223> OTHER INFORMATION: Synthetic construct

<400> SEQUENCE: 341

Met Arg Leu Phe Gly Tyr Ala Arg Val Ser Thr Ser Gln Gln Ser Leu
1               5                   10                  15

Asp Ile Gln Val Arg Ala Leu Lys Asp Ala Gly Val Lys Ala Asn Arg
            20                  25                  30
```

Ile Phe Thr Asp Lys Ala Ser Gly Ser Ser Cys Asp Arg Lys Gly Leu
            35                  40                  45

Asp Leu Leu Arg Met Lys Val Glu Glu Gly Asp Val Ile Leu Val Lys
 50                  55                  60

Lys Leu Asp Arg Leu Gly Arg Asp Thr Ala Asp Met Ile Gln Leu Ile
 65                  70                  75                  80

Lys Glu Phe Asp Ala Gln Gly Val Ser Ile Arg Phe Ile Asp Asp Gly
                    85                  90                  95

Ile Ser Thr Asp Gly Glu Met Gly Lys Met Val Val Thr Ile Leu Ser
                100                 105                 110

Ala Val Ala Gln Ala Glu Arg Gln Arg Ile Leu Glu Arg Thr Asn Glu
            115                 120                 125

Gly Arg Gln Glu Ala Met Ala Lys Gly Val Val Phe Gly Arg Lys Arg
130                 135                 140

<210> SEQ ID NO 342
<211> LENGTH: 141
<212> TYPE: PRT
<213> ORGANISM: Artificial Sequence
<220> FEATURE:
<223> OTHER INFORMATION: Synthetic construct

<400> SEQUENCE: 342

Met Leu Ile Gly Tyr Val Arg Val Ser Thr Asn Asp Gln Asn Thr Asp
 1               5                  10                  15

Leu Gln Arg Asn Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Lys Arg Leu Gln Lys Gly Asp Thr Leu Val Val Trp Lys Leu Asp
 50                  55                  60

Arg Leu Gly Arg Ser Met Lys His Leu Ile Ser Leu Val Gly Glu Leu
 65                  70                  75                  80

Arg Glu Arg Gly Ile Asn Phe Arg Ser Leu Thr Asp Ser Ile Asp Thr
                    85                  90                  95

Ser Ser Pro Met Gly Arg Phe Phe Phe His Val Met Gly Ala Leu Ala
                100                 105                 110

Glu Met Glu Arg Glu Leu Ile Ile Glu Arg Thr Met Ala Gly Leu Ala
            115                 120                 125

Ala Ala Arg Asn Lys Gly Arg Ile Gly Gly Arg Pro Pro
130                 135                 140

<210> SEQ ID NO 343
<211> LENGTH: 44
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature

```
<222> LOCATION: (11)..(16)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (29)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t

<400> SEQUENCE: 343
rnnrnnrnnr nnnnnnaaab nwwnvtttnn nnnnynnynn ynny            44

<210> SEQ ID NO 344
<211> LENGTH: 44
<212> TYPE: DNA
<213> ORGANISM: Artificial Sequence
<220> FEATURE:
<223> OTHER INFORMATION: Synthetic construct

<400> SEQUENCE: 344
gctgatgcag atacagaaac caaggttttc ttacttgctg ctgc            44

<210> SEQ ID NO 345
<211> LENGTH: 44
<212> TYPE: DNA
<213> ORGANISM: Artificial Sequence
<220> FEATURE:
<223> OTHER INFORMATION: Synthetic construct

<400> SEQUENCE: 345
gtggatggag cagccaatag gttccttttcc tccccttag cccc            44

<210> SEQ ID NO 346
<211> LENGTH: 44
<212> TYPE: DNA
<213> ORGANISM: Artificial Sequence
<220> FEATURE:
<223> OTHER INFORMATION: Synthetic construct

<400> SEQUENCE: 346
agggaagtca atccagaaac catcctttat cccttcctgt cctt            44

<210> SEQ ID NO 347
<211> LENGTH: 44
<212> TYPE: DNA
<213> ORGANISM: Artificial Sequence
<220> FEATURE:
<223> OTHER INFORMATION: Synthetic construct

<400> SEQUENCE: 347
ggaaatgtaa aagtagaaac taaagtttct gctttcattc ttcc            44
```

<210> SEQ ID NO 348
<211> LENGTH: 44
<212> TYPE: DNA
<213> ORGANISM: Artificial Sequence
<220> FEATURE:
<223> OTHER INFORMATION: Synthetic construct

<400> SEQUENCE: 348
ggaagaagga tgagagaaac taacctttgt ggaacccctg cagc                            44

<210> SEQ ID NO 349
<211> LENGTH: 44
<212> TYPE: DNA
<213> ORGANISM: Artificial Sequence
<220> FEATURE:
<223> OTHER INFORMATION: Synthetic construct

<400> SEQUENCE: 349
aacggcagaa gaagaaaaat tatactttct tttccattgt tttc                            44

<210> SEQ ID NO 350
<211> LENGTH: 44
<212> TYPE: DNA
<213> ORGANISM: Artificial Sequence
<220> FEATURE:
<223> OTHER INFORMATION: Synthetic construct

<400> SEQUENCE: 350
gaggtaaata cttgataaat gttgcttttt tcccccatta ccct                            44

<210> SEQ ID NO 351
<211> LENGTH: 44
<212> TYPE: DNA
<213> ORGANISM: Artificial Sequence
<220> FEATURE:
<223> OTHER INFORMATION: Synthetic construct

<400> SEQUENCE: 351
attgtggatg gagtaaaaat gatcctttaa tacatttcta catt                            44

<210> SEQ ID NO 352
<211> LENGTH: 44
<212> TYPE: DNA
<213> ORGANISM: Artificial Sequence
<220> FEATURE:
<223> OTHER INFORMATION: Synthetic construct

<400> SEQUENCE: 352
ataggagaaa atttggaaag tataattttt cagactactc tttt                            44

<210> SEQ ID NO 353
<211> LENGTH: 43
<212> TYPE: DNA
<213> ORGANISM: Artificial Sequence
<220> FEATURE:
<223> OTHER INFORMATION: Synthetic construct

<400> SEQUENCE: 353
acagaagaca ttaagaaaac ctaacttgac ctcctatggt tcc                             43

<210> SEQ ID NO 354
<211> LENGTH: 44
<212> TYPE: DNA
<213> ORGANISM: Artificial Sequence
<220> FEATURE:
<223> OTHER INFORMATION: Synthetic construct

<400> SEQUENCE: 354
ggcaggacag ctaactaatg aaaggtttgg tgtgtgtctg tctt                44

<210> SEQ ID NO 355
<211> LENGTH: 44
<212> TYPE: DNA
<213> ORGANISM: Artificial Sequence
<220> FEATURE:
<223> OTHER INFORMATION: Synthetic construct

<400> SEQUENCE: 355
agggatgagg cctcataaag taaagtttttt tgtttgtttg tttc                44

<210> SEQ ID NO 356
<211> LENGTH: 44
<212> TYPE: DNA
<213> ORGANISM: Artificial Sequence
<220> FEATURE:
<223> OTHER INFORMATION: Synthetic construct

<400> SEQUENCE: 356
acagtcaaag tatttgaaag ttaactttt tcgtcagctc ttcc                44

<210> SEQ ID NO 357
<211> LENGTH: 44
<212> TYPE: DNA
<213> ORGANISM: Artificial Sequence
<220> FEATURE:
<223> OTHER INFORMATION: Synthetic construct

<400> SEQUENCE: 357
gaaattgtgg acaattaaat tatcctttct gggcccctta tttc                44

<210> SEQ ID NO 358
<211> LENGTH: 44
<212> TYPE: DNA
<213> ORGANISM: Artificial Sequence
<220> FEATURE:
<223> OTHER INFORMATION: Synthetic construct

<400> SEQUENCE: 358
gaaattggaa ggaaaaaaat tatcctttat ggtgtaatac ttat                44

<210> SEQ ID NO 359
<211> LENGTH: 44
<212> TYPE: DNA
<213> ORGANISM: Artificial Sequence
<220> FEATURE:
<223> OTHER INFORMATION: Synthetic construct

<400> SEQUENCE: 359
aaaacagctg gctttgaaag gaaactttta actactatcc tgcc                44

<210> SEQ ID NO 360
<211> LENGTH: 44
<212> TYPE: DNA
<213> ORGANISM: Artificial Sequence
<220> FEATURE:
<223> OTHER INFORMATION: Synthetic construct

<400> SEQUENCE: 360
atagtaagtg ctcaataaat gttcgtttat atcatcattg tggc                44

<210> SEQ ID NO 361

```
<211> LENGTH: 44
<212> TYPE: DNA
<213> ORGANISM: Artificial Sequence
<220> FEATURE:
<223> OTHER INFORMATION: Synthetic construct

<400> SEQUENCE: 361
aaagatggaa caaacaaaat taaggtttag tacattataa ttcc            44

<210> SEQ ID NO 362
<211> LENGTH: 43
<212> TYPE: DNA
<213> ORGANISM: Artificial Sequence
<220> FEATURE:
<223> OTHER INFORMATION: Synthetic construct

<400> SEQUENCE: 362
gcgggaggcg tgtccaaacc atggtttaca gcacgcctcc cgc             43

<210> SEQ ID NO 363
<211> LENGTH: 44
<212> TYPE: DNA
<213> ORGANISM: Artificial Sequence
<220> FEATURE:
<223> OTHER INFORMATION: Synthetic construct

<400> SEQUENCE: 363
gctgatgcag atcgagaaac caaggttttc ttacttgctg ctgc            44

<210> SEQ ID NO 364
<211> LENGTH: 44
<212> TYPE: DNA
<213> ORGANISM: Artificial Sequence
<220> FEATURE:
<223> OTHER INFORMATION: Synthetic construct

<400> SEQUENCE: 364
gtggatggag cagccaatag gttcctttcc tcccccttag cccc            44

<210> SEQ ID NO 365
<211> LENGTH: 44
<212> TYPE: DNA
<213> ORGANISM: Artificial Sequence
<220> FEATURE:
<223> OTHER INFORMATION: Synthetic construct

<400> SEQUENCE: 365
agggaagtca atccagaaac catcctttat cccttcctgt cctt            44

<210> SEQ ID NO 366
<211> LENGTH: 35
<212> TYPE: DNA
<213> ORGANISM: Artificial Sequence
<220> FEATURE:
<223> OTHER INFORMATION: Synthetic construct

<400> SEQUENCE: 366
agatacagaa accgttttct tacttgctgc tggcc                      35

<210> SEQ ID NO 367
<211> LENGTH: 38
<212> TYPE: DNA
<213> ORGANISM: Artificial Sequence
<220> FEATURE:
<223> OTHER INFORMATION: Synthetic construct

<400> SEQUENCE: 367
```

```
tcagggaagt catcctttat cccttcctgt ccttagct                                 38

<210> SEQ ID NO 368
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t

<400> SEQUENCE: 368
tccasssnna tnnsssacag                                                     20

<210> SEQ ID NO 369
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (17)..(20)
<223> OTHER INFORMATION: n is a, c, g, or t

<400> SEQUENCE: 369
nnnnaaanna tnntttnnnn                                                     20
```